(12) United States Patent
Parham et al.

(10) Patent No.: US 10,377,766 B2
(45) Date of Patent: Aug. 13, 2019

(54) HETEROCYCLIC COMPOUNDS WITH BENZO(C)COUMARIN-STRUCTURES

(71) Applicant: Merck Patent GmbH, Darmstadt (DE)

(72) Inventors: Amir Hossain Parham, Frankfurt am Main (DE); Teresa Mujica-Fernaud, Darmstadt (DE); Thomas Eberle, Landau (DE); Anja Jatsch, Frankfurt am Main (DE); Jonas Valentin Kroeber, Frankfurt am Main (DE); Tobias Grossmann, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 17 days.

(21) Appl. No.: 15/513,410

(22) PCT Filed: Aug. 27, 2015

(86) PCT No.: PCT/EP2015/001750
§ 371 (c)(1),
(2) Date: Mar. 22, 2017

(87) PCT Pub. No.: WO2016/045769
PCT Pub. Date: Mar. 31, 2016

(65) Prior Publication Data
US 2017/0298077 A1    Oct. 19, 2017

(30) Foreign Application Priority Data
Sep. 25, 2014  (EP) .................................. 14003317

(51) Int. Cl.
| | | |
|---|---|---|
| *C07D 311/80* | (2006.01) |
| *C07D 493/14* | (2006.01) |
| *C07D 405/14* | (2006.01) |
| *C07D 405/04* | (2006.01) |
| *C07D 407/04* | (2006.01) |
| *C07D 407/10* | (2006.01) |
| *C07D 407/12* | (2006.01) |
| *C07D 407/14* | (2006.01) |
| *C07D 409/10* | (2006.01) |
| *C07D 409/14* | (2006.01) |
| *C07D 413/04* | (2006.01) |
| *C07D 417/04* | (2006.01) |
| *C07D 417/10* | (2006.01) |
| *C07D 471/04* | (2006.01) |
| *C07D 491/052* | (2006.01) |
| *C07D 493/04* | (2006.01) |
| *C07D 513/04* | (2006.01) |
| *H01L 51/00* | (2006.01) |
| *C07D 311/94* | (2006.01) |
| *C09K 11/06* | (2006.01) |
| *H01L 51/50* | (2006.01) |

(52) U.S. Cl.
CPC .......... *C07D 493/14* (2013.01); *C07D 311/80* (2013.01); *C07D 311/94* (2013.01); *C07D 405/04* (2013.01); *C07D 405/14* (2013.01); *C07D 407/04* (2013.01); *C07D 407/10* (2013.01); *C07D 407/12* (2013.01); *C07D 407/14* (2013.01); *C07D 409/10* (2013.01); *C07D 409/14* (2013.01); *C07D 413/04* (2013.01); *C07D 417/04* (2013.01); *C07D 417/10* (2013.01); *C07D 471/04* (2013.01); *C07D 491/052* (2013.01); *C07D 493/04* (2013.01); *C07D 513/04* (2013.01); *C09K 11/06* (2013.01); *H01L 51/0058* (2013.01); *H01L 51/0062* (2013.01); *H01L 51/0064* (2013.01); *H01L 51/0072* (2013.01); *H01L 51/0073* (2013.01); *H01L 51/5012* (2013.01); *C09K 2211/1018* (2013.01); *H01L 51/0085* (2013.01); *H01L 51/0087* (2013.01); *Y02E 10/549* (2013.01)

(58) Field of Classification Search
None
See application file for complete search history.

(56) References Cited

U.S. PATENT DOCUMENTS

| | | |
|---|---|---|
| 2007/0051922 A1 | 3/2007 | Nakatani et al. |
| 2009/0039765 A1 | 2/2009 | Uetani et al. |
| 2015/0179940 A1 | 6/2015 | Mujica-Fernaud et al. |
| 2016/0301005 A1 | 10/2016 | Pfister et al. |
| 2016/0326429 A1 | 11/2016 | Parham et al. |

FOREIGN PATENT DOCUMENTS

| | | |
|---|---|---|
| EP | 2468725 A1 | 6/2012 |
| WO | WO-03099901 A1 | 12/2003 |
| WO | WO-2014015935 A2 | 1/2014 |
| WO | WO-2015082056 A1 | 6/2015 |
| WO | WO-2015106789 A1 | 7/2015 |

OTHER PUBLICATIONS

International Search Report for PCT/EP2015/001750 dated Nov. 11, 2015.
Written Opinion of the International Searching Authority or PCT/EP2015/001750 dated Nov. 11, 2015.

*Primary Examiner* — Heidi Reese
(74) *Attorney, Agent, or Firm* — Drinker Biddle & Reath LLP

(57) ABSTRACT

The invention relates to heterocyclic compounds with benzo[c]coumarin structures and to electronic devices, in particular organic electroluminescent devices, containing said compounds.

23 Claims, No Drawings

HETEROCYCLIC COMPOUNDS WITH BENZO(C)COUMARIN-STRUCTURES

CROSS-REFERENCE TO RELATED APPLICATIONS

This application is a national stage application (under 35 U.S.C. § 371) of PCT/EP2015/001750, filed Aug. 27, 2015, which claims benefit of European Application No. 14003317.6, filed Sep. 25, 2014, both of which are incorporated herein by reference in their entirety.

The present invention relates to heterocyclic compounds having benzo[c]coumarin structures suitable for use in electronic devices. The present invention further relates to processes for preparation thereof and to electronic devices.

BACKGROUND OF THE INVENTION

Electronic devices containing organic, organometallic and/or polymeric semiconductors are becoming increasingly important, and are being used in many commercial products for reasons of cost and because of their performance. Examples here include organic-based charge transport materials (for example triarylamine-based hole transporters) in photocopiers, organic or polymeric light-emitting diodes (OLEDs or PLEDs) and in readout and display devices or organic photoreceptors in photocopiers. Organic solar cells (O-SCs), organic field-effect transistors (O-FETs), organic thin-film transistors (O-TFTs), organic integrated circuits (O-ICs), organic optical amplifiers and organic laser diodes (O-lasers) are at an advanced stage of development and may have great future significance.

Many of these electronic devices, irrespective of the respective end use, have the following general layer structure which can be adjusted for the particular application:
(1) substrate,
(2) electrode, frequently metallic or inorganic, but also composed of organic or polymeric conductive materials,
(3) charge injection layer(s) or interlayer(s), for example to compensate for unevenness in the electrode ("planarization layer"), frequently composed of a conductive doped polymer,
(4) organic semiconductors,
(5) possibly further charge transport, charge injection or charge blocker layers,
(6) counterelectrode, materials as specified in (2),
(7) encapsulation.

The above arrangement is the general structure of an organic electronic device, it being possible to combine various layers, such that the result in the simplest case is an arrangement composed of two electrodes with an organic layer in between. In this case, the organic layer fulfills all functions including the emission of light in the case of OLEDs. A system of this kind is described, for example, in WO 90/13148 A1, based on poly(p-phenylenes).

Electronic devices containing polymeric compounds having benzo[c]coumarin structures are known from publications including JP 2009-073808 A, WO 2005/33174 A, WO 2004/39859 A and WO 2003/99901 A.

Known electronic devices have a useful profile of properties. However, there is a constant need to improve the properties of these devices.

These properties especially include the energy efficiency with which an electronic device solves the problem defined. In the case of organic light-emitting diodes, which may be based either on low molecular weight compounds or on polymeric materials, the light yield in particular should be sufficiently high that a minimum amount of electrical power has to be applied to achieve a particular luminous flux. In addition, a minimum voltage should also be necessary to achieve a defined luminance. A further particular problem is the lifetime of the electronic devices.

BRIEF SUMMARY OF THE INVENTION

It is therefore an object of the present invention to provide novel compounds which lead to electronic devices having improved properties. It is a particular object to provide hole transport materials, hole injection materials, hole blocker materials, electron injection materials, electron blocker materials and/or electron transport materials which exhibit improved properties in relation to efficiency, operating voltage and/or lifetime. Moreover, the compounds should be processible in a very simple manner, and especially exhibit good solubility and film formation.

A further object can be considered that of providing electronic devices having excellent performance very inexpensively and in constant quality.

Furthermore, it should be possible to use or adapt the electronic devices for many purposes. More particularly, the performance of the electronic devices should be maintained over a broad temperature range.

It has been found that, surprisingly, these objects and others which are not specified explicitly but can be inferred or discerned directly from the connections discussed herein by way of introduction are achieved by compounds having all the features of claim 1. Appropriate modifications to the compounds of the invention are protected in the dependent claims that refer back to claim 1.

DETAILED DESCRIPTION OF THE INVENTION

The invention thus provides a compound comprising at least one structure of the formula (I)

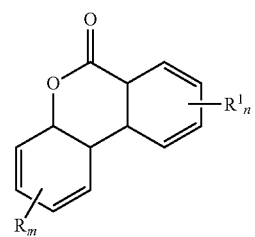

Formula (I)

where the symbols used are as follows:
R is the same or different at each instance and is H, D, F, Cl, Br, I, CHO, C(=O)Ar$^1$, P(=O)(Ar$^1$)$_2$, S(=O)Ar$^1$, S(=O)$_2$Ar$^1$, CN, NO$_2$, Si(R$^2$)$_3$, B(OR$^2$)$_2$, OSO$_2$R$^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R$^2$ radicals, where one or more nonadjacent CH$_2$ groups may be replaced by C≡C, Si(R$^2$)$_2$, Ge(R$^2$)$_2$, Sn(R$^2$)$_2$, C=O, C=S, C=Se, P(=O)(R$^2$), SO, SO$_2$, O, S or CONR$^2$ and where one or more hydrogen atoms may be replaced by D, F, Cl, Br, I, CN or NO$_2$, or an aromatic or heteroaromatic ring system which has 5 to 40 aromatic ring atoms, each of which may be substituted by one or more R$^2$ radicals, or an aryloxy or heteroaryloxy group which has 5 to 40 aromatic ring atoms and may be substituted by one or more $R^2$ radicals, or a combination of these systems; at the same time, two or more adjacent R substituents may also form a mono- or polycyclic aliphatic or aromatic ring system with one another, with the ring to which R is bonded, with a ring to which R is adjacent or with an $R^1$ radical;

$R^1$ is the same or different at each instance and is H, D, F, Cl, Br, I, CHO, C(=O)Ar$^1$, P(=O)(Ar$^1$)$_2$, S(=O)Ar$^1$, S(=O)$_2$Ar$^1$, CN, NO$_2$, Si(R$^2$)$_3$, B(OR$^2$)$_2$, OSO$_2$R$^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent CH$_2$ groups may be replaced by R$^2$C=CR$^2$, C≡C, Si(R$^2$)$_2$, Ge(R$^2$)$_2$, Sn(R$^2$)$_2$, C=O, C=S, C=Se, P(=O)(R$^2$), SO, SO$_2$, O, S or CONR$^2$ and where one or more hydrogen atoms may be replaced by D, F, Cl, Br, I, CN or NO$_2$, or an aromatic or heteroaromatic ring system which has 5 to 40 aromatic ring atoms, each of which may be substituted by one or more $R^2$ radicals, or an aryloxy or heteroaryloxy group which has 5 to 40 aromatic ring atoms and may be substituted by one or more $R^2$ radicals, or a combination of these systems; at the same time, two or more adjacent $R^1$ substituents may also form a mono- or polycyclic aliphatic or aromatic ring system with one another, with the ring to which $R^1$ is bonded, with a ring to which $R^1$ is adjacent or with an R radical;

$R^2$ is the same or different at each instance and is H, D, F, Cl, Br, I, CHO, C(=O)Ar$^1$, P(=O)(Ar$^1$)$_2$, S(=O)Ar$^1$, S(=O)$_2$Ar$^1$, CN, NO$_2$, Si(R$^3$)$_3$, B(OR$^3$)$_2$, OSO$_2$R$^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, where one or more nonadjacent CH$_2$ groups may be replaced by CC, Si(R$^3$)$_2$, Ge(R$^3$)$_2$, Sn(R$^3$)$_2$, C=O, C=S, C=Se, P(=O)(R$^3$), SO, SO$_2$, O, S or CONR$^3$ and where one or more hydrogen atoms may be replaced by D, F, Cl, Br, I, CN or NO$_2$, or an aromatic or heteroaromatic ring system which has 5 to 40 aromatic ring atoms, each of which may be substituted by one or more $R^3$ radicals, or an aryloxy or heteroaryloxy group which has 5 to 40 aromatic ring atoms and may be substituted by one or more $R^3$ radicals, or a combination of these systems; at the same time, two or more adjacent $R^2$ substituents may also form a mono- or polycyclic aliphatic or aromatic ring system with one another;

$Ar^1$ is the same or different at each instance and is an aromatic or heteroaromatic ring system which has 5 to 30 aromatic ring atoms and may be substituted by one or more $R^2$ radicals; at the same time, it is also possible for two $Ar^1$ radicals bonded to the same phosphorus atom to be joined to one another by a single bond or a bridge selected from B(R$^3$), C(R$^3$)$_2$, Si(R$^3$)$_2$, C=O, C=NR$^3$, C=C(R$^3$)$_2$, O, S, S=O, SO$_2$, N(R$^3$), P(R$^3$) and P(=O)R$^3$;

$R^3$ is the same or different at each instance and is H, D, F or an aliphatic, aromatic and/or heteroaromatic hydrocarbyl radical having 1 to 20 carbon atoms, in which hydrogen atoms may also be replaced by F; at the same time, two or more adjacent $R^3$ substituents may also form a mono- or polycyclic, aliphatic or aromatic ring system with one another;

m, n are each independently 0, 1, 2, 3 or 4;

with the proviso that the sum of m and n is not less than 1;

at least one of the R and/or $R^1$ groups in formula (I) is at least one L group; and L is an aromatic group having 10 to 40 carbon atoms, preferably an aromatic group having 10 to 20 carbon atoms, or a heteroaromatic group having 6 to 40 carbon atoms, preferably a heteroaromatic group having 6 to 20 carbon atoms, where the aromatic and/or heteroaromatic group comprises at least two adjacent aromatic and/or heteroaromatic rings, each of which may be fused or unfused and/or may be substituted by one or more $R^2$ radicals.

In this context, "adjacent carbon atoms" means that the carbon atoms are bonded directly to one another. In addition, "adjacent radicals" in the definition of the radicals means that these radicals are bonded to the same carbon atom or to adjacent carbon atoms. These definitions apply correspondingly, inter alia, to the terms "adjacent groups" and "adjacent substituents".

More particularly, the obligatory L group has an aromatic and/or heteroaromatic group comprising at least two adjacent aromatic and/or heteroaromatic rings. Accordingly, the rings may be joined to one another via a bond, such that the L group may, for example, comprise a biphenyl group. In addition, the rings may be fused, such that, for example, two carbon atoms belong to the at least two aromatic or heteroaromatic rings, as is the case, for example, in a naphthyl group.

An aryl group in the context of this invention contains 6 to 40 carbon atoms; a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused aryl or heteroaryl group, for example naphthalene, anthracene, phenanthrene, quinoline, isoquinoline, etc.

An aromatic ring system in the context of this invention contains 6 to 60 carbon atoms in the ring system. A heteroaromatic ring system in the context of this invention contains 1 to 60 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be interrupted by a nonaromatic unit (preferably less than 10% of the atoms other than H), for example a carbon, nitrogen or oxygen atom or a carbonyl group. For example, systems such as 9,9'-spirobifluorene, 9,9-diarylfluorene, triarylamine, diaryl ethers, stilbene, etc. shall also be regarded as aromatic ring systems in the context of this invention, and likewise systems in which two or more aryl groups are interrupted, for example, by a linear or cyclic alkyl group or by a silyl group. In addition, systems in which two or more aryl or heteroaryl groups are bonded directly to one another, for example biphenyl or terphenyl, shall likewise be regarded as an aromatic or heteroaromatic ring system.

A cyclic alkyl, alkoxy or thioalkoxy group in the context of this invention is understood to mean a monocyclic, bicyclic or polycyclic group.

In the context of the present invention, a $C_1$- to $C_{40}$-alkyl group in which individual hydrogen atoms or $CH_2$ groups may also be replaced by the abovementioned groups are understood to mean, for example, the methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl)cyclohex-1-yl and 1-(n-decyl)cyclohex-1-yl radicals. An alkenyl group is understood to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is understood to mean, for example, ethynyl, propynyl, butynyl, pentynyl, hexynyl, heptynyl or octynyl. A $C_1$- to $C_{40}$-alkoxy group is understood to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system which has 5-60 aromatic ring atoms and may also be substituted in each case by the abovementioned radicals and which may be joined to the aromatic or heteroaromatic system via any desired positions is understood to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

In a preferred configuration, it may be the case that the sum total of the indices m and n is not more than 6, preferably not more than 5, especially preferably not more than 4, particularly preferably not more than 3. Especially preferably, the sum total of the indices m and n is 1 or 2.

It may further be the case that the structure of formula (I) preferably has not more than 4, more preferably not more than 3 and especially preferably one or two L groups.

Preferably, the L group in formula (I) may comprise at least three aromatic or heteroaromatic rings which may be unfused or fused.

Preference is further given to compounds which are characterized in that the L group in formula (I) comprises at least one biphenyl, fluorenyl and/or spirobifluorenyl group.

In addition, surprising advantages are exhibited by compounds of formula (I) where the index m is 1 or 2 and at least one of the R radicals is an L group, where the index n is preferably 0.

In addition, it is advantageously possible to use compounds of formula (I) where the index n is 1 or 2 and at least one of the $R^1$ radicals is an L group, where the index m is preferably 0.

In addition, it may be the case that, in formula (I), the index m is 1 or 2 and the index n is 1 or 2, where at least one of the R radicals is an L group and at least one of the $R^1$ radicals is an L group.

If n and m are not less than 1, the R and $R^1$ radicals may be the same. It may additionally be the case that the R and $R^1$ radicals are different, this being preferable. The criterion for a difference here is that a structural element binds to the benzo[c]coumarin structure at another site. For example, the R radical differs from an $R^1$ radical if R is a group of the structure L-2 shown below, while $R^1$ is a structure of formula L-3.

Preference is given to compounds comprising structures of the formula (I) in which at least one L radical is a group selected from the formulae (L-1) to (L-14)

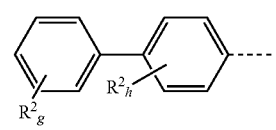

Formula (L-1)

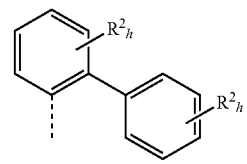

Formula (L-2)

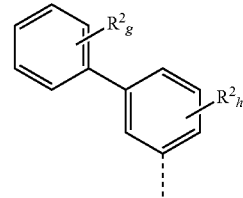

Formula (L-3)

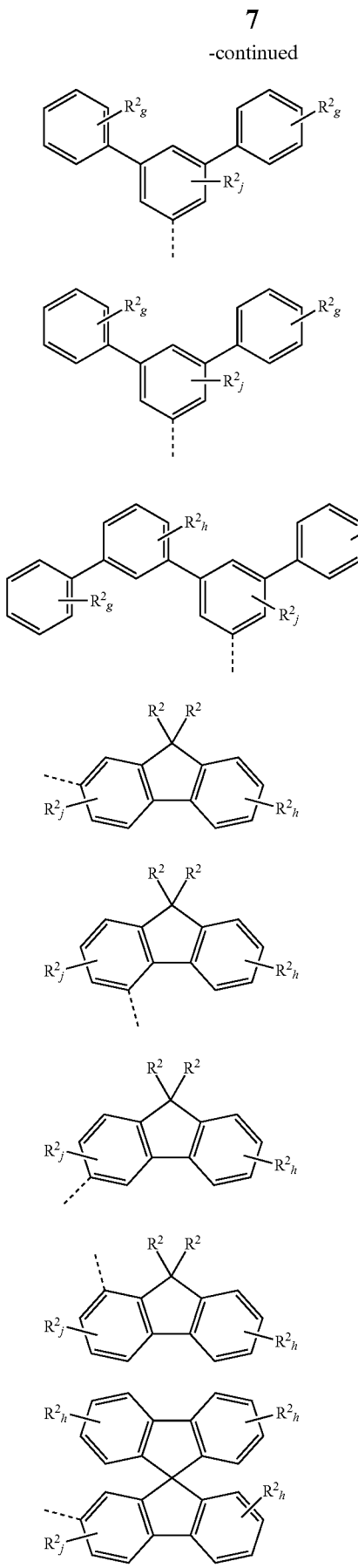

where the dotted bond marks the attachment position, g is 0, 1, 2, 3, 4 or 5, h is 0, 1, 2, 3 or 4, j is 0, 1, 2 or 3, Y is O, S or N(R$^1$), and R$^1$ and R$^2$ have the definitions given above for formula (I).

It may preferably be the case that the L group in formula (I) comprises at least one heteroaryl group having a nitrogen atom.

Preference is further given to compounds of formula (I) where the L group in formula (I) comprises at least one carbazole, diazine, triazine, benzothiophene and/or benzofuran group.

Preference is given to compounds comprising structures of the formula (I) where, in the structure of formula (I), at least one L radical is a group selected from the formulae (L-15) to (L-39)

Formula (L-18)
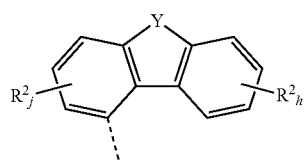
Formula (L-19)
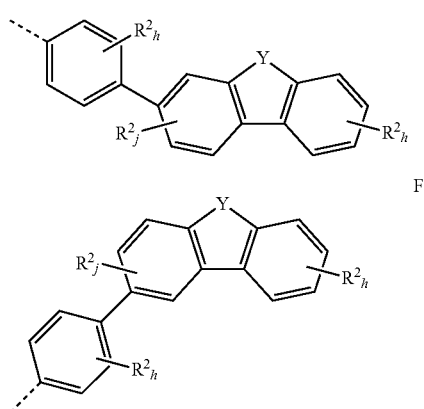
Formula (R¹-20)
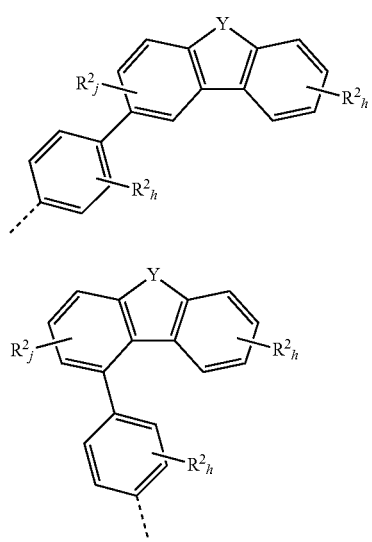
Formula (L-21)
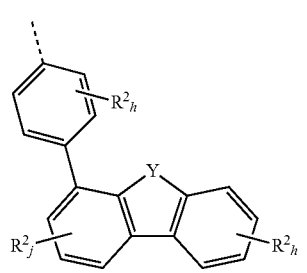
Formula (L-22)
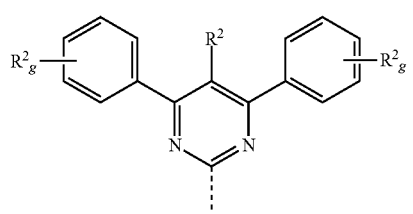
Formula (L-23)
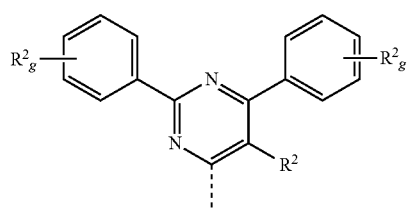
Formula (L-24)
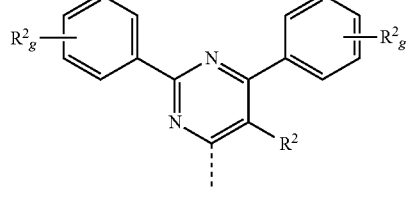
Formula (L-25)
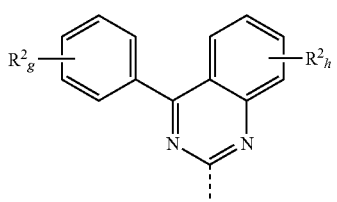
Formula (L-26)
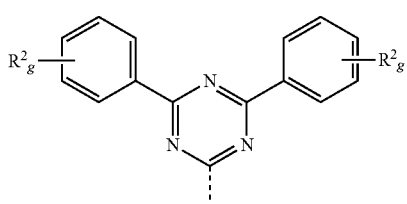
Formula (L-27)
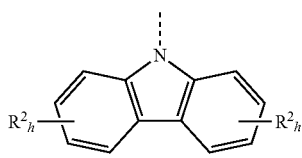
Formula (L-28)
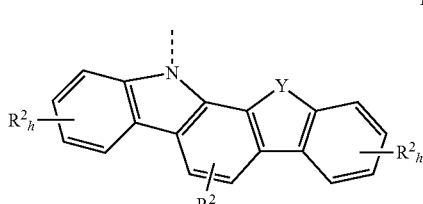
Formula (L-29)
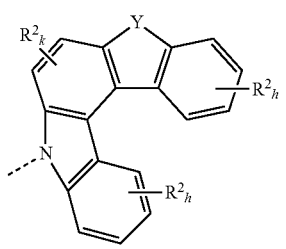
Formula (L-30)
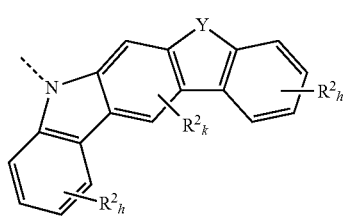
Formula (L-31)
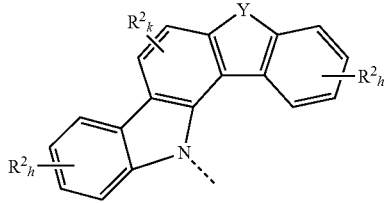

Formula (L-32)
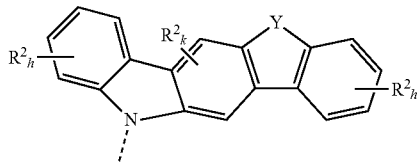

Formula (L-33)
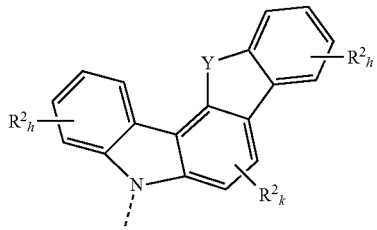

Formula (L-34)
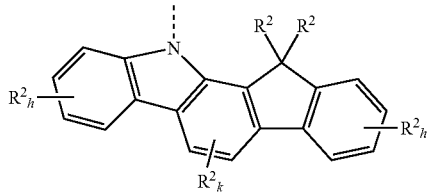

Formula (L-35)
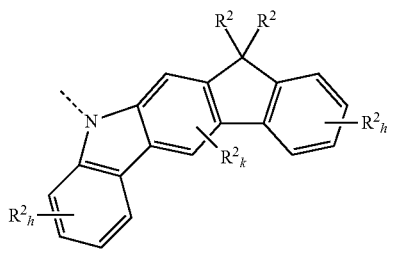

Formula (L-36)
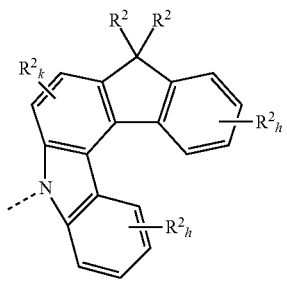

Formula (L-37)
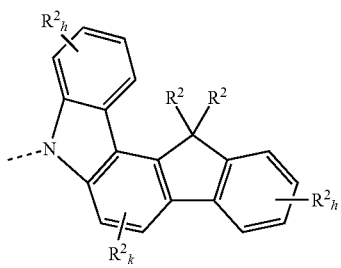

Formula (L-38)
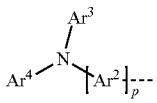

Formula (L-39)
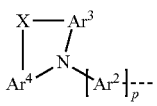

where the dotted bond marks the attachment position, g is 0, 1, 2, 3, 4 or 5, h is 0, 1, 2, 3 or 4, j is 0, 1, 2 or 3, k is 0, 1 or 2, Y is O, S or N(R'), and $R^1$ and $R^2$ have the definitions given above for formula (I). Preferably, the sum total of the indices g, h, j and k in a structure of the formulae (L-1) to (L-39) is not more than 5, preferably 0, 1, 2 or 3 and more preferably 0 or 1.

Preference is given to compounds comprising structures of the formula (I) where, in the structure of formula (I), at least one L radical is a group selected from the formulae (L-40) to (L-42)

Formula (L-40)
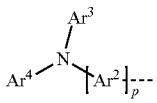

Formula (L-41)
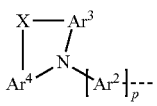

Formula (L-42)
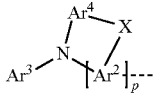

where the dotted bond marks the attachment position and $Ar^2$, $Ar^3$, $Ar^4$ are each independently an aryl group having 6 to 40 carbon atoms or a heteroaryl group having 3 to 40 carbon atoms, each of which may be substituted by one or more $R^1$ radicals;

p is 0 or 1 and

X is a bond, $CR^1{}_2$, C=O, N(R'), B(R'), $SiR^1{}_2$, O or S, preferably $CR^1{}_2$, C=O, N($Ar^1$), O or S, where the $R^1$ and $Ar^1$ radicals have the definitions given above for formula (I).

The structure of the formula (I) or of one of the preferred embodiments of this structure comprises at least one L group as detailed above. The type of the functional group L affects the properties of the compound, these properties being adjustable over a wide range.

For compounds which are preferably used as hole transport material (HTM) or electron blocker layer (EBL), L may preferably be a radical having at least one diarylamino group. In the case of use of a carbazole derivative as structural element of the L group, compounds obtained include those which can be used preferentially as triplet matrix material (TMM), more preferably as electron-conducting triplet matrix material (e-TMM) or as hole blocker layer (HBL). If L is an aromatic system, especially an aryl group which more preferably does not comprise any heteroatoms, the material can be used surprisingly advantageously as electron transport material (ETM). In this context, it should be emphasized that the compounds obtained generally have a significantly better profile of properties through the presence of the benzo[c]coumarin structural element than comparable compounds according to the prior art. Particular preference is given especially to compounds comprising structures of the formula (I), or the preferred embodiments detailed above or hereinafter, which can be used as matrix material or as electron transport material.

In a particular embodiment of the present invention, the L group in the structure of formula (I) may preferably be a carbazole, indenocarbazole, indolocarbazole, arylamine or diarylamine group. Compounds of the formula (I) having at least one carbazole, indenocarbazole, indolocarbazole, arylamine or diarylamine group can be used with preference as matrix material.

In addition, the L group in the structure of formula (I) may preferably be a pyridine, pyrimidine, pyrazine, pyridazine, triazine, dibenzofuran, dibenzothiophene, fluorene, spirobifluorene, anthracene or benzimidazole group. Compounds of the formula (I) having at least one pyridine, pyrimidine, pyrazine, pyridazine, triazine, dibenzofuran, dibenzothiophene, fluorene, spirobifluorene, anthracene or benzimidazole group can be used advantageously as electron transport material (ETM).

As well as at least one L group, an inventive structure of formula (I) may comprise further substituents which do correspond to the definition of R or $R^1$ but do not correspond to the definition of L detailed above, for example for formula (I). More preferably, a structure of formula (I) has not more than three and preferably not more than two R and/or $R^1$ radicals that do not correspond to the definition of L. Especially preferably, a structure of formula (I) has not more than one R and/or $R^1$ radical that does not correspond to the definition of L. More preferably, all R and/or $R^1$ radicals correspond to the definition of L.

Preference is further given to compounds of formula (I) in which the structure of formula (I) comprises not more than one reactive group. Preferably, the reactive group is selected from triflate, bromine, iodine, chlorine, boronic acid and boronic ester, more preferably from Br, Cl and $B(OR^2)_2$.

Particularly preferred compounds comprise structures of the following formulae (II), (III), (IV), (V), (VI), (VII), (VIII) and/or (IX):

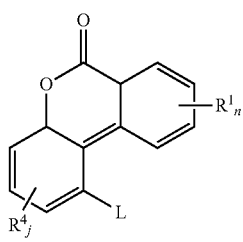

Formula (II)

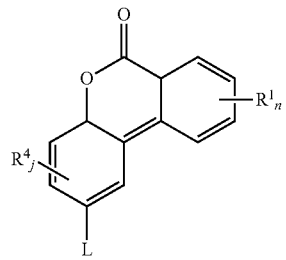

Formula (III)

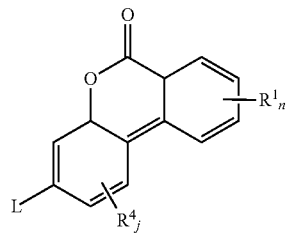

Formula (IV)

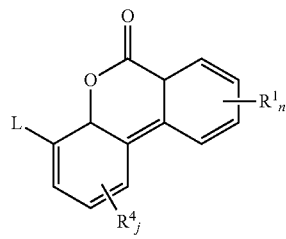

Formula (V)

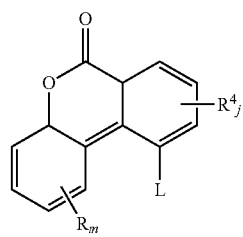

Formula (VI)

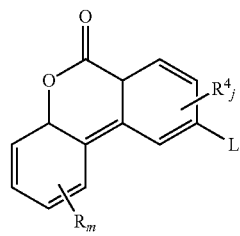

Formula (VII)

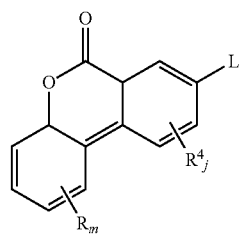

Formula (VIII)

Formula (IX)

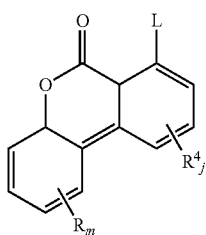

where the symbols R, $R^1$, L shown and the indices m and n have the definitions detailed above for formula (I), the index j is 0, 1, 2 or 3, preferably 0, 1 or 2 and more preferably 0 or 1 and $R^4$ is the same or different at each instance and is H, D, F, Cl, Br, I, CHO, C(=O)$Ar^1$, P(=O)($Ar^1$)$_2$, S(=O)$Ar^1$, S(=O)$_2Ar^1$, CN, NO$_2$, Si($R^2$)$_3$, B(O$R^2$)$_2$, OSO$_2R^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent CH$_2$ groups may be replaced by $R^2$C=C$R^2$, C≡C, Si($R^2$)$_2$, Ge($R^2$)$_2$, Sn($R^2$)$_2$, C=O, C=S, C=Se, P(=O)($R^2$), SO, SO$_2$, O, S or CON$R^2$ and where one or more hydrogen atoms may be replaced by D, F, Cl, Br, I, CN or NO$_2$, or an aromatic or heteroaromatic ring system which has 5 to 40 aromatic ring atoms, each of which may be substituted by one or more $R^2$ radicals, or an aryloxy or heteroaryloxy group which has 5 to 40 aromatic ring atoms and may be substituted by one or more $R^2$ radicals, where the $R^2$ and $Ar^1$ radicals have the definition given above for formula (I), or a combination of these systems; at the same time, two or more adjacent $R^4$ substituents may also form a mono- or polycyclic aliphatic or aromatic ring system with one another, with the ring to which $R^4$ is bonded, with a ring to which $R^4$ is adjacent or with an R or $R^1$ radical.

Particularly preferred compounds include structures according to the following formulae:
(X), (XI), (XII), (XIII), (XIV), (XV), (XVI) and/or (XVII)

Formula (X)

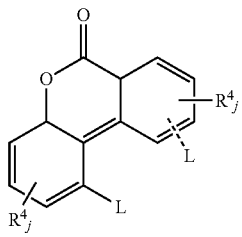

Formula (XI)

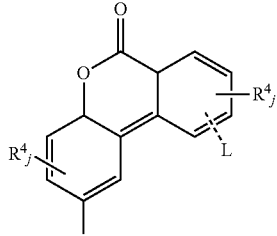

Formula (XII)

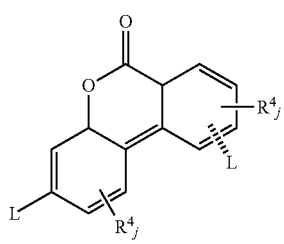

Formula (XIII)

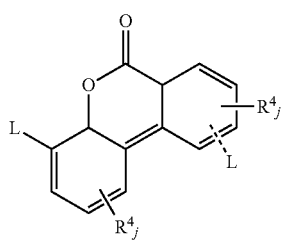

Formula (XIV)

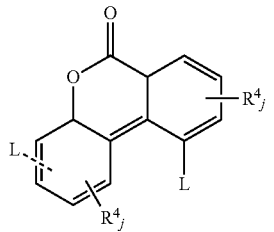

Formula (XV)

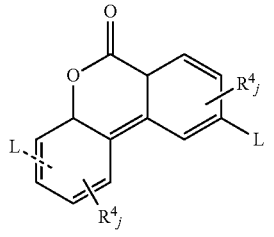

Formula (XVI)

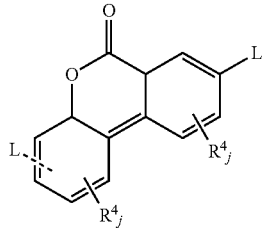

Formula (XVII)

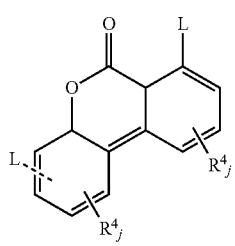

where the symbols R, $R^1$, L shown and the indices m and n have the definitions detailed above for formula (I), and the index j is the same or different at each instance and is 0, 1, 2 or 3 and $R^4$ is the same or different at each instance and is H, D, F, Cl, Br, I, CHO, C(=O)$Ar^1$, P(=O)($Ar^1$)$_2$, S(=O)$Ar^1$, S(=O)$_2Ar^1$, CN, NO$_2$, Si($R^2$)$_3$, B(O$R^2$)$_2$, OSO$_2R^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent $CH_2$ groups may be replaced by $R^2C=CR^2$, $C\equiv C$, $Si(R^2)_2$, $Ge(R^2)_2$, $Sn(R^2)_2$, $C=O$, $C=S$, $C=Se$, $P(=O)(R^2)$, SO, $SO_2$, O, S or $CONR^2$ and where one or more hydrogen atoms may be replaced by D, F, Cl, Br, I, CN or $NO_2$, or an aromatic or heteroaromatic ring system which has 5 to 40 aromatic ring atoms, each of which may be substituted by one or more $R^2$ radicals, or an aryloxy or heteroaryloxy group which has 5 to 40 aromatic ring atoms and may be substituted by one or more $R^2$ radicals, where the $R^2$ and $Ar^1$ radicals have the definitions given for formula (I), or a combination of these systems; at the same time, two or more adjacent $R^4$ substituents may also form a mono- or polycyclic aliphatic or aromatic ring system with one another, with the ring to which $R^4$ is bonded or with a ring to which $R^4$ is adjacent.

It may preferably be the case that the $R^4$ radical in the formulae (II), (III), (IV), (V), (VI), (VII), (VIII) and/or (IX) and the formulae (X), (XI), (XII), (XIII), (XIV), (XV), (XVI) and/or (XVII) is not a group that corresponds to the definition of the L radical in formula (I).

Preferably, the compound having structures of formula (I) may comprise R and/or $R^1$ radicals in which these R and/or $R^1$ radicals are the same or different at each instance and are preferably selected from the group consisting of H, D, F, Br, I, CN, $Si(R^2)_3$, $B(OR^2)_2$, $C(=O)Ar^1$, a straight-chain alkyl group having 1 to 10 carbon atoms or a straight-chain alkoxy group having 1 to 10 carbon atoms or an alkenyl group having 2 to 10 carbon atoms or a branched or cyclic alkoxy group having 3 to 10 carbon atoms or a branched or cyclic alkyl group having 3 to 10 carbon atoms, each of which may be substituted by one or more $R^2$ radicals, where one or more hydrogen atoms may be replaced by D or F, or an aromatic or heteroaromatic ring system which has 5 to 30 aromatic ring atoms and may be substituted in each case by one or more $R^2$ radicals; at the same time, two adjacent R or $R^1$ radicals together or R or $R^1$ radicals together with $R^2$ radicals may also form a mono- or polycyclic, aliphatic or aromatic ring system. More preferably, these R or $R^1$ radicals are the same or different at each instance and are selected from the group consisting of H, D, F, a straight-chain alkoxy group having 1 to 6 carbon atoms or a branched or cyclic alkoxy group having 3 to 10 carbon atoms, a straight-chain alkyl group having 1 to 6 carbon atoms or a branched or cyclic alkyl group having 3 to 10 carbon atoms, where one or more hydrogen atoms may be replaced by D or F, or an aromatic or heteroaromatic ring system which has 5 to 24 aromatic ring atoms and may be substituted in each case by one or more $R^2$ radicals; at the same time, two adjacent R or $R^1$ radicals together or R or $R^1$ radicals together with $R^2$ radicals may also form a mono- or polycyclic, aliphatic or aromatic ring system. More preferably, at least one of the R or $R^1$ radicals in formula (I) may be an aryl group or a heteroaryl group which has 6 to 18 carbon atoms and may be substituted by up to three $R^2$ radicals.

Preferably, the compound having structures of formula (I) may comprise $R^2$ radicals, where these $R^2$ radicals are the same or different at each instance and are preferably selected from the group consisting of H, D, F, Cl, Br, I, CHO, $C(=O)Ar^1$, $P(=O)(Ar^1)_2$, $S(=O)Ar^1$, $S(=O)_2Ar^1$, CN, $NO_2$, $Si(R^3)_3$, $B(OR^3)_2$, $OSO_2R^3$, a straight-chain alkyl, alkoxy or thioalkoxy group having 1 to 10 carbon atoms or a branched or cyclic alkyl, alkoxy or thioalkoxy group having 3 to 10 carbon atoms, each of which may be substituted by one or more $R^3$ radicals, where one or more nonadjacent $CH_2$ groups may be replaced by $C\equiv C$, $Si(R^3)_2$, $Ge(R^3)_2$, $Sn(R^3)_2$, $C=O$, $C=S$, $C=Se$, $P(=O)(R^3)$, S, $SO_2$, O, S or $CONR^3$ and where one or more hydrogen atoms may be replaced by D, F, Cl, Br, I, CN or $NO_2$, or an aromatic or heteroaromatic ring system which has 5 to 24 aromatic ring atoms and may be substituted in each case by one or more $R^3$ radicals, or an aryloxy or heteroaryloxy group which has 5 to 24 aromatic ring atoms and may be substituted by one or more $R^3$ radicals, or a combination of these systems; at the same time, two or more adjacent $R^2$ substituents may also form a mono- or polycyclic, aliphatic or aromatic ring system with one another. More preferably, at least one of the $R^2$ radicals in formula (I) may be an aryl group or a heteroaryl group which has 6 to 18 carbon atoms and may be substituted by up to three $R^3$ radicals.

Particularly preferred compounds include structures according to the following formulae 1 to 247:

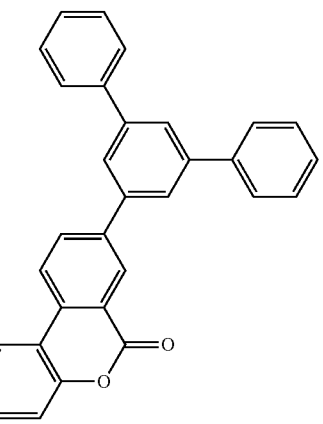

Formula 1

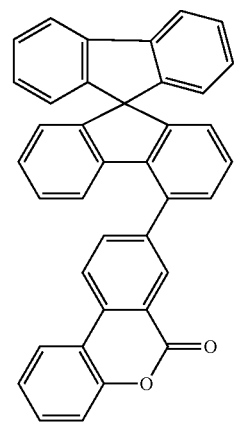

Formula 2

Formula 3
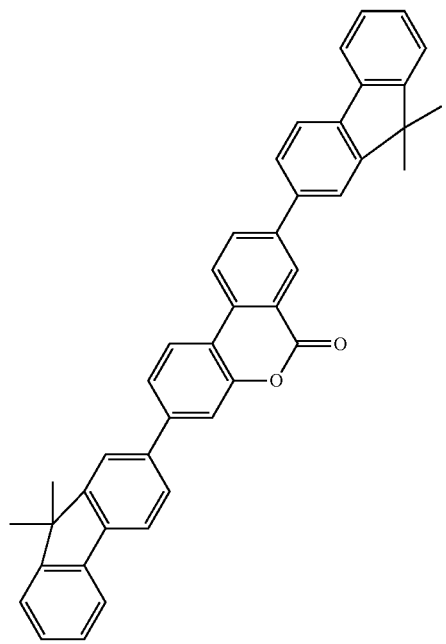
Formula 6
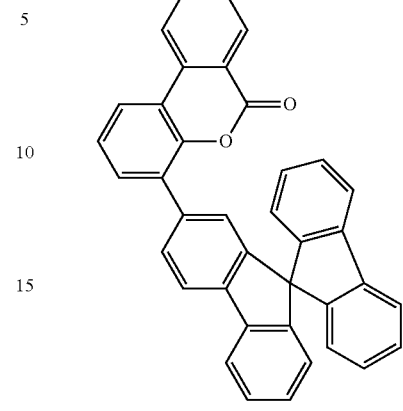
Formula 7
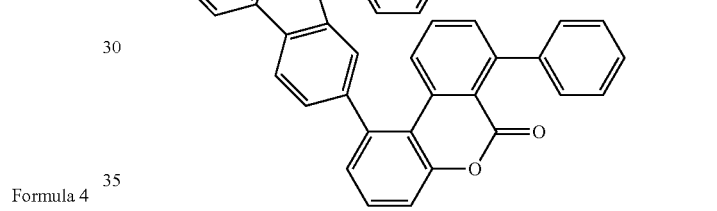
Formula 4
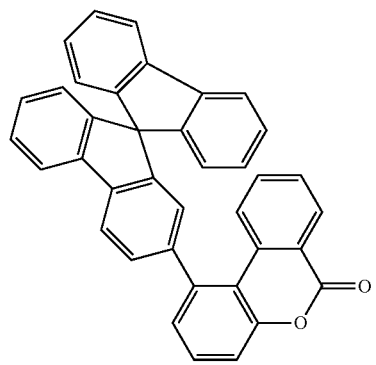
Formula 8
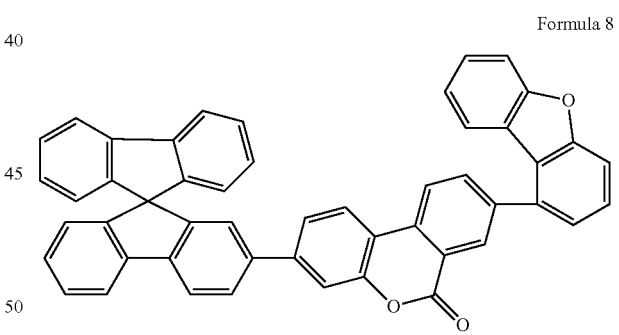
Formula 5
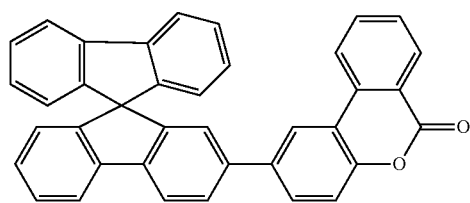
Formula 9
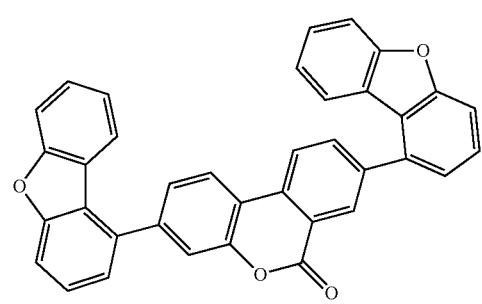

Formula 10
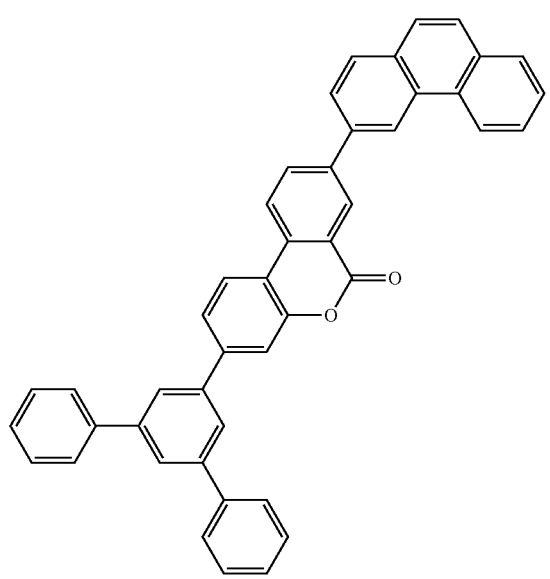
Formula 11
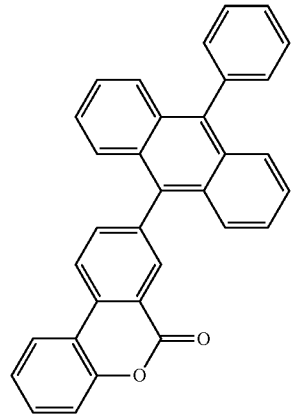
Formula 12
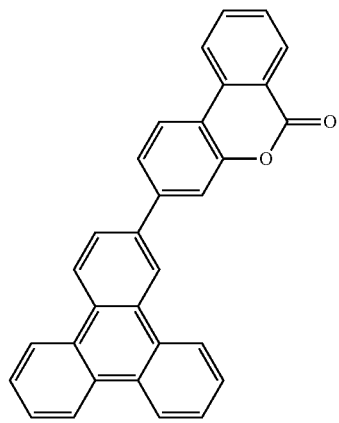
Formula 13
Formula 14
Formula 15
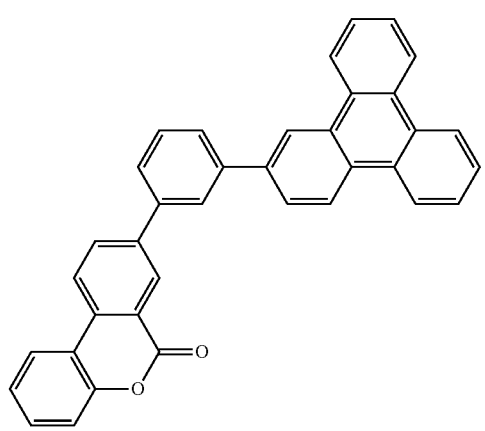
Formula 16
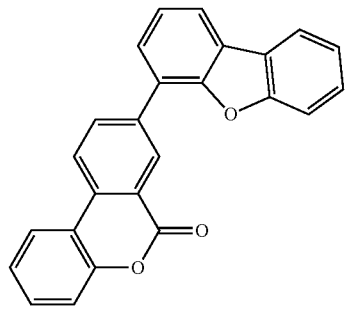

Formula 17
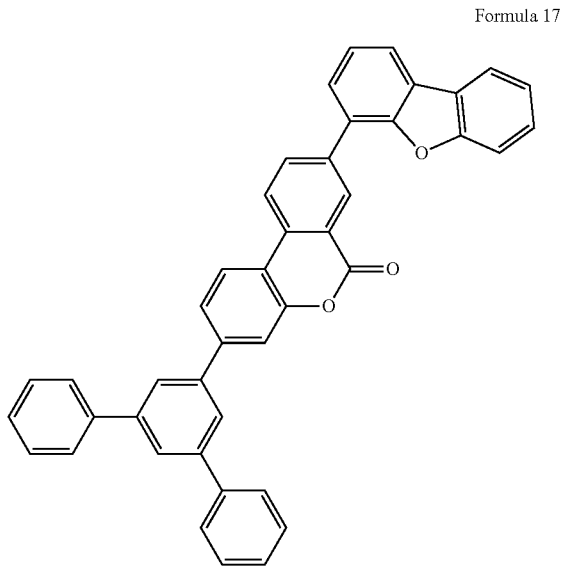
Formula 18
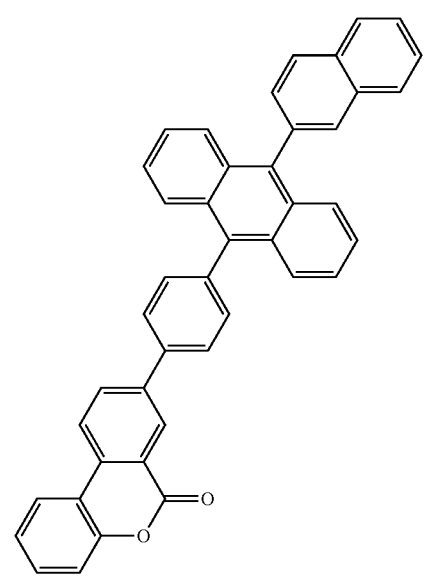
Formula 19
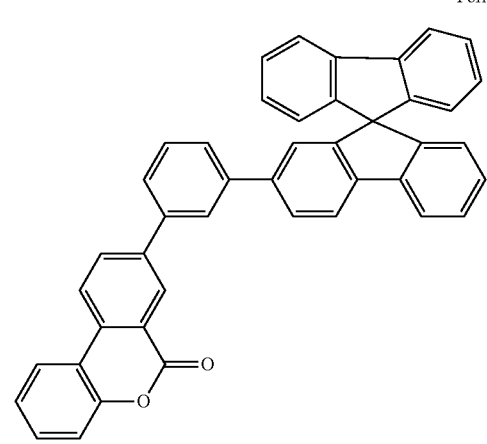
Formula 20
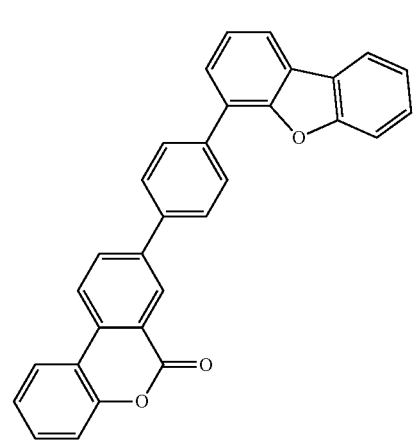
Formula 21
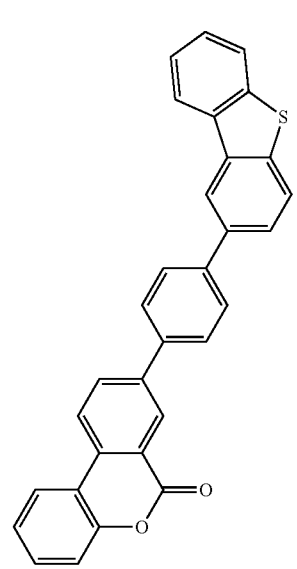
Formula 22
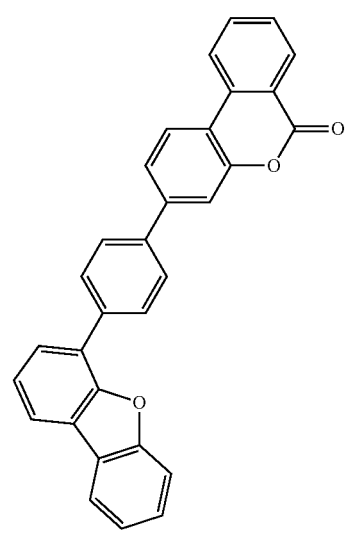

Formula 23
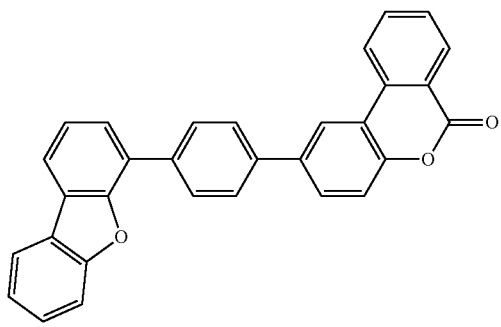
Formula 24
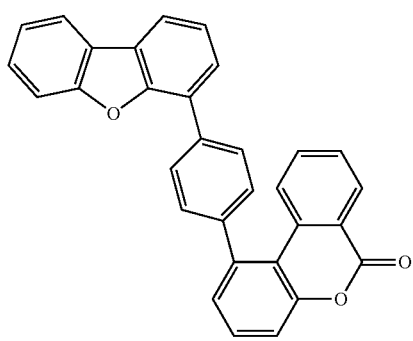
Formula 25
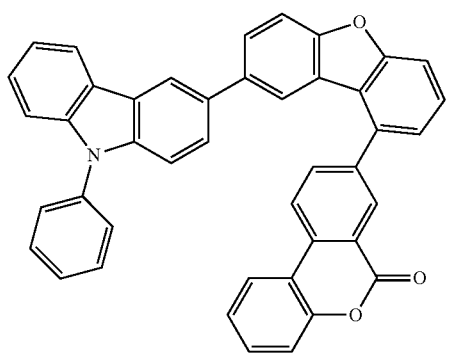
Formula 26
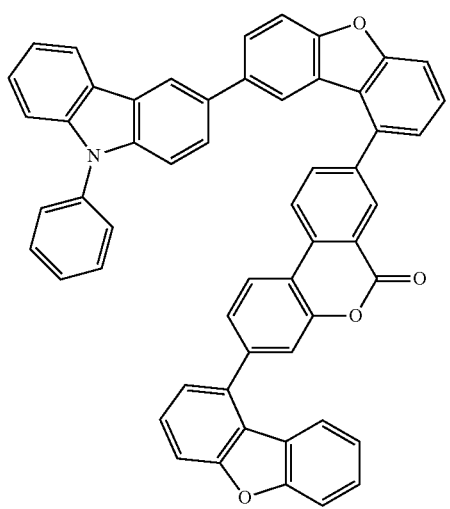
Formula 27
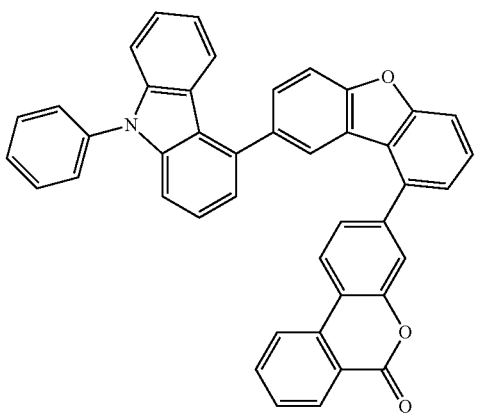
Formula 28
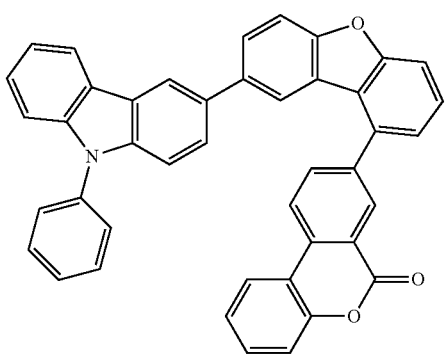
Formula 29
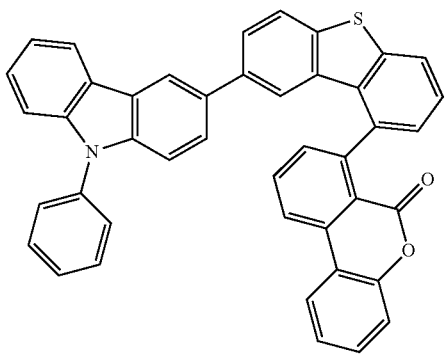
Formula 30
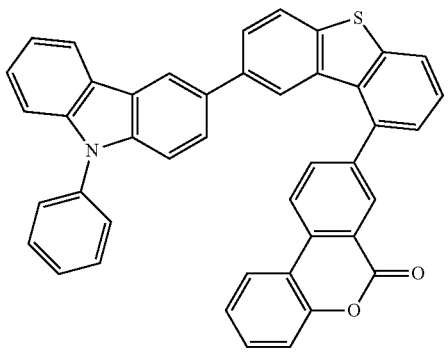

Formula 31
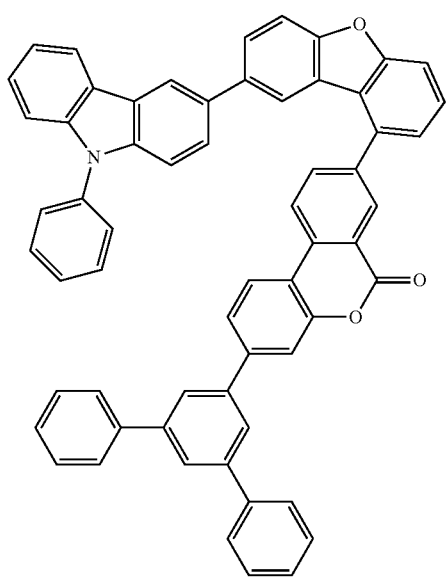
Formula 32
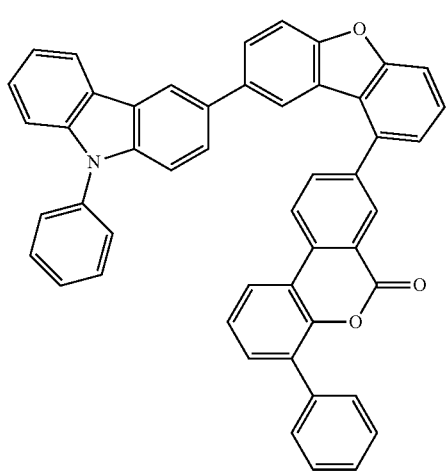
Formula 33
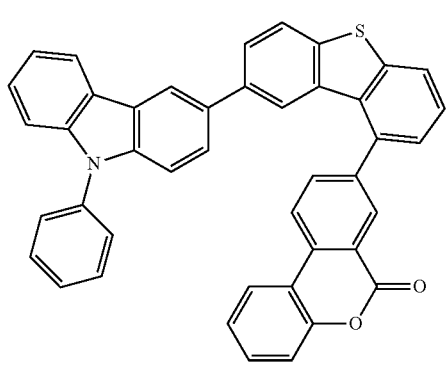
Formula 34
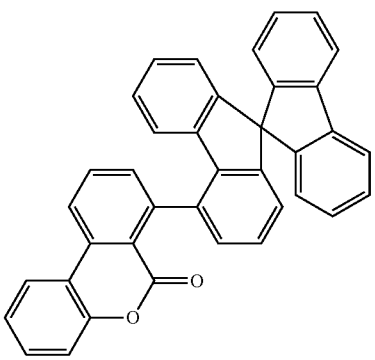
Formula 35
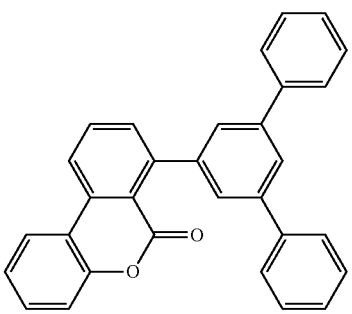
Formula 36
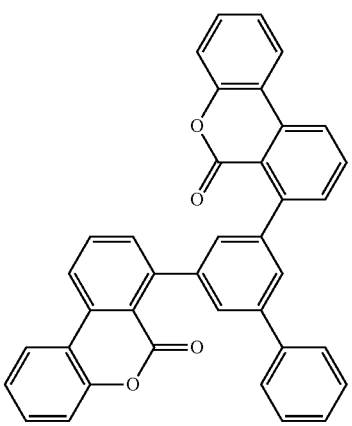
Formula 37
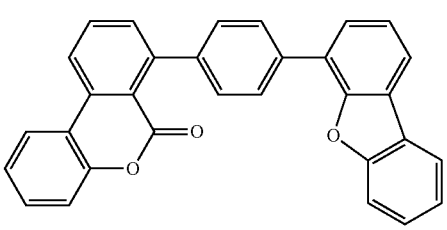
Formula 38
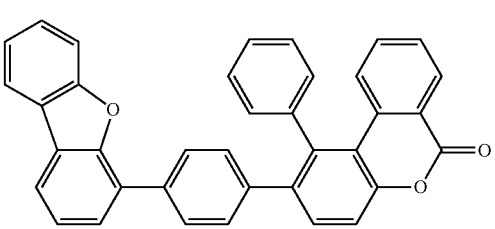

Formula 39
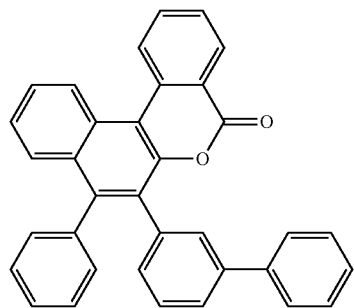
Formula 40
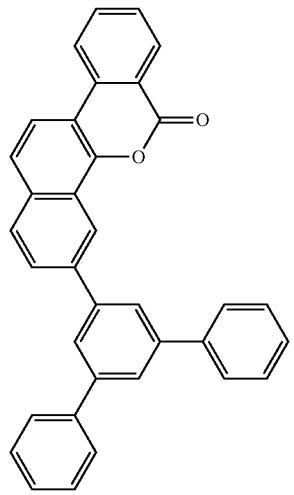
Formula 41
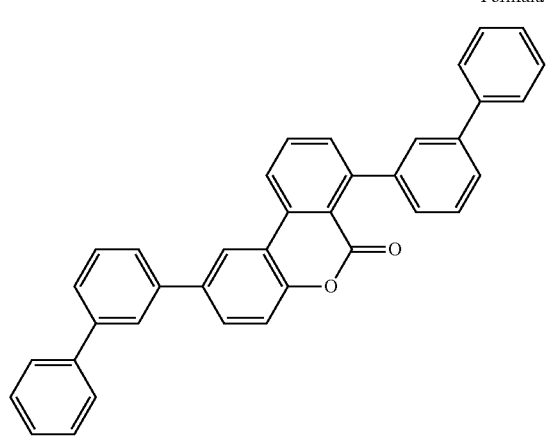
Formula 42
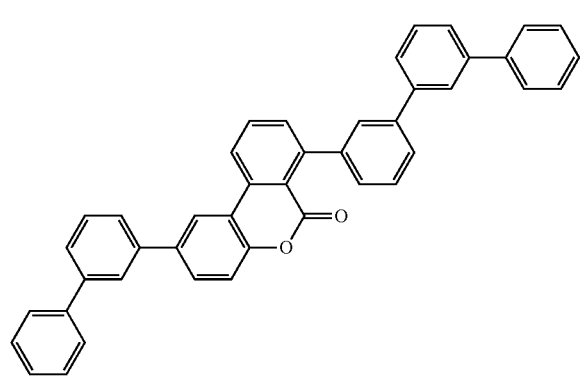
Formula 43
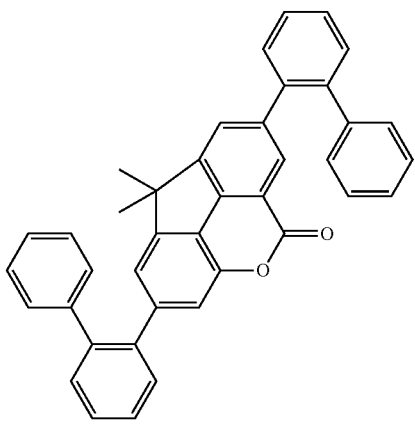
Formula 44
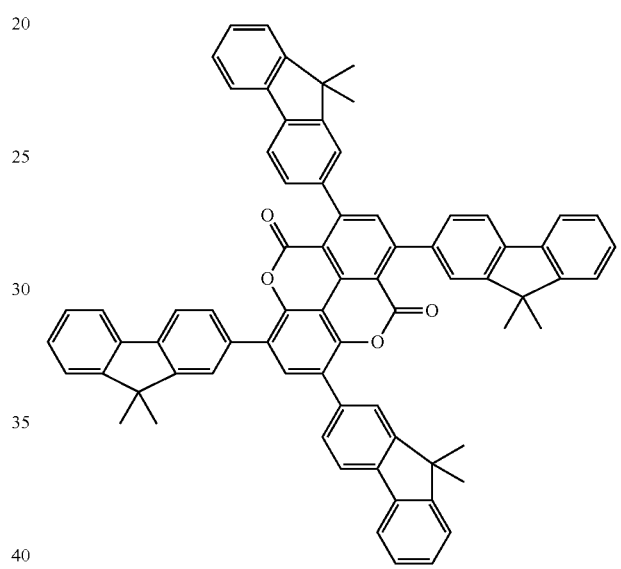
Formula 45
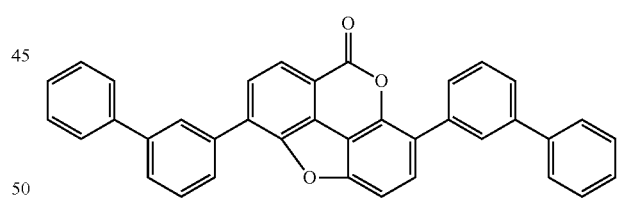
Formula 46
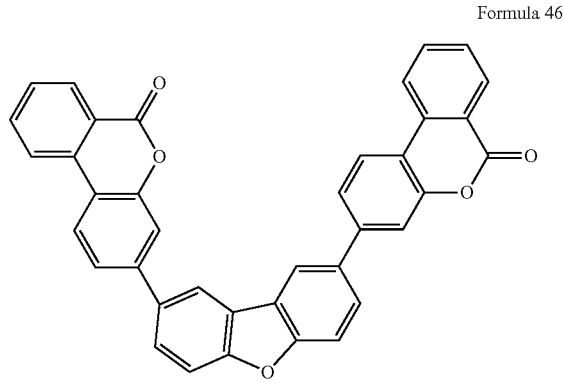

Formula 47
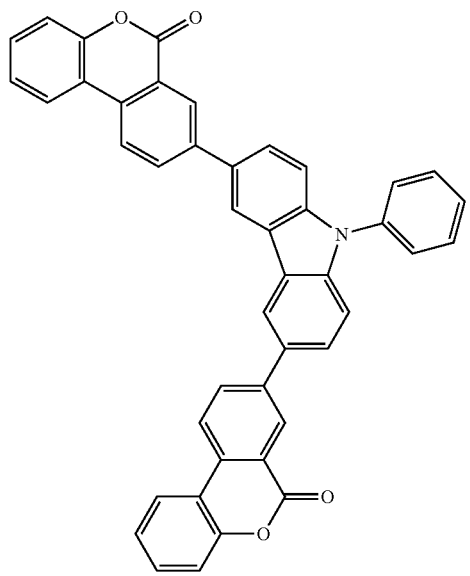
Formula 48
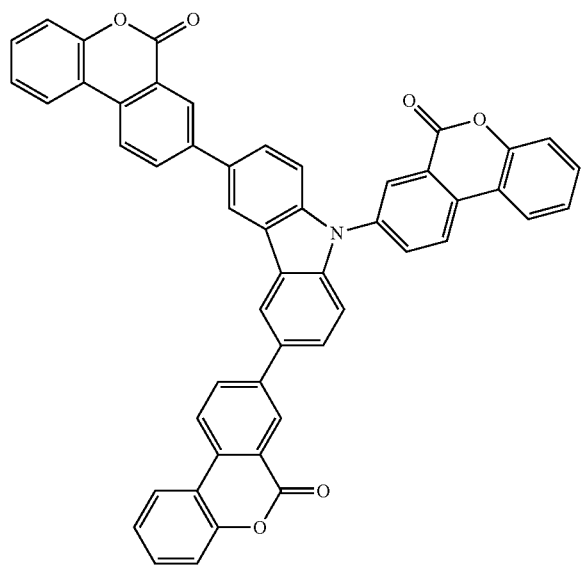
Formula 49
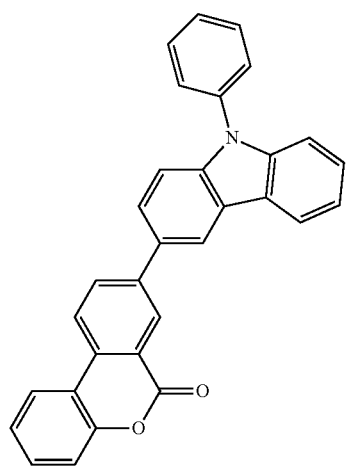
Formula 50
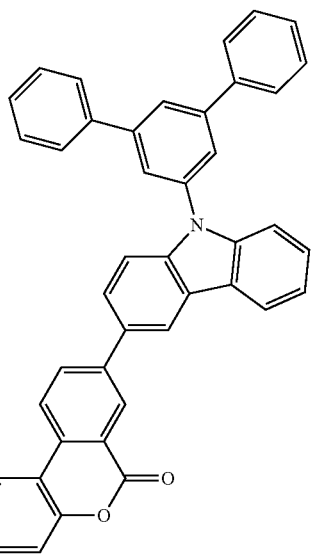
Formula 51
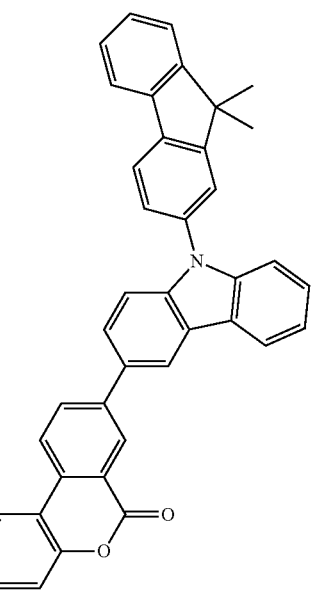

Formula 52
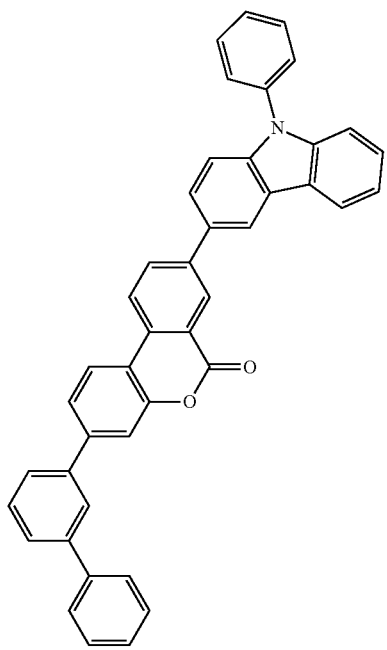
Formula 53
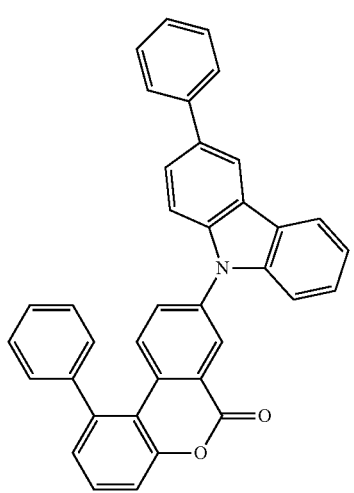
Formula 54
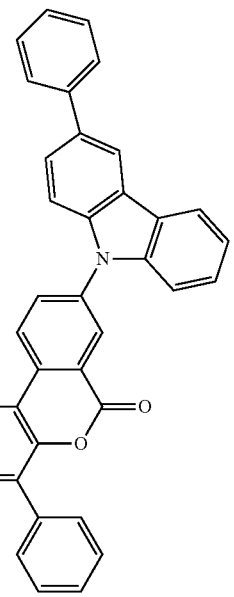
Formula 55
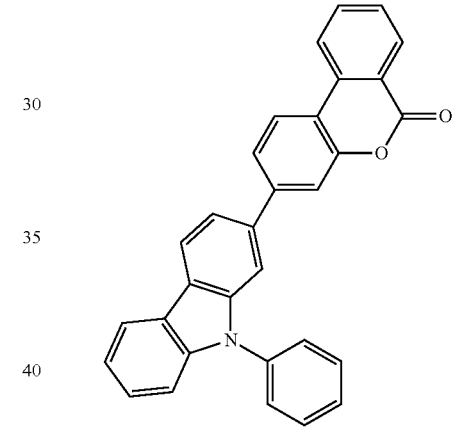
Formula 56
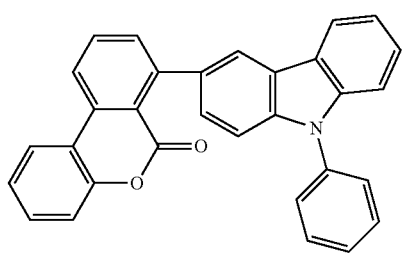
Formula 57
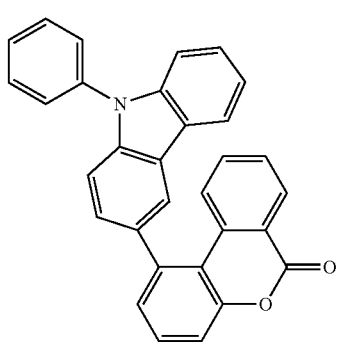

Formula 58
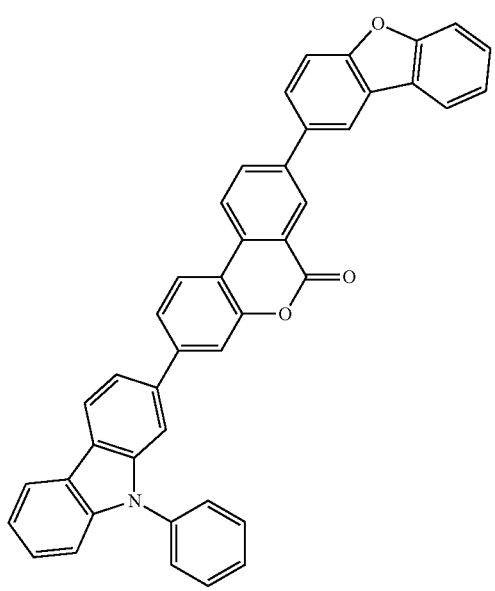
Formula 59
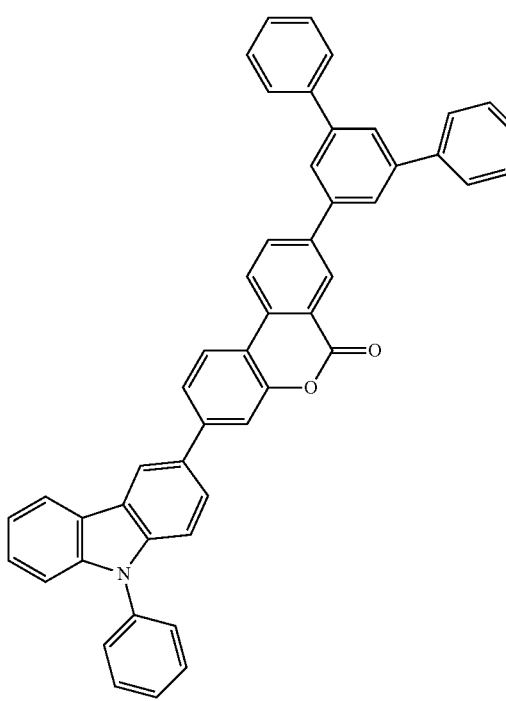
Formula 60
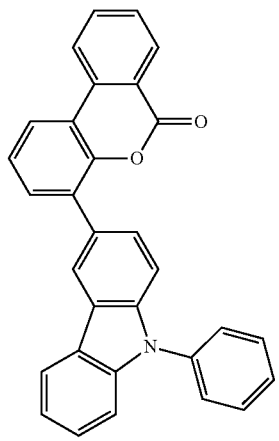
Formula 61
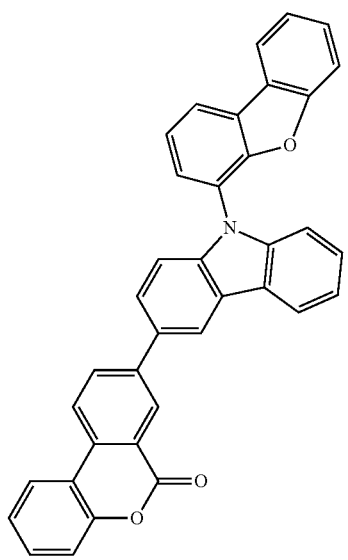
Formula 62
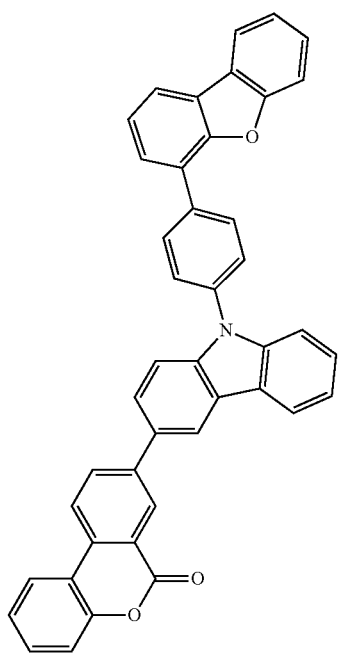

Formula 63
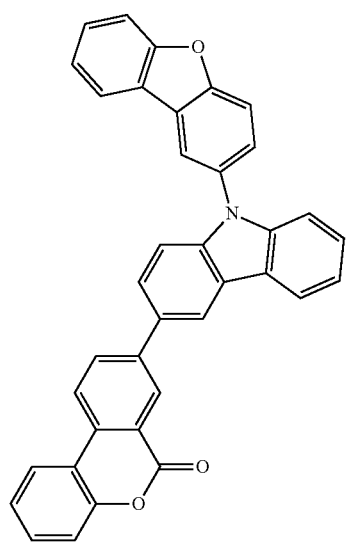
Formula 64
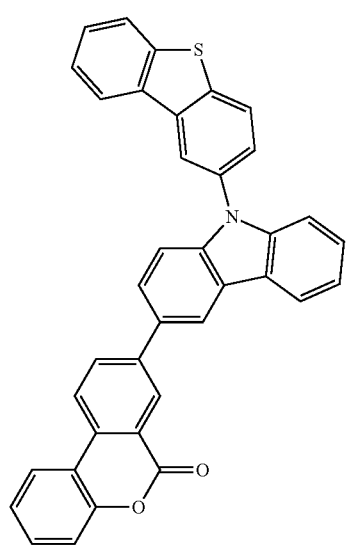
Formula 65
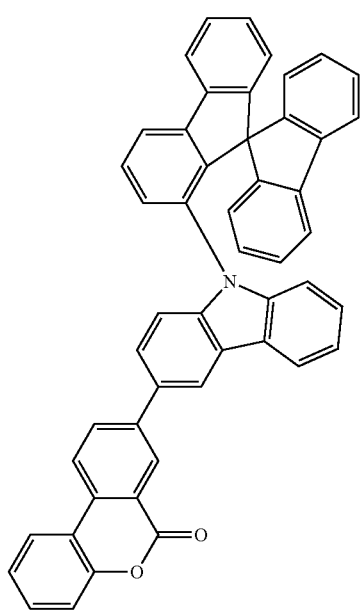
Formula 66
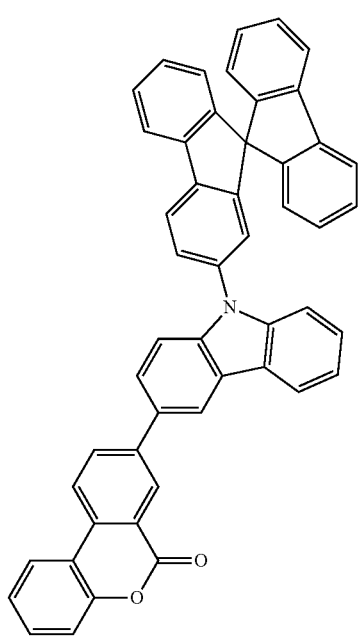

Formula 67
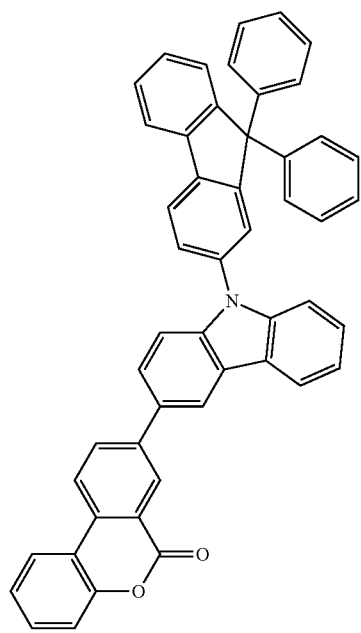
Formula 68
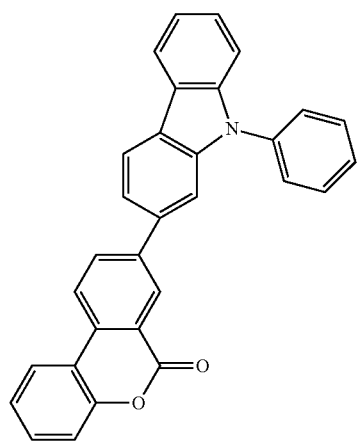
Formula 69
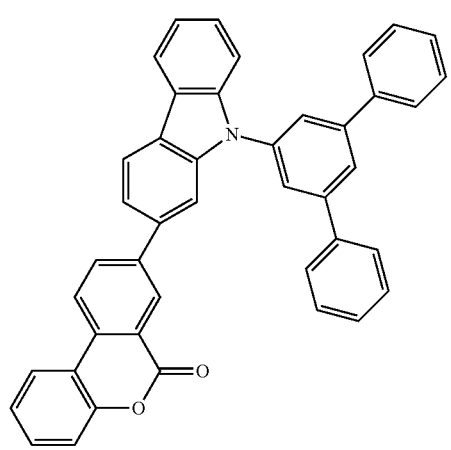
Formula 70
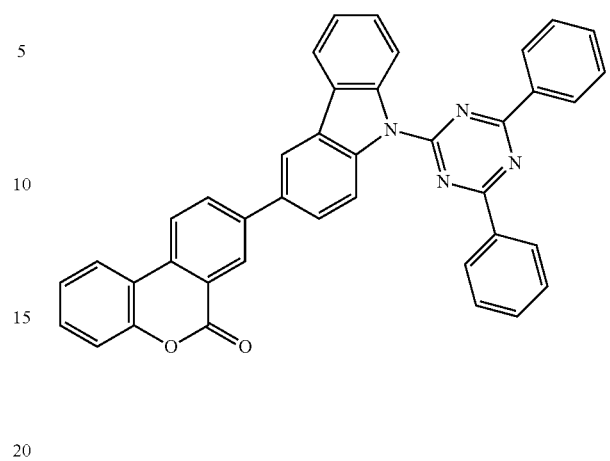
Formula 71
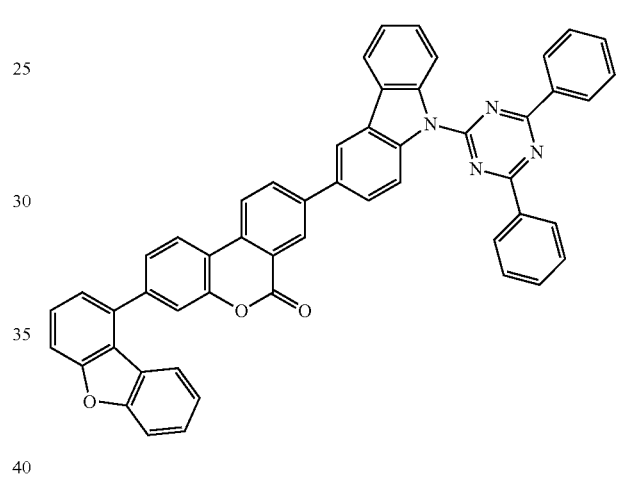
Formula 72
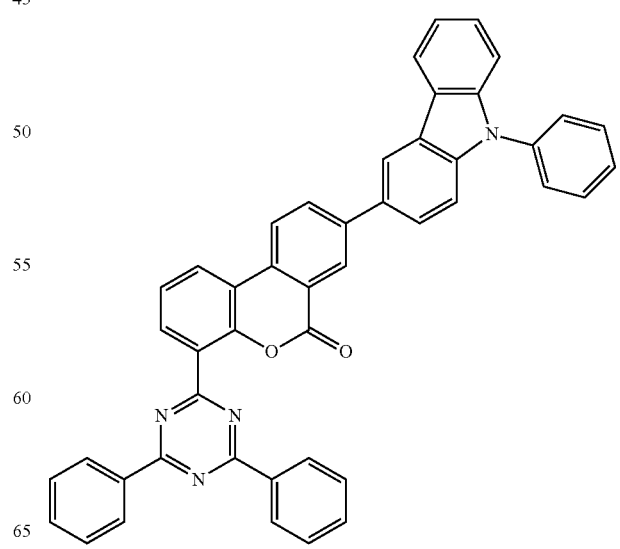

Formula 73
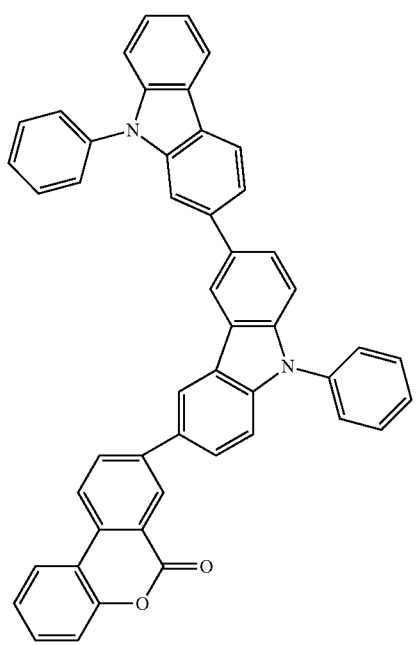
Formula 75
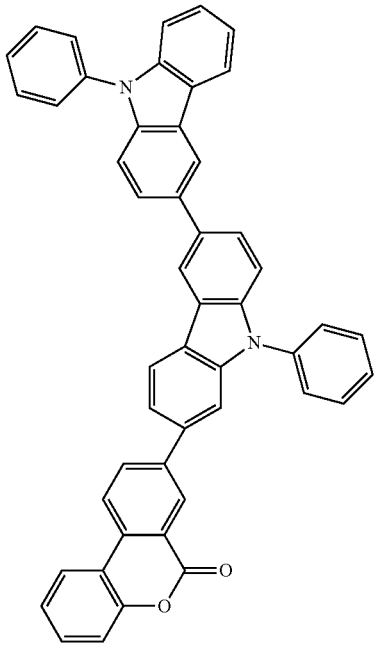
Formula 76
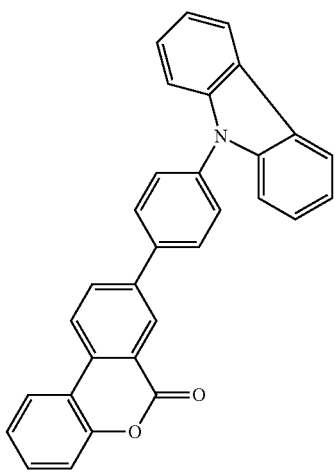
Formula 74
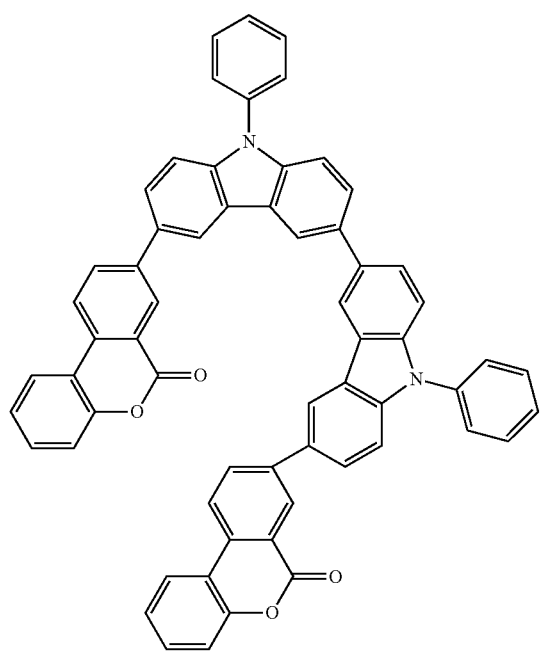
Formula 77
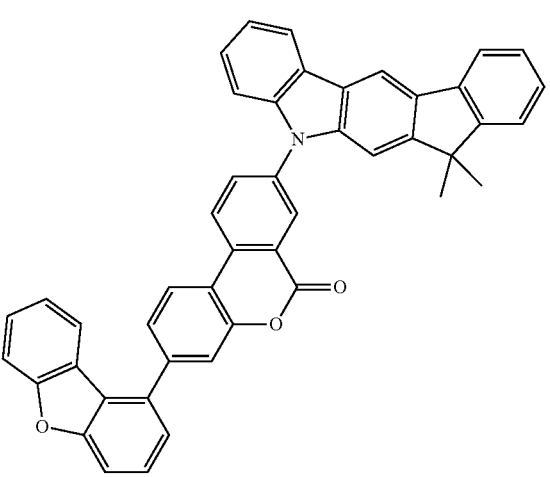

Formula 78
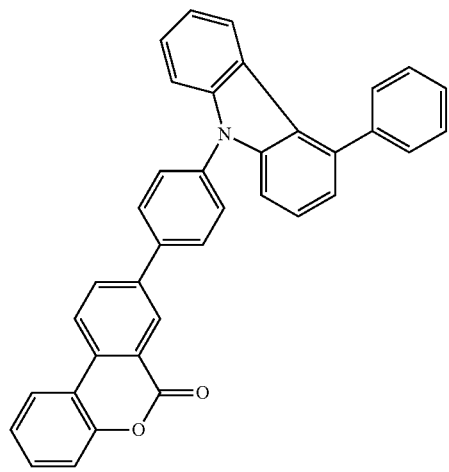
Formula 79
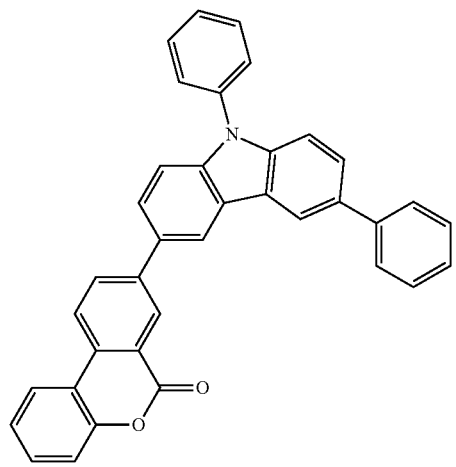
Formula 80
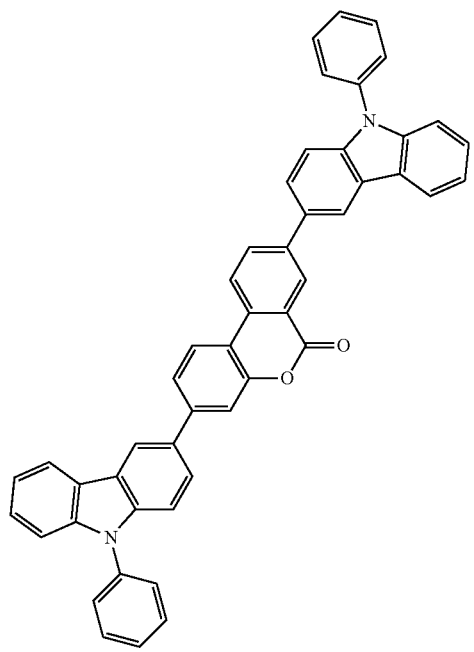
Formula 81
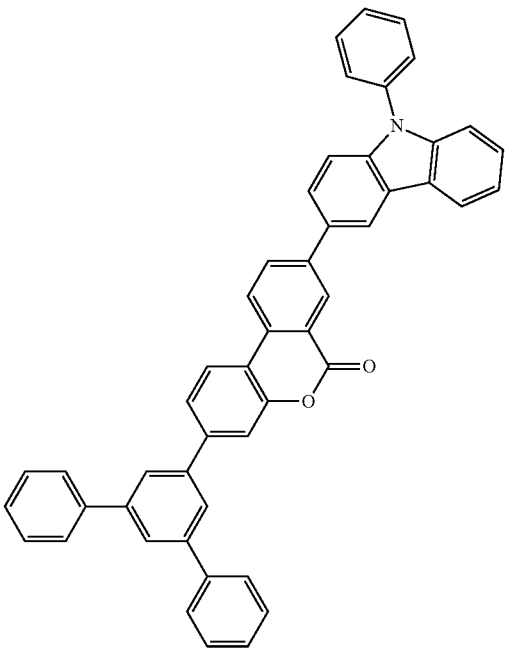
Formula 82
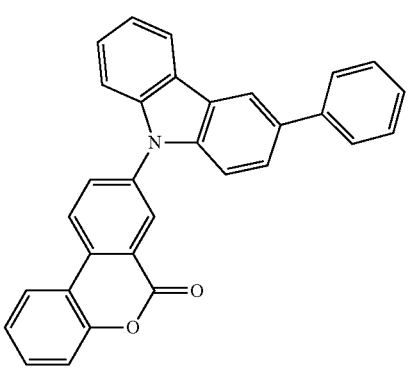

Formula 83
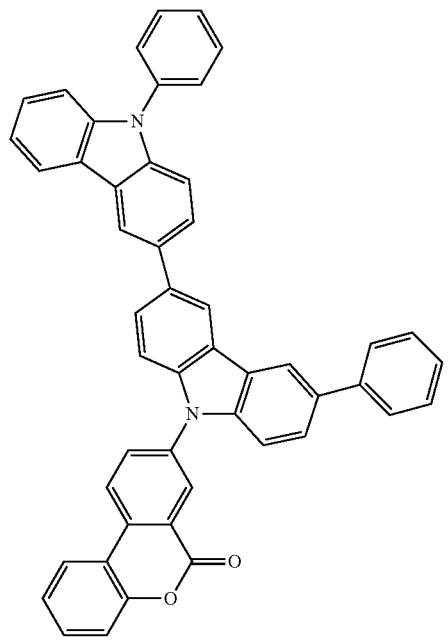
Formula 85
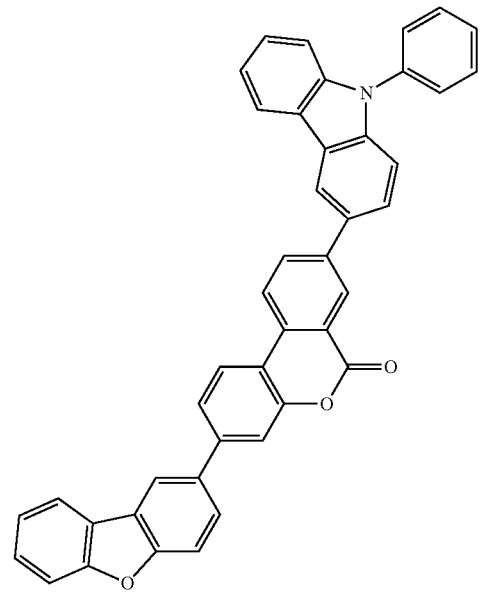
Formula 86
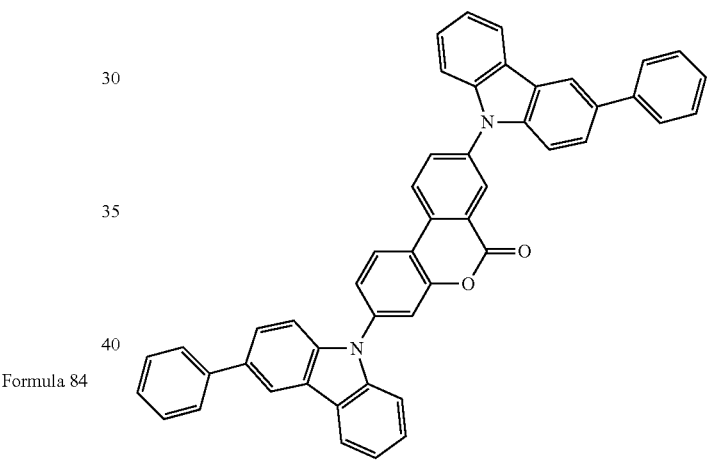
Formula 84
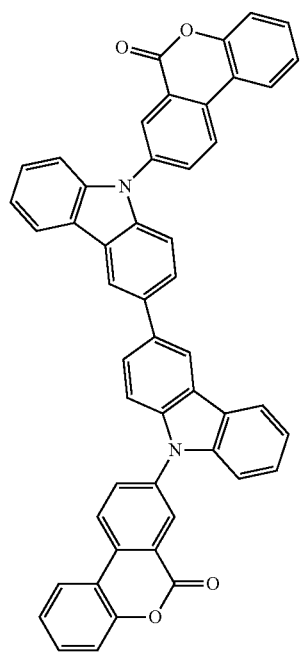
Formula 87
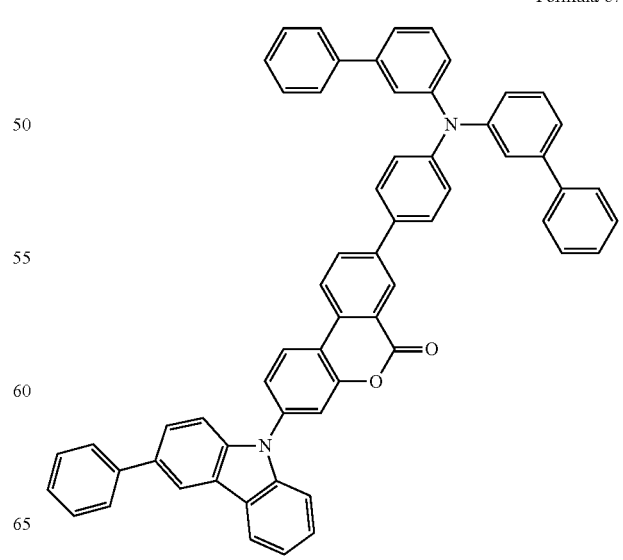

-continued
Formula 88
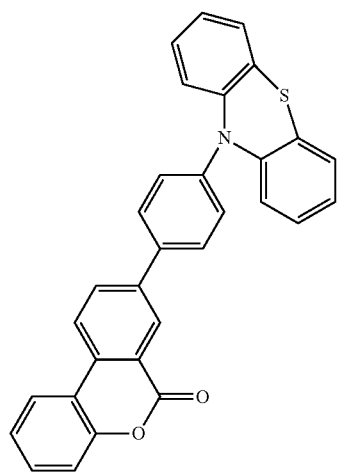
Formula 89
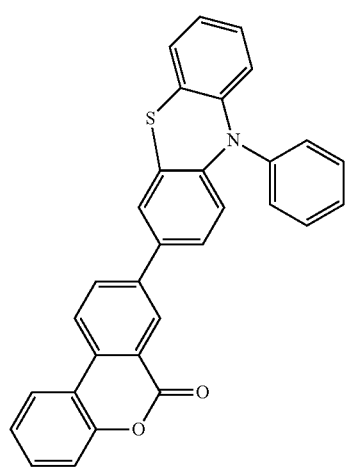
Formula 90
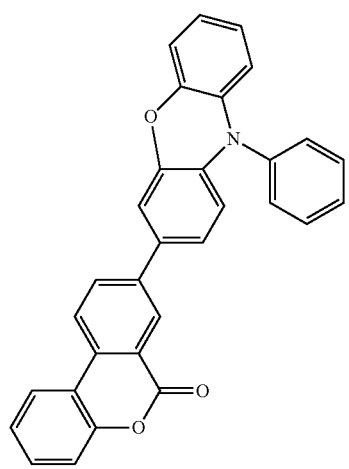
Formula 91
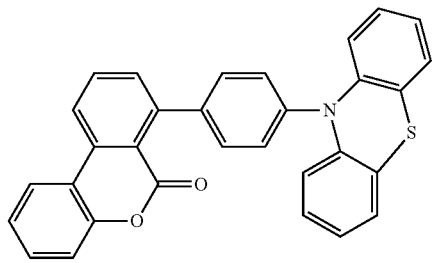
Formula 92
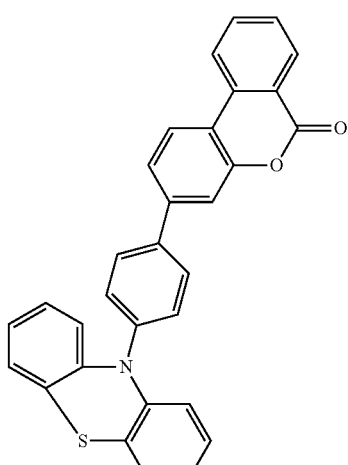
Formula 93
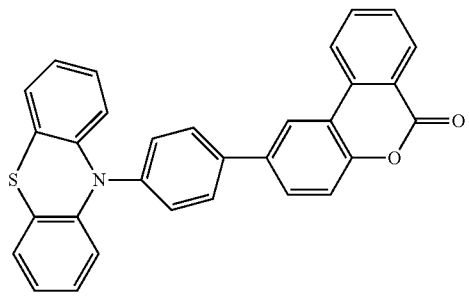
Formula 94
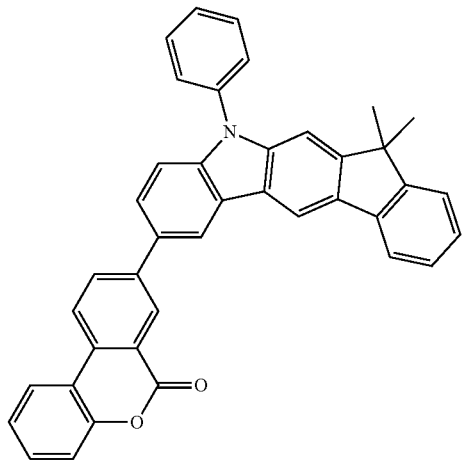

Formula 95
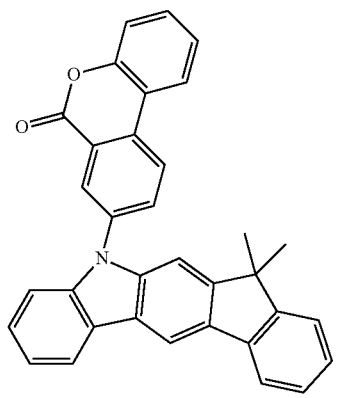
Formula 96
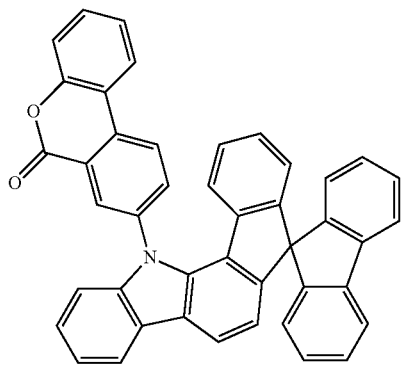
Formula 97
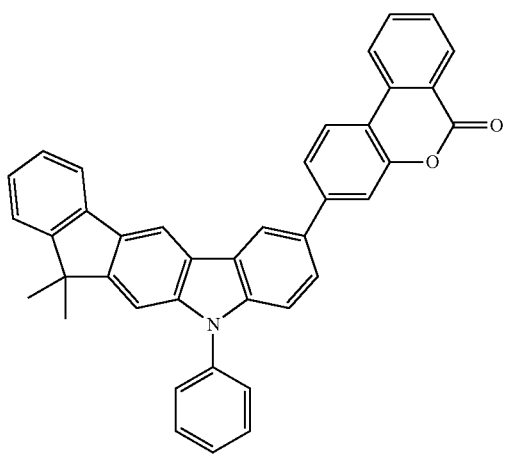
Formula 98
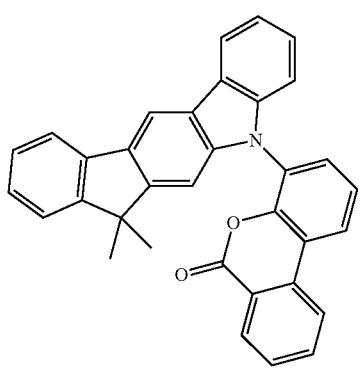
Formula 99
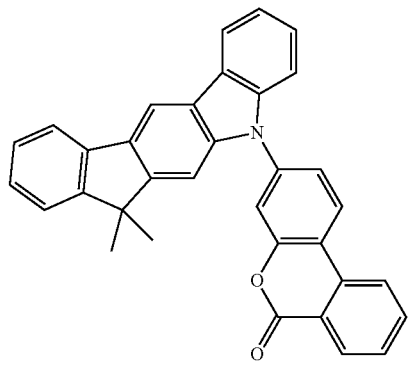
Formula 100
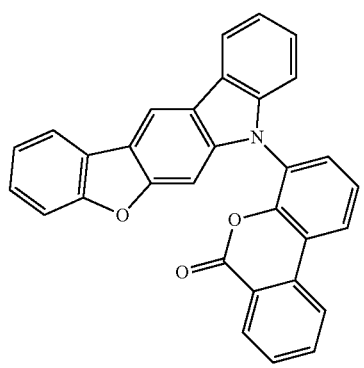
Formula 101
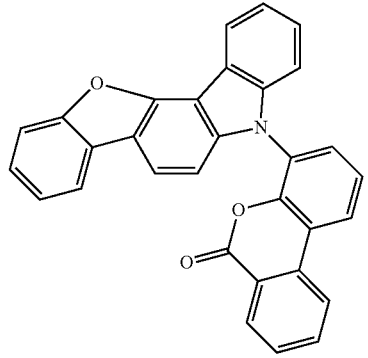
Formula 102
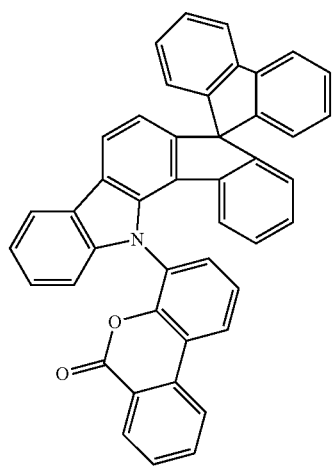

Formula 103
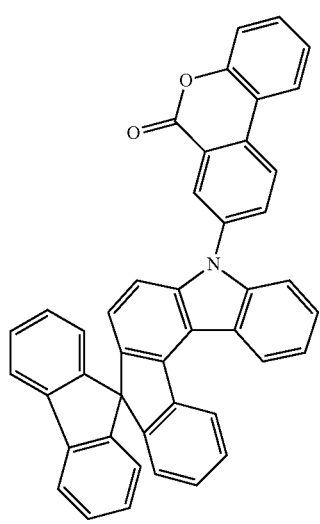
Formula 104
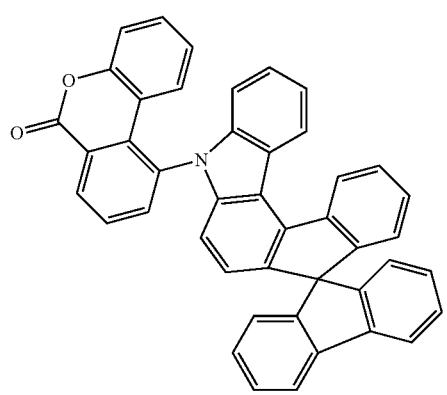
Formula 105
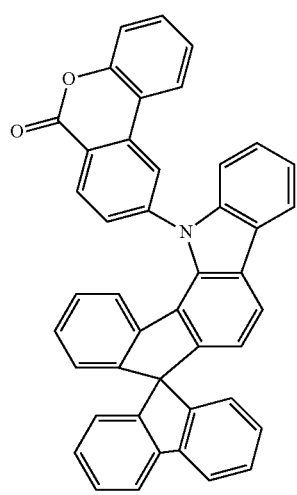
Formula 106
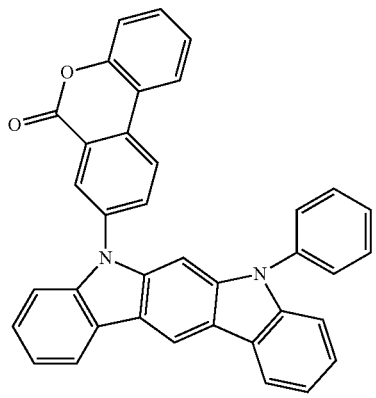
Formula 107
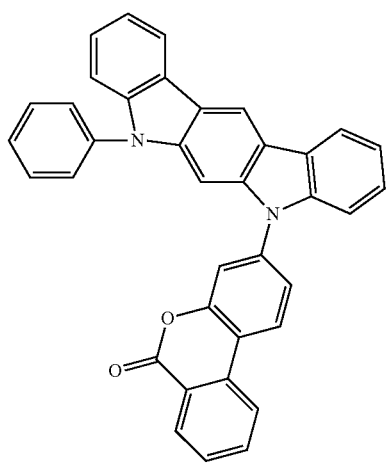
Formula 108
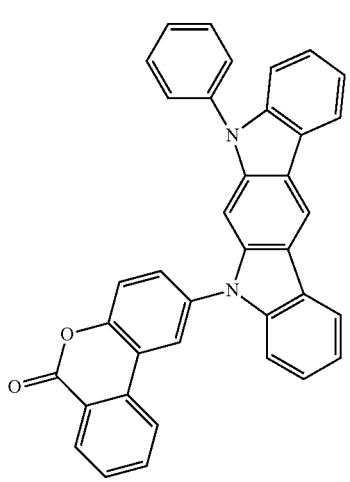

Formula 109
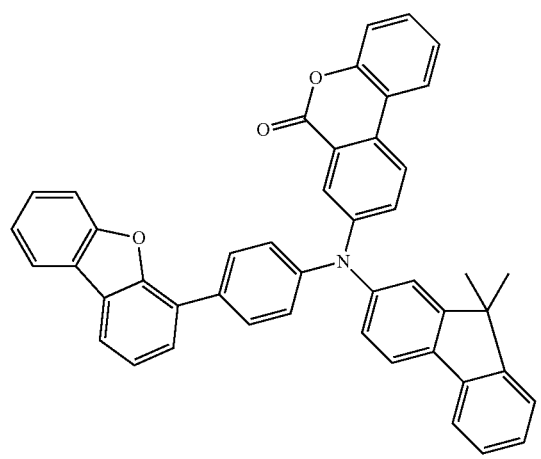
Formula 110
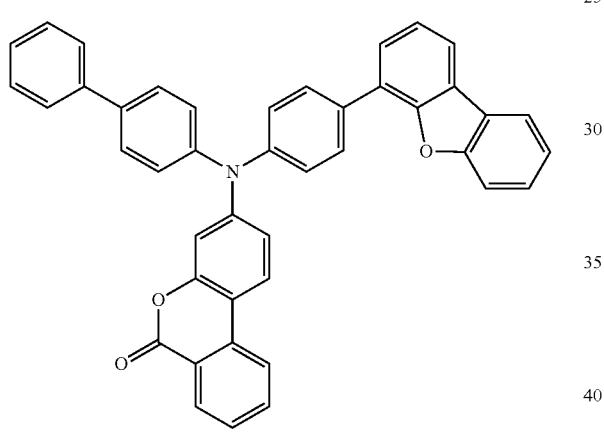
Formula 111
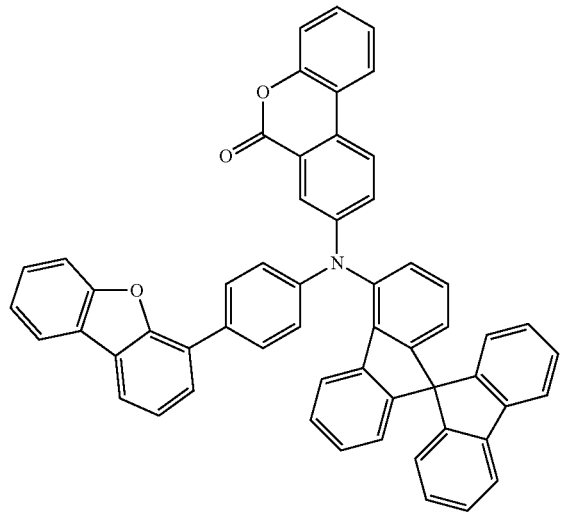
Formula 112
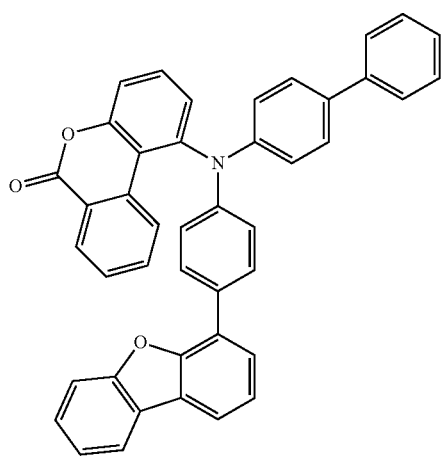
Formula 113
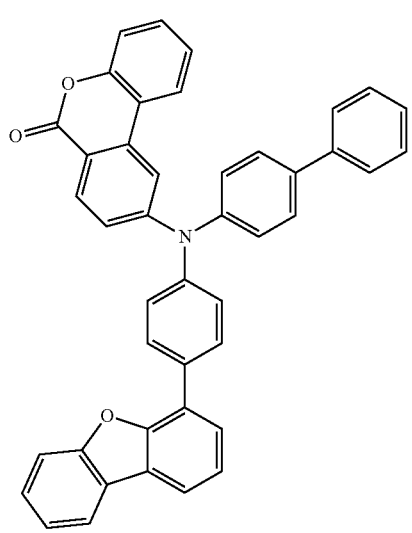
Formula 114
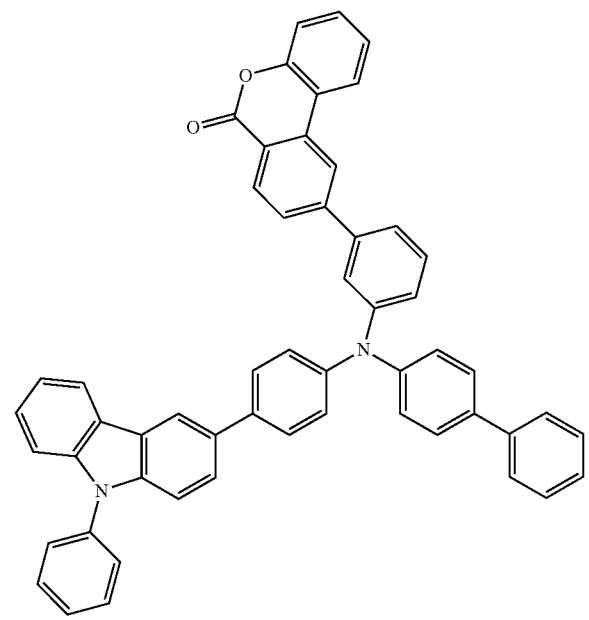

Formula 115
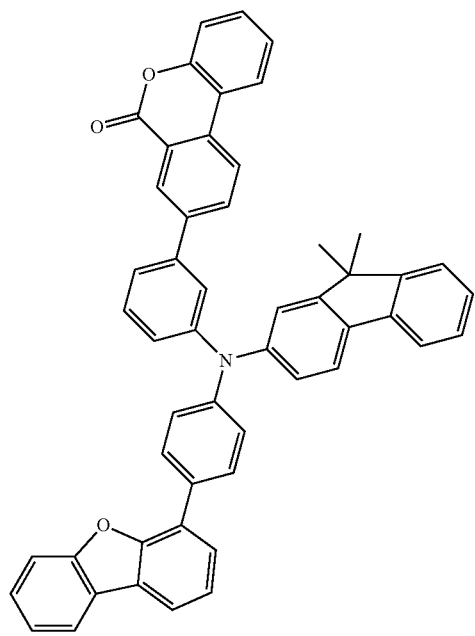
Formula 116
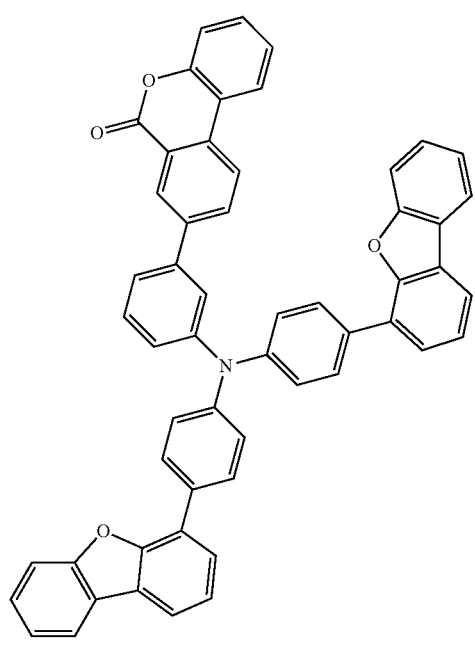
Formula 117
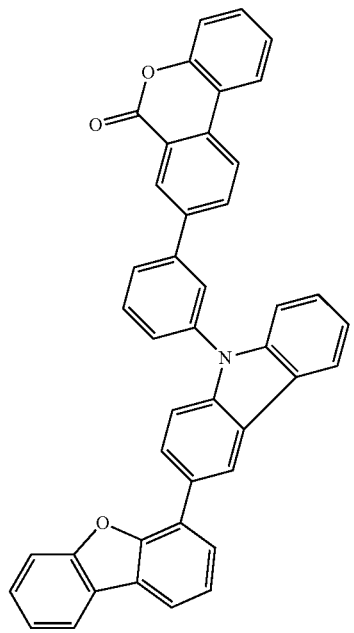
Formula 118
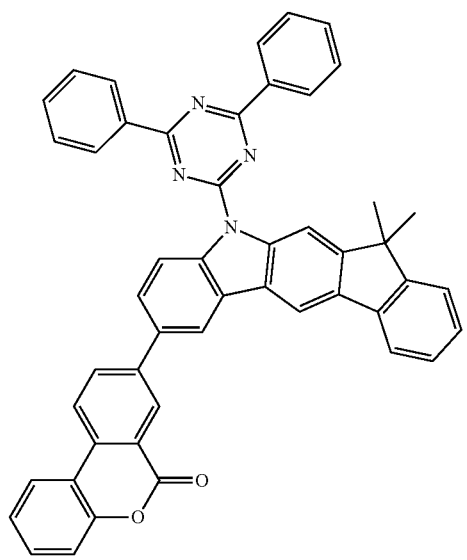

Formula 119
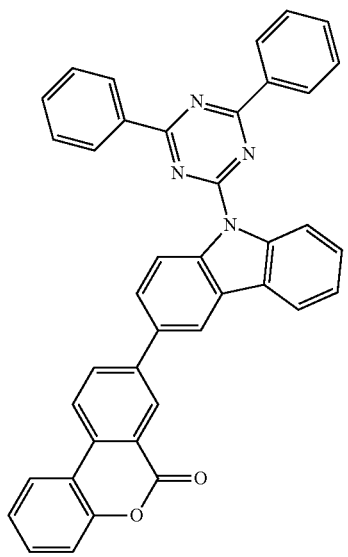
Formula 120
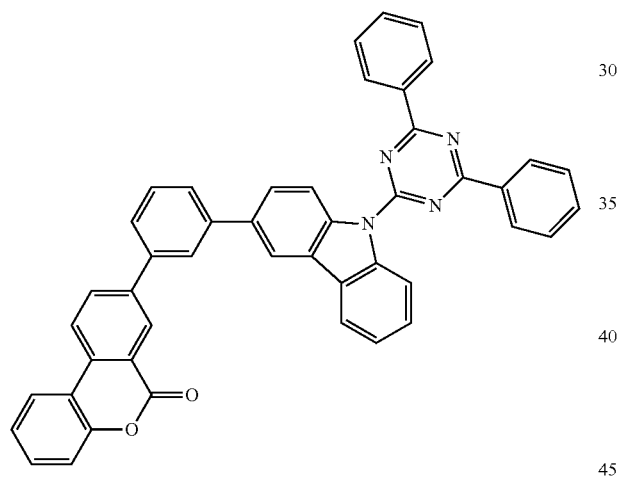
Formula 121
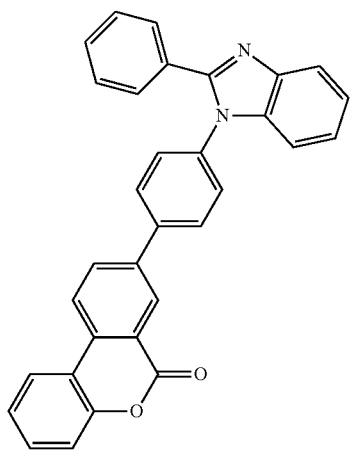
Formula 122
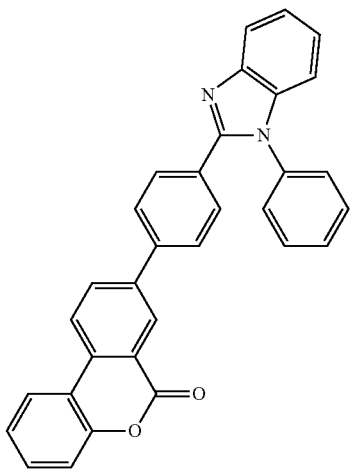
Formula 123
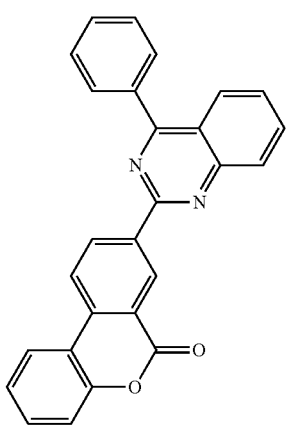
Formula 124
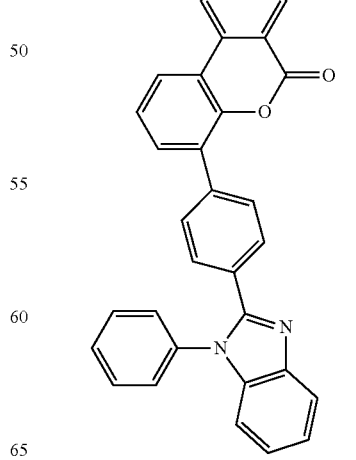

Formula 125
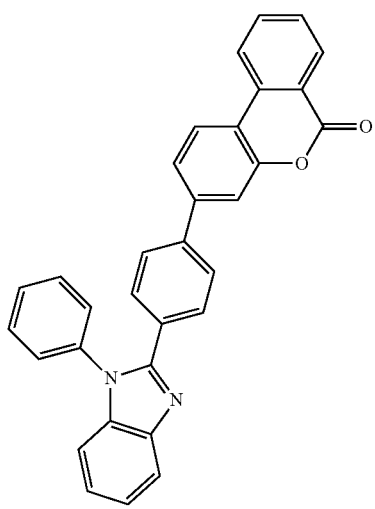
Formula 126
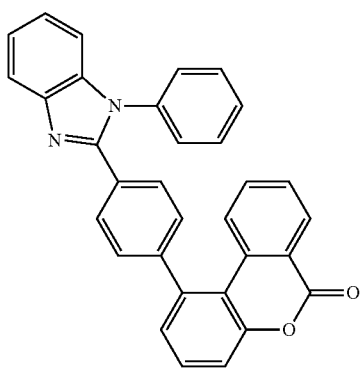
Formula 127
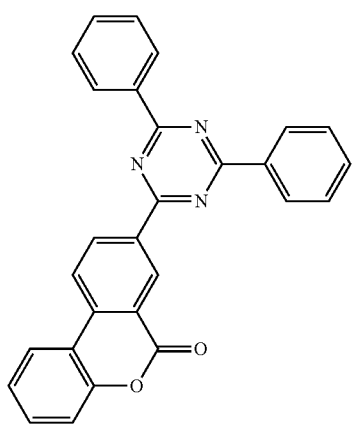
Formula 128
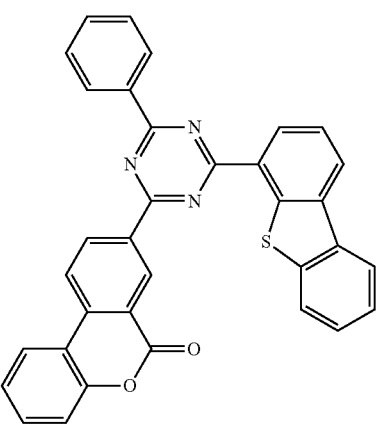
Formula 129
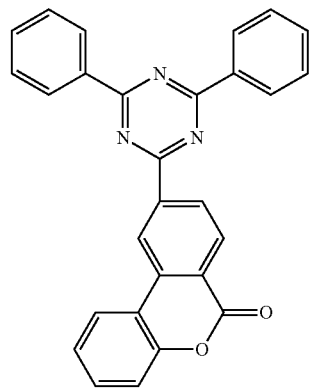
Formula 130
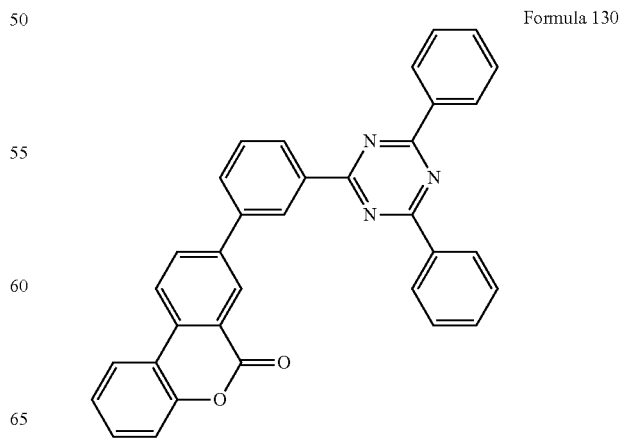

Formula 131
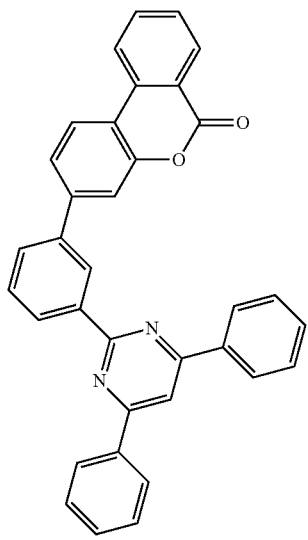
Formula 132
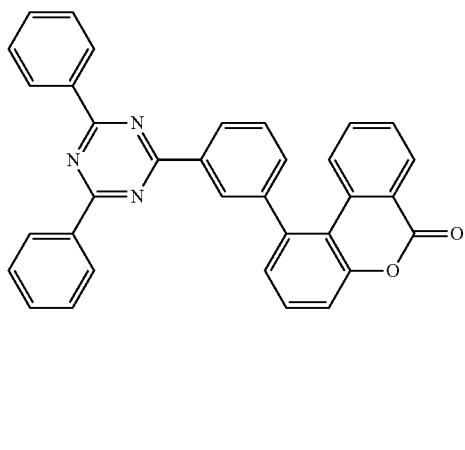
Formula 133
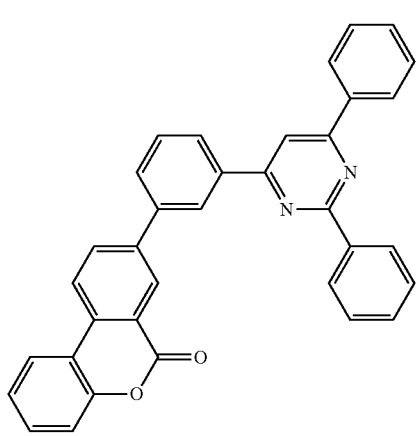
Formula 134
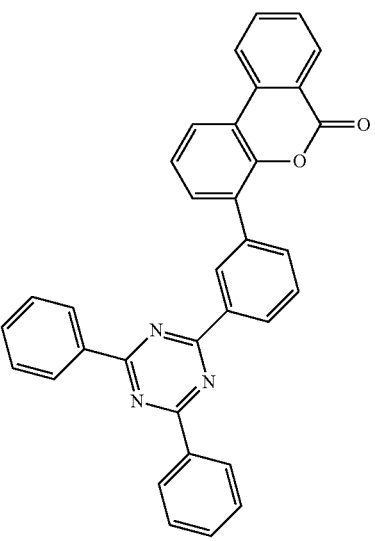
Formula 135
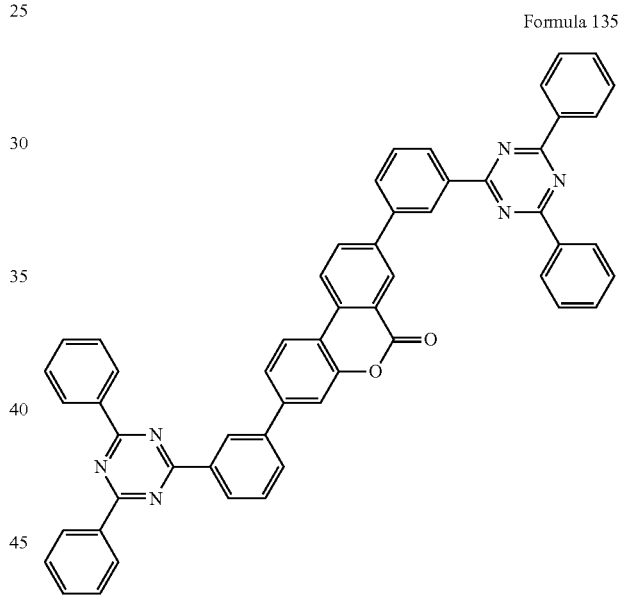
Formula 136
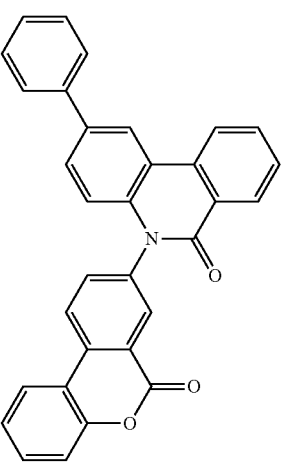

Formula 137
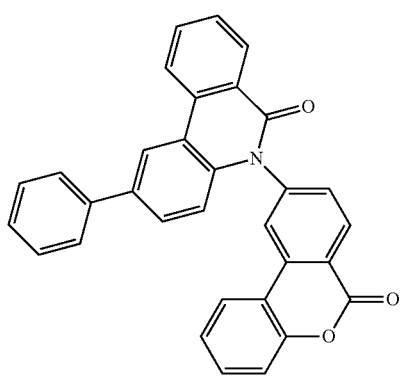
Formula 140
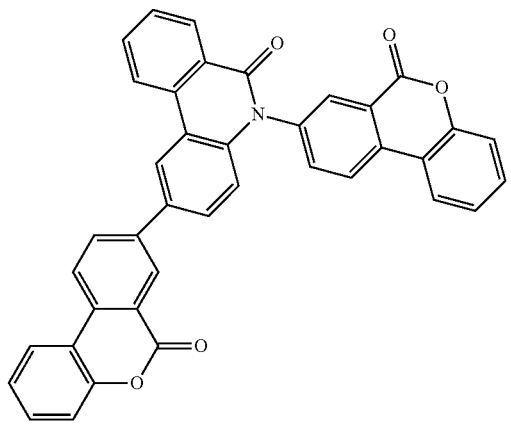
Formula 138
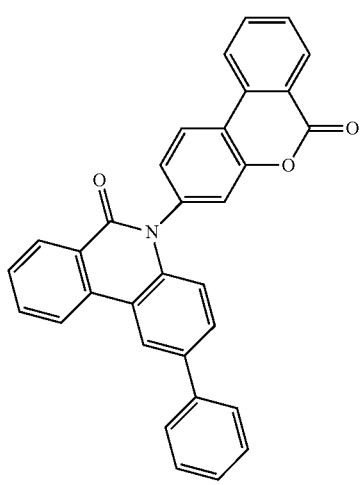
Formula 141
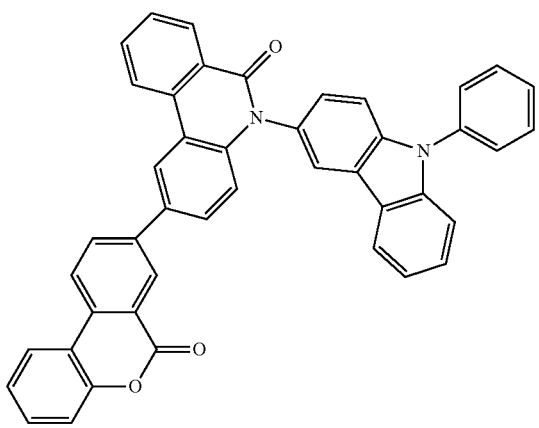
Formula 139
Formula 142
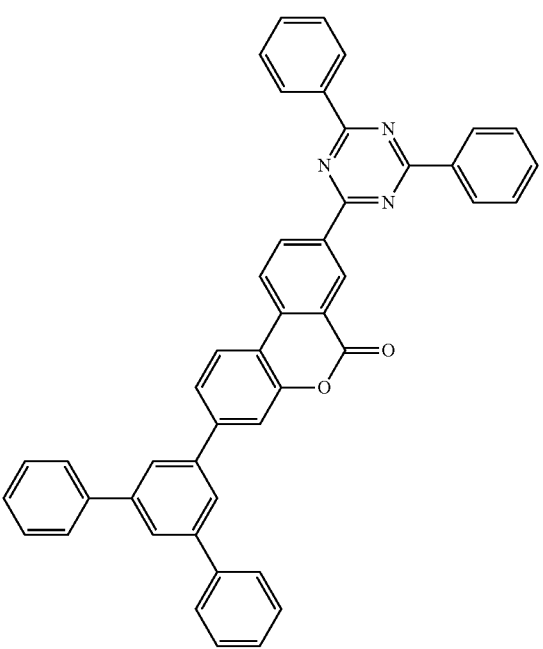

Formula 143
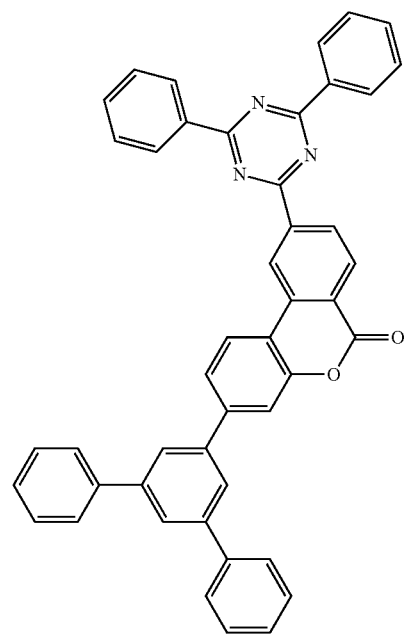
Formula 144
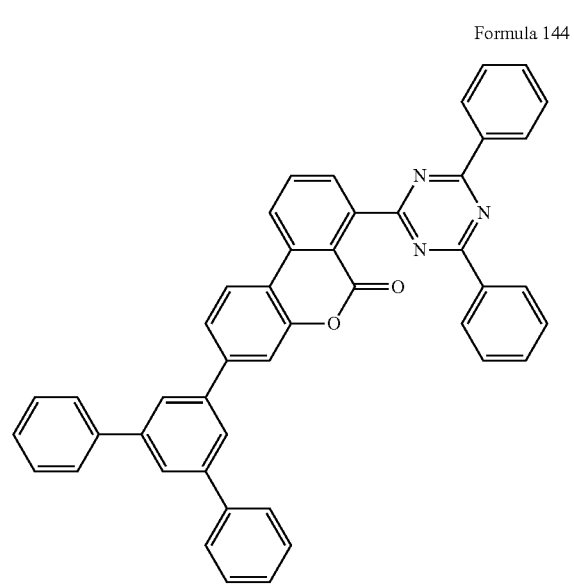
Formula 145
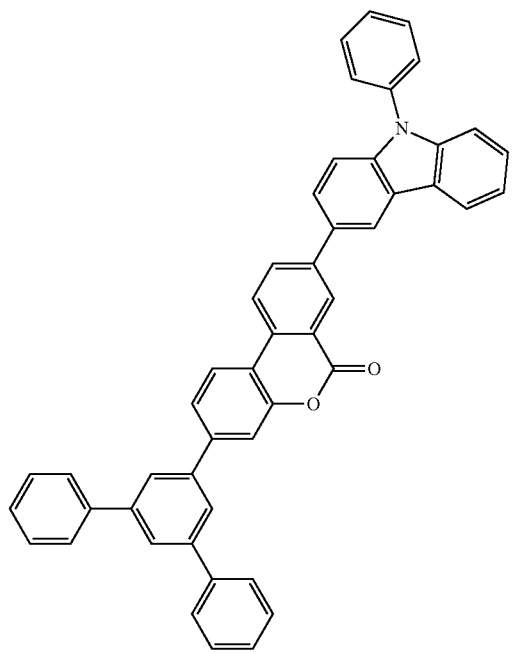
Formula 146
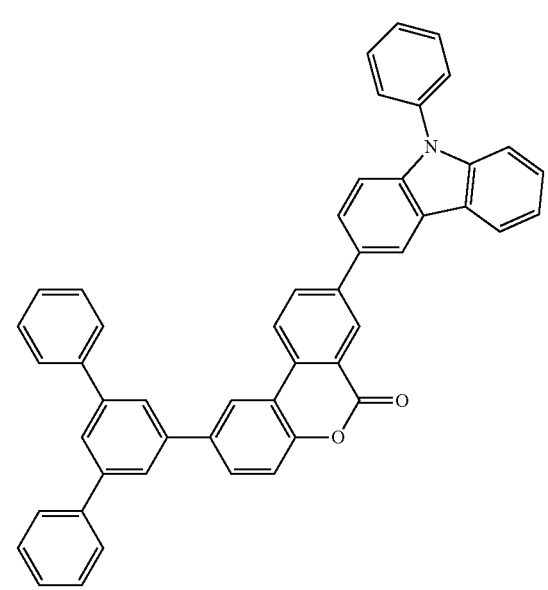

Formula 147
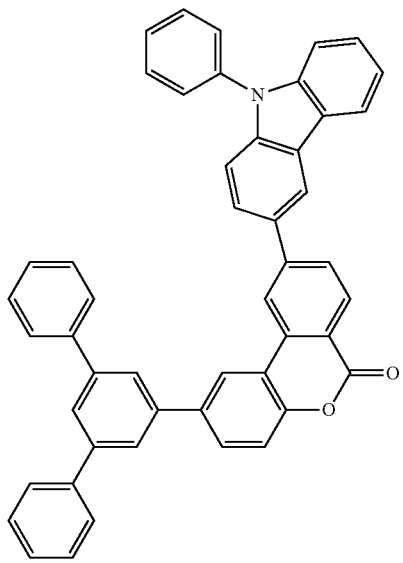
Formula 148
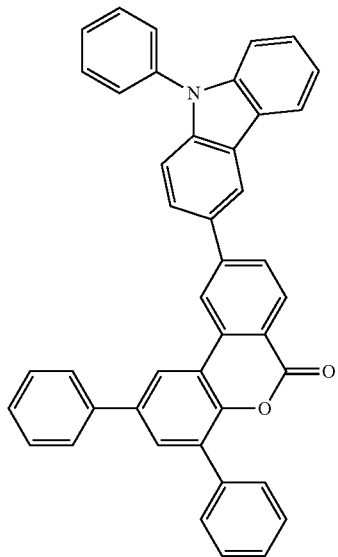
Formula 149
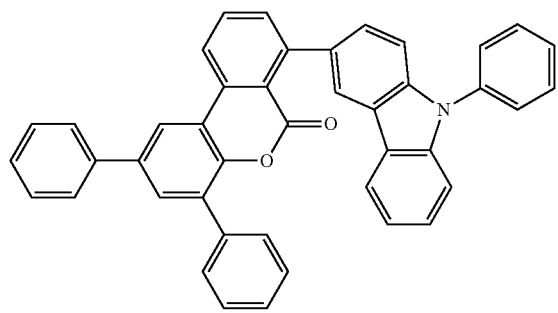
Formula 150
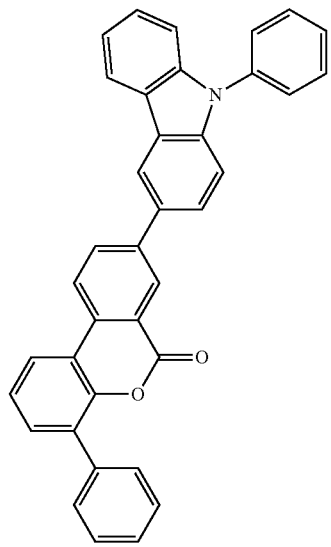
Formula 151
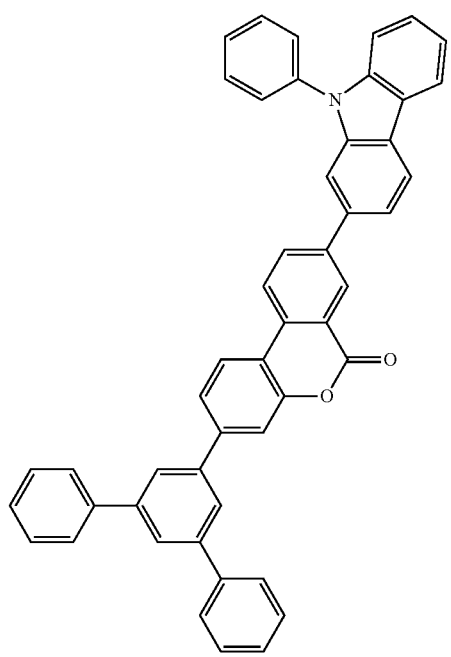

-continued
Formula 152
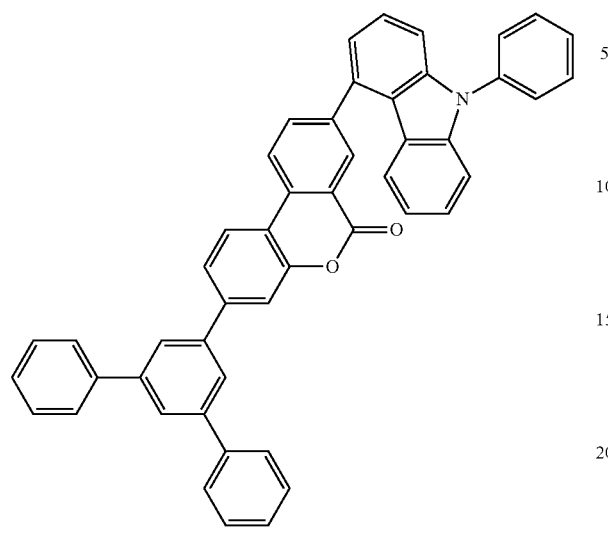
Formula 153
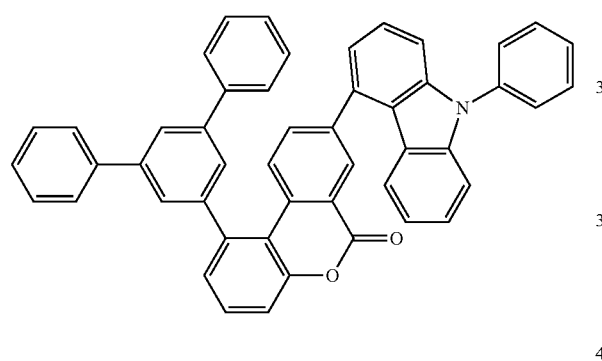
Formula 154
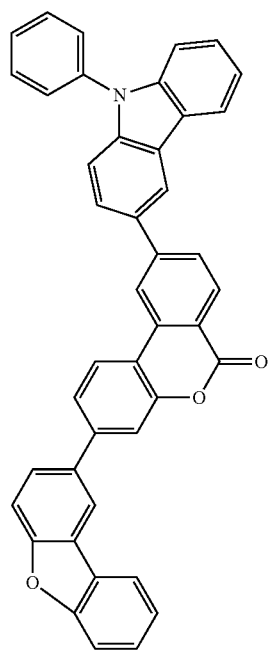
-continued
Formula 155
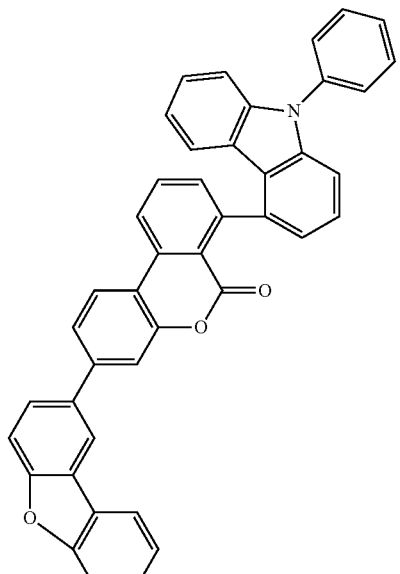
Formula 156
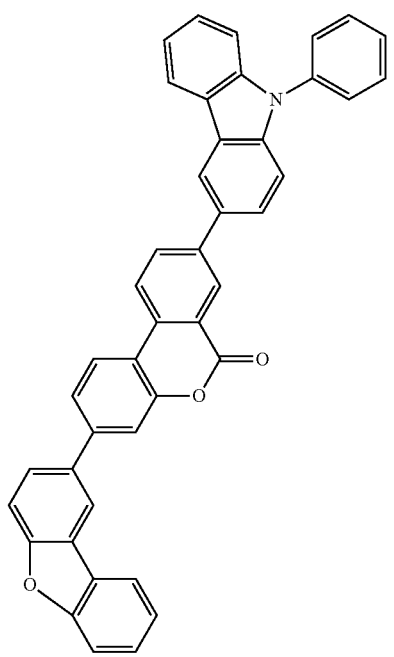

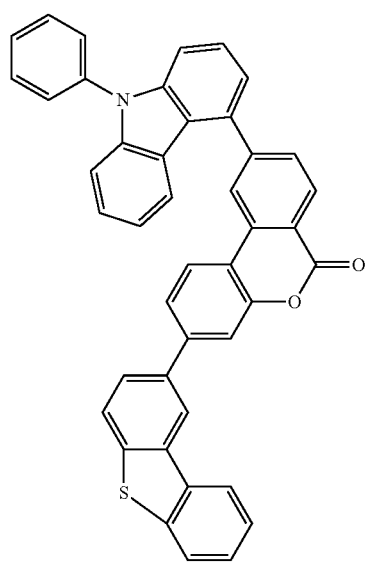
Formula 157
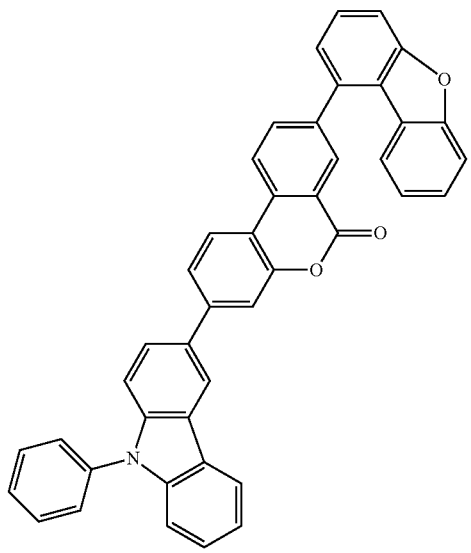
Formula 159
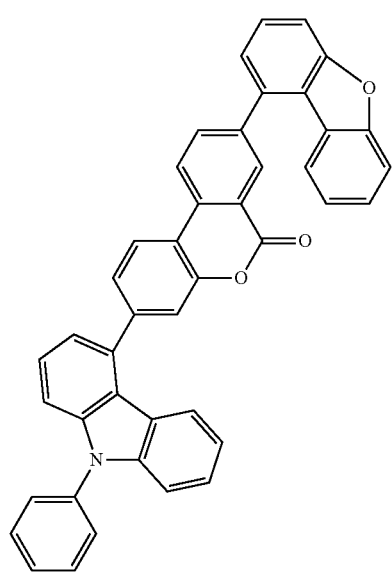
Formula 158
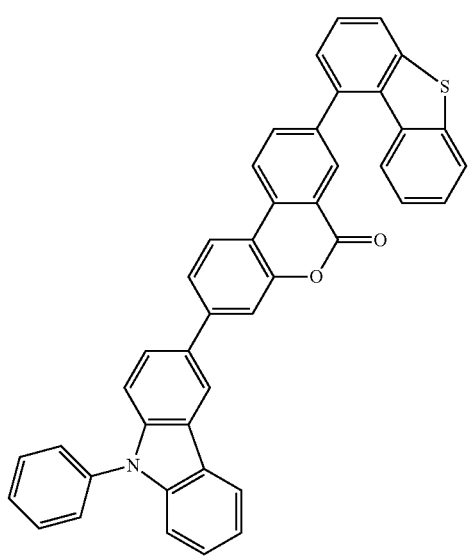
Formula 160

Formula 161
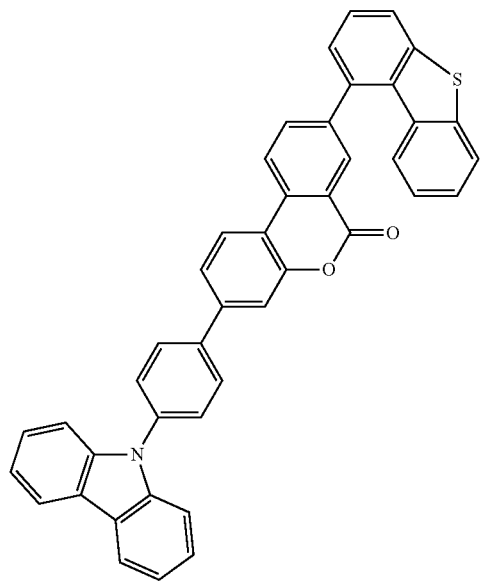
Formula 162
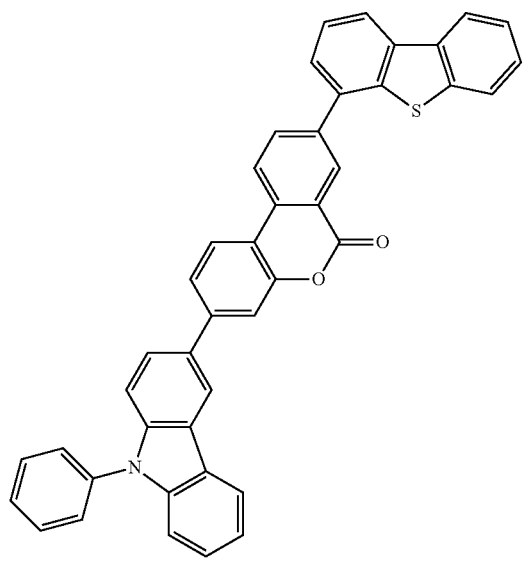
Formula 163
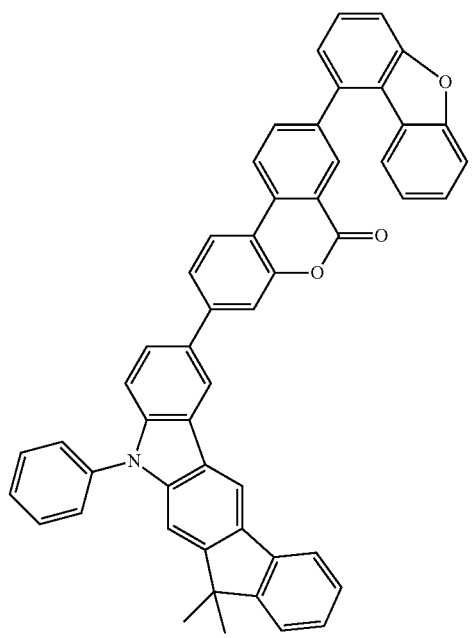
Formula 164
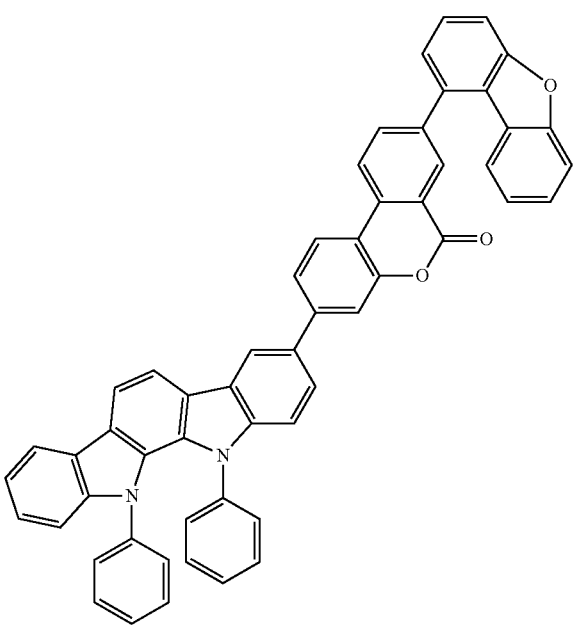

Formula 165
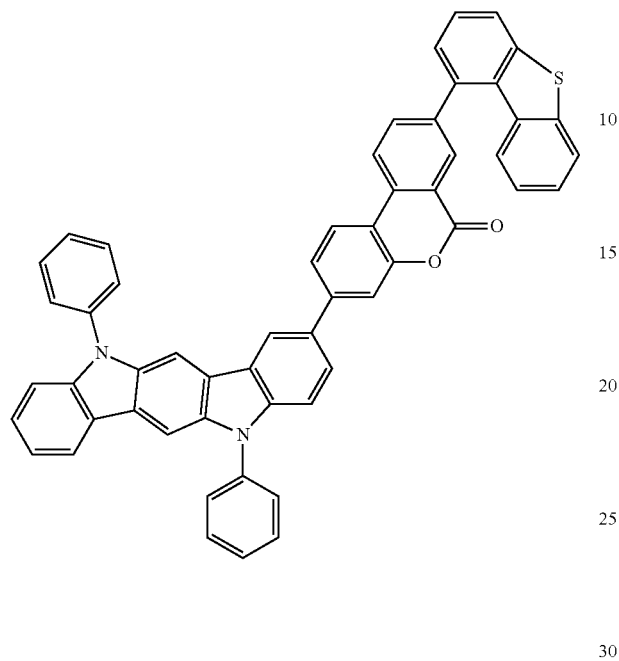
Formula 166
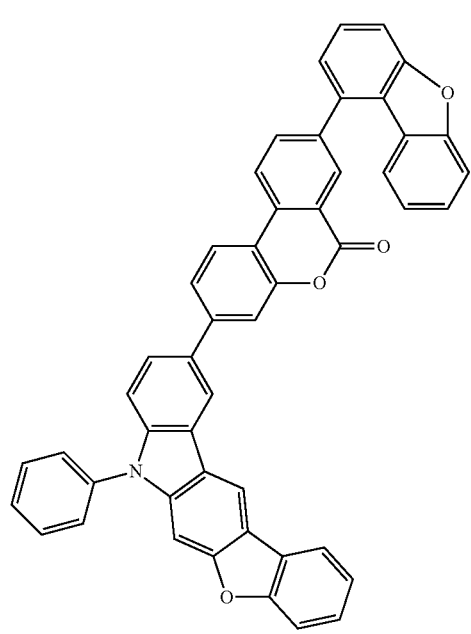
Formula 167
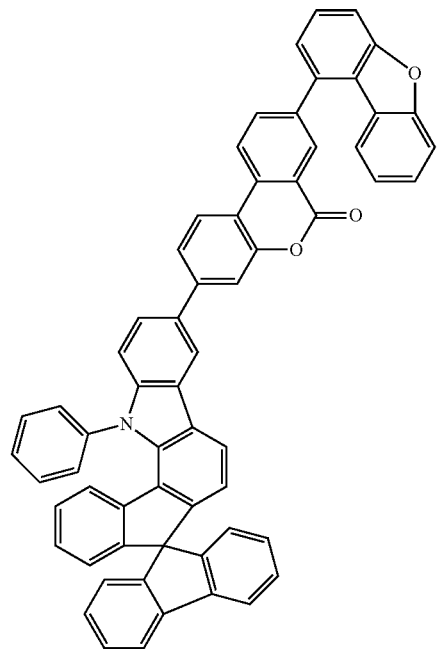
Formula 168
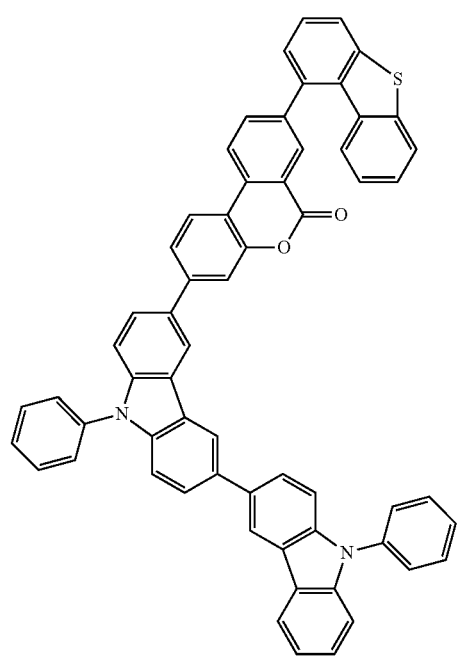

Formula 169
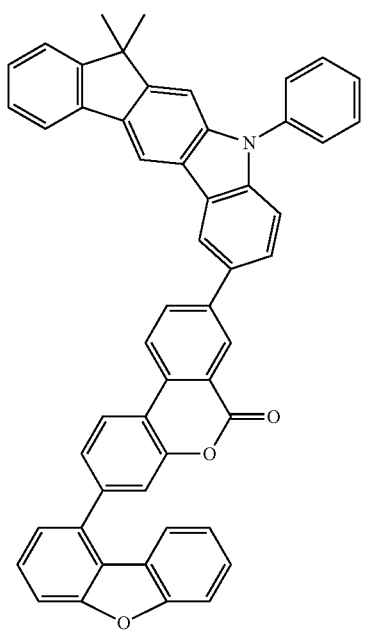
Formula 171
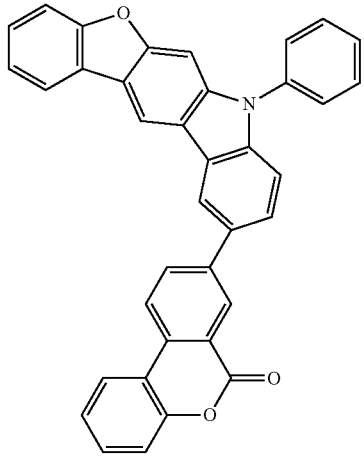
Formula 172
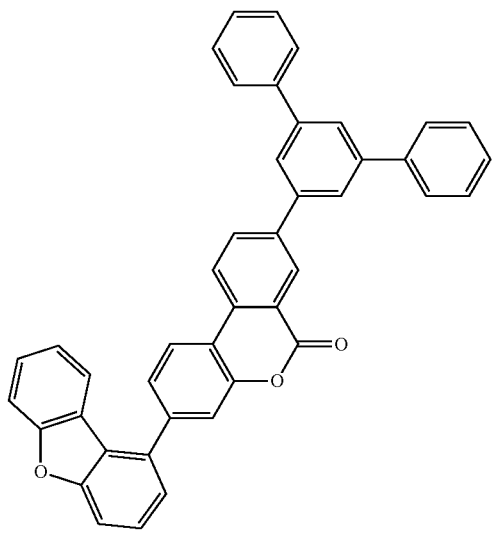
Formula 170
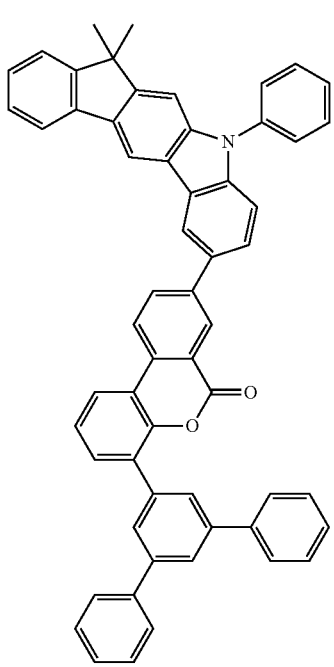
Formula 173
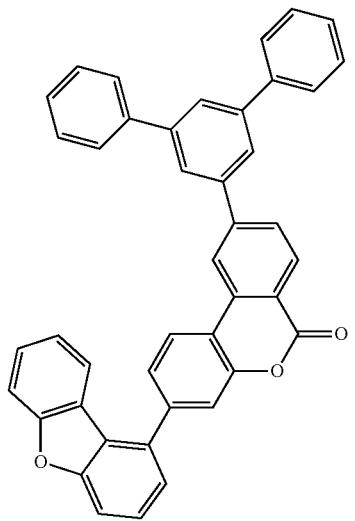

Formula 174
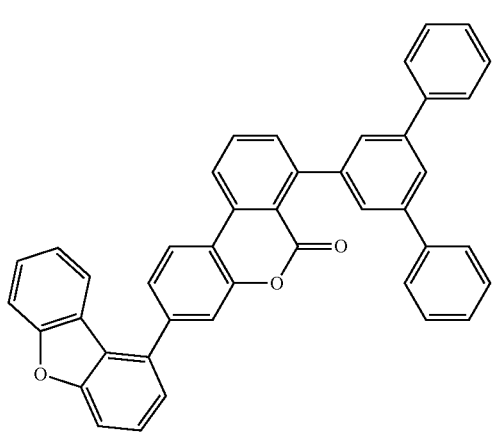
Formula 172
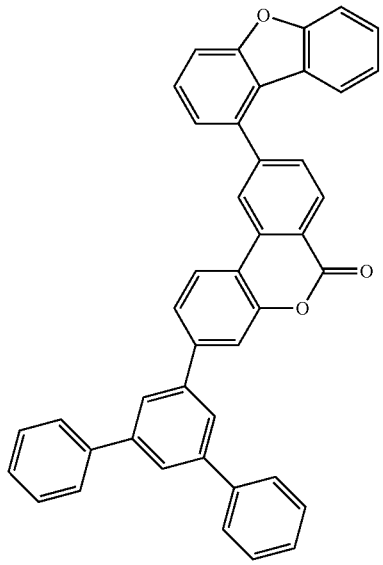
Formula 173
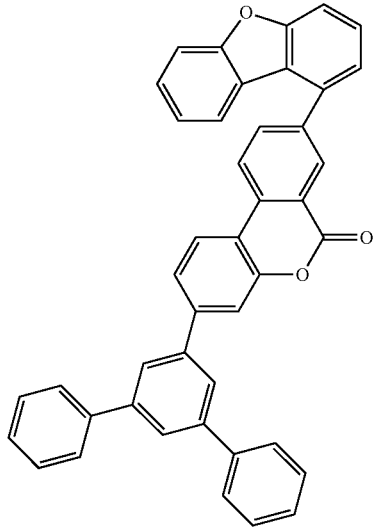
Formula 174
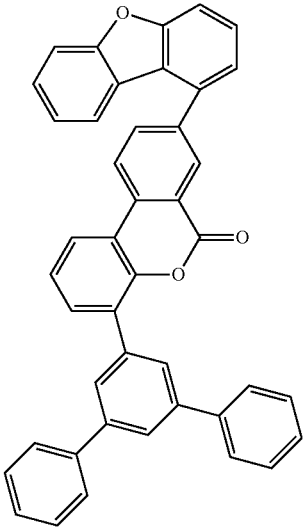
Formula 175
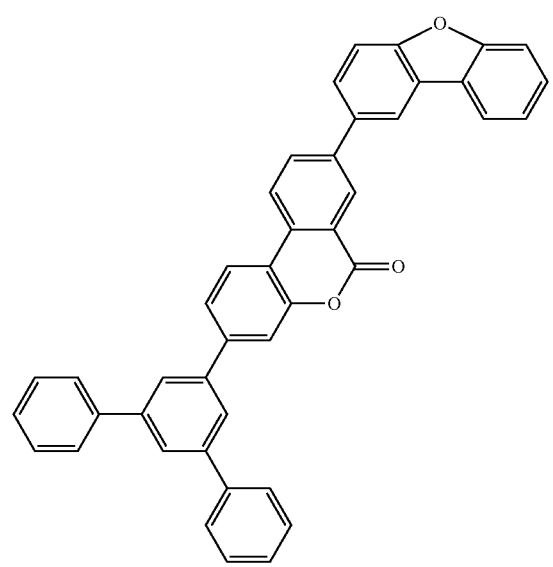
Formula 176
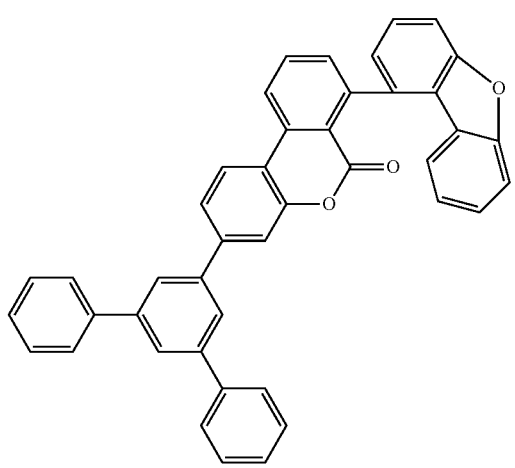

Formula 177
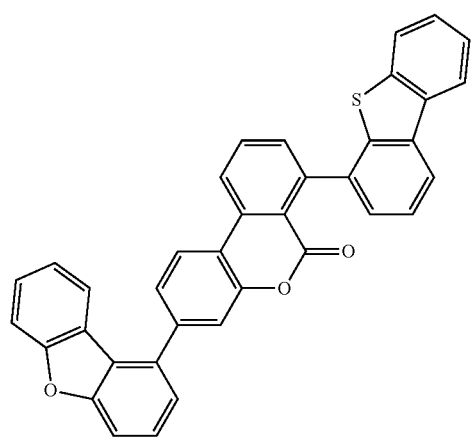
Formula 180
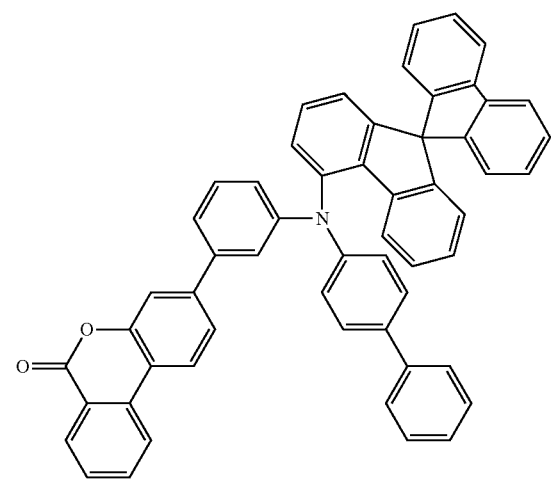
Formula 178
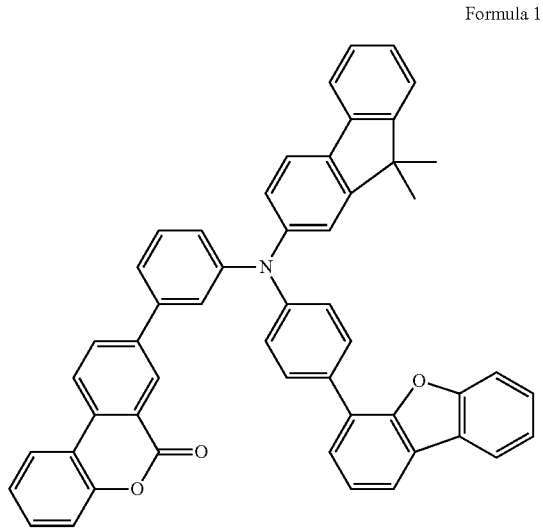
Formula 181
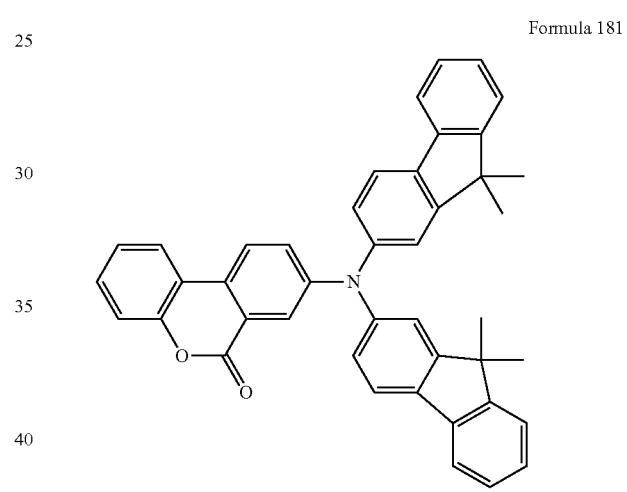
Formula 179
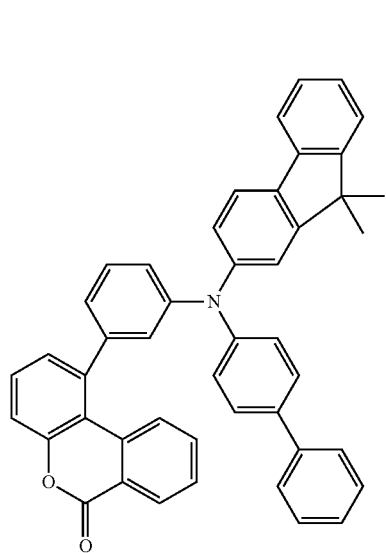
Formula 182
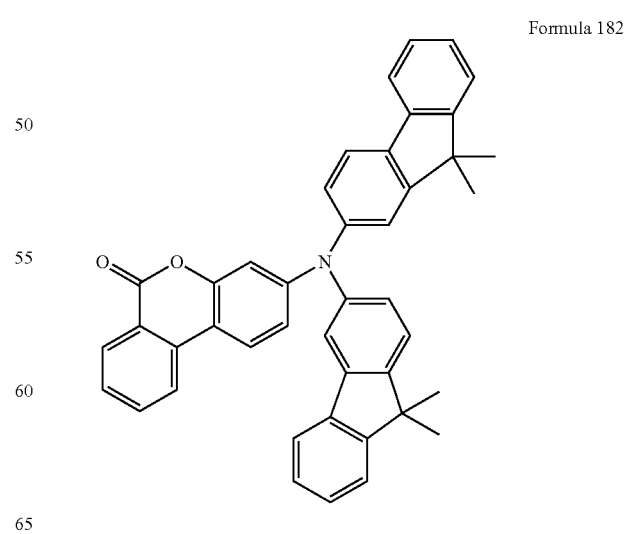

Formula 183
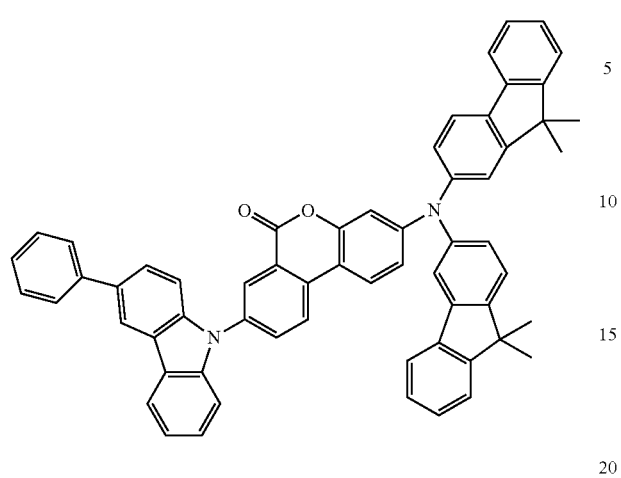
Formula 184
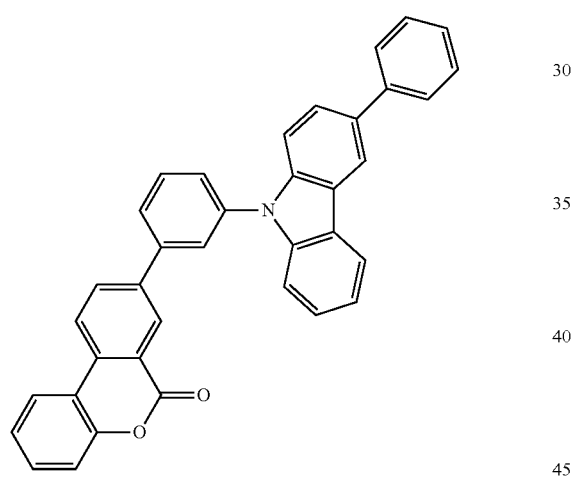
Formula 185
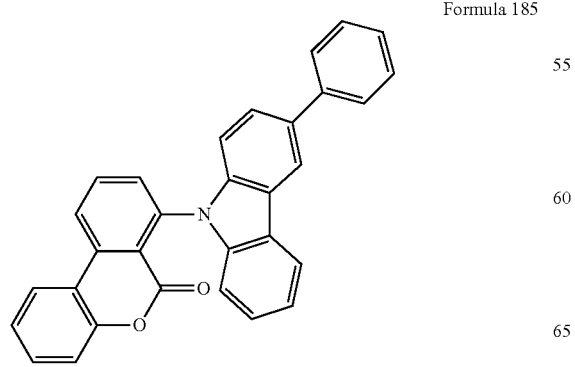
Formula 186
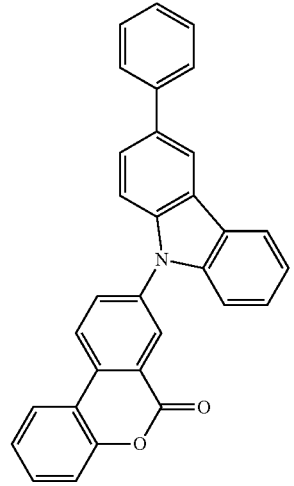
Formula 187
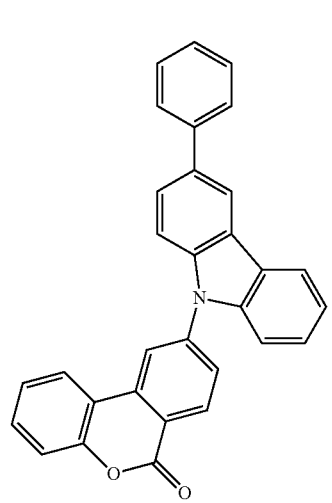
Formula 188
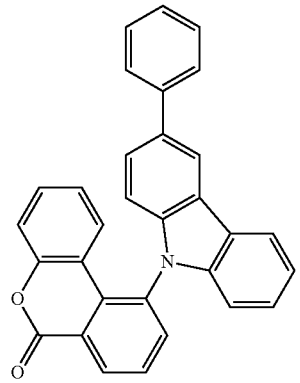

Formula 189
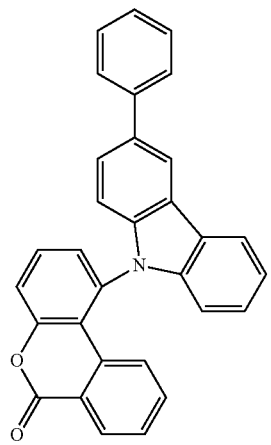
Formula 190
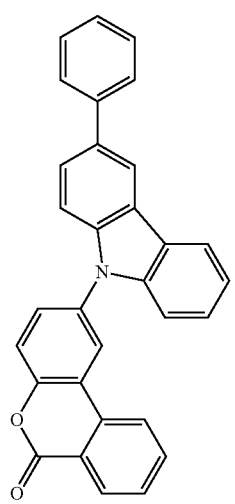
Formula 191
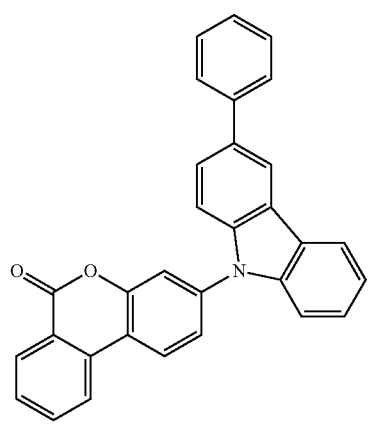
Formula 192
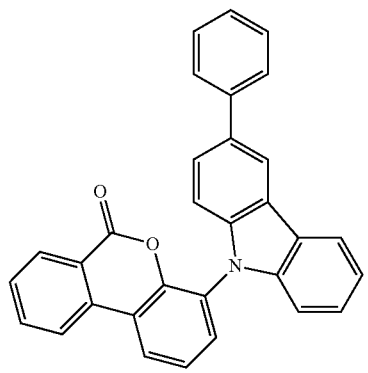
Formula 193
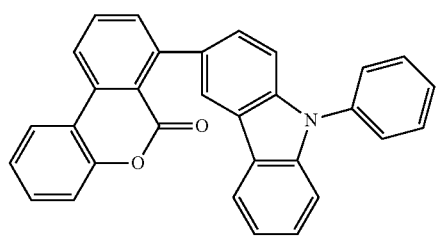
Formula 194
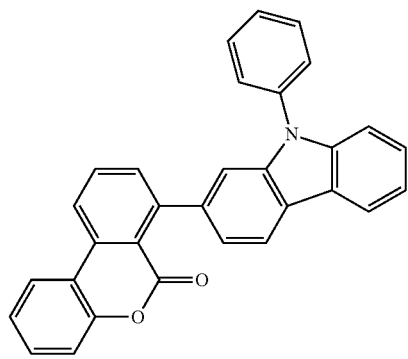
Formula 195
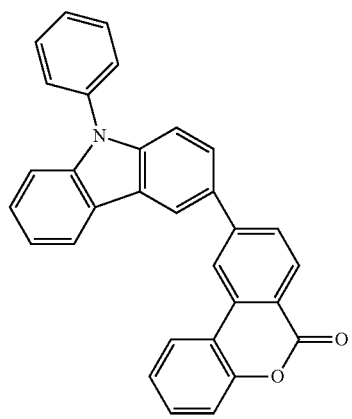

-continued
Formula 196
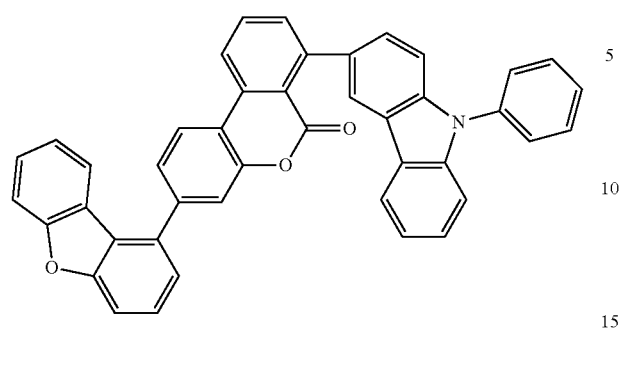
Formula 197
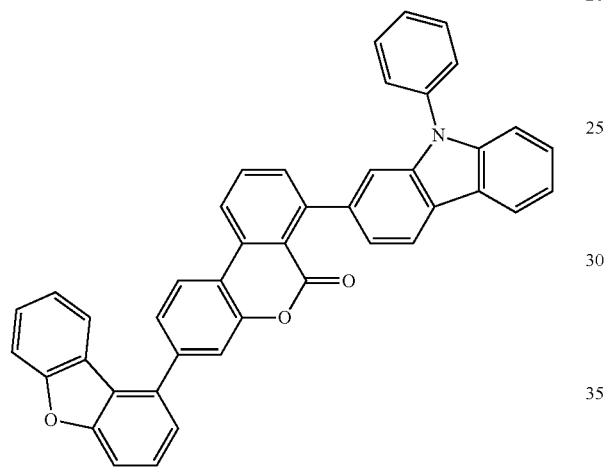
Formula 198
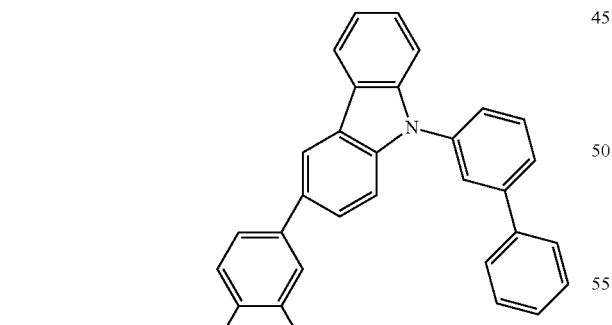
Formula 199
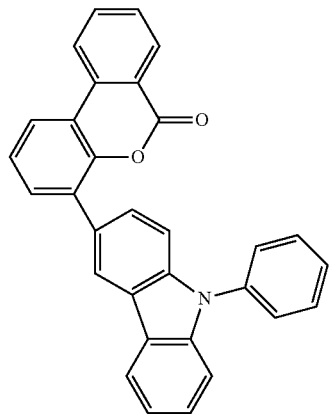
Formula 200
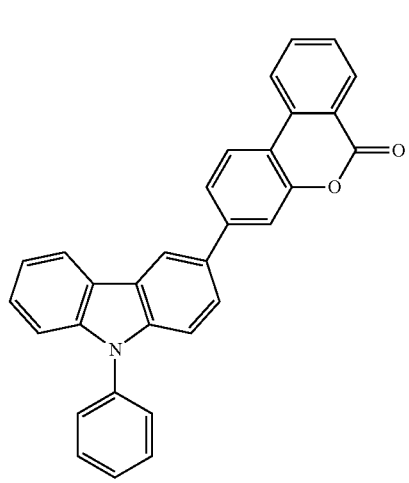
Formula 201
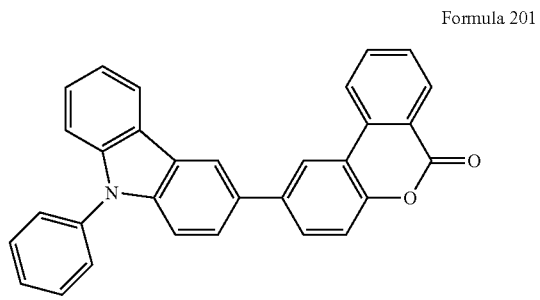

Formula 202
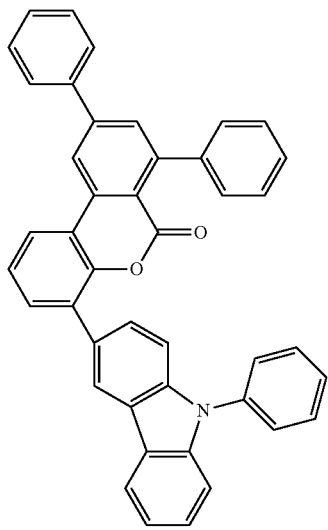
Formula 203
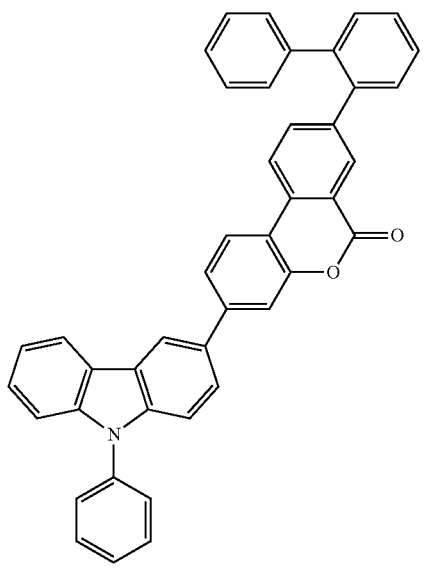
Formula 204
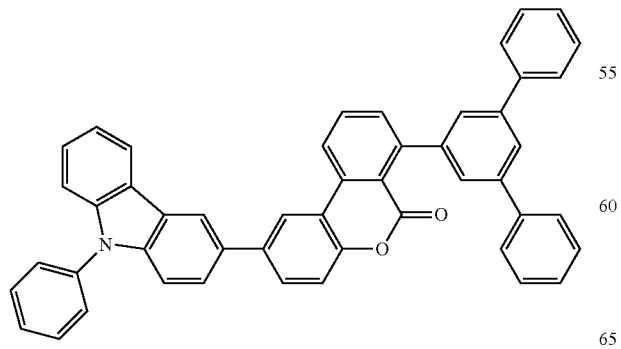
Formula 205
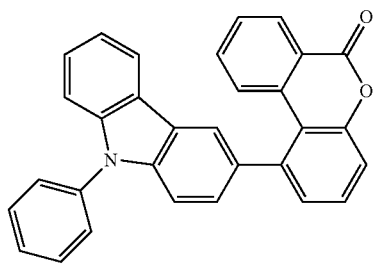
Formula 206
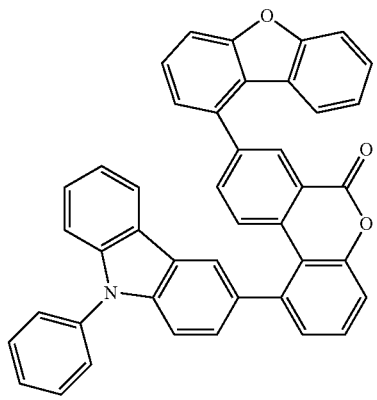
Formula 207
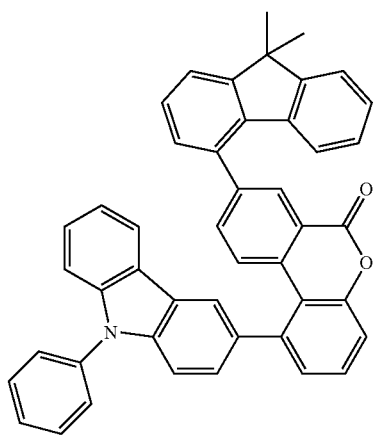

Formula 208
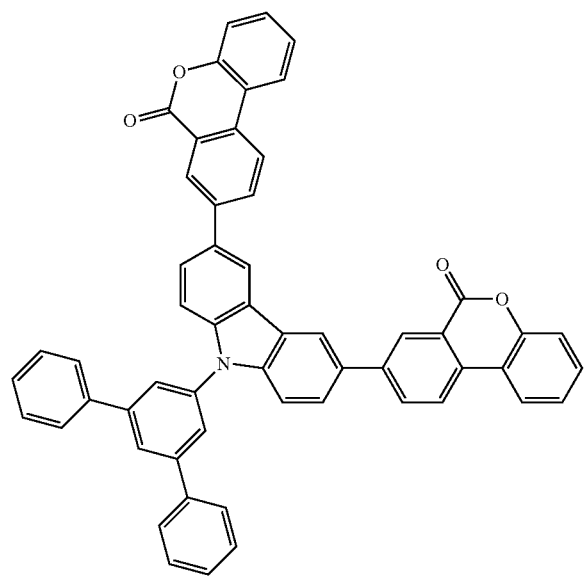
Formula 209
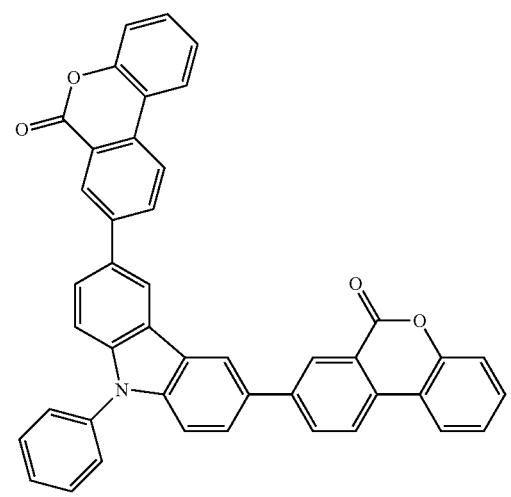
Formula 210
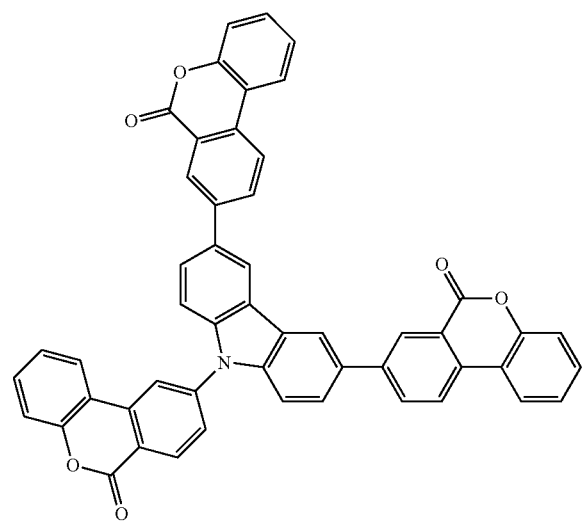
Formula 211
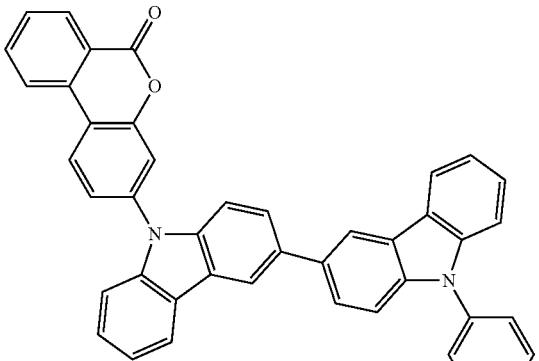
Formula 212
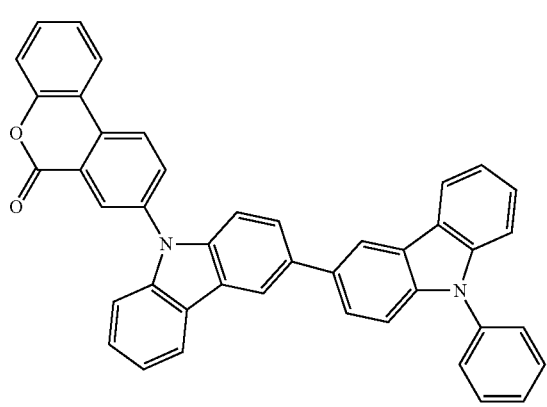
Formula 213
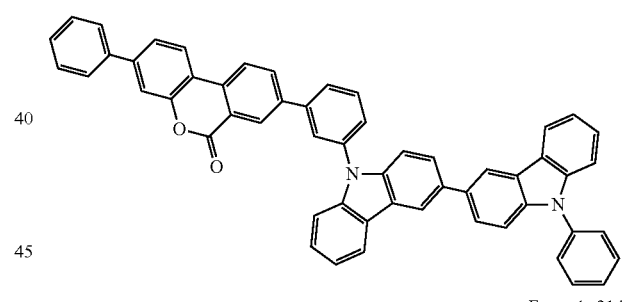
Formula 214
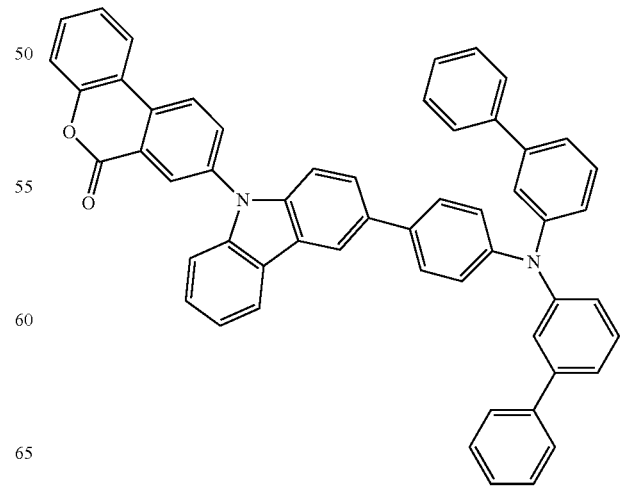

Formula 215
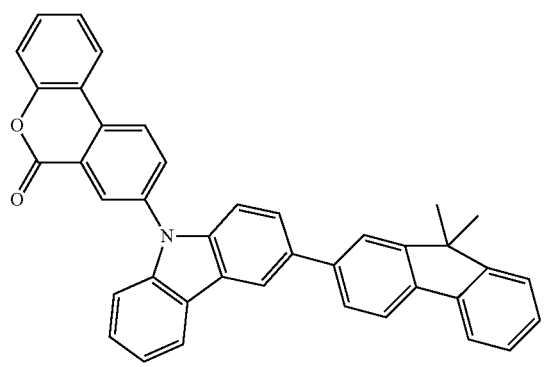
Formula 216
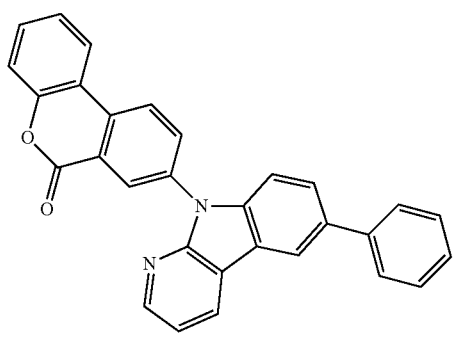
Formula 217
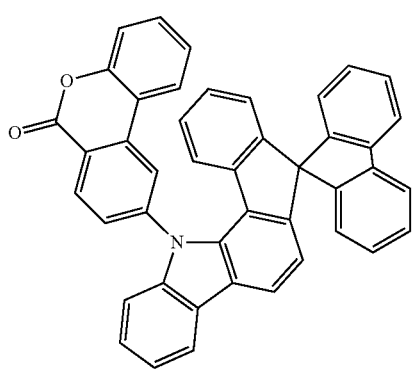
Formula 218
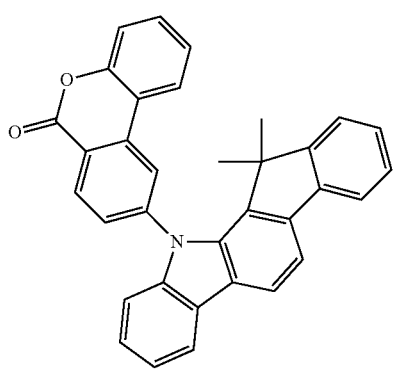
Formula 219
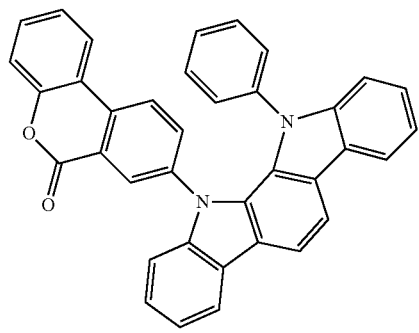
Formula 220
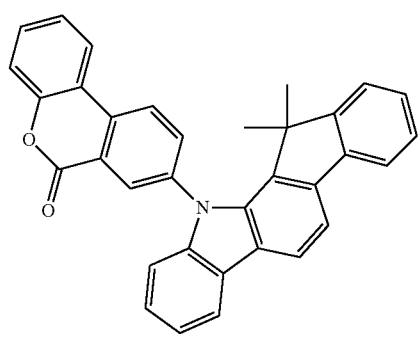
Formula 221
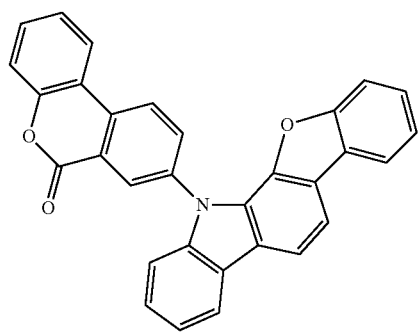
Formula 222
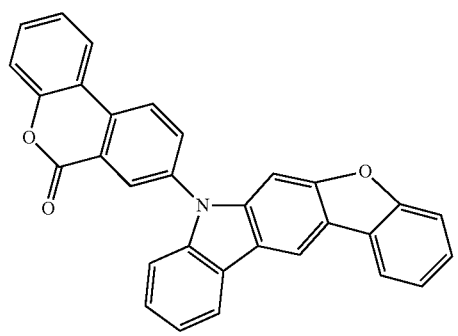

Formula 223
Formula 224
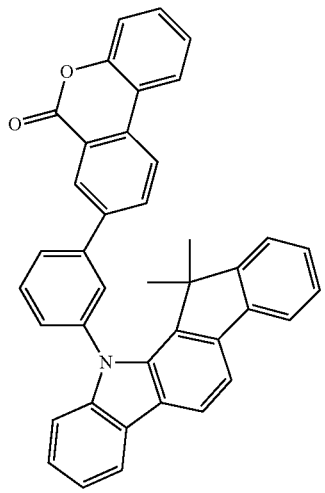
Formula 225
Formula 226
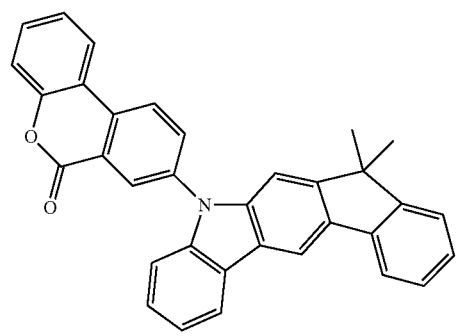
Formula 227
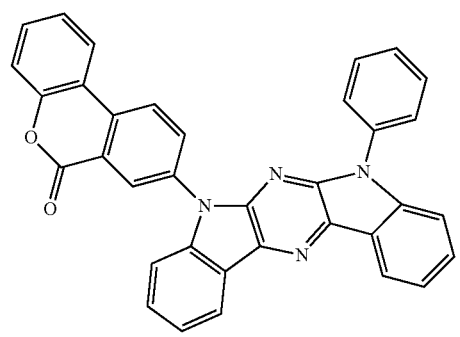
Formula 228
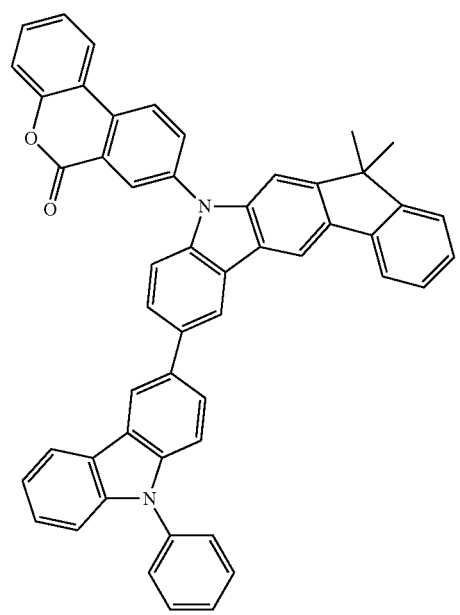

Formula 229
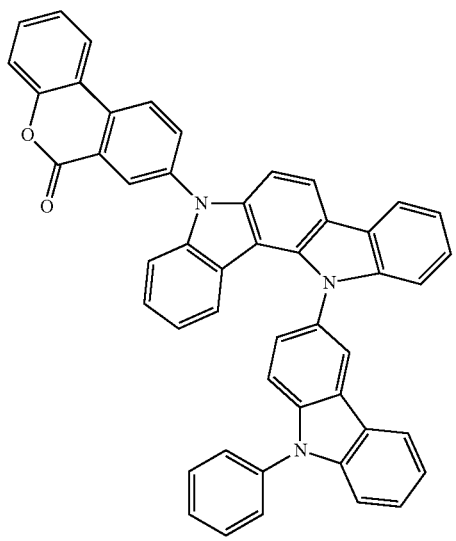
Formula 230
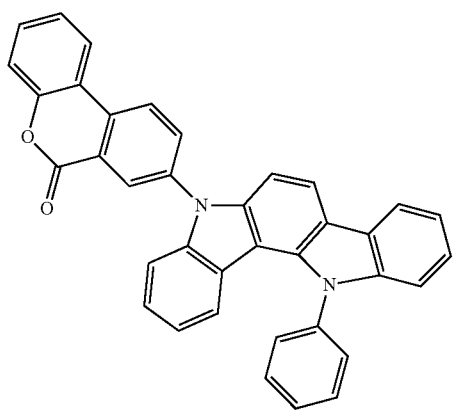
Formula 231
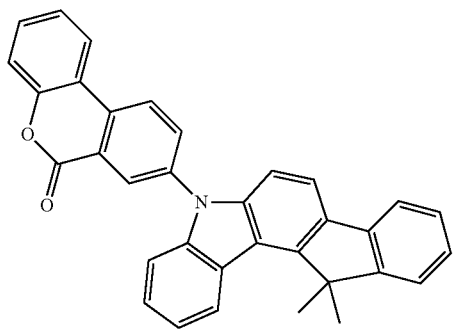
Formula 232
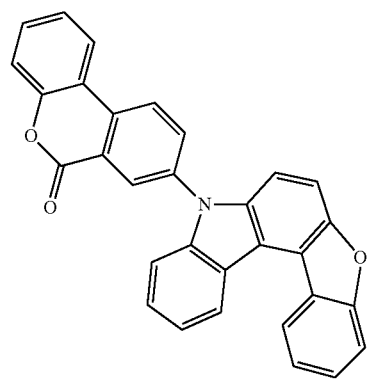
Formula 233
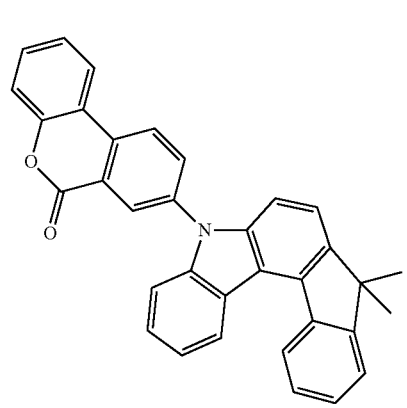
Formula 234
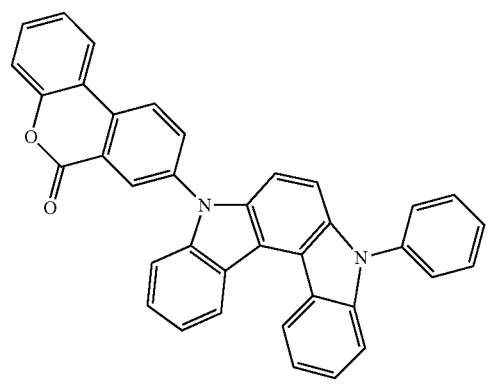
Formula 235
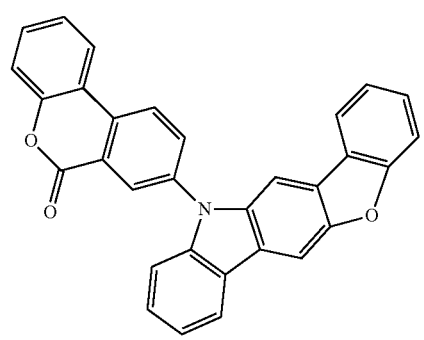

Formula 236
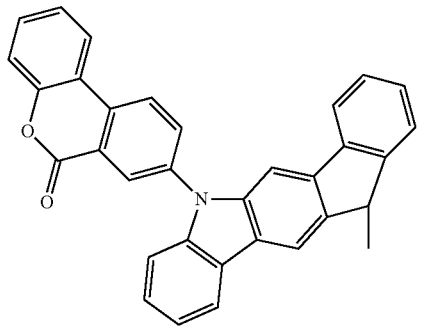
Formula 237
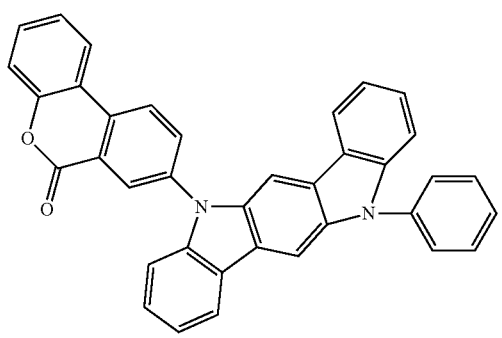
Formula 238
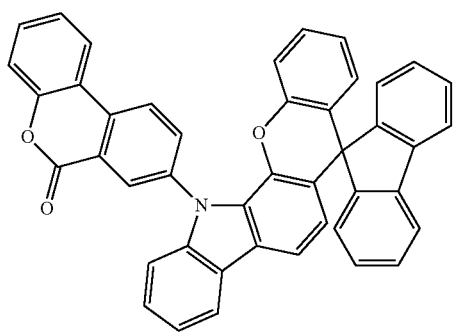
Formula 239
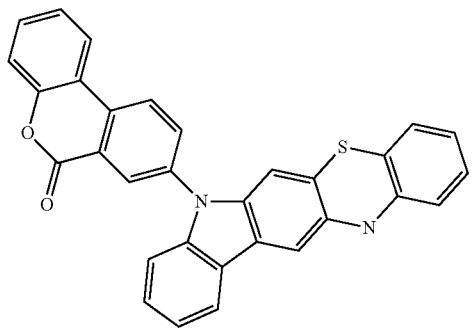
Formula 240
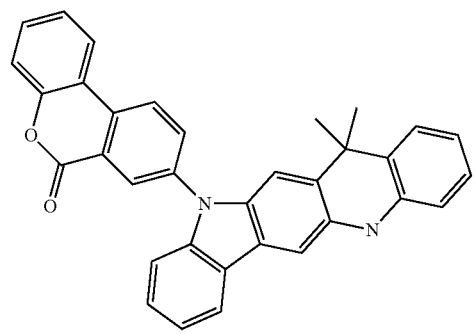
Formula 241
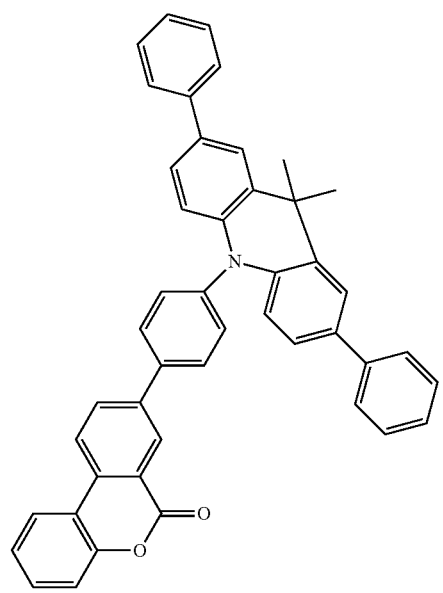
Formula 242
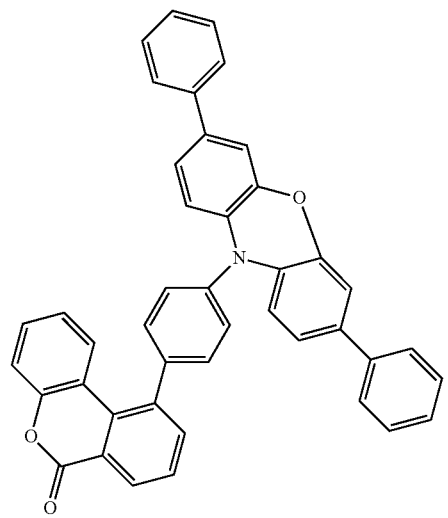

Formula 243

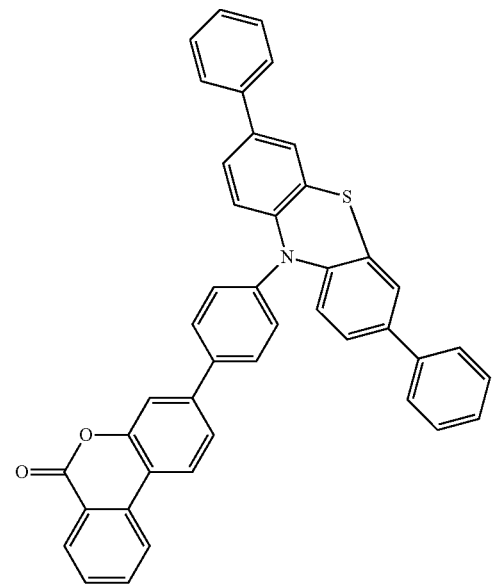

Formula 244

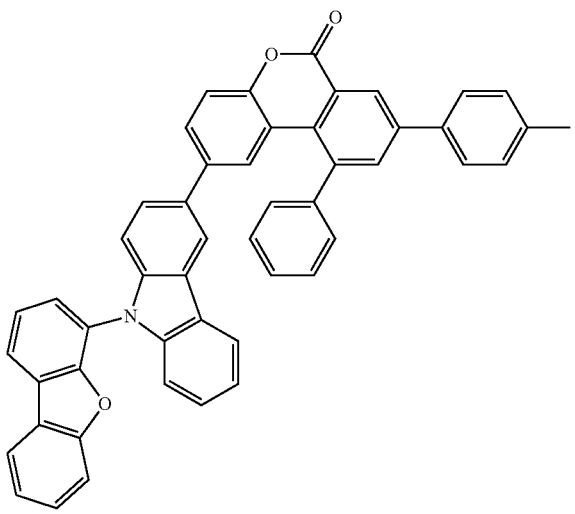

Formula 245

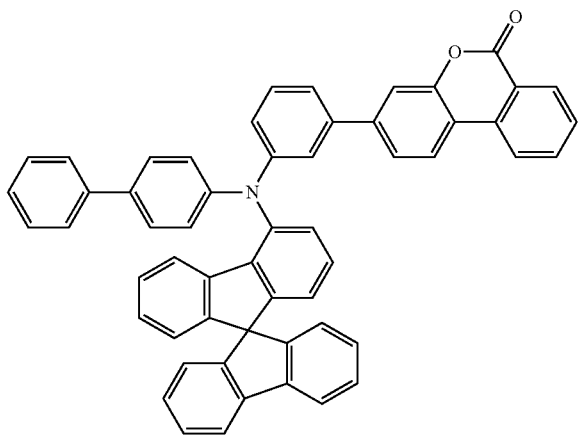

Formula 246

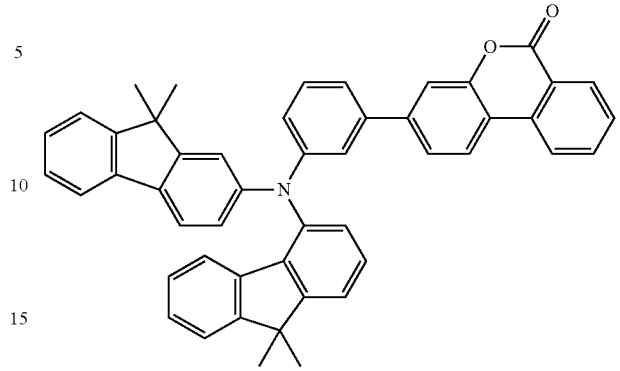

Formula 247

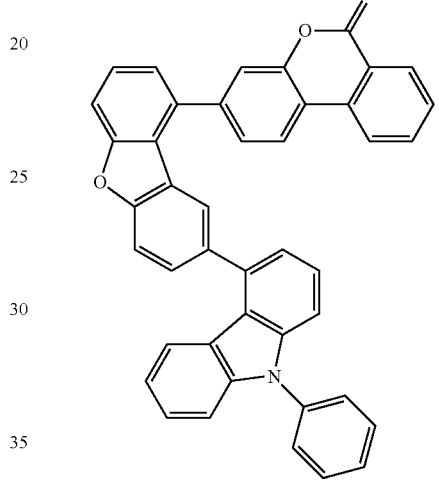

Preferred embodiments of compounds of the invention are detailed specifically in the examples, these compounds being usable alone or in combination with further compounds for all purposes of the invention.

Provided that the conditions specified in claim 1 are complied with, the abovementioned preferred embodiments can be combined with one another as desired. In a particularly preferred embodiment of the invention, the abovementioned preferred embodiments apply simultaneously.

The compounds of the invention are preparable in principle by various processes. However, the processes described hereinafter have been found to be particularly suitable.

The present invention therefore further provides a process for preparing the compounds comprising structures of formula (I), in which a coumarin compound is joined to an aryl and/or heteroaryl group via a coupling reaction.

The coumarin compound, which preferably comprises at least one benzo[c]coumarin structural element, can be effected, inter alia, by oxidation from a corresponding dibenzofuran compound or by a ring closure reaction, for example by the reaction of an aromatic carboxylic acid compound, for example a benzoic acid compound, with a phenol compound. The necessary conditions for this are known to those skilled in the art, and the specific details given in the examples will support the person skilled in the art in conducting these reactions.

Particularly suitable and preferred coupling reactions which all lead to C—C bond formation and/or C—N bond formation are those according to BUCHWALD, SUZUKI, YAMAMOTO, STILLE, HECK, NEGISHI, SONOGASHIRA and HIYAMA. These reactions are widely known, and the examples will provide the person skilled in the art with further pointers.

In all the synthesis schemes which follow, the compounds are shown with a small number of substituents to simplify the structures. This does not rule out the presence of any desired further substituents in the processes.

An illustrative implementation is given by the schemes which follow, without any intention that these should impose a restriction. The component steps of the individual schemes may be combined with one another as desired.

For example, according to scheme 1, proceeding from a dibenzofuran compound, it is possible, for example, to prepare a benzo[c]coumarin compound by an oxidation, in which case the oxidation can be effected, for example, by sodium percarbonate. Alternatively, proceeding from a reactive bromobenzoic acid, it is possible to obtain a reactive benzo[c]coumarin compound by a ring closure reaction with a phenylboronic acid compound. Proceeding from this reactive benzo[c]coumarin compound, it is possible to attach a carbazole structure, for example, via a Buchwald coupling. In addition, it is possible, for example, to join an aryl group onto the benzo[c]coumarin compound via a Suzuki reaction.

Scheme 1

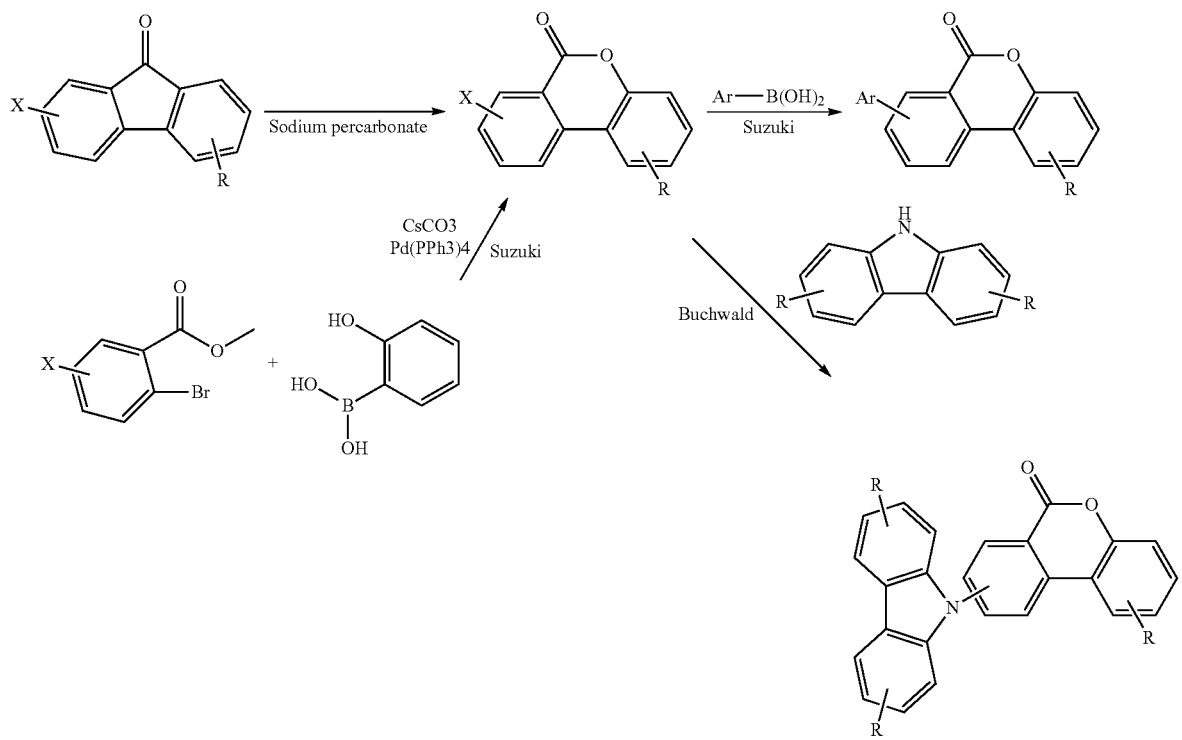

X=halogen or triflate, where the triflate can also be obtained in an intermediate reaction from an ether or a hydroxyl group, as will be elucidated in detail in the examples.

In reactions according to scheme 2, proceeding from corresponding dibromide, the synthesis of disubstituted derivatives is shown.

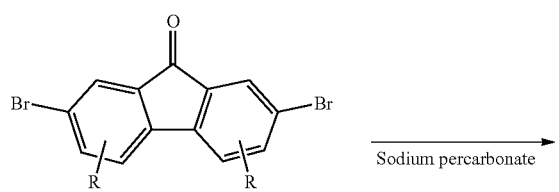

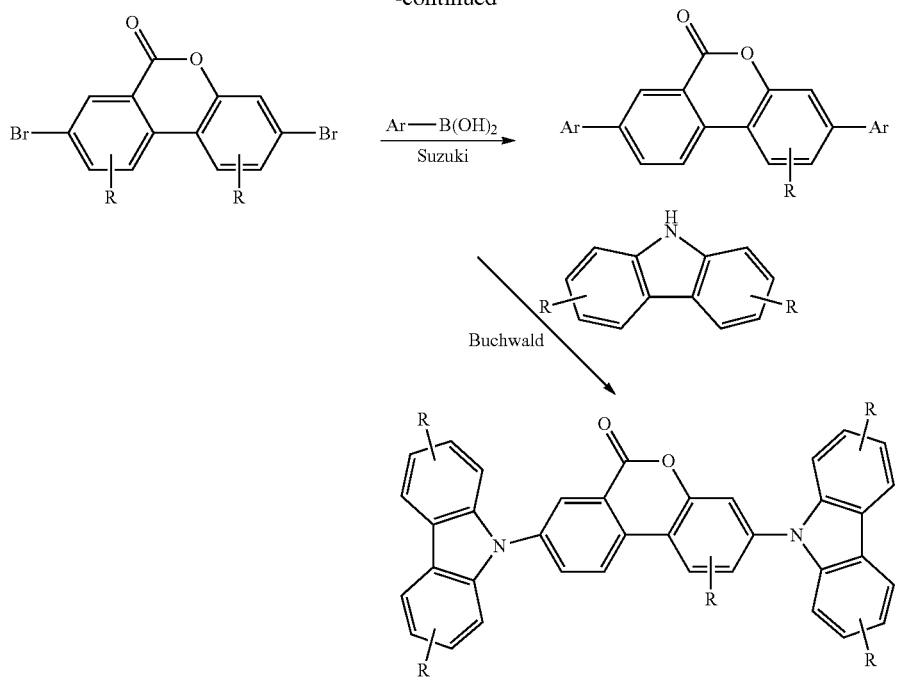

According to scheme 3, two or more identical or different substituents can be joined stepwise to a benzo[c]coumarin compound having groups of correspondingly different reactivity. Compounds having hydroxyl and/or ether groups can preferably be used for this purpose. The position of the substitution can be fixed via the corresponding starting material.

Scheme 3

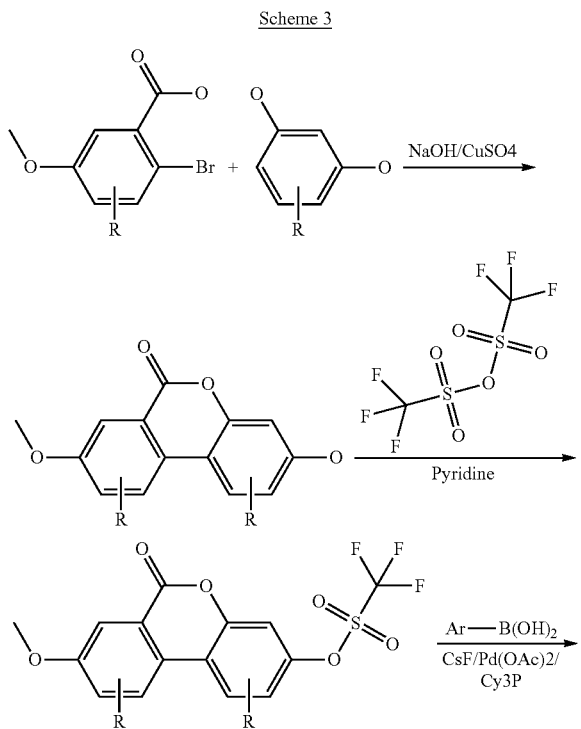

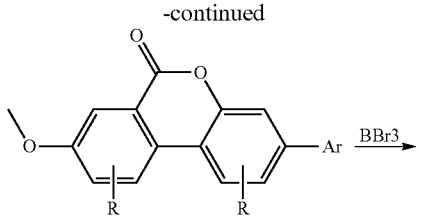

The processes shown for synthesis of the compounds of the invention should be understood by way of example. The person skilled in the art will be able to develop alternative synthesis routes within the scope of his common knowledge in the art.

The principles of the preparation processes detailed above are known in principle from the literature for similar compounds and can be adapted easily by the person skilled in the art for preparation of the compounds of the invention. Further information can be found in the examples.

It is possible by these processes, if necessary followed by purification, for example recrystallization or sublimation, to obtain the compounds of the invention comprising structures of formula (I) in high purity, preferably more than 99% (determined by means of $^1$H NMR and/or HPLC).

The compounds of the invention may also have suitable substituents, for example by relatively long alkyl groups (about 4 to 20 carbon atoms), especially branched alkyl groups, or optionally substituted aryl groups, for example xylyl, mesityl or branched terphenyl or quaterphenyl groups, which bring about solubility in standard organic solvents, for example toluene or xylene, at room temperature in a sufficient concentration soluble, in order to be able to process the complexes from solution. These soluble compounds are of particularly good suitability for processing from solution, for example by printing methods. In addition, it should be emphasized that the compounds of the invention comprising at least one structure of the formula (I) already have enhanced solubility in these solvents.

The compounds of the invention may also be mixed with a polymer. It is likewise possible to incorporate these compounds covalently into a polymer. This is especially possible with compounds substituted by reactive leaving groups such as bromine, iodine, chlorine, boronic acid or boronic ester, or by reactive polymerizable groups such as olefins or oxetanes. These may find use as monomers for production of corresponding oligomers, dendrimers or polymers. The oligomerization or polymerization is preferably effected via the halogen functionality or the boronic acid functionality or via the polymerizable group. It is additionally possible to crosslink the polymers via groups of this kind. The compounds of the invention and polymers may be used in the form of a crosslinked or uncrosslinked layer.

The invention therefore further provides oligomers, polymers or dendrimers containing one or more of the above-detailed structures of the formula (I) or compounds of the invention, wherein one or more bonds of the compounds of the invention or of the structures of the formula (I) to the polymer, oligomer or dendrimer are present. According to the linkage of the structures of the formula (I) or of the compounds, these therefore form a side chain of the oligomer or polymer or are bonded within the main chain. The polymers, oligomers or dendrimers may be conjugated, partly conjugated or nonconjugated. The oligomers or polymers may be linear, branched or dendritic. For the repeat units of the compounds of the invention in oligomers, dendrimers and polymers, the same preferences apply as described above.

For preparation of the oligomers or polymers, the monomers of the invention are homopolymerized or copolymerized with further monomers. Preference is given to copolymers wherein the units of formula (I) or the above-recited preferred embodiments are present to an extent of 0.01 to 99.9 mol %, preferably 5 to 90 mol %, more preferably 20 to 80 mol %. Suitable and preferred comonomers which form the polymer base skeleton are chosen from fluorenes (for example according to EP 842208 or WO 2000/022026), spirobifluorenes (for example according to EP 707020, EP 894107 or WO 2006/061181), paraphenylenes (for example according to WO 92/18552), carbazoles (for example according to WO 2004/070772 or WO 2004/113468), thiophenes (for example according to EP 1028136), dihydrophenanthrenes (for example according to WO 2005/014689), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers may contain still further units, for example hole transport units, especially those based on triarylamines, and/or electron transport units.

In addition, the present compounds may have a relatively low molecular weight. The present invention accordingly further provides a compound comprising one or more structures of the formula (I) and having a molecular weight of preferably not more than 10 000 g/mol, more preferably not more than 5000 g/mol, particularly preferably not more than 4000 g/mol, especially preferably not more than 3000 g/mol, specifically preferably not more than 2000 g/mol and most preferably not more than 1000 g/mol.

In addition, it is a feature of preferred compounds of the invention that they are sublimable. These compounds generally have a molar mass of less than about 1200 g/mol.

Additionally of particular interest are compounds of the invention which feature a high glass transition temperature. In this connection, preference is given especially to compounds of the invention comprising structures of the general formula (I) having a glass transition temperature of at least 70° C., more preferably of at least 110° C., even more preferably of at least 125° C. and especially preferably of at least 150° C., determined in accordance with DIN 51005.

The present invention still further provides a formulation comprising a compound of the invention or an oligomer, polymer or dendrimer of the invention and at least one further compound. The further compound may preferably be a solvent. The further compound may alternatively be a further organic or inorganic compound which is likewise used in the electronic device, for example a matrix material. This further compound may also be polymeric.

Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The present invention still further provides a composition comprising a compound of the invention and at least one further organic functional material. Functional materials are generally the organic or inorganic materials introduced between the anode and cathode. Preferably, the organic functional material is selected from the group consisting of fluorescent emitters, phosphorescent emitters, host materials, matrix materials, electron transport materials, electron injection materials, hole conductor materials, hole injection materials, n-dopants, wide band gap materials, electron blocker materials and hole blocker materials.

The present invention therefore also relates to a composition comprising at least one compound comprising structures of formula (I) and at least one further matrix material. According to a particular aspect of the present invention, the further matrix material has hole-transporting properties.

The present invention further provides a composition comprising at least one compound comprising at least one structure of formula (I) and at least one wide band gap material, a wide band gap material being understood to mean a material in the sense of the disclosure of U.S. Pat. No. 7,294,849. These systems exhibit particularly advantageous performance data in electroluminescent devices.

Preferably, the additional compound may have a band gap of 2.5 eV or more, preferably 3.0 eV or more, very preferably of 3.5 eV or more. One way of calculating the band gap is via the energy levels of the highest occupied molecular orbital (HOMO) and the lowest unoccupied molecular orbital (LUMO).

Molecular orbitals, especially also the highest occupied molecular orbital (HOMO) and the lowest unoccupied molecular orbital (LUMO), the energy levels thereof and the energy of the lowest triplet state $T_1$ and that of the lowest excited singlet state Si of the materials are determined via quantum-chemical calculations. For calculation of organic substances without metals, an optimization of geometry is first conducted by the "Ground State/Semi-empirical/Default Spin/AM1/Charge 0/Spin Singlet" method. Subsequently, an energy calculation is effected on the basis of the optimized geometry. This is done using the "TD-SCF/DFT/Default Spin/B3PW91" method with the "6-31G(d)" basis set (charge 0, spin singlet). For metal-containing compounds, the geometry is optimized via the "Ground State/Hartree-Fock/Default Spin/LanL2 MB/Charge 0/Spin Singlet" method. The energy calculation is effected analogously to the above-described method for the organic substances, except that the "LanL2DZ" basis set is used for the metal atom and the "6-31G(d)" basis set for the ligands. The HOMO energy level HEh or LUMO energy level LEh is obtained from the energy calculation in Hartree units. This is used to determine the HOMO and LUMO energy levels in electron volts, calibrated by cyclic voltammetry measurements, as follows:

HOMO(eV)=((*HEh*\*27.212)−0.9899)/1.1206

LUMO(eV)=((*LEh*\*27.212)−2.0041)/1.385

These values are to be regarded as HOMO and LUMO energy levels of the materials in the context of this application.

The lowest triplet state $T_1$ is defined as the energy of the triplet state having the lowest energy, which is apparent from the quantum-chemical calculation described.

The lowest excited singlet state $S_1$ is defined as the energy of the excited singlet state having the lowest energy, which is apparent from the quantum-chemical calculation described.

The method described herein is independent of the software package used and always gives the same results. Examples of frequently utilized programs for this purpose are "Gaussian09 W" (Gaussian Inc.) and Q-Chem 4.1 (Q-Chem, Inc.).

The present invention also relates to a composition comprising at least one compound comprising structures of formula (I) and at least one phosphorescent emitter, the term "phosphorescent emitter" also being understood to mean phosphorescent dopants.

The term "phosphorescent dopants" typically encompasses compounds where the emission of light is effected through a spin-forbidden transition, for example a transition from an excited triplet state or a state having a higher spin quantum number, for example a quintet state.

Suitable phosphorescent dopants are especially compounds which, when suitably excited, emit light, preferably in the visible region, and also contain at least one atom of atomic number greater than 20, preferably greater than 38, and less than 84, more preferably greater than 56 and less than 80. Preference is given to using, as phosphorescent dopants, compounds containing copper, molybdenum, tungsten, rhenium, ruthenium, osmium, rhodium, iridium, palladium, platinum, silver, gold or europium, especially compounds containing iridium, platinum or copper.

In the context of the present application, all luminescent iridium, platinum or copper complexes are considered to be phosphorescent compounds. Examples of phosphorescent dopants are adduced in a section which follows.

A dopant in a system comprising a matrix material and a dopant is understood to mean that component having the smaller proportion in the mixture. Correspondingly, a matrix material in a system comprising a matrix material and a dopant is understood to mean that component having the greater proportion in the mixture.

Preferred phosphorescent dopants for use in mixed matrix systems are the preferred phosphorescent dopants specified hereinafter.

Examples of phosphorescent dopants can be found in applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used for phosphorescent OLEDs according to the prior art and as known to those skilled in the art in the field of organic electroluminescent devices are suitable for use in the devices of the invention.

Explicit examples of phosphorescent dopants are adduced in the following table:

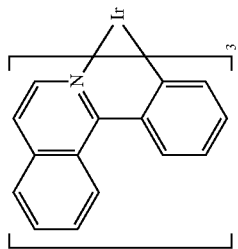
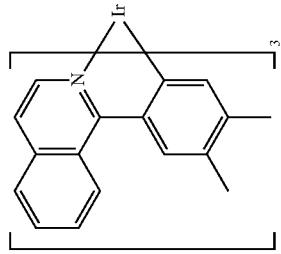
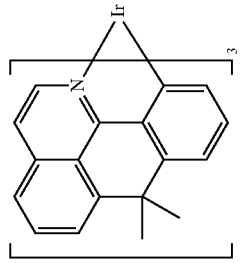
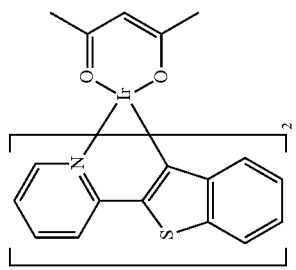
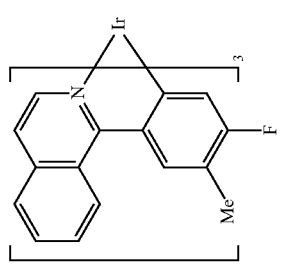
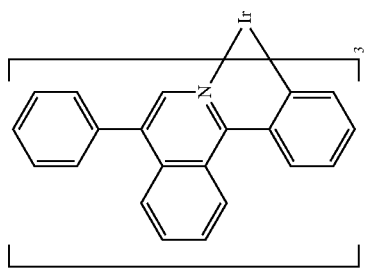
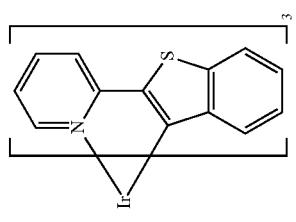
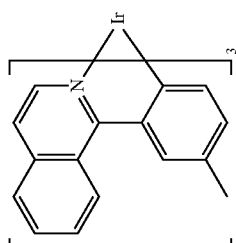
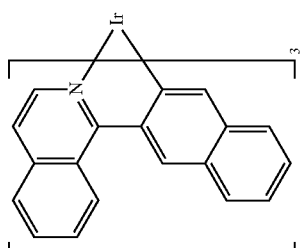

-continued
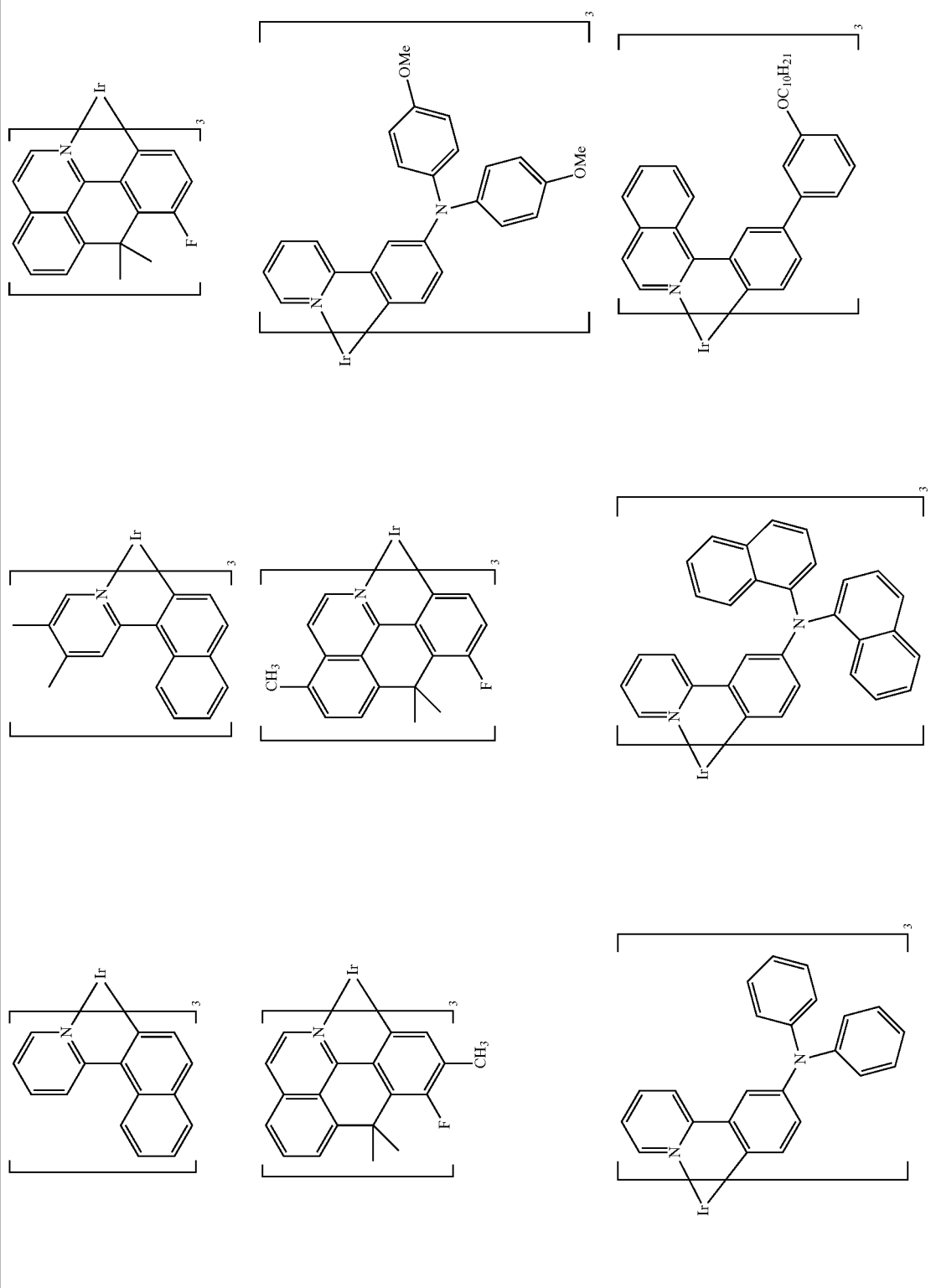

-continued
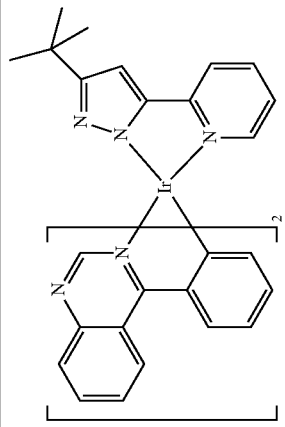 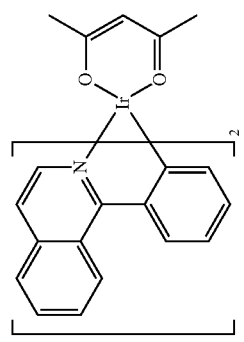 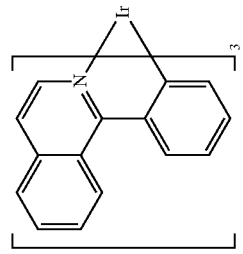
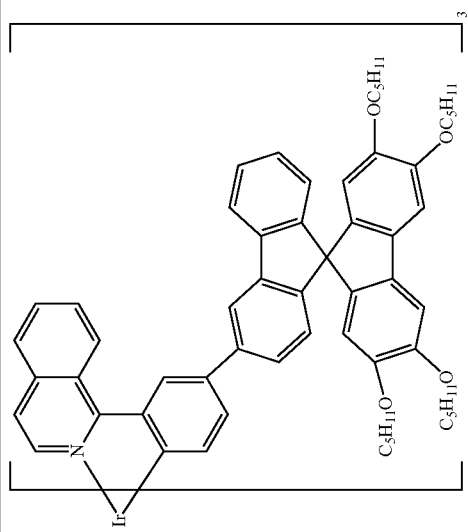 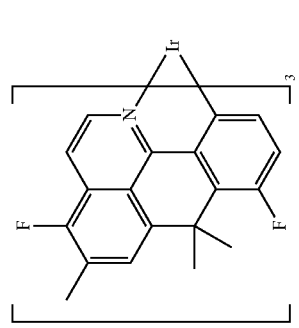 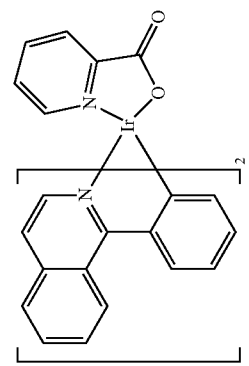
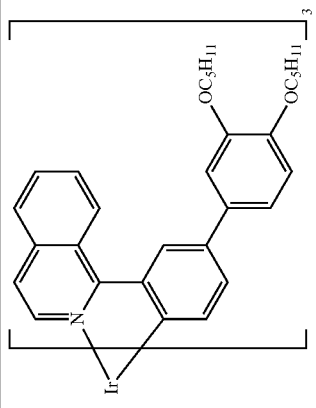 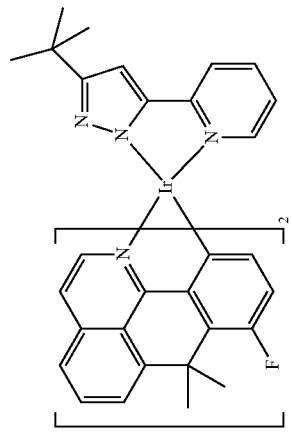 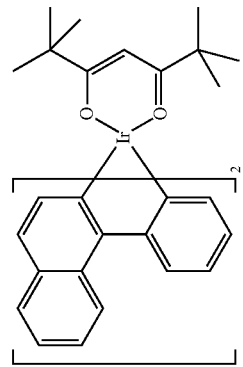

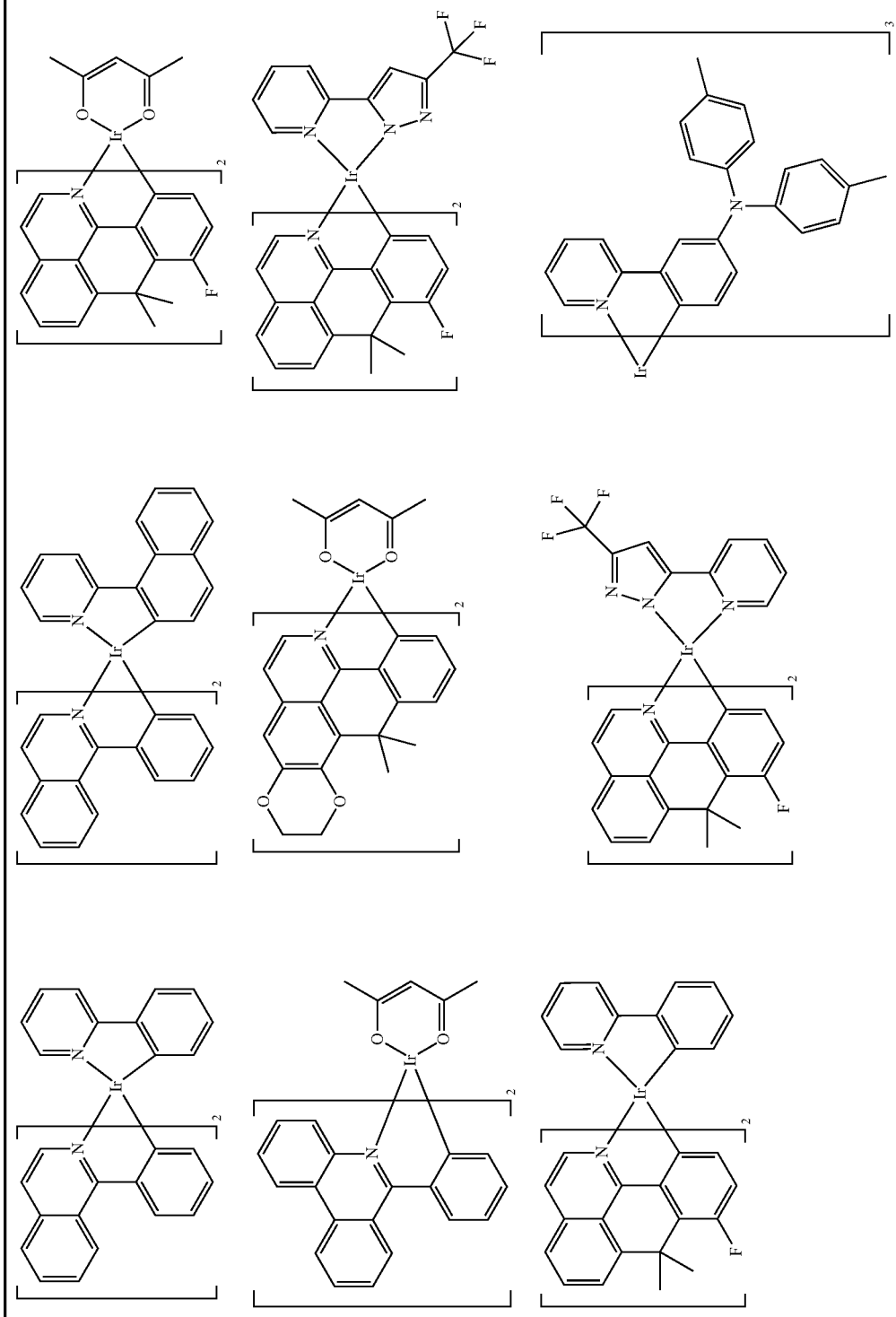

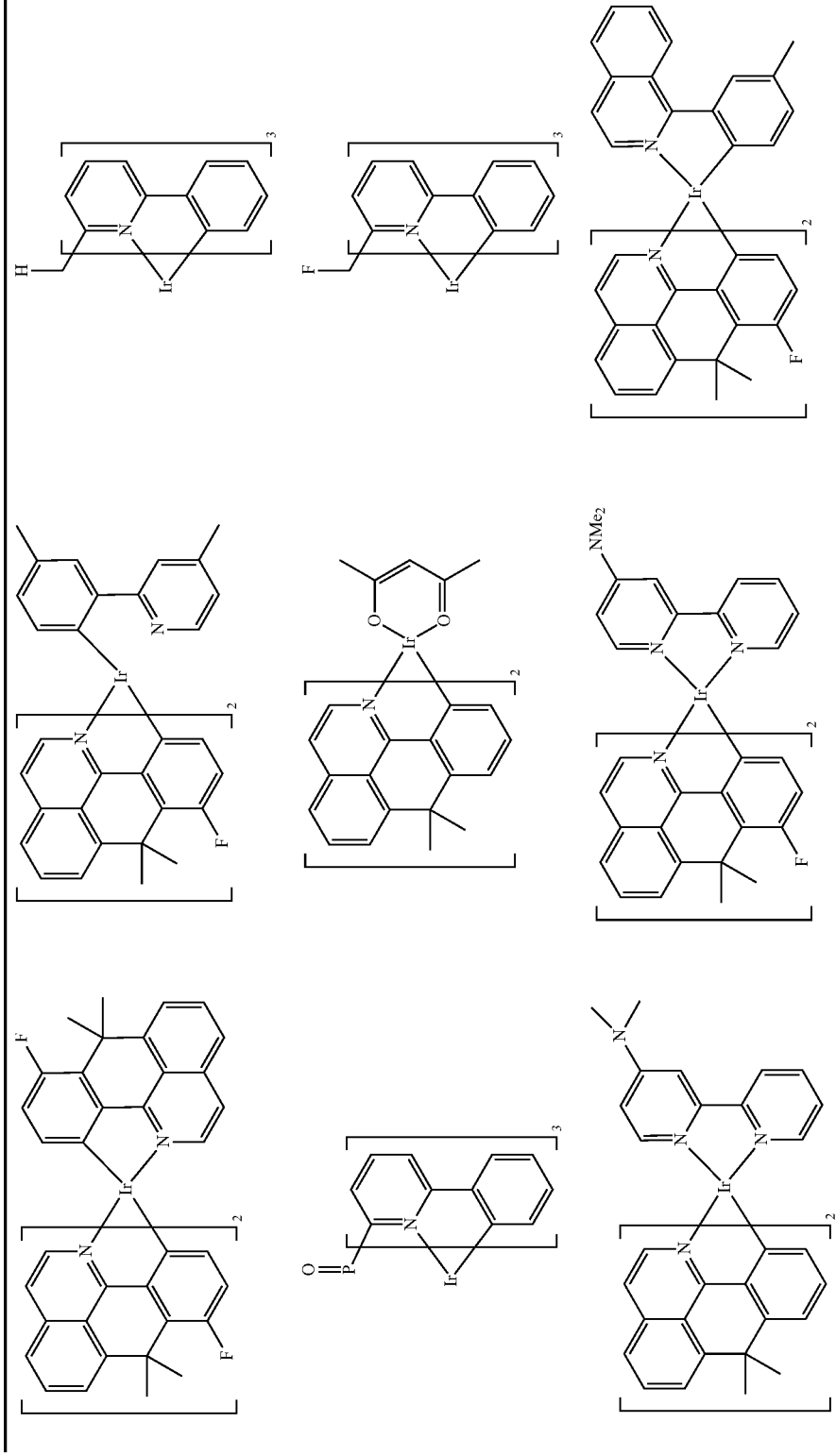

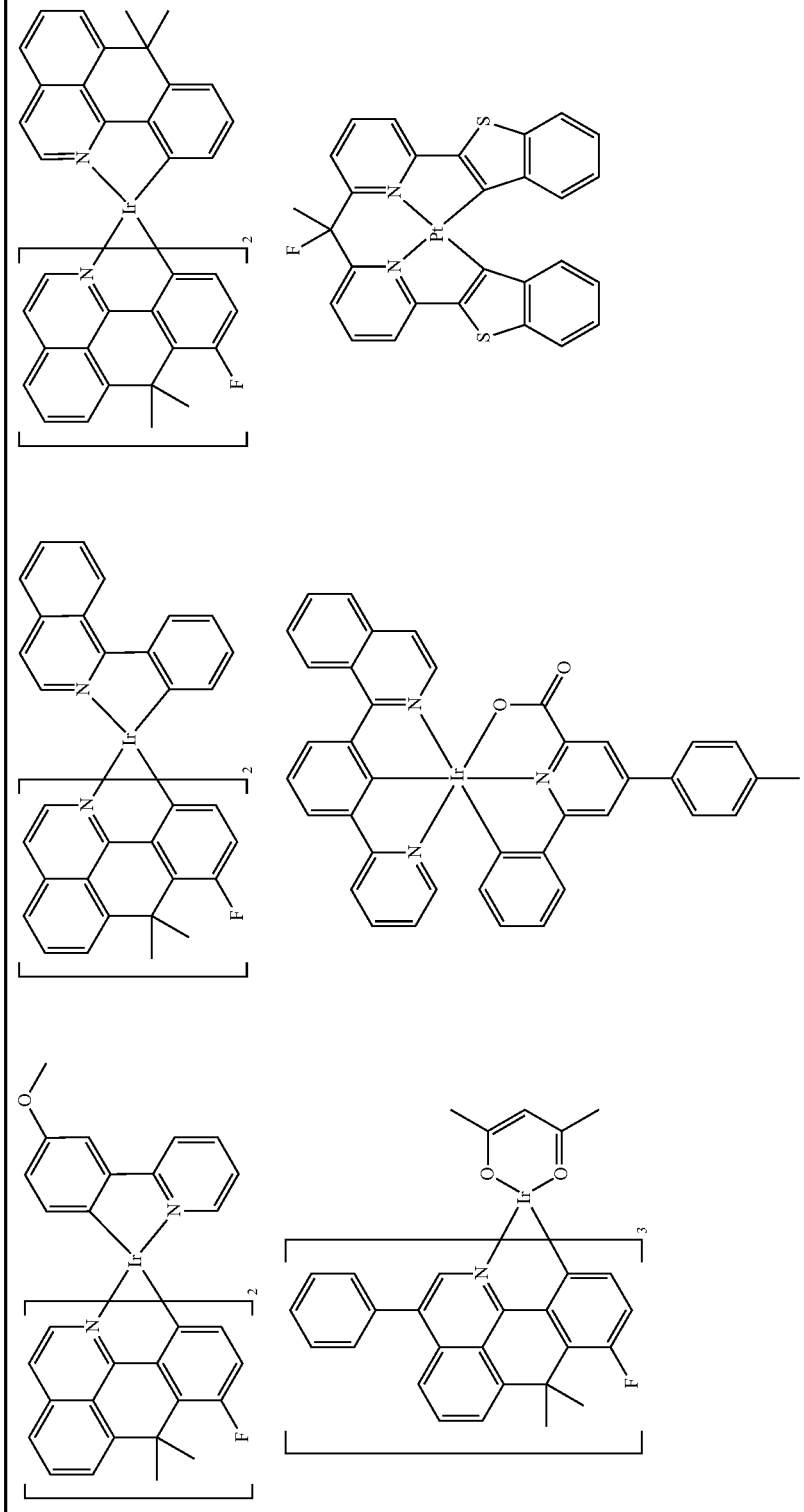

-continued
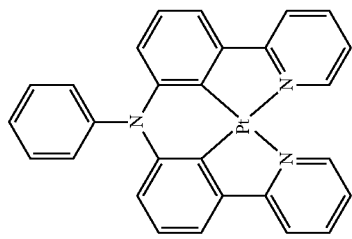
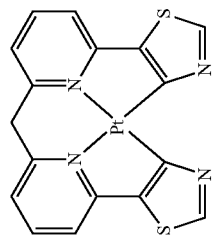
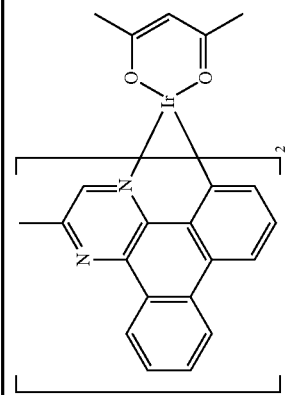
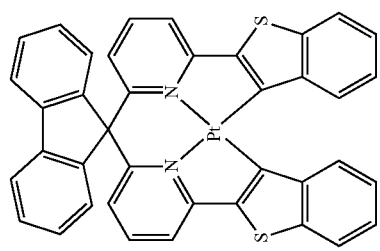
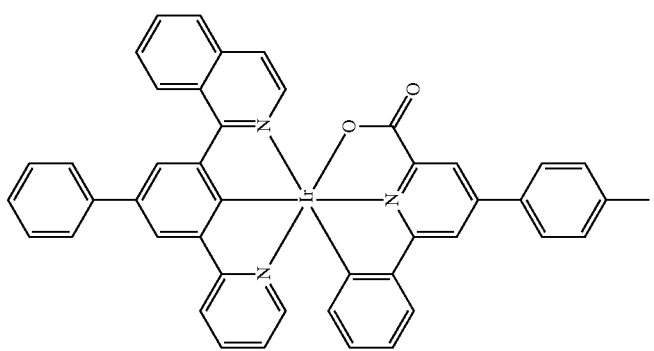
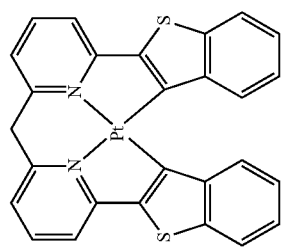

-continued
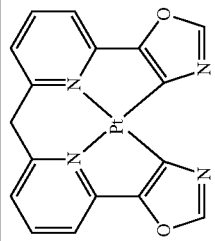 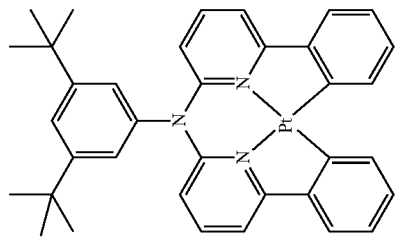
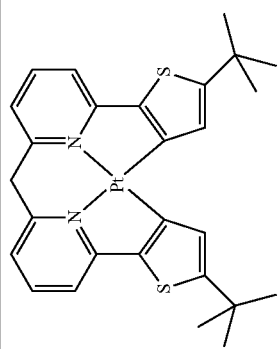 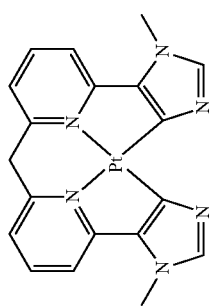
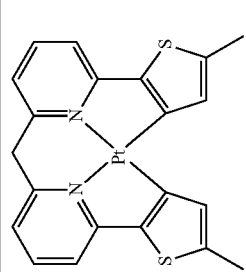 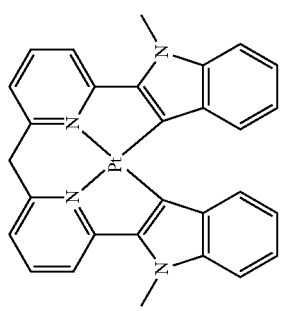

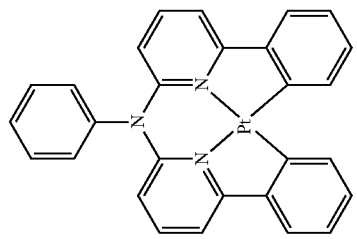
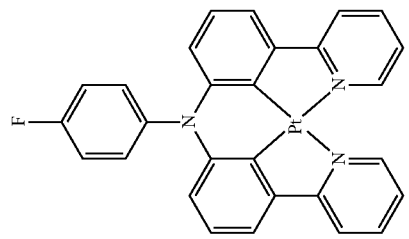
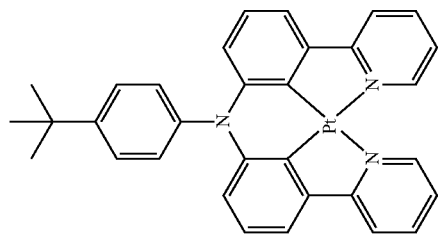
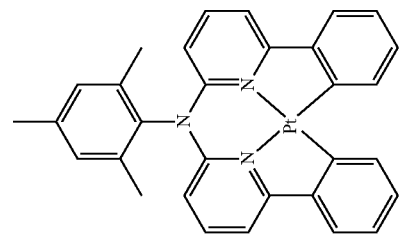
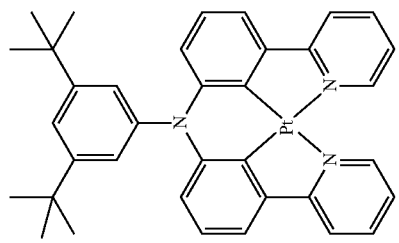
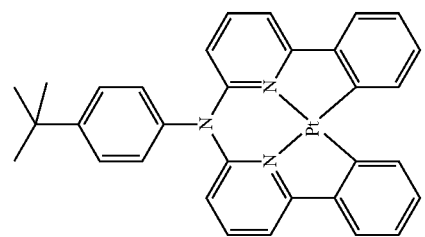

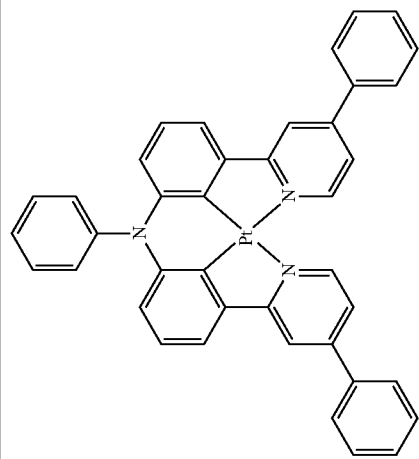
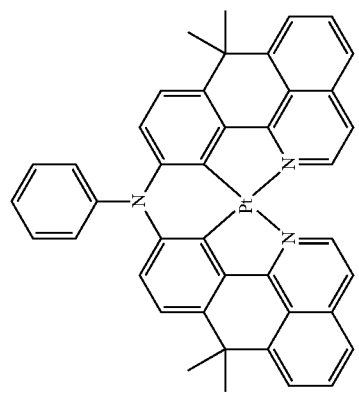
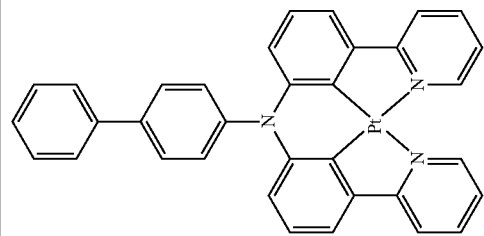
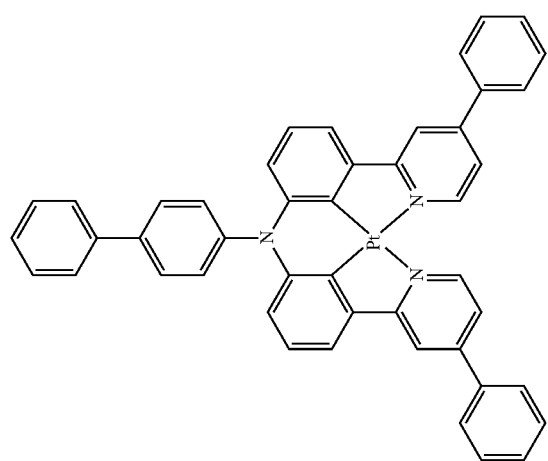
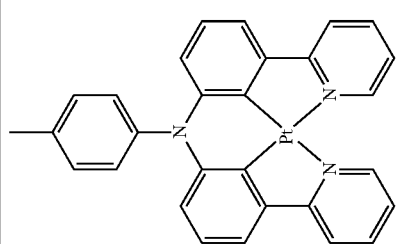
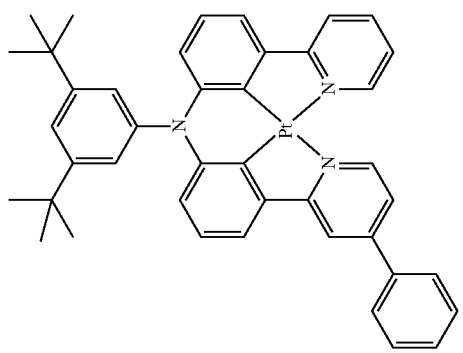

-continued
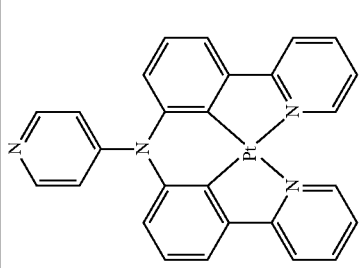 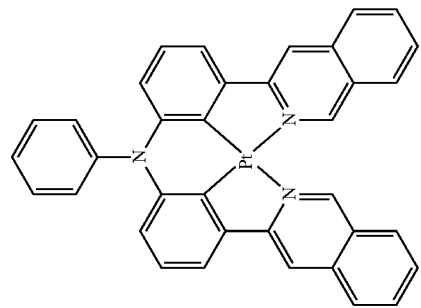
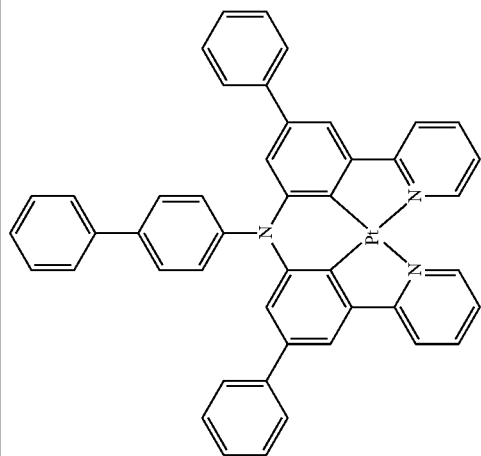 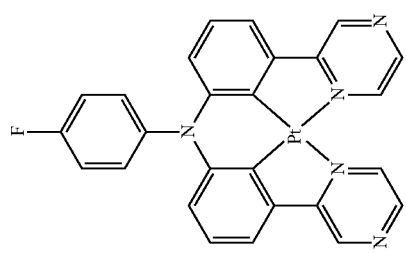
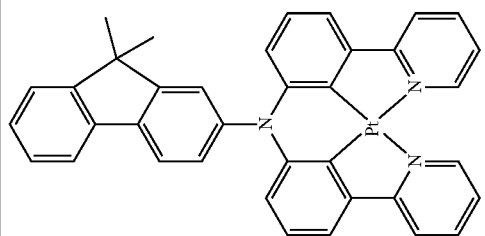 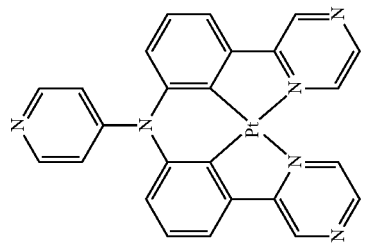

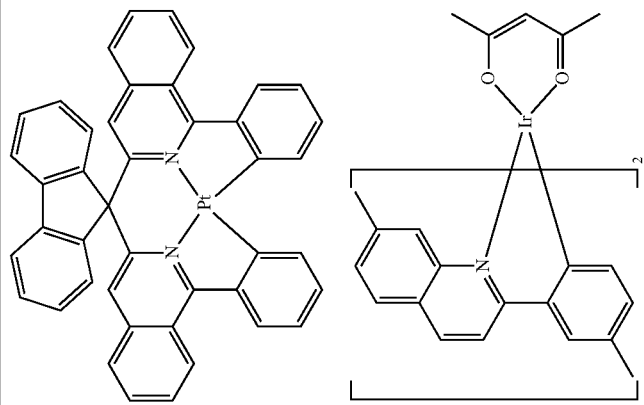
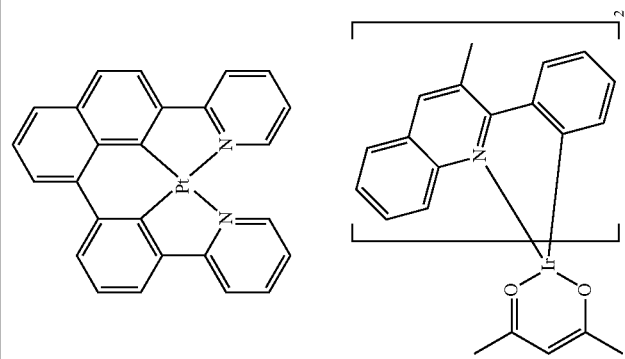
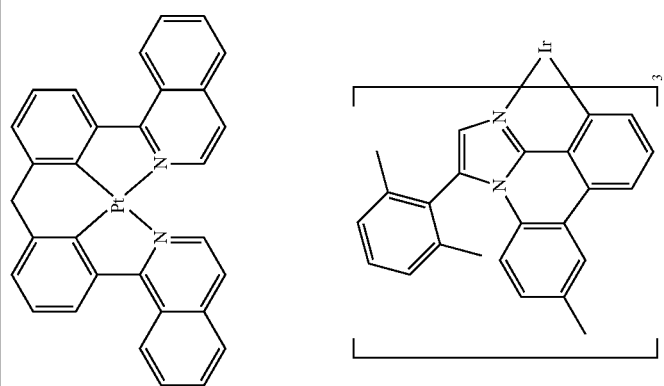

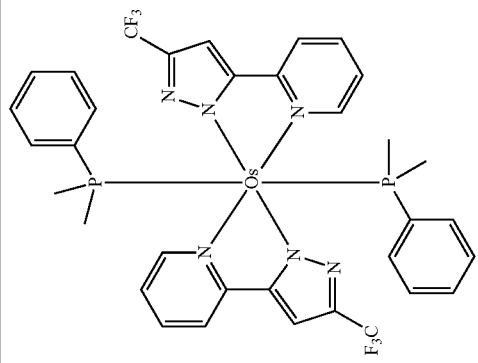 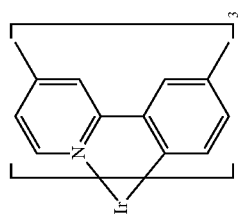 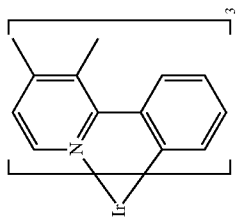
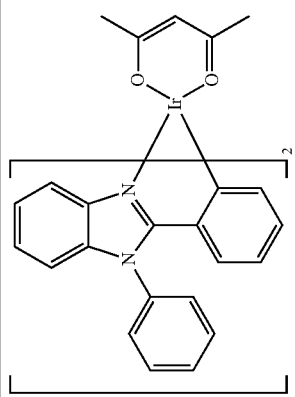 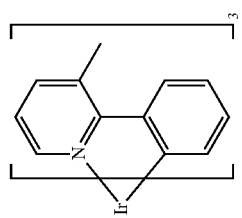 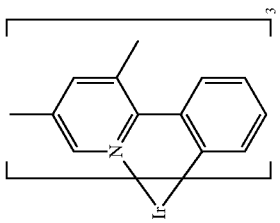
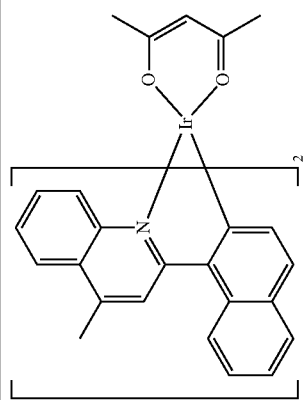 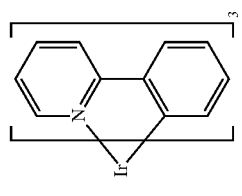 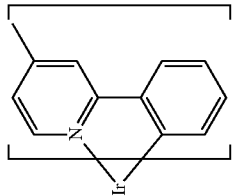

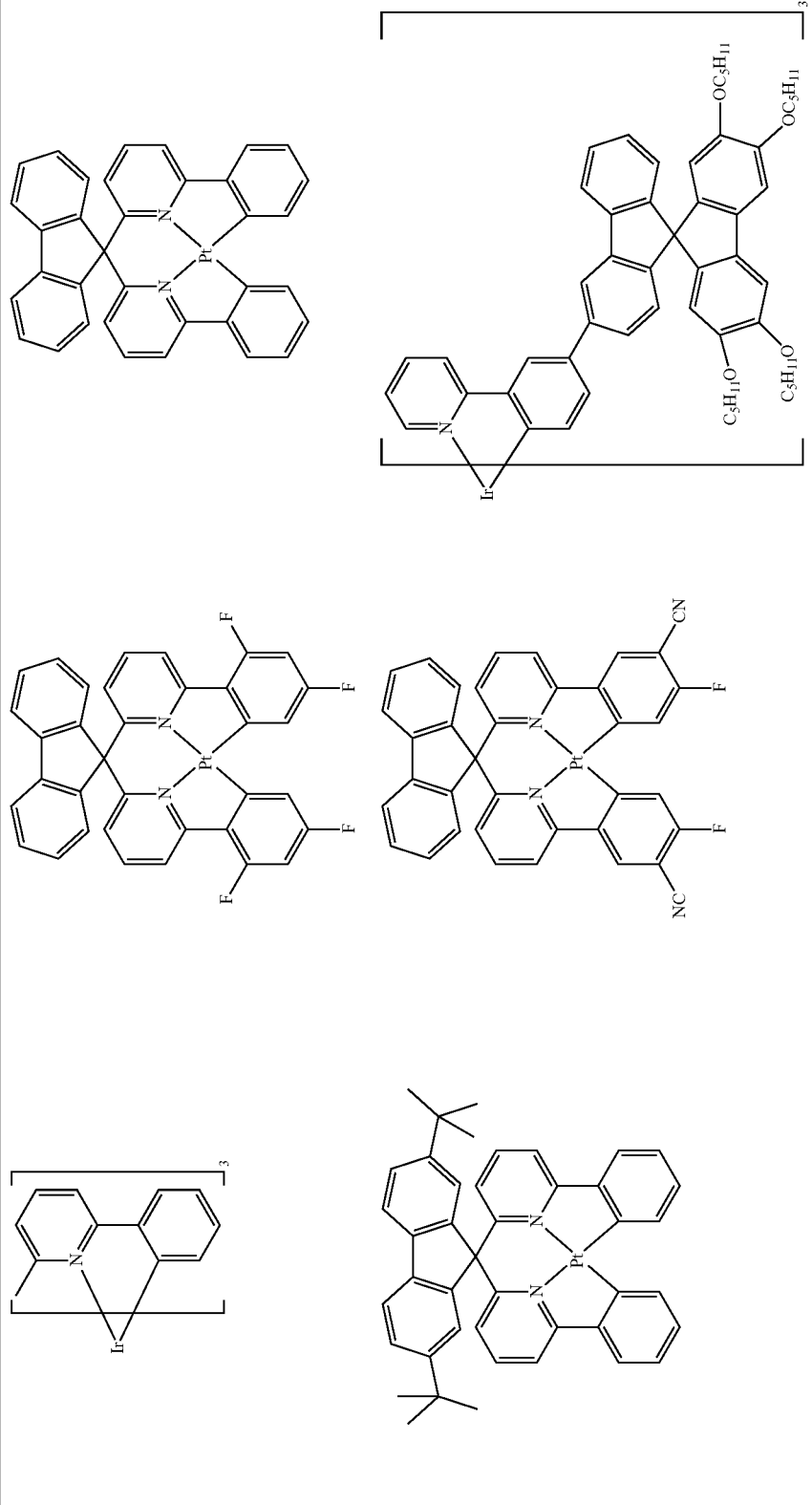

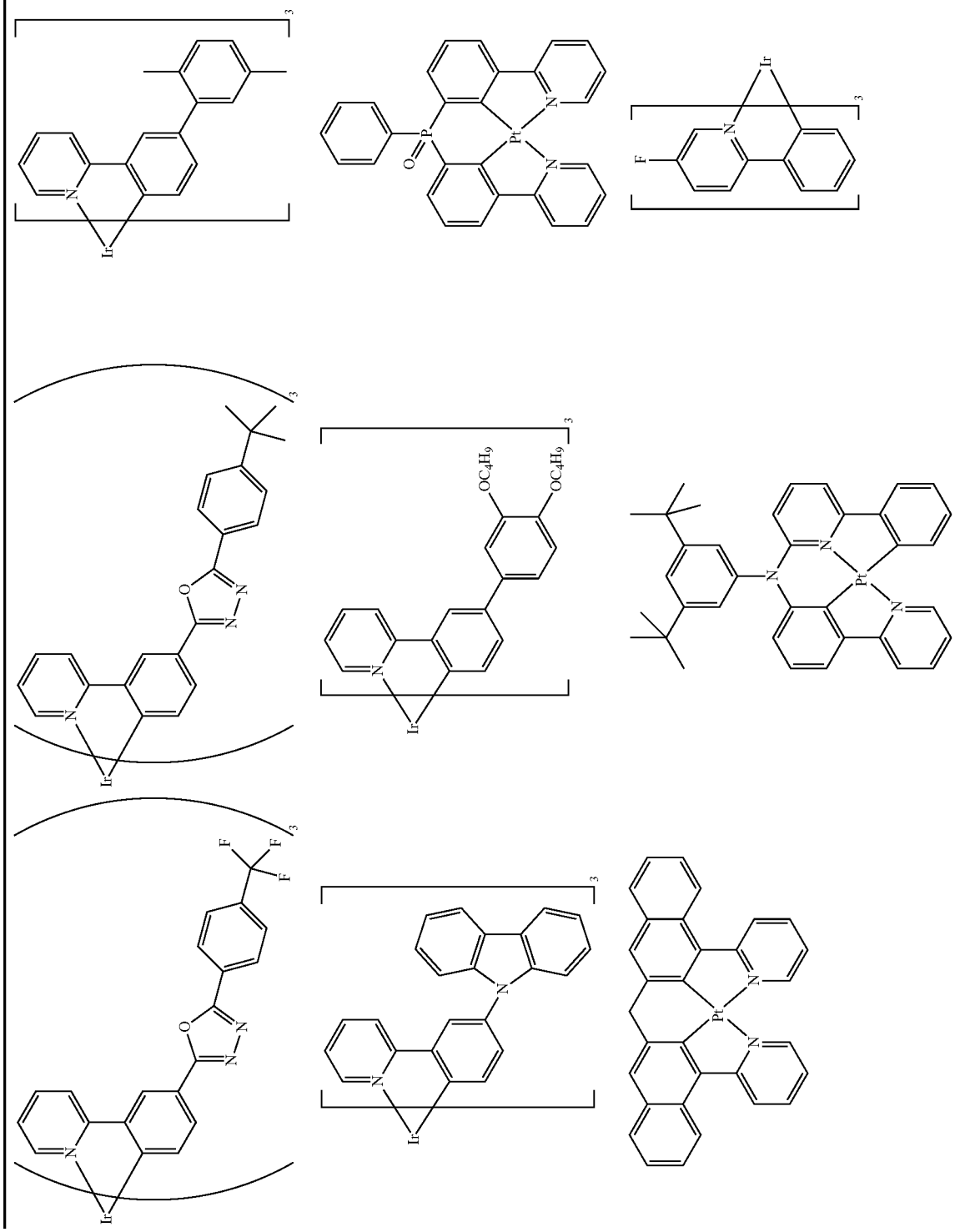

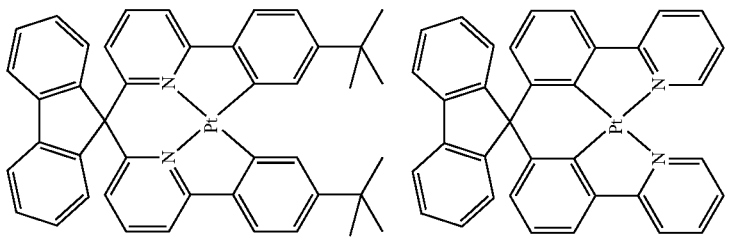
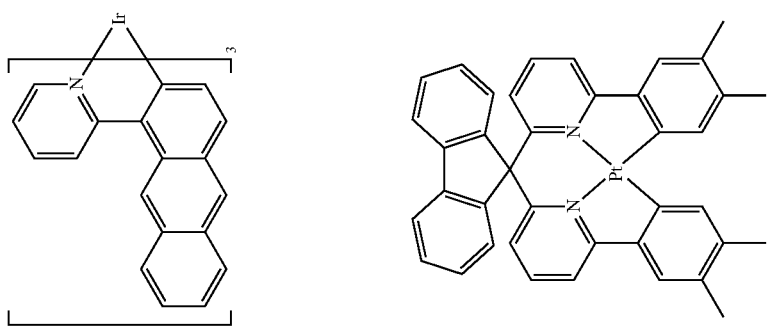
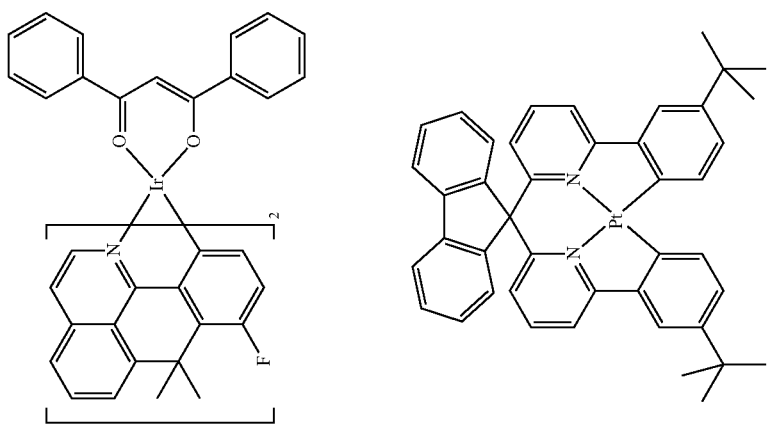

-continued
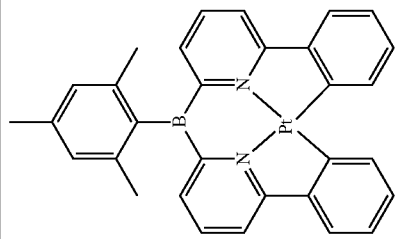 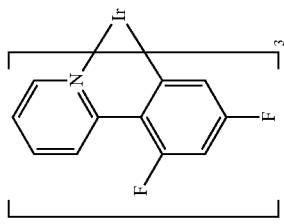
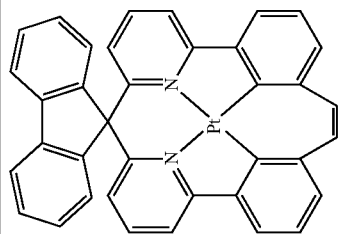 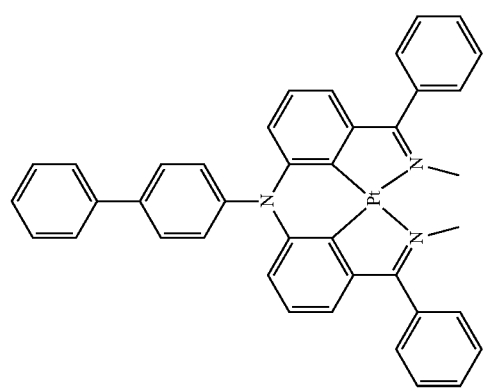
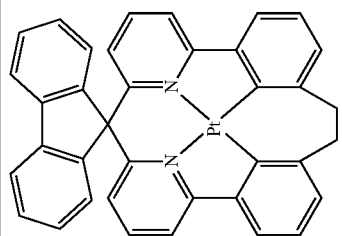 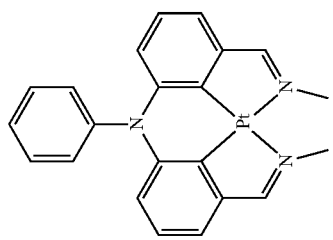

-continued
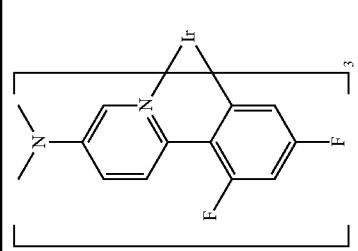 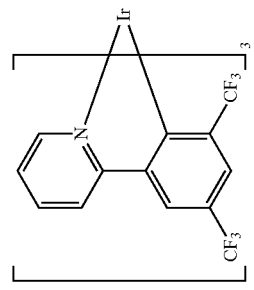 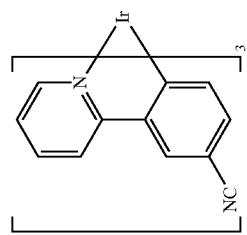
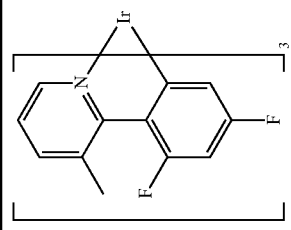 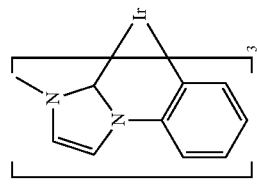 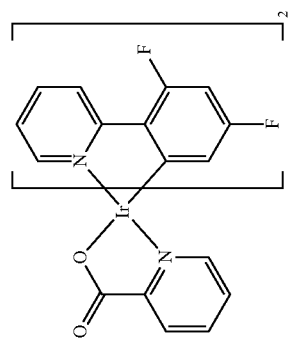
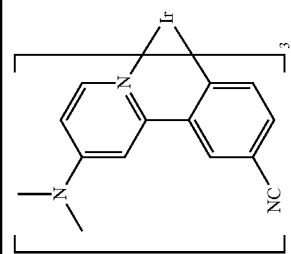 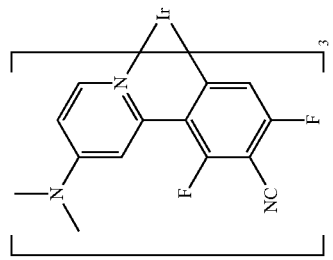 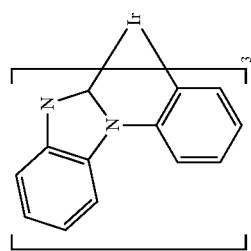

-continued
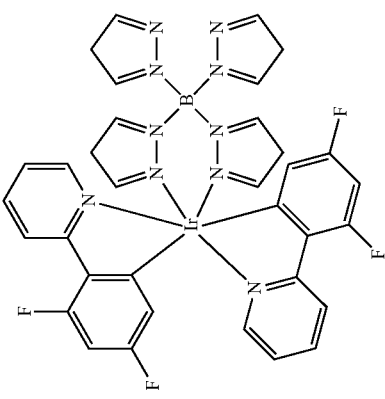
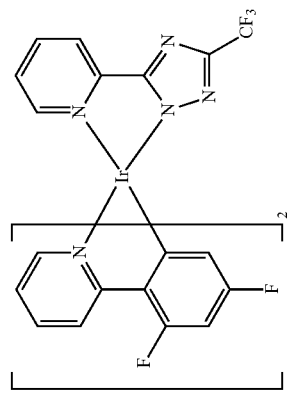
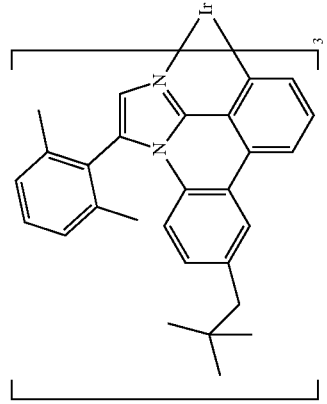
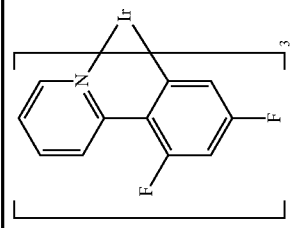
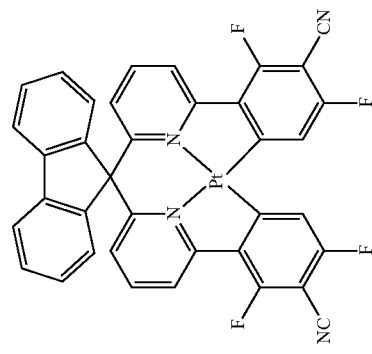
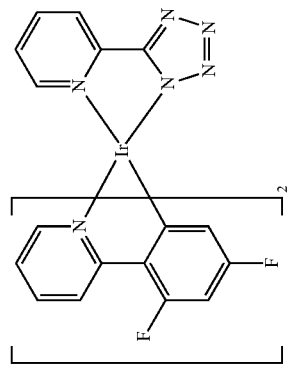
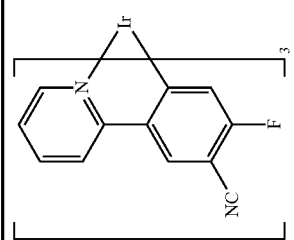
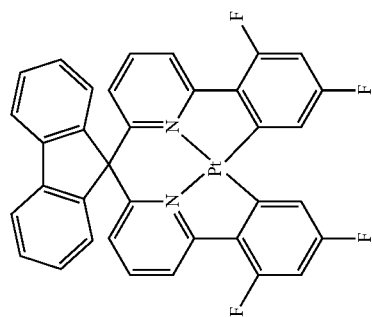
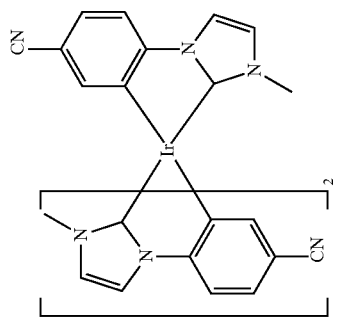

-continued
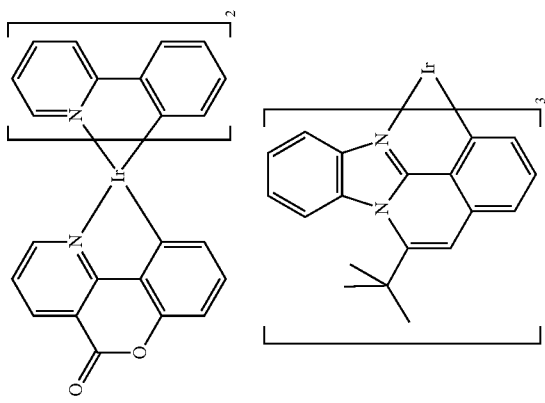
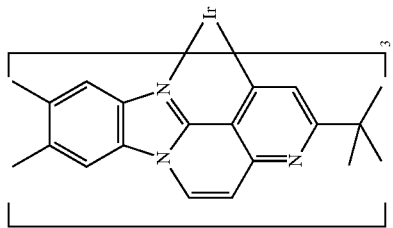
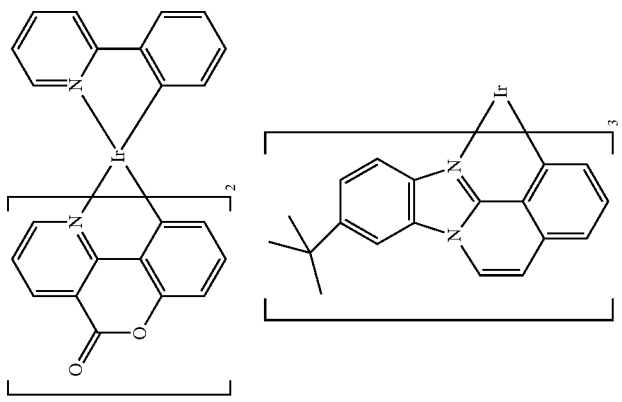
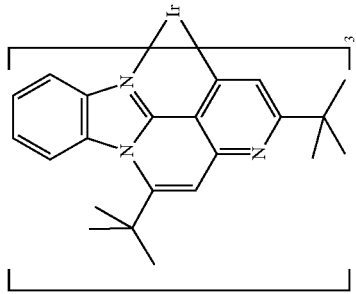
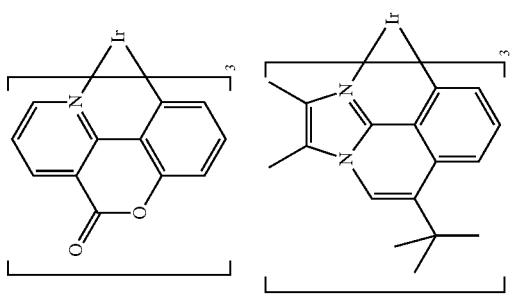
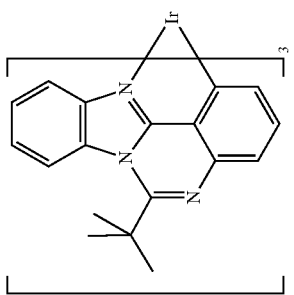

The above-described compound comprising structures of the formula (I) or the above-detailed preferred embodiments can preferably be used as active component in an electronic device. An electronic device is understood to mean any device comprising anode, cathode and at least one layer, said layer comprising at least one organic or organometallic compound. The electronic device of the invention thus comprises anode, cathode and at least one layer containing at least one compound comprising structures of the formula (I). Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), organic electrical sensors, light-emitting electrochemical cells (LECs) and organic laser diodes (O-lasers), containing at least one compound comprising structures of the formula (I) in at least one layer. Particular preference is given to organic electroluminescent devices. Active components are generally the organic or inorganic materials introduced between the anode and cathode, for example charge injection, charge transport or charge blocker materials, but especially emission materials and matrix materials.

A preferred embodiment of the invention is organic electroluminescent devices. The organic electroluminescent device comprises cathode, anode and at least one emitting layer. Apart from these layers, it may comprise still further layers, for example in each case one or more hole injection layers, hole transport layers, hole blocker layers, electron transport layers, electron injection layers, exciton blocker layers, electron blocker layers, charge generation layers and/or organic or inorganic p/n junctions. At the same time, it is possible that one or more hole transport layers are p-doped, for example with metal oxides such as $MoO_3$ or $WO_3$ or with (per)fluorinated electron-deficient aromatic systems, and/or that one or more electron transport layers are n-doped. It is likewise possible for interlayers to be introduced between two emitting layers, these having, for example, an exciton-blocking function and/or controlling the charge balance in the electroluminescent device. However, it should be pointed out that not necessarily every one of these layers need be present.

In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are three-layer systems where the three layers exhibit blue, green and orange or red emission (for the basic construction see, for example, WO 2005/011013), or systems having more than three emitting layers. The system may also be a hybrid system wherein one or more layers fluoresce and one or more other layers phosphoresce.

In a preferred embodiment of the invention, the organic electroluminescent device contains the compound of the invention comprising structures of formula (I) or the above-detailed preferred embodiments as matrix material, preferably as electron-conducting matrix material, in one or more emitting layers, preferably in combination with a further matrix material, preferably a hole-conducting matrix material. An emitting layer comprises at least one emitting compound.

The matrix material used may generally be any materials which are known for the purpose according to the prior art. The triplet level of the matrix material is preferably higher than the triplet level of the emitter.

Suitable matrix materials for the compounds of the invention are ketones, phosphine oxides, sulfoxides and sulfones, for example according to WO 2004/013080, WO 2004/093207, WO 2006/005627 or WO 2010/006680, triarylamines, carbazole derivatives, e.g. CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, indolocarbazole derivatives, for example according to WO 2007/063754 or WO 2008/056746, indenocarbazole derivatives, for example according to WO 2010/136109 or WO 2011/000455, azacarbazoles, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, diazasilole derivatives, for example according to WO 2010/054729, diazaphosphole derivatives, for example according to WO 2010/054730, triazine derivatives, for example according to WO 2010/015306, WO 2007/063754 or WO 2008/056746, zinc complexes, for example according to EP 652273 or WO 2009/062578, dibenzofuran derivatives, for example according to WO 2009/148015, or bridged carbazole derivatives, for example according to US 2009/0136779, WO 2010/050778, WO 2011/042107 or WO 2011/088877.

It may also be preferable to use a plurality of different matrix materials as a mixture, especially at least one electron-conducting matrix material and at least one hole-conducting matrix material. Preference is likewise given to the use of a mixture of a charge-transporting matrix material and an electrically inert matrix material having no significant involvement, if any, in the charge transport, as described, for example, in WO 2010/108579.

It is further preferable to use a mixture of two or more triplet emitters together with a matrix. In this case, the triplet emitter having the shorter-wave emission spectrum serves as co-matrix for the triplet emitter having the longer-wave emission spectrum.

More preferably, it is possible to use a compound of the invention comprising structures of formula (I), in a preferred embodiment, as matrix material in an emission layer of an organic electronic device, especially in an organic electroluminescent device, for example in an OLED or OLEC. In this case, the matrix material containing compound comprising structures of formula (I) is present in the electronic device in combination with one or more dopants, preferably phosphorescent dopants.

The proportion of the matrix material in the emitting layer in this case is between 50.0% and 99.9% by volume, preferably between 80.0% and 99.5% by volume, and more preferably between 92.0% and 99.5% by volume for fluorescent emitting layers and between 85.0% and 97.0% by volume for phosphorescent emitting layers.

Correspondingly, the proportion of the dopant is between 0.1% and 50.0% by volume, preferably between 0.5% and 20.0% by volume, and more preferably between 0.5% and 8.0% by volume for fluorescent emitting layers and between 3.0% and 15.0% by volume for phosphorescent emitting layers.

An emitting layer of an organic electroluminescent device may also comprise systems comprising a plurality of matrix materials (mixed matrix systems) and/or a plurality of dopants. In this case too, the dopants are generally those materials having the smaller proportion in the system and the matrix materials are those materials having the greater proportion in the system. In individual cases, however, the proportion of a single matrix material in the system may be less than the proportion of a single dopant.

In a further preferred embodiment of the invention, the compound comprising structures of formula (I) is used as a component of mixed matrix systems. The mixed matrix systems preferably comprise two or three different matrix materials, more preferably two different matrix materials. Preferably, in this case, one of the two materials is a material having hole-transporting properties and the other material is a material having electron-transporting properties. The desired electron-transporting and hole-transporting properties of the mixed matrix components may, however, also be combined mainly or entirely in a single mixed matrix component, in which case the further mixed matrix component(s) fulfill(s) other functions. The two different matrix materials may be present in a ratio of 1:50 to 1:1, preferably 1:20 to 1:1, more preferably 1:10 to 1:1 and most preferably 1:4 to 1:1. Preference is given to using mixed matrix systems in phosphorescent organic electroluminescent devices. One source of more detailed information about mixed matrix systems is the application WO 2010/108579.

The present invention further provides an electronic device, preferably an organic electroluminescent device, comprising one or more compounds of the invention and/or at least one oligomer, polymer or dendrimer of the invention in one or more electron-conducting layers, as electron-conducting compound.

Preferred cathodes are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag, in which case combinations of the metals such as Mg/Ag, Ca/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). Likewise useful for this purpose are organic alkali metal complexes, e.g. Liq (lithium quinolinate). The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable either the irradiation of the organic material (O-SC) or the emission of light (OLED/PLED, O-laser). Preferred anode materials here are conductive mixed metal oxides. Particular preference is given to indium tin oxide (ITO) or indium zinc oxide (IZO). Preference is further given to conductive doped organic materials, especially conductive doped polymers, for example PEDOT, PANI or derivatives of these polymers. It is further preferable when a p-doped hole transport material is applied to the anode as hole injection layer, in which case suitable p-dopants are metal oxides, for example $MoO_3$ or $WO_3$, or (per)fluorinated electron-deficient aromatic systems. Further suitable p-dopants are HAT-CN (hexacyanohexaazatriphenylene) or the compound NPD9 from Novaled. Such a layer simplifies hole injection into materials having a low HOMO, i.e. a large HOMO in terms of magnitude.

In the further layers, it is generally possible to use any materials as used according to the prior art for the layers, and the person skilled in the art is able, without exercising inventive skill, to combine any of these materials with the materials of the invention in an electronic device.

The device is correspondingly (according to the application) structured, contact-connected and finally hermetically sealed, since the lifetime of such devices is severely shortened in the presence of water and/or air.

Additionally preferred is an electronic device, especially an organic electroluminescent device, which is characterized in that one or more layers are coated by a sublimation process. In this case, the materials are applied by vapor deposition in vacuum sublimation systems at an initial pressure of typically less than $10^{-5}$ mbar, preferably less than $10^{-6}$ mbar. It is also possible that the initial pressure is even lower or even higher, for example less than $10^{-7}$ mbar.

Preference is likewise given to an electronic device, especially an organic electroluminescent device, which is characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured (for example M. S. Arnold et al., *Appl. Phys. Lett.* 2008, 92, 053301).

Preference is additionally given to an electronic device, especially an organic electroluminescent device, which is characterized in that one or more layers are produced from solution, for example by spin-coating, or by any printing method, for example screen printing, flexographic printing, offset printing or nozzle printing, but more preferably LITI (light-induced thermal imaging, thermal transfer printing) or inkjet printing. For this purpose, soluble compounds are needed, which are obtained, for example, through suitable substitution.

The electronic device, especially the organic electroluminescent device, can also be produced as a hybrid system by applying one or more layers from solution and applying one or more other layers by vapor deposition. For example, it is possible to apply an emitting layer comprising a compound of the invention comprising structures of formula (I) and a matrix material from solution, and to apply a hole blocker layer and/or an electron transport layer thereto by vapor deposition under reduced pressure.

These methods are known in general terms to those skilled in the art and can be applied without difficulty to electronic devices, especially organic electroluminescent devices comprising compounds of the invention comprising structures of formula (I) or the above-detailed preferred embodiments.

The electronic devices of the invention, especially organic electroluminescent devices, are notable for one or more of the following surprising advantages over the prior art:
1. Electronic devices, especially organic electroluminescent devices comprising compounds, oligomers, polymers or dendrimers having structures of formula (I), especially as electron-conducting and/or as hole-conducting materials, have a very good lifetime.
2. Electronic devices, especially organic electroluminescent devices comprising compounds, oligomers, polymers or dendrimers having structures of formula (I) as electron-conducting and/or as hole-conducting materials, have excellent efficiency. More particularly, the efficiency is much higher compared to analogous compounds containing no structural unit of formula (I).
3. The compounds, oligomers, polymers or dendrimers of the invention having structures of the formula (I) exhibit very high stability and lead to compounds having a very long lifetime.
4. With compounds, oligomers, polymers or dendrimers having structures of formula (I), it is possible to avoid the formation of optical loss channels in electronic devices, especially organic electroluminescent devices. As a result, these devices feature a high PL efficiency and hence high EL efficiency of emitters, and excellent energy transmission of the matrices to dopants.
5. The use of compounds, oligomers, polymers or dendrimers having structures of formula (I) in layers of electronic devices, especially organic electroluminescent devices, leads to a high mobility of the electron conductor structures and/or the hole conductor structures.
6. Compounds, oligomers, polymers or dendrimers having structures of formula (I) feature excellent thermal stability, where compounds having a molar mass of less than about 1200 g/mol have good sublimability.
7. Compounds, oligomers, polymers or dendrimers having structures of formula (I) have excellent glass film formation.
8. Compounds, oligomers, polymers or dendrimers having structures of formula (I) form very good films from solutions.
9. The compounds, oligomers, polymers or dendrimers comprising structures of formula (I) have a surprisingly high triplet level $T_1$, this being particularly true of compounds which are used as electron-conducting materials.

These abovementioned advantages are not accompanied by a deterioration in the further electronic properties.

The present invention further provides for the use of a compound of the invention and/or an oligomer, polymer or dendrimer of the invention in an electronic device as hole transport material, hole injection material, hole blocker material, electron injection material, electron blocker material and/or electron transport material.

It should be pointed out that variations of the embodiments described in the present invention are covered by the scope of this invention. Any feature disclosed in the present invention may, unless this is explicitly ruled out, be exchanged for alternative features which serve the same purpose or an equivalent or similar purpose. Thus, any feature disclosed in the present invention, unless stated otherwise, should be considered as an example of a generic series or as an equivalent or similar feature.

All features of the present invention may be combined with one another in any manner, unless particular features and/or steps are mutually exclusive. This is especially true of preferred features of the present invention. Equally, features of non-essential combinations may be used separately (and not in combination).

It should also be pointed out that many of the features, and especially those of the preferred embodiments of the present invention, are themselves inventive and should not be regarded merely as some of the embodiments of the present invention. For these features, independent protection may be sought in addition to or as an alternative to any currently claimed invention.

The technical teaching disclosed with the present invention may be abstracted and combined with other examples.

The invention is illustrated in detail by the examples which follow, without any intention of restricting it thereby.

The person skilled in the art will be able to use the details given, without exercising inventive skill, to produce further electronic devices of the invention and hence to execute the invention over the entire scope claimed.

EXAMPLES

The syntheses which follow, unless stated otherwise, are conducted under a protective gas atmosphere in dried solvents. The metal complexes are additionally handled with exclusion of light or under yellow light. The solvents and reagents can be purchased, for example, from Sigma-ALDRICH or ABCR. The respective figures in square brackets or the numbers quoted for individual compounds relate to the CAS numbers of the compounds known from the literature.

Preparation Examples a) 1-Bromodibenzofuran

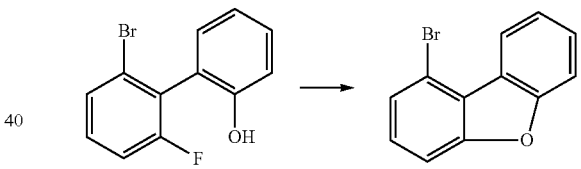

111 g (416 mmol) of 6'-bromo-2'-fluorobiphenyl-2-ol are dissolved in 2 L of DMF (max. 0.003% $H_2O$) SeccoSolv® and cooled to 5° C. 20 g (449 mmol) of sodium hydride (60% suspension in paraffin oil) are added to this solution in portions and, once the addition has ended, the mixture is stirred for 20 min, and then the mixture is heated to 100° C. for 45 min. After the cooling, 500 mL of ethanol are added gradually to the mixture, which is completely concentrated by rotary evaporation and then purified by chromatography. Yield: 90 g (367 mmol), 88.5% of theory.

The following compounds are prepared in an analogous manner:

| | Reactant 1 | Product | Yield |
|---|---|---|---|
| a1 | ![Reactant 1 structure] | ![Product structure] | 73% |

| | Reactant 1 | Product | Yield |
|---|---|---|---|
| a2 | 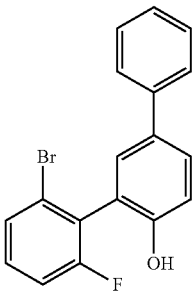 [SMILES: Oc1ccc(-c2ccccc2)cc1-c1c(F)cccc1Br] | 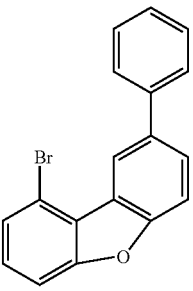 [SMILES: Brc1cccc2oc3ccc(-c4ccccc4)cc3c12] | 79% | b) Dibenzofuran-1-boronic acid

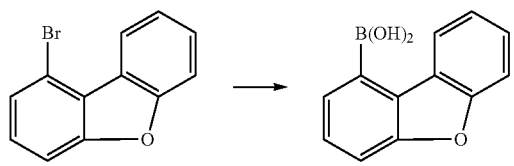 [SMILES: Brc1cccc2oc3ccccc3c12 ; OB(O)c1cccc2oc3ccccc3c12]

180 g (728 mmol) of 1-bromodibenzofuran are dissolved in 1500 mL of dry THF and cooled to 78° C. At this temperature, 305 mL (764 mmol/2.5 M in hexane) of n-BuLi are added within about 5 min, and then the mixture is stirred at −78° C. for a further 2.5 h. At this temperature, 151 g (1456 mmol) of trimethyl borate are added very rapidly and the reaction is allowed to come gradually to RT (about 18 h). The reaction solution is washed with water and the precipitated solids and the organic phase are subjected to azeotropic drying with toluene. The crude product is extracted while stirring from toluene/methylene chloride at about 40° C. and filtered off with suction. Yield: 146 g (690 mmol), 95% of theory.

The following compounds are prepared in an analogous manner:

| | Reactant 1 | Product | Yield |
|---|---|---|---|
| b1 | 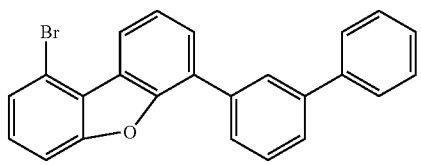 [SMILES: Brc1cccc2oc3c(-c4cccc(-c5ccccc5)c4)cccc3c12] | 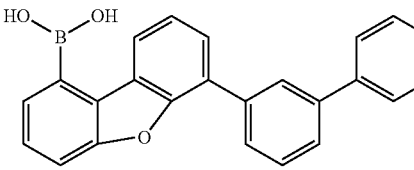 | 73% |
| b2 | 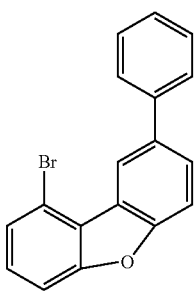 [SMILES: Brc1cccc2oc3ccc(-c4ccccc4)cc3c12] | 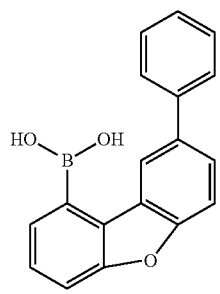 [SMILES: OB(O)c1cccc2oc3ccc(-c4ccccc4)cc3c12] | 79% |
| b3 | 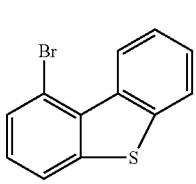  [65642-94-6] | 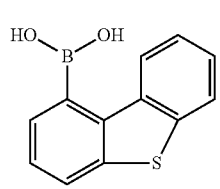 [SMILES: OB(O)c1cccc2sc3ccccc3c12] | 73% | c) Synthesis of 5"-chloro-[1,3';1',1";3",1'";3'",1""]quinquephenyl

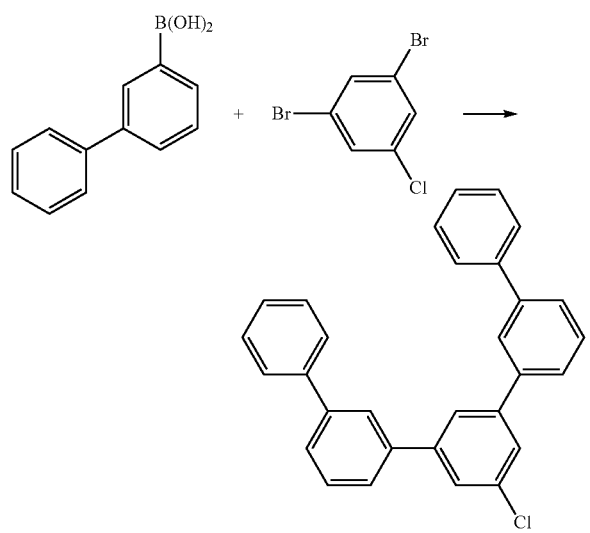

29 g (148 mmol) of 3-biphenylboronic acid, 20 g (74 mmol) of 1-chloro-3,5-dibromobenzene and 60 g (596 mmol) of sodium carbonate are suspended in 500 mL of THF and 300 mL of water. 6.5 g (5.6 mmol) of tetrakis(triphenylphosphine)palladium(0) are added to this suspension, and the reaction mixture is heated under reflux for 16 h. After cooling, the organic phase is removed, filtered through silica gel, washed three times with 200 mL of water and then concentrated to dryness. The residue is recrystallized from toluene. The yield is 22 g (53 mmol), corresponding to 71% of theory.

In an analogous manner, it is possible to obtain the following compounds:

| Example | Reactant 1 | Reactant 2 | Product | Yield |
|---|---|---|---|---|
| c1 | (1-chloro-3,5-dibromobenzene) | (phenylboronic acid) | (5'-chloro-1,1':3',1''-terphenyl) | 95% |
| c2 | (1-chloro-3,5-dibromobenzene) | (9-phenyl-9H-carbazol-3-yl boronic acid) [854952-58-2] | (bis-carbazolyl chlorobenzene product) | 73% |

-continued

| Example | Reactant 1 | Reactant 2 | Product | Yield |
|---|---|---|---|---|
| c3 | | [1314221-56-1] | | 83% |

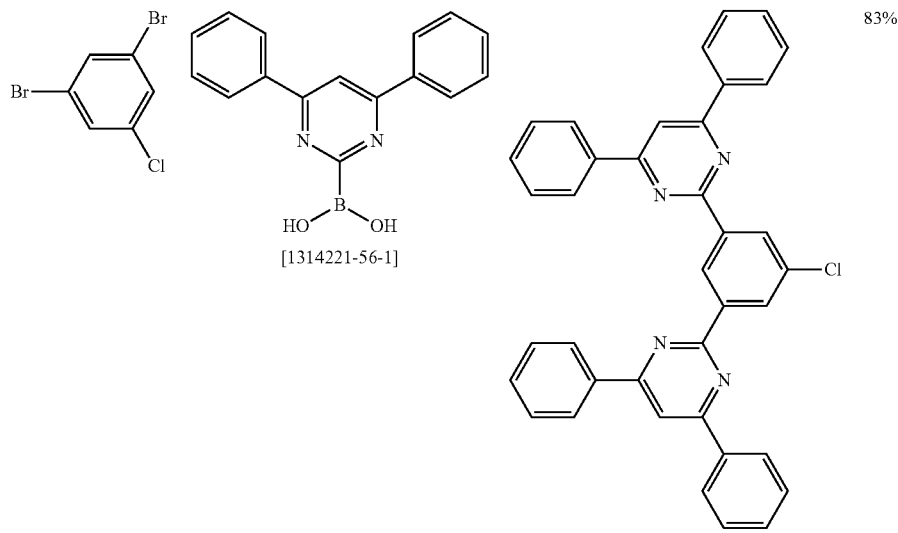

d) Synthesis of 4,4,5,5-tetramethyl-2-[1,3';1',1'';3'',1''';3''',1'''']quinquephenyl-5''-yl-[1,3,2]dioxaborolane

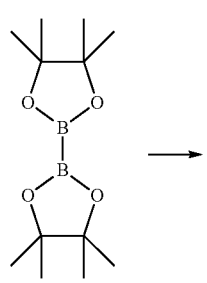

+

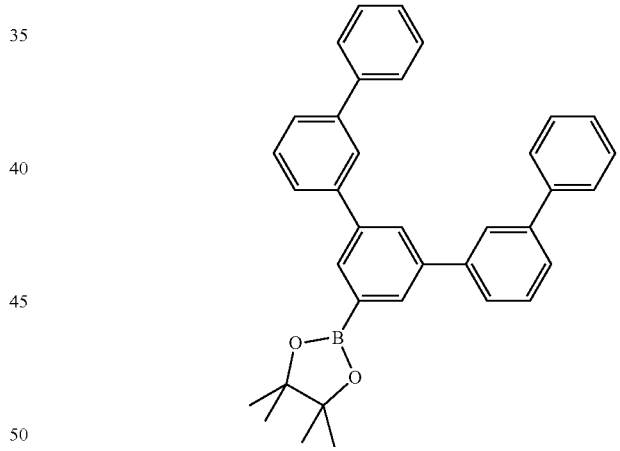

-continued 75 g (126 mmol) of 5''-chloro-[1,3';1',1'';3'',1''';3''',1'''']quinquephenyl, 41.6 g of bis(pinacolato)diborane (163 mmol), 21 g (214 mmol) of potassium acetate and 18 g (25 mmol) of tricyclohexylphosphinepalladium dichloride are heated to reflux in 1 L of 1,4-dioxane while stirring vigorously for 2 days. The reaction mixture is filtered through Celite at room temperature.

The solvent is removed under reduced pressure, and the remaining solids are recrystallized in acetonitrile. The solids formed are filtered off and washed with heptane. The yield is 82 g (119 mmol), corresponding to 95% of theory.

In an analogous manner, it is possible to obtain the following compounds:

| Example | Reactant 1 | Product | Yield |
|---|---|---|---|
| d1 | 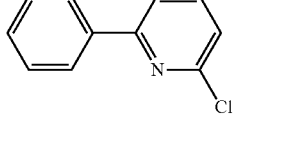 | 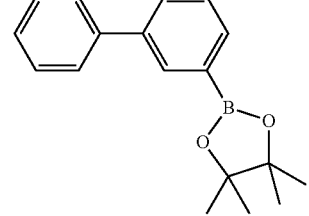 | 90% |
| d2 | 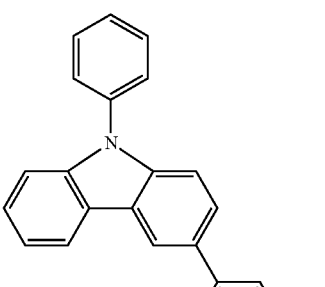 | 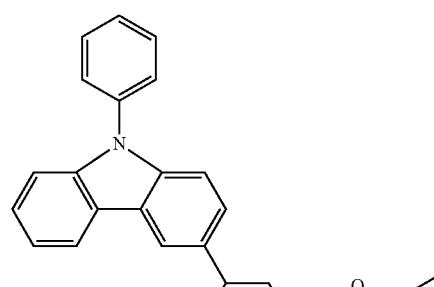 | 84% |
| d3 | 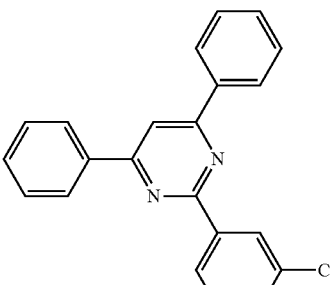 | 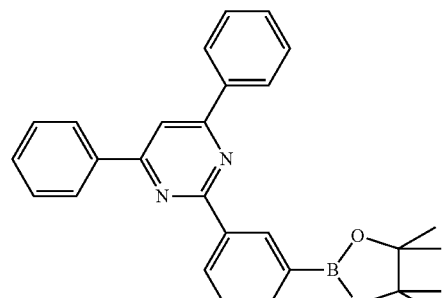 | 75% | e) Synthesis of 8-bromodibenzo[b,d]pyran-6-one f) 8-(9-Phenyl-9H-carbazol-3-yl)benzo[c]chromen-6-one

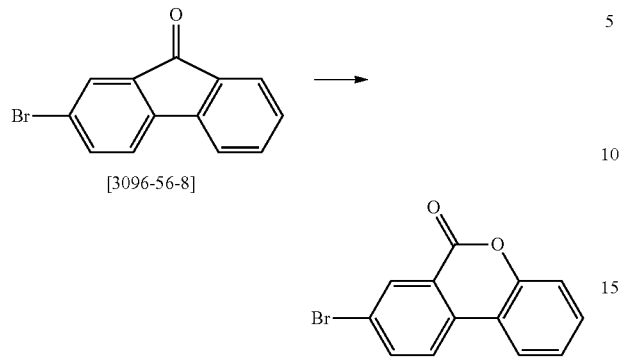

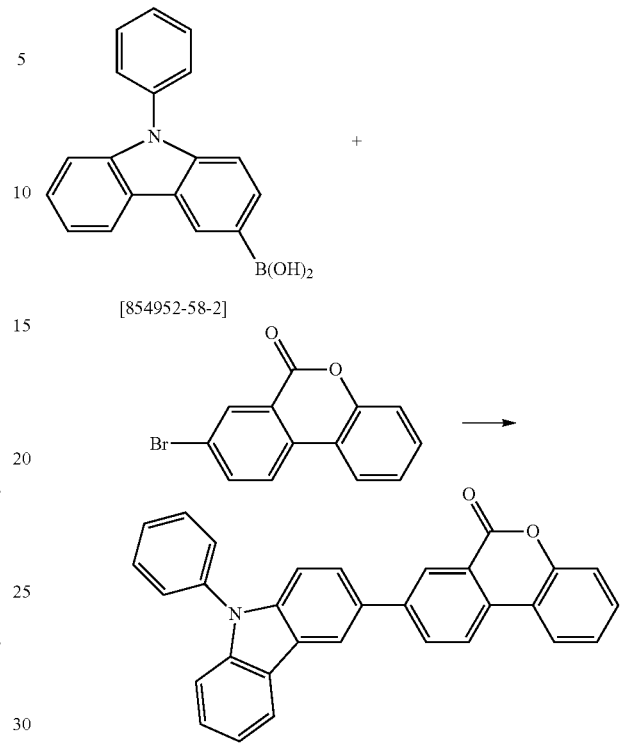

100 g (386 mmol) of 2-bromofluorenone are initially charged in 1000 mL of trifluoroacetic acid and cooled to 0° C. Added gradually to this solution are 100 g (637 mmol) of sodium percarbonate (13%-14% active oxygen), and the reaction mixture is stirred at 10-15° C. for 1 h. Subsequently, stirring of the mixture continues at room temperature overnight. 1000 mL of water are added to the reaction mixture, and the organic phase is removed and then concentrated to dryness. The residue is triturated with heptane, filtered off with suction and dried at 50° C. under reduced pressure.

Yield: 92 g (334 mmol), 86% of theory.

In an analogous manner, it is possible to prepare the following compounds:

| Example | Reactant 1 | Product | Yield |
|---|---|---|---|
| e1 | [52086-14-3] | [52086-14-3] | 50% |
| e2 | [171669-72-0] | [171669-72-0] | 63% |
| e3 | [1470370-96-7] | [1470370-95-7] | 61% |

17 g (67 mmol) of 9-phenyl-9H-carbazole-3-boronic acid, 22.2 g (81 mmol) of 8-bromo-6H-dibenzo[b,d]pyran-6-one and 136 g (980 mmol) of tripotassium phosphate are suspended in 1000 mL of THF and 300 mL of water. Added to this suspension are 178 mg (0.67 mmol) of triphenylphosphine and then 152 mg (0.67 mmol) of palladium(II) acetate, and the reaction mixture is heated under reflux for 16 h. After cooling, the organic phase is removed, filtered through silica gel, washed three times with 200 mL of water and then concentrated to dryness. The residue is recrystallized from toluene/heptane and finally sublimed under high vacuum ($p=5\times10^{-5}$ mbar, T=377° C.). The yield is 23 g (54 mmol), corresponding to 82% of theory.

In an analogous manner, it is possible to obtain the following compounds:

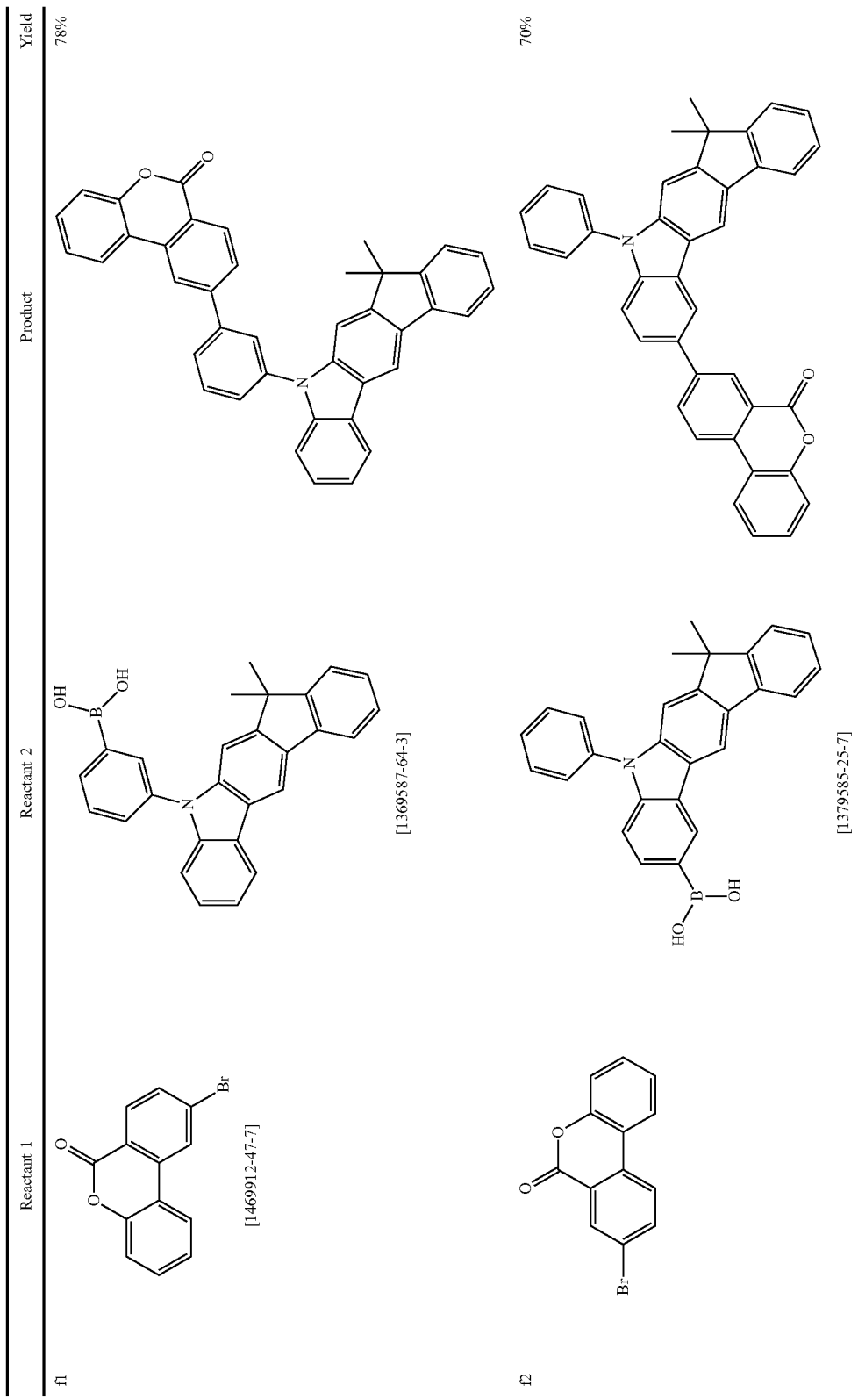

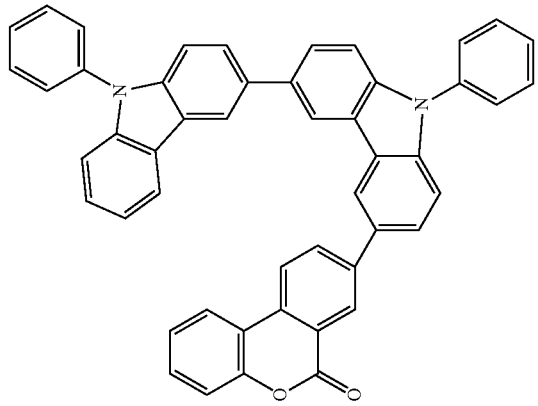
| Reactant 1 | Reactant 2 | Product | Yield |
|---|---|---|---|
| | [1572537-61-1] | | 75% |

| | Reactant 1 | Reactant 2 | Product | Yield |
|---|---|---|---|---|
| I4 | 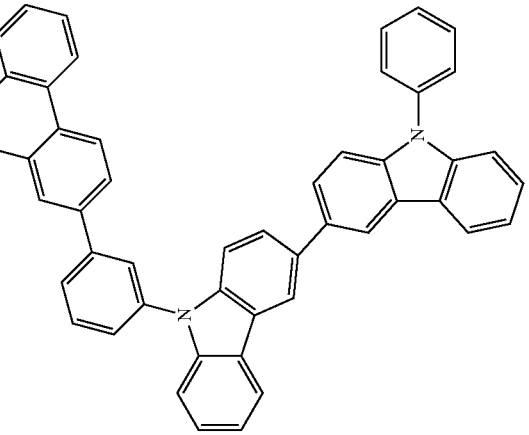 | 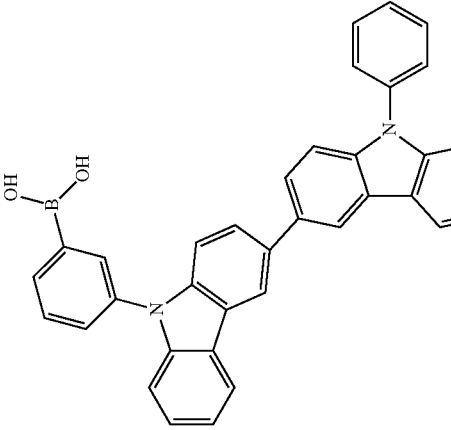  [1398394-64-3] | 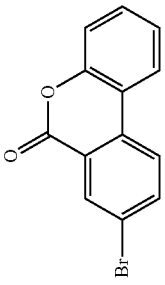 | 77% |

| Reactant 1 | Reactant 2 | Product | Yield |
|---|---|---|---|
| f5 [1443434-82-9] | [1420067-45-3] | | 75% |
| f6 [1000391-25-2] | [854952-58-2] | | 62% |

| | Reactant 1 | Reactant 2 | Product | Yield |
|---|---|---|---|---|
| f7 | 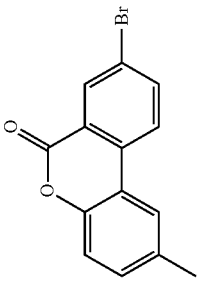 [100527-53-5] | 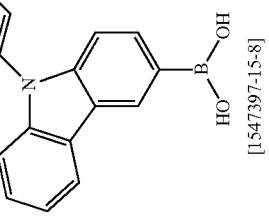 [1547397-15-8] | | 83% |
| f8 | 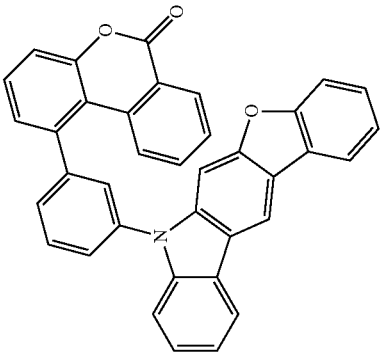 [928307-80-6] | 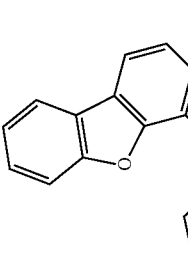 [1369587-56-3] | | 84% |

-continued
| | Reactant 1 | Reactant 2 | Product | Yield |
|---|---|---|---|---|
| f9 | 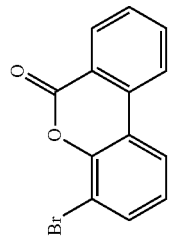 [158097-94-0] | 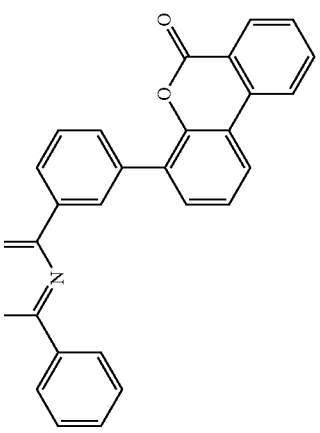 [1269506-31-7] | 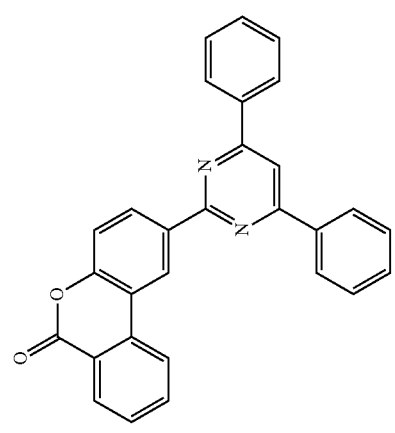 | 79% |
| f10 | 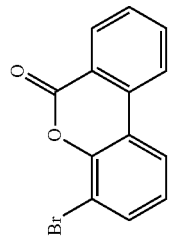 [151648-54-3] | 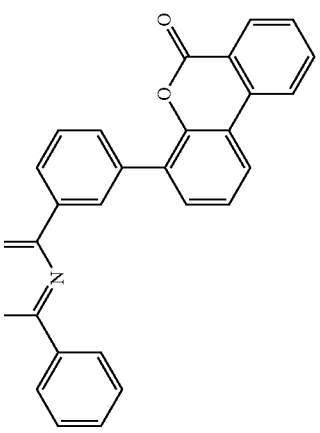 [1314221-56-1] | 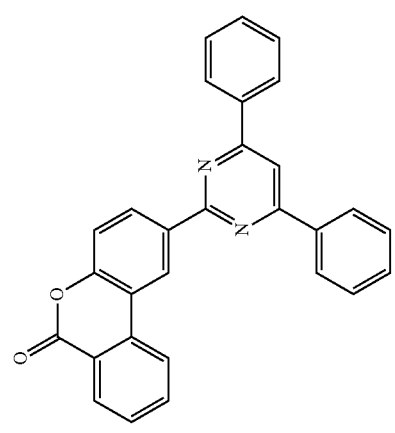 | 83% |

| | Reactant 1 | Reactant 2 | Product | Yield |
|---|---|---|---|---|
| f11 | 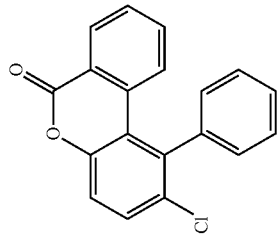 [1130141-14-8] | 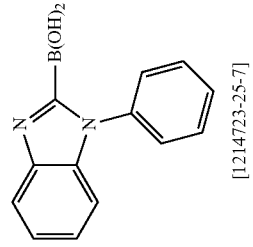 [1214723-25-7] | 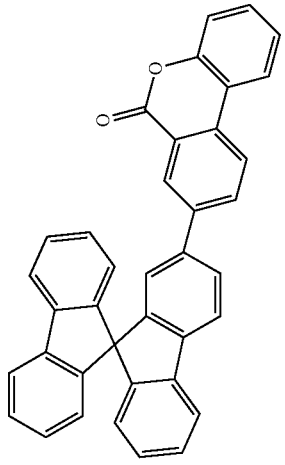 | 75% |
| f12 | 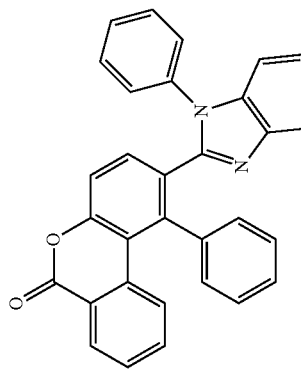 | 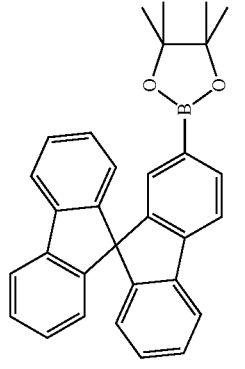 [1557257-88-1] | 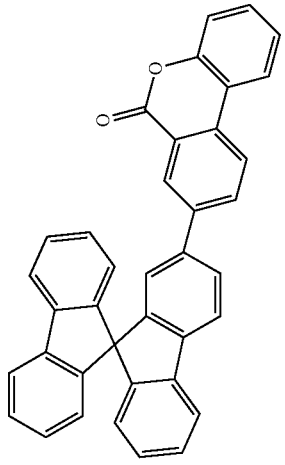 | 77% |

| | Reactant 1 | Reactant 2 | Product | Yield |
|---|---|---|---|---|
| f13 | 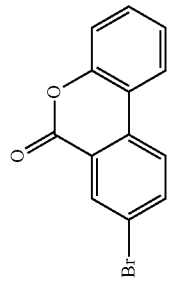 | 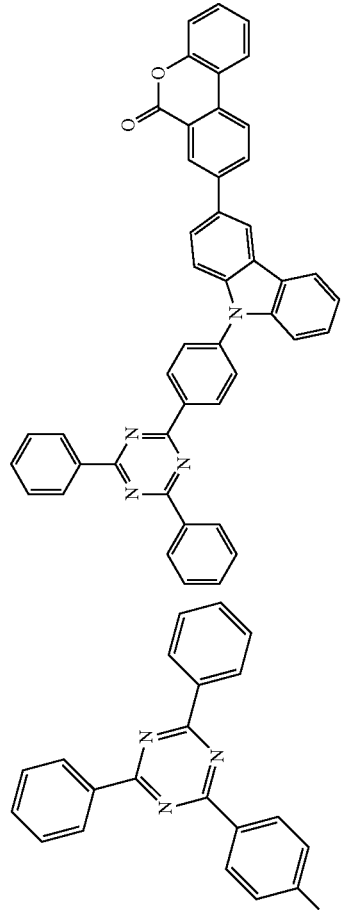 | 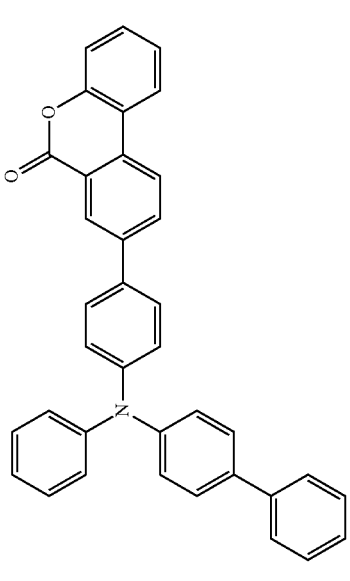 | 74% |
| f14 | 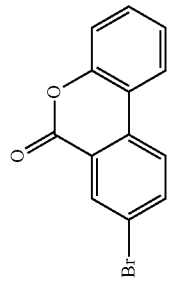 | 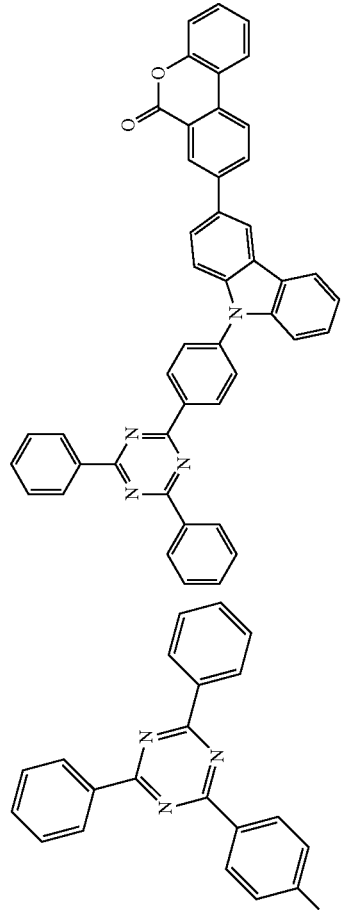 [1084334-86-0] | 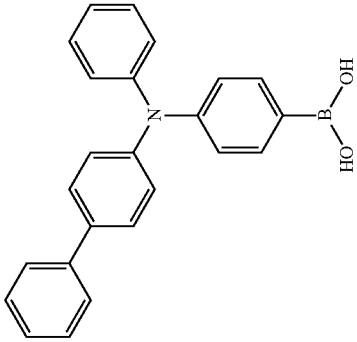 | 69% |

-continued

| | Reactant 1 | Reactant 2 | Product | Yield |
|---|---|---|---|---|
| f15 | [585529-39-1] | [B(OH)₂ compound] | | 68% |
| f16 | [52086-14-3] | [1379585-25-7] | | 80% |

-continued

| | Reactant 1 | Reactant 2 | Product | Yield |
|---|---|---|---|---|
| f17 | [1470370-96-7] | [1434286-69-7] | | 71% |
| f18 | | [1146340-38-6] | | 69% |

| Reactant 1 | Reactant 2 | Product | Yield |
|---|---|---|---|
| f19 [1433966-13-6] | [1572537-61-1] | | 71% |

| | Reactant 1 | Reactant 2 | Product | Yield |
|---|---|---|---|---|
| f20 | (4-methylphenyl, phenyl-substituted bromo-benzocoumarin) | (dibenzofuran-N-carbazole boronic acid) [1547397-15-8] | (coupled product) | 71% |

In an analogous manner, it is possible to prepare the following compound with 0.5 eq. of boronic acid or bromide.

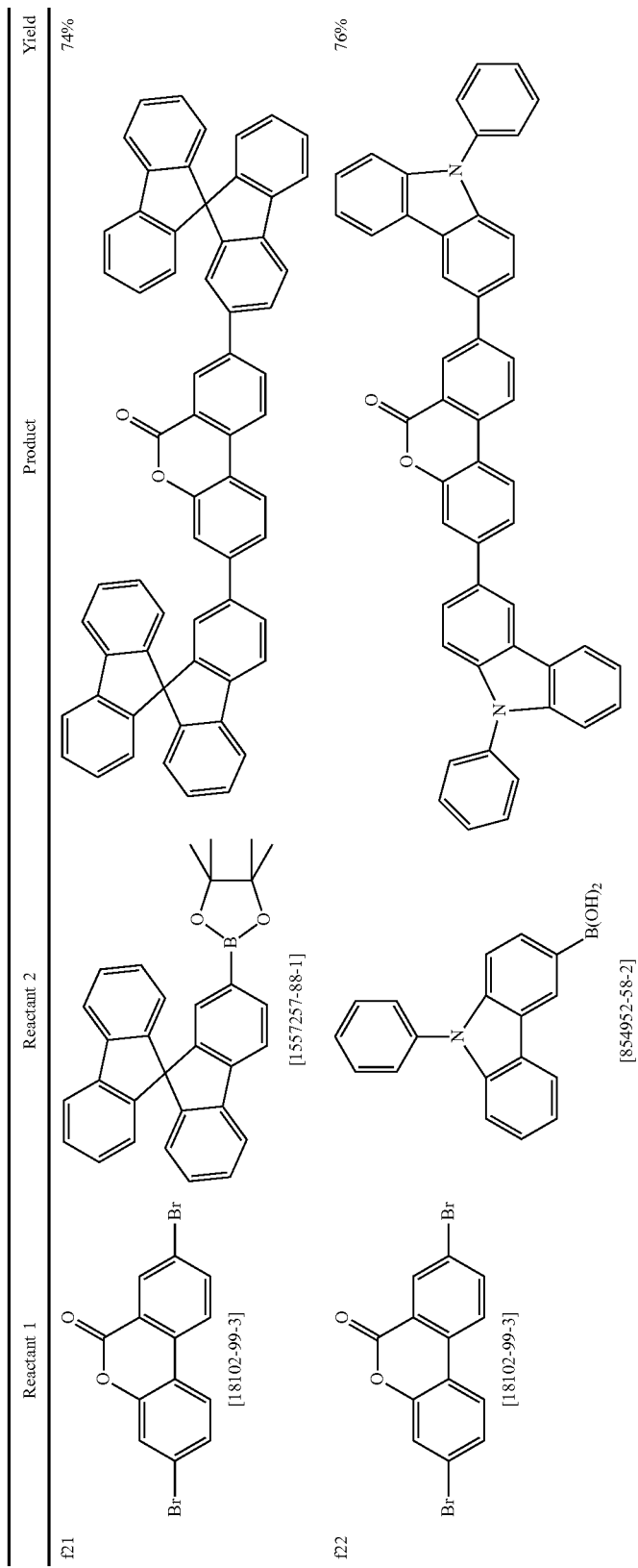

| | Reactant 1 | Reactant 2 | Product | Yield |
|---|---|---|---|---|
| f23 | [171669-72-0] | [654664-63-8] | | 70% |
| f24 | | [1197989-83-5] | | 72% | g) 3-Hydroxy-8-methoxybenzo[c]chromen-6-one h) 8-Methoxy-6-oxo-6H-benzo[c]chromen-3-yl trifluoromethanesulfonate

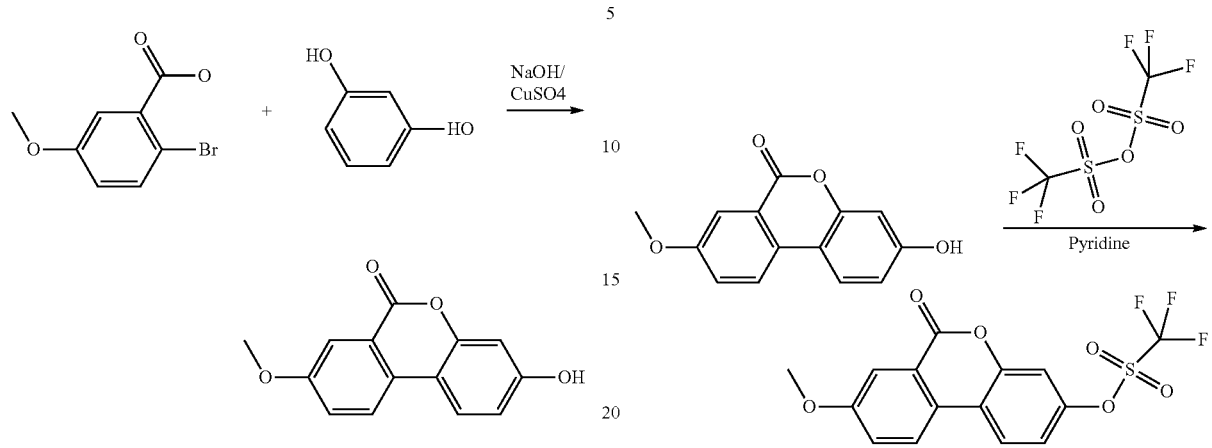

83 g (343 mmol) of sodium hydroxide are dissolved in 1000 mL of water. 80 g (346 mmol) of 2-bromo-5-methoxybenzoic acid and 76.5 g (695 mmol) of benzene-1,3-diol are added and the mixture is boiled under reflux for 30 min. Added to this suspension is a solution of 7 g (28 mmol) of copper sulfate pentahydrate dissolved in 300 mL of water, and the reaction mixture is heated under reflux for 1 h. After cooling, the solids are filtered off, mixed washed once with 200 mL of heptane and then concentrated to dryness. The yield is 50 g (165 mmol), corresponding to 80% of theory.

In an analogous manner, it is possible to obtain the following compounds:

83 g (343 mmol) of 3-hydroxy-8-methoxybenzo[c]chromen-6-one are suspended in 1200 mL of dichloromethane at 0° C. 37 mL (267 mmol) of triethylamine, 57 mL (343 mmol) of trifluoromethanesulfonate in 250 mL of dichloromethane, in such a way that the temperature does not rise above 5° C. The mixture is stirred at 0° C. for a further 1 h, then stirring is continued at room temperature overnight. The solids are filtered off, mixed washed once with 200 mL of water/MeOH and then concentrated to dryness. The yield is 102 g (275 mmol), corresponding to 80% of theory.

In an analogous manner, it is possible to obtain the following compounds:

| | Reactant 1 | Reactant 2 | Product | Yield |
|---|---|---|---|---|
| g1 | [22921-68-2] | | | 80% |
| g2 | [72135-36-5] | | | 87% |
| g3 | [88377-29-1] | | | 85% |

| Reactant 1 | Product | Yield |
|---|---|---|
| h1 | | 81% |
| h2 | | 82% |
| h3 | | 79% | j) 8-Methoxy-3-(9-phenyl-9H-carbazol-3-yl)benzo[c]chromen-6-one

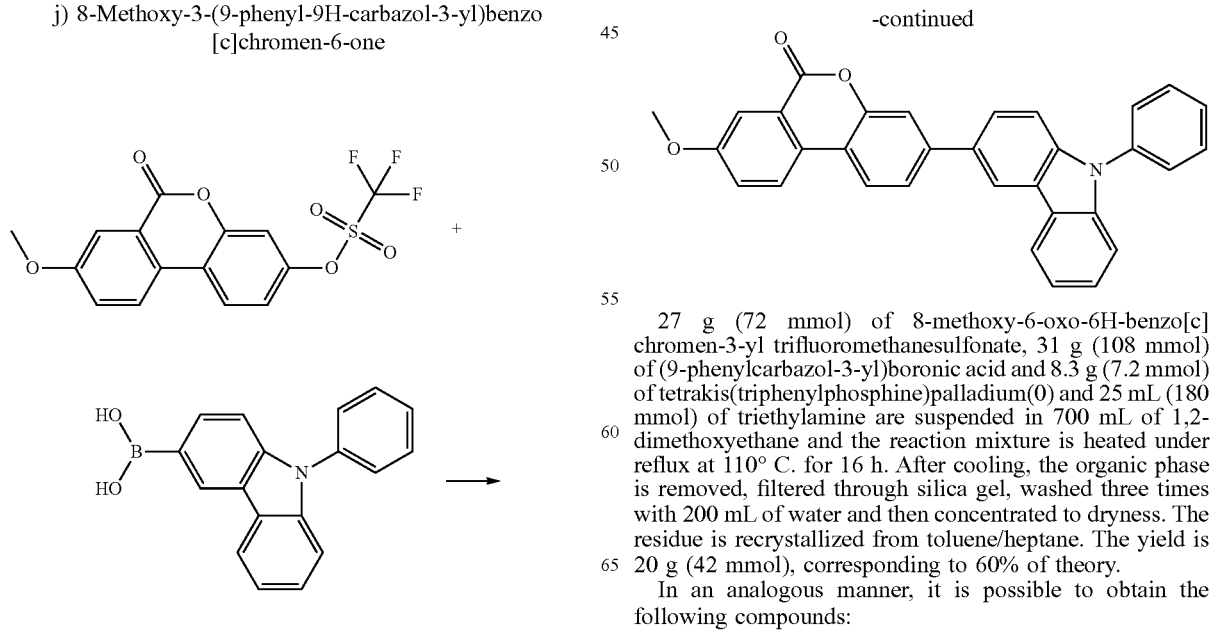

27 g (72 mmol) of 8-methoxy-6-oxo-6H-benzo[c]chromen-3-yl trifluoromethanesulfonate, 31 g (108 mmol) of (9-phenylcarbazol-3-yl)boronic acid and 8.3 g (7.2 mmol) of tetrakis(triphenylphosphine)palladium(0) and 25 mL (180 mmol) of triethylamine are suspended in 700 mL of 1,2-dimethoxyethane and the reaction mixture is heated under reflux at 110° C. for 16 h. After cooling, the organic phase is removed, filtered through silica gel, washed three times with 200 mL of water and then concentrated to dryness. The residue is recrystallized from toluene/heptane. The yield is 20 g (42 mmol), corresponding to 60% of theory.

In an analogous manner, it is possible to obtain the following compounds:

| | Reactant 1 | Reactant 2 | Product | Yield |
|---|---|---|---|---|
| j1 | | [1421789-05-0] | | 63% |
| j2 | | [1162753-18-5] | | 68% |
| j3 | | [854952-58-2] | | 72% |
| j4 | | [1148340-36-6] | | 75% |
| j5 | | | | 70% |
| j6 | | | | 76% |

-continued

| | Reactant 1 | Reactant 2 | Product | Yield |
|---|---|---|---|---|
| j7 | | [854952-58-2] | | 81% |
| j8 | | [854952-58-2] | | 82% |
| j9 | | [854952-58-2] | | 79% |
| j10 | | [1547492-13-6] | | 78% | i) 8-Hydroxy-3-(9-phenyl-9H-carbazol-3-yl)benzo[c]chromen-6-one

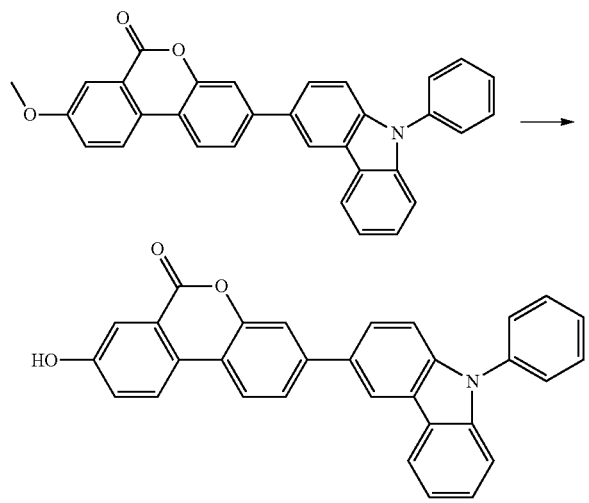

83 g (178 mmol) of 8-methoxy-3-(9-phenyl-9H-carbazol-3-yl)benzo[c]-chromen-6-one and 1500 mL of dichloromethane are cooled to 0° C., 100 mL (1054 mmol) of tribromoborane are added gradually and the mixture is stirred at room temperature for 16 h. Thereafter, hydrolysis is effected with 100 mL of methanol and the solids are filtered off with suction. The residue is recrystallized from heptane. The yield is 46 g (103 mmol), corresponding to 57% of theory.

In an analogous manner, it is possible to obtain the following compounds:

| | Reactant 1 | Product | Yield |
|---|---|---|---|
| i1 | | | 65% |
| i2 | | | 64% |
| i3 | | | 70% |
| i4 | | | 65% |

-continued

| | Reactant 1 | Product | Yield |
|---|---|---|---|
| i5 | | | 60% |
| i6 | | | 71% |
| i7 | | | 69% |
| i8 | | | 78% |
| i9 | | | 73% |
| i10 | | | 67% |

211
k) 6-Oxo-3-(9-phenyl-9H-carbazol-3-yl)-6H-benzo[c]chromen-8-yl trifluoromethanesulfonate
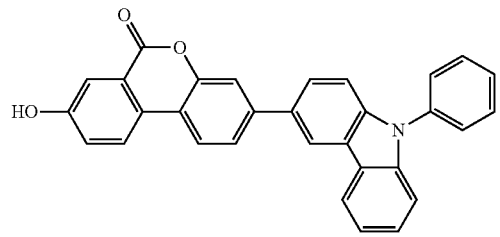
→
212
-continued
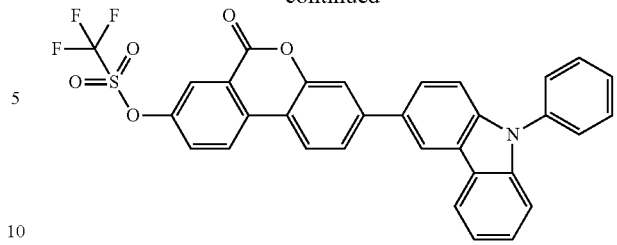
In an analogous manner, it is possible to obtain the following compounds by method (h). The residue is recrystallized from toluene. The yield is 81% of theory.
In an analogous manner, it is possible to obtain the following compounds:
| | Reactant 1 | Product | Yield |
|---|---|---|---|
| k1 | | | 80% |
| k2 | | | 78% |
| k3 | | | 84% |
| k4 | | | 73% |

-continued
| | Reactant 1 | Product | Yield |
|---|---|---|---|
| k5 | 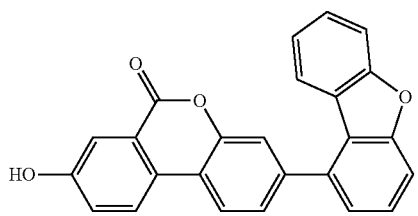 [SMILES: O=c1oc2cc(-c3cccc4oc5ccccc5c34)ccc2c2ccc(O)cc12] | 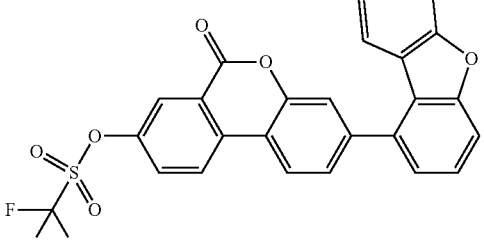 | 72% |
| k6 | 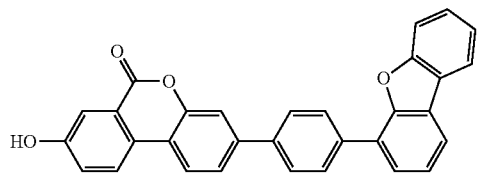 [SMILES: O=c1oc2cc(-c3ccc(-c4cccc5c4oc4ccccc45)cc3)ccc2c2ccc(O)cc12] | 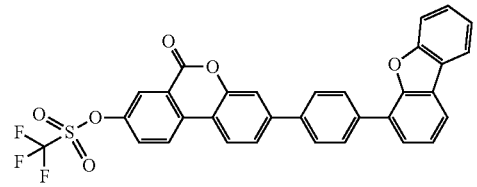 [SMILES: O=c1oc2cc(-c3ccc(-c4cccc5c4oc4ccccc45)cc3)ccc2c2ccc(OS(=O)(=O)C(F)(F)F)cc12] | 71% |
| k7 | 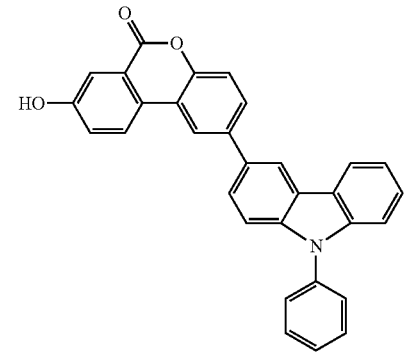 [SMILES: O=c1oc2ccc(-c3ccc4c(c3)c3ccccc3n4-c3ccccc3)cc2c2ccc(O)cc12] | 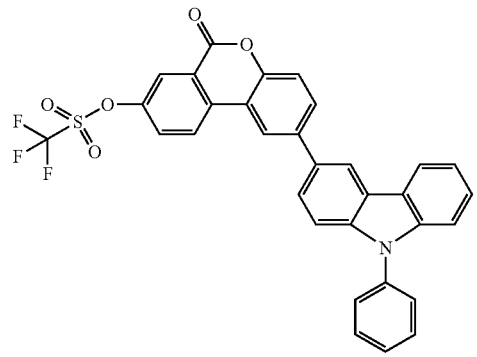 [SMILES: O=c1oc2ccc(-c3ccc4c(c3)c3ccccc3n4-c3ccccc3)cc2c2ccc(OS(=O)(=O)C(F)(F)F)cc12] | 79% |
| k8 | 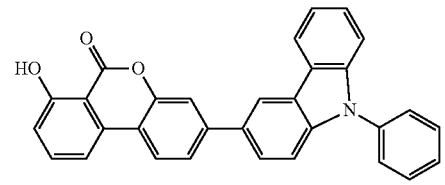 [SMILES: O=c1oc2cc(-c3ccc4c(c3)c3ccccc3n4-c3ccccc3)ccc2c2cccc(O)c12] | 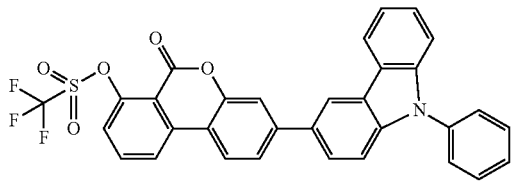 [SMILES: O=c1oc2cc(-c3ccc4c(c3)c3ccccc3n4-c3ccccc3)ccc2c2cccc(OS(=O)(=O)C(F)(F)F)c12] | 72% |
| k9 | 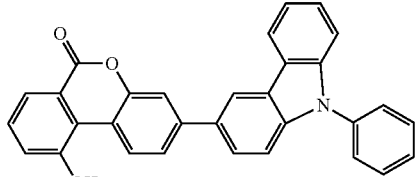 | 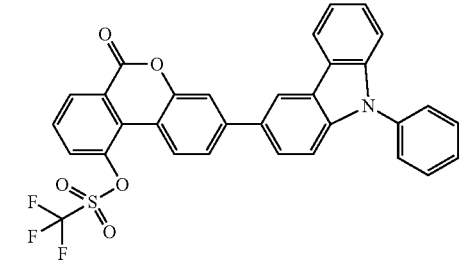 [SMILES: O=c1oc2cc(-c3ccc4c(c3)c3ccccc3n4-c3ccccc3)ccc2c2c(OS(=O)(=O)C(F)(F)F)cccc12] | 75% |
| k10 | 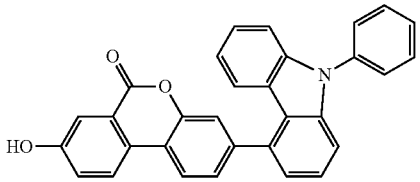 | 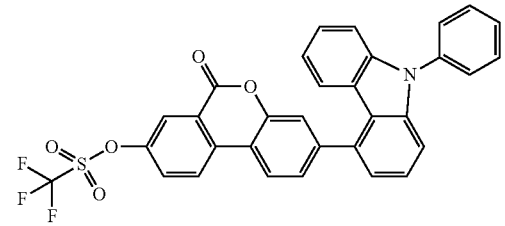 [SMILES: O=c1oc2cc(-c3cccc4c3c3ccccc3n4-c3ccccc3)ccc2c2ccc(OS(=O)(=O)C(F)(F)F)cc12] | 74% | l) Dibenzofuran-1-yl-3-(9-phenyl-9H-carbazol-3-yl)benzo[c]chromen-6-one
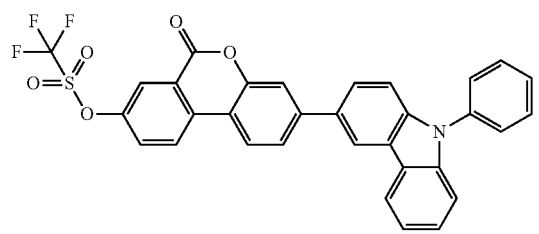
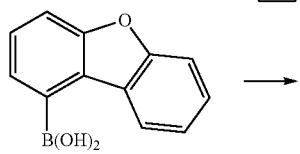
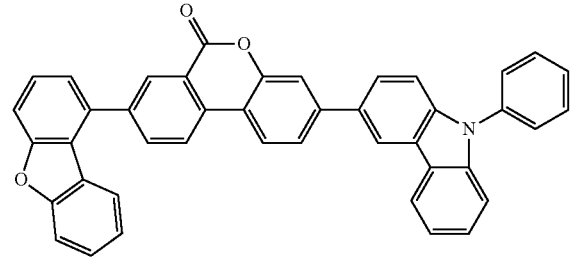
In an analogous manner, it is possible to obtain the following compounds by method (j). The residue is recrystallized from toluene/heptane and finally sublimed under high vacuum (p=5×10$^{-5}$ mbar, T=377° C.). The yield is 75% of theory.
In an analogous manner, it is possible to obtain the following compounds:

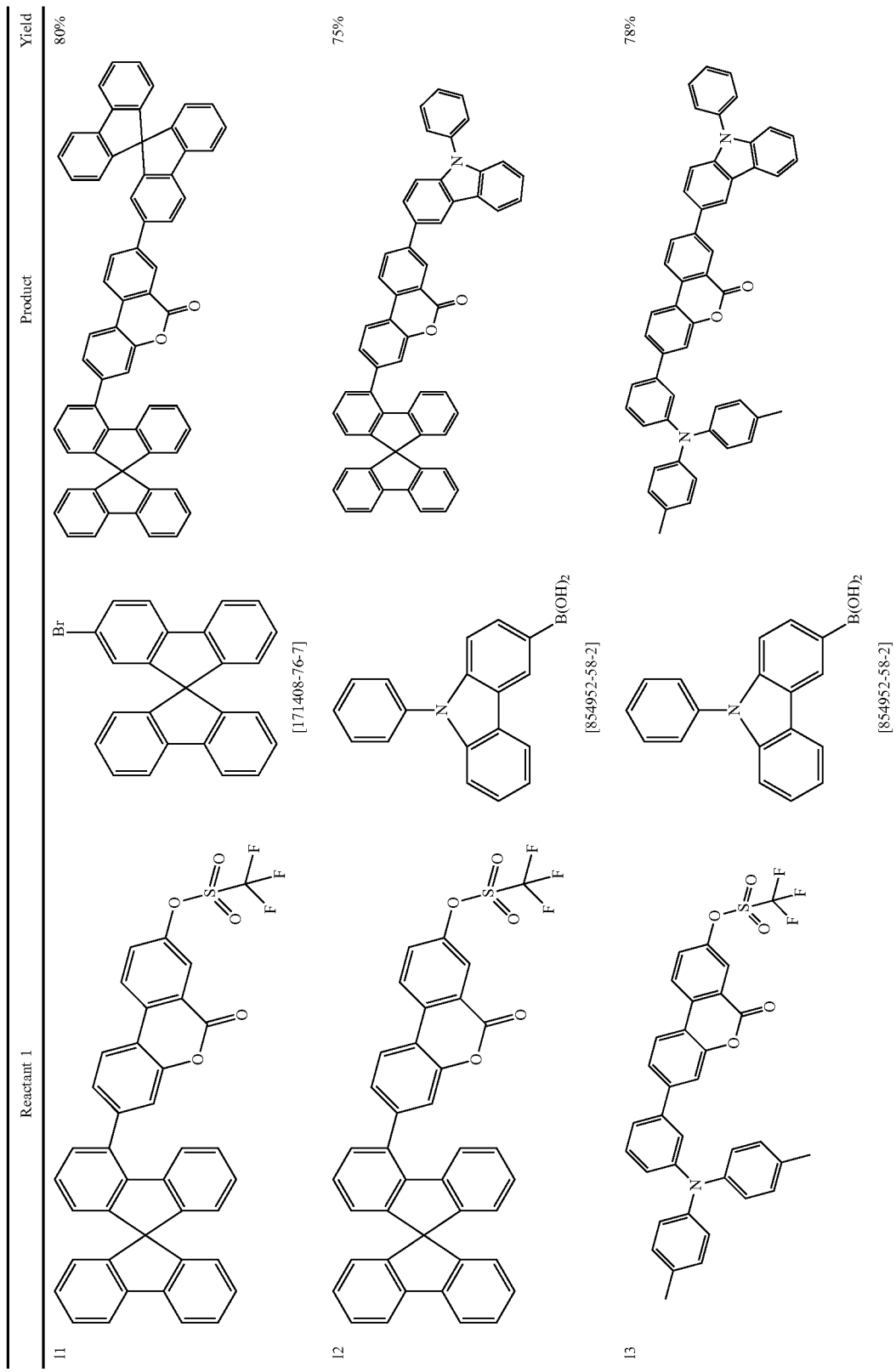

| | Reactant 1 | Product | Yield |
|---|---|---|---|
| 14 | 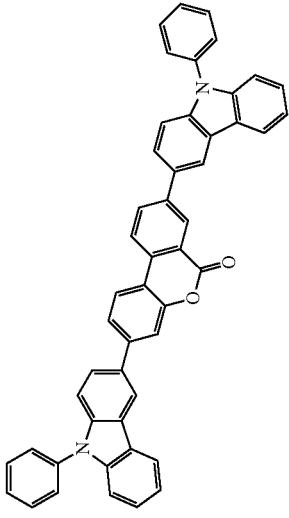 | 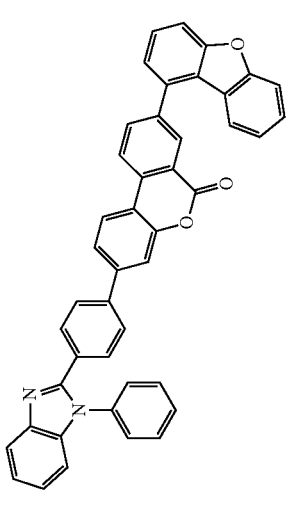 | 84% |
| 15 | 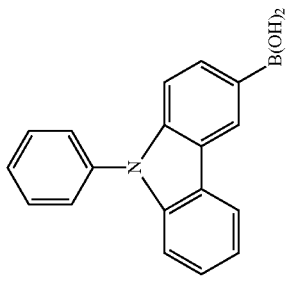 | 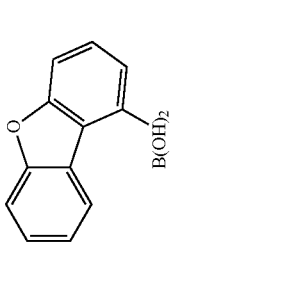 | 73% |
| 16 | 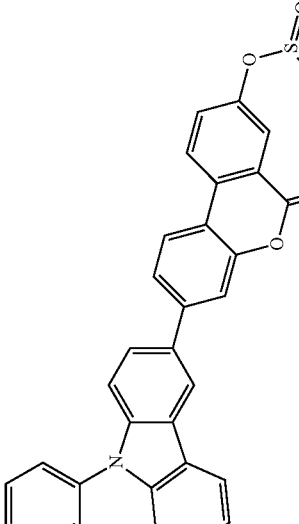 | 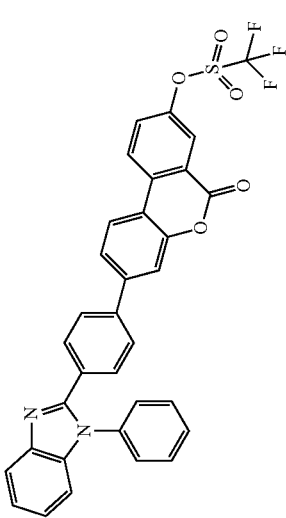 | 72% |

-continued

| Reactant 1 | | Product | Yield |
|---|---|---|---|
| 17 | [854952-58-2] | | 71% |
| 18 | [171408-76-7] | | 79% |

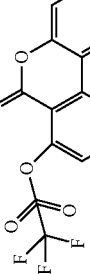

| | Reactant 1 | | Yield |
|---|---|---|---|
| I12 | | | 73% |
| I13 | | | 74% | m) 8-(12,12-Dimethyl-12H-10-azaindeno[2,1-b]fluoren-10-yl)benzo[c]chromen-6-one

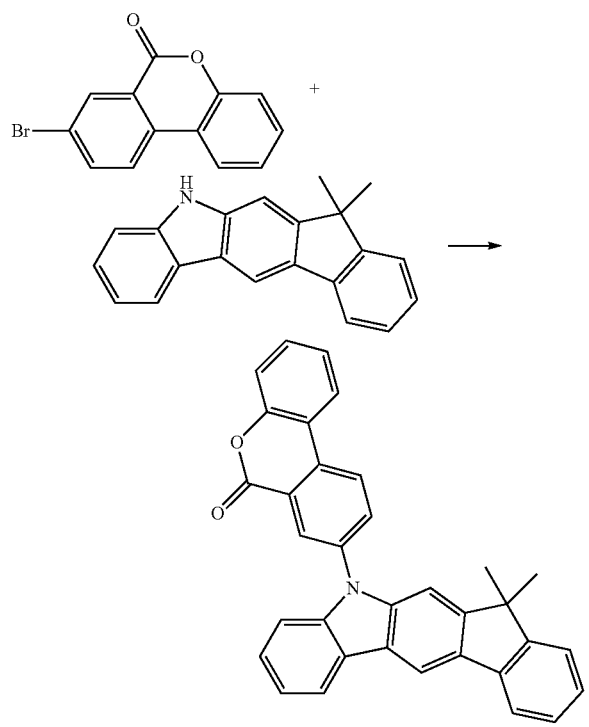

31 g (115 mmol) of 8-bromo-6H-dibenzo[b,d]pyran-6-one, 27.7 g (98 mmol) of 12,12-dimethyl-10,12-dihydro-10-azaindeno[2,1-b]fluorene and 30.5 g of NaOtBu are suspended in 1.5 L of p-xylene. To this suspension are added 0.5 g (2.11 mmol) of Pd(OAc)$_2$ and 6 mL of a 1 M tri-tert-butylphosphine (1 M solution in toluene). The reaction mixture is heated under reflux for 16 h. After cooling, the organic phase is removed, washed three times with 200 mL each time of water and then concentrated to dryness. The residue is subjected to hot extraction with toluene, recrystallized from toluene and finally sublimed under high vacuum. The purity is 99.9% by HPLC. The yield is 33 g (69 mmol), corresponding to 71% of theory.

The following compounds can be prepared in an analogous manner:

| | Reactant 1 | Reactant 2 | Product | Yield |
|---|---|---|---|---|
| m1 | 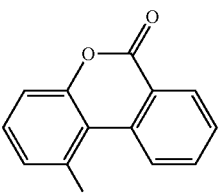 [928307-80-6] | 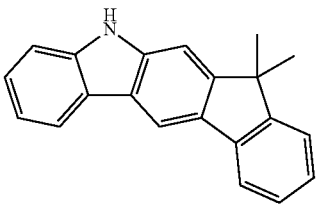 [1257220-47-5] | 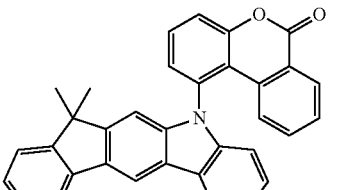 | 70% |
| m2 | 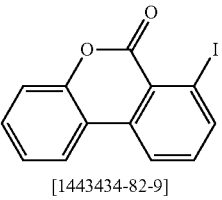 [SMILES: O=c1oc2ccccc2c2cccc(I)c12] [1443434-82-9] | 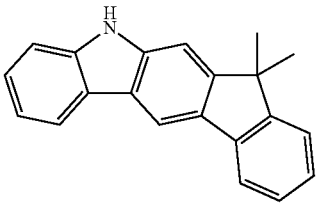 [1257220-47-5] | 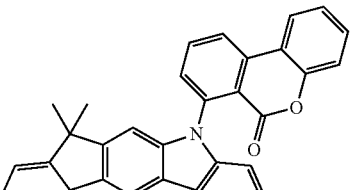 | 74% |

-continued
| | Reactant 1 | Reactant 2 | Product | Yield |
|---|---|---|---|---|
| m3 | 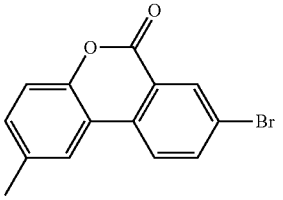 [100527-53-5] | 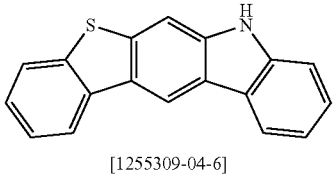 [SMILES: c1ccc2c(c1)[nH]c1cc3sc4ccccc4c3cc12] [1255309-04-6] | 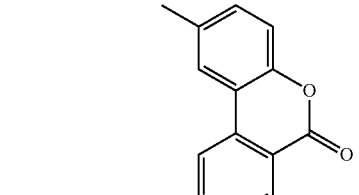 | 81% |
| m4 | 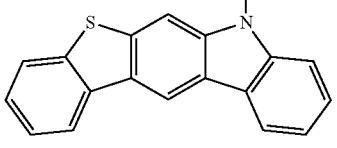 [158097-94-0] | 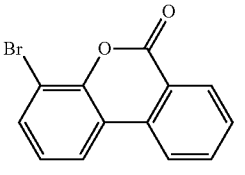 [103012-26-6] | 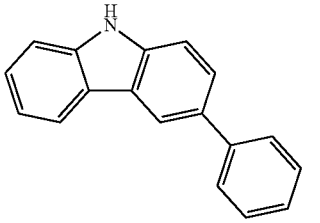 | 80% |
| m5 | 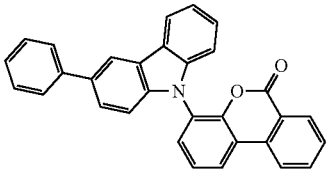 [SMILES: O=c1oc2c(-n3c4ccccc4c4cc(-c5ccccc5)ccc43)cccc2c2ccccc12] | 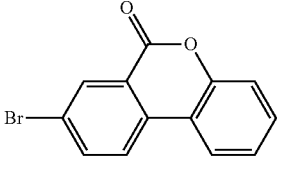 [SMILES: O=c1oc2ccccc2c2ccc(Br)cc12] [1060735-14-9] | 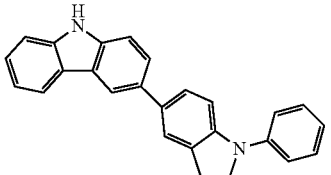 | 79% |
| m6 | 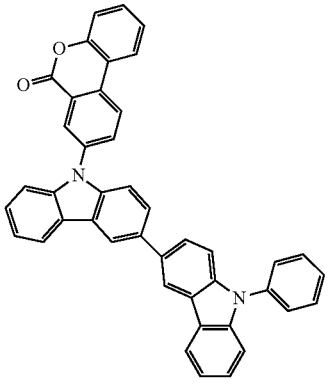 [SMILES: O=c1oc2ccccc2c2ccc(-n3c4ccccc4c4cc(-c5ccc6c(c5)c5ccccc5n6-c5ccccc5)ccc43)cc12] | 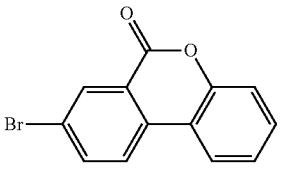 [SMILES: O=c1oc2ccccc2c2ccc(Br)cc12] [1024598-06-8] | 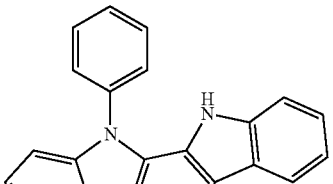 | 62% |

-continued
| | Reactant 1 | Reactant 2 | Product | Yield |
|---|---|---|---|---|
| m7 | 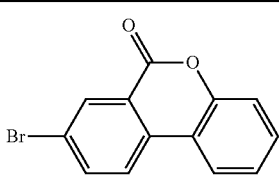 | 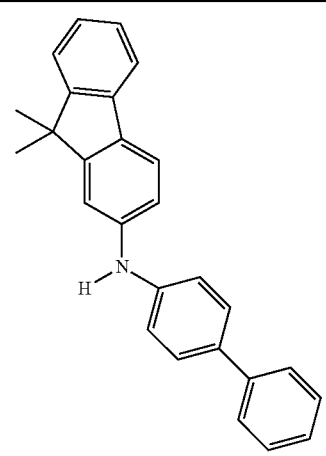<br>[1386375-27-4] | 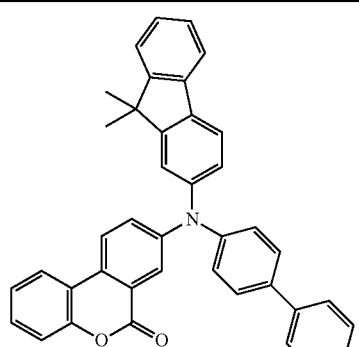 | 75% |
| m8 | 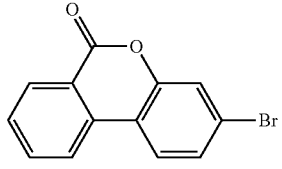<br>[1433988-13-6] | 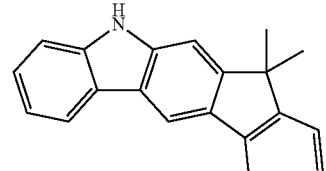<br>[1257220-47-5] | 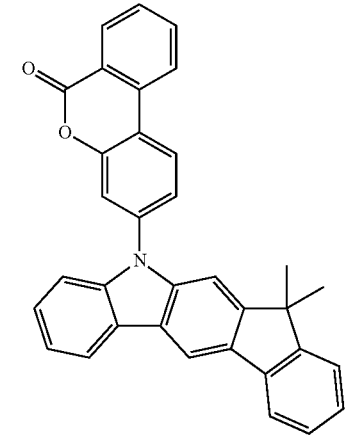 [SMILES: CC1(C)c2ccccc2-c2cc3c4ccccc4n(-c4ccc5c(c4)oc(=O)c4ccccc45)c3cc21] | 79% |
| m9 | 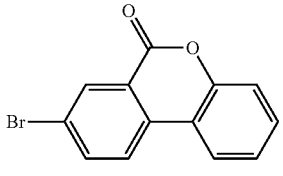 | 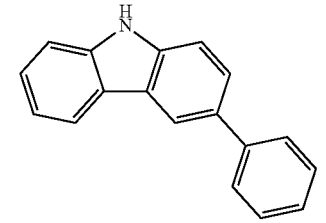<br>[103012-26-6] | 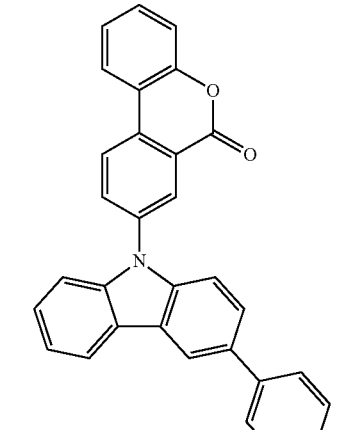 | 81% |

| Reactant 1 | Reactant 2 | Product | Yield |
|---|---|---|---|
| m10 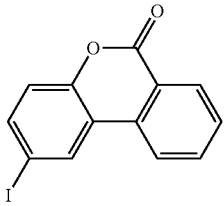 [151648-54-3] | 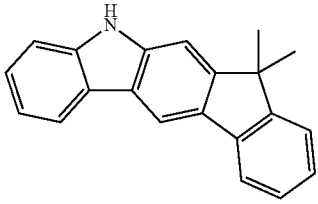 [1257220-47-5] | 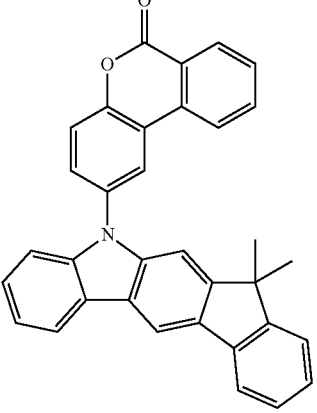 | 78% |

Production of the OLEDs

In use examples R1 to R16 which follow (see tables 1 and 2), the data of various OLEDs are presented.

Pretreatment for Examples R1-R16:

Glass plaques coated with structured ITO (indium tin oxide) of thickness 50 nm, for improved processing, are coated with 20 nm of PEDOT:PSS (poly(3,4-ethylenedioxythiophene) poly(styrenesulfonate), purchased as CLEV-IOS™ P VP AI 4083 from Heraeus Precious Metals GmbH, Germany, spun on from aqueous solution). These coated glass plaques form the substrates to which the OLEDs are applied.

The OLEDs basically have the following layer structure: substrate/hole transport layer (HTL)/optional interlayer (IL)/ electron blocker layer (EBL)/emission layer (EML)/optional hole blocker layer (HBL)/electron transport layer (ETL)/ optional electron injection layer (EIL) and finally a cathode. The cathode is formed by an aluminum layer of thickness 100 nm. The exact structure of the OLEDs can be found in Table 1. The materials required for production of the OLEDs are shown in Table 3.

All materials are applied by thermal vapor deposition in a vacuum chamber. In this case, the emission layer always consists of at least one matrix material (host material) and an emitting dopant (emitter) which is added to the matrix material(s) in a particular proportion by volume by coevaporation. Details given in such a form as IC1:IC3:TEG1 (55%:35%:10%) mean here that the material IC1 is present in the layer in a proportion by volume of 55%, IC3 in a proportion of 35% and TEG1 in a proportion of 10%. Analogously, the electron transport layer may also consist of a mixture of two materials.

The OLEDs are characterized in a standard manner. For this purpose, the electroluminescence spectra, the current efficiency (measured in cd/A), the power efficiency (measured in lm/W) and the external quantum efficiency (EQE, measured in percent) as a function of luminance, calculated from current-voltage-luminance characteristics (IUL characteristics) assuming Lambertian emission characteristics, and also the lifetime are determined. The electroluminescence spectra are determined at a luminance of 1000 cd/m², and the CIE 1931 x and y color coordinates are calculated therefrom. The parameter U1000 in Table 2 refers to the voltage which is required for a luminance of 1000 cd/m². CE1000 and PE1000 respectively refer to the current and power efficiencies which are achieved at 1000 cd/m². Finally, EQE1000 refers to the external quantum efficiency at an operating luminance of 1000 cd/m².

The data for the various OLEDs are collated in Table 2. Examples R1-R16 show data for OLEDs of the invention. The structures of the invention are used here as matrix material in the emission layer (EML) and for conduction of electrons in the electron transport layer (ETL). In addition, the structures of the invention can be used as hole blocker layer (HBL).

TABLE 1

Structure of the OLEDs

| Ex. | HTL thickness | IL thickness | EBL thickness | EML thickness | HBL thickness | ETL thickness | EIL thickness |
|---|---|---|---|---|---|---|---|
| R1 | SpA1 70 nm | HATCN 5 nm | SpMA1 90 nm | EG1:TEG1 (90%:10%) 30 nm | IC1 10 nm | ST2:LiQ (50%:50%) 30 nm | — |
| R2 | SpA1 70 nm | HATCN 5 nm | SpMA1 90 nm | EG2:TEG1 (90%:10%) 30 nm | IC1 10 nm | ST2:LiQ (50%:50%) 30 nm | — |
| R3 | SpA1 70 nm | HATCN 5 nm | SpMA1 90 nm | EG3:TEG1 (90%:10%) 30 nm | IC1 10 nm | ST2:LiQ (50%:50%) 30 nm | — |
| R4 | SpA1 70 nm | HATCN 5 nm | SpMA1 90 nm | EG4:TEG1 (90%:10%) 30 nm | IC1 10 nm | ST2:LiQ (50%:50%) 30 nm | — |
| R5 | SpA1 70 nm | HATCN 5 nm | SpMA1 90 nm | IC1:TEG1 (90%:10%) 30 nm | IC1 10 nm | EG5:LiQ (50%:50%) 30 nm | — |

TABLE 1-continued

Structure of the OLEDs

| Ex. | HTL thickness | IL thickness | EBL thickness | EML thickness | HBL thickness | ETL thickness | EIL thickness |
|---|---|---|---|---|---|---|---|
| R6 | SpA1 70 nm | HATCN 5 nm | SpMA1 90 nm | IC1:TEG1 (90%:10%) 30 nm | IC1 10 nm | EG6:ST2 (60%:40%) 30 nm | LiF 1 nm |
| R7 | SpA1 70 nm | HATCN 5 nm | SpMA1 90 nm | EG7:IC3:TEG1 (65%:30%:5%) 30 nm | IC1 10 nm | ST2:LiQ (50%:50%) 30 nm | — |
| R8 | SpA1 70 nm | HATCN 5 nm | SpMA1 90 nm | EG8:TEG1 (90%:10%) 30 nm | IC1 10 nm | ST2:LiQ (50%:50%) 30 nm | — |
| R9 | SpA1 70 nm | HATCN 5 nm | SpMA1 90 nm | IC1:TEG1 (90%:10%) 30 nm | EG9 10 nm | ST2:LiQ (50%:50%) 30 nm | — |
| R10 | SpA1 70 nm | HATCN 5 nm | SpMA1 90 nm | IC1:TEG1 (90%:10%) 30 nm | IC1 10 nm | EG10:LiQ (50%:50%) 30 nm | — |
| R11 | HATCN 5 nm | SpMA1 70 nm | SpMA2 15 nm | IC1:EG11:TEY1 (45%:45%:10%) 25 nm | — | ST2 45 nm | LiQ 3 nm |
| R12 | HATCN 5 nm | SpMA1 70 nm | SpMA2 15 nm | L1:EG12:TEY1 (45%:45%:10%) 25 nm | — | ST2 45 nm | LiQ 3 nm |
| R13 | SpA1 90 nm | HATCN 5 nm | SpMA1 130 nm | EG13:TER3 (92%:8%) 40 nm | — | ST2:LiQ (50%:50%) 40 nm | — |
| R14 | SpA1 70nm | HATCN 5 nm | SpMA1 90 nm | IC1:TEG1 (90%:10%) 30 nm | IC1 10 nm | EG14:LiQ (50%:50%) 30 nm | — |
| R15 | SpA1 70 nm | HATCN 5 nm | SpMA1 90 nm | EG15:TEG1 (90%:10%) 30 nm | IC1 10 nm | ST2:LiQ (50%:50%) 30 nm | — |
| R16 | SpA1 70 nm | HATCN 5 nm | SpMA1 90 nm | EG16:TEG1 (90%:10%) 30 nm | IC1 10 nm | ST2:LiQ (50%:50%) 30 nm | — |

TABLE 2

Data of the OLEDs

| Ex. | U1000 (V) | CE1000 (cd/A) | PE1000 (lm/W) | EQE 1000 | CIE x/y at 1000 cd/m$^2$ |
|---|---|---|---|---|---|
| R1 | 3.6 | 57 | 50 | 15.7% | 0.31/0.64 |
| R2 | 3.3 | 58 | 55 | 15.5% | 0.33/0.64 |
| R3 | 3.6 | 56 | 49 | 15.4% | 0.34/0.62 |
| R4 | 3.4 | 60 | 55 | 16.1% | 0.33/0.63 |
| R5 | 3.4 | 64 | 59 | 17.2% | 0.33/0.63 |
| R6 | 3.6 | 64 | 56 | 17.4% | 0.32/0.64 |
| R7 | 3.4 | 57 | 53 | 15.5% | 0.30/0.65 |
| R8 | 3.3 | 60 | 57 | 16.5% | 0.32/0.64 |
| R9 | 3.5 | 61 | 55 | 17.2% | 0.32/0.63 |
| R10 | 3.3 | 64 | 61 | 17.0% | 0.34/0.63 |
| R11 | 2.9 | 84 | 91 | 25.1% | 0.45/0.54 |
| R12 | 3.1 | 82 | 83 | 24.0% | 0.43/0.56 |
| R13 | 4.7 | 11 | 7 | 12.2% | 0.67/0.33 |
| R14 | 3.5 | 60 | 54 | 17.0% | 0.33/0.62 |
| R15 | 3.3 | 58 | 55 | 15.6% | 0.33/0.63 |
| R16 | 3.2 | 57 | 56 | 15.3% | 0.32/0.64 |

TABLE 3

Structural formulae of the materials for the OLEDs

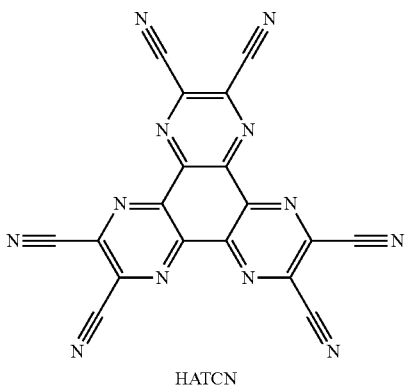

HATCN

TABLE 3-continued
Structural formulae of the materials for the OLEDs
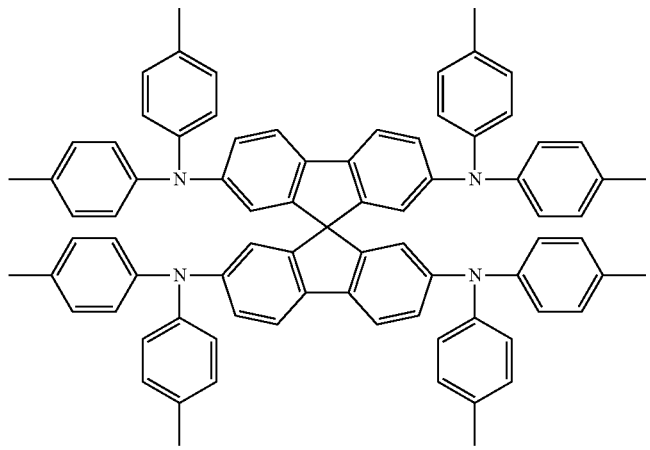
SpA1
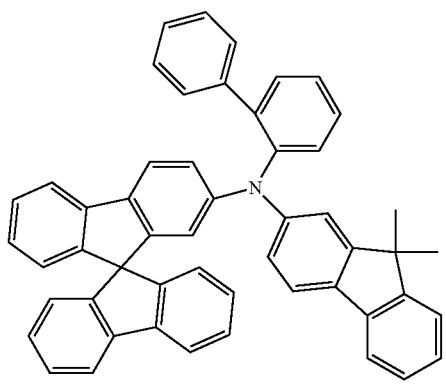 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA1
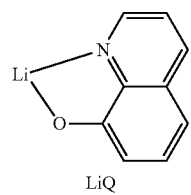
LiQ
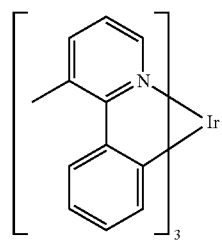
TEG1

TABLE 3-continued
Structural formulae of the materials for the OLEDs
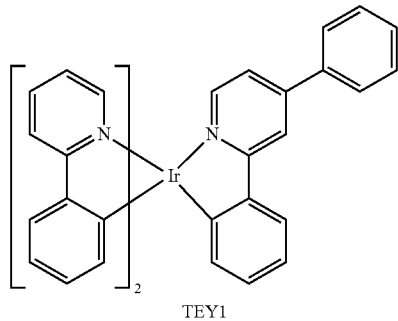
TEY1
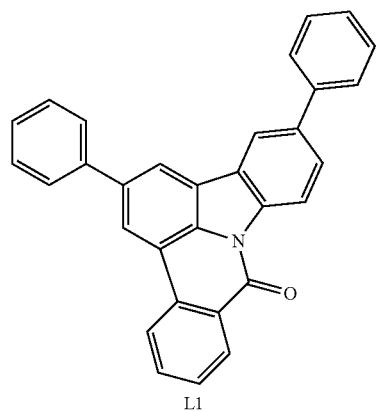
L1
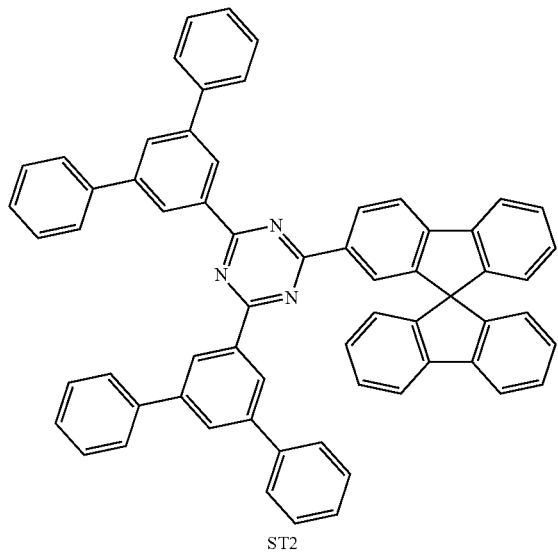
ST2
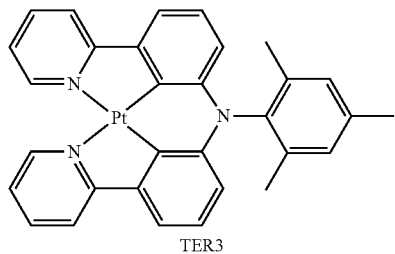
TER3

TABLE 3-continued
Structural formulae of the materials for the OLEDs
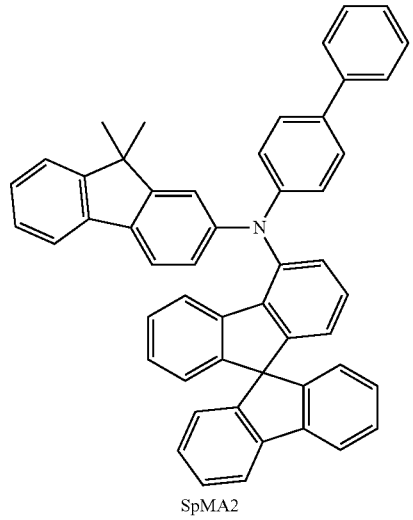
SpMA2
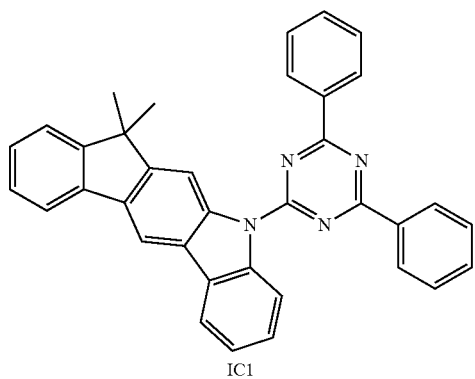
IC1
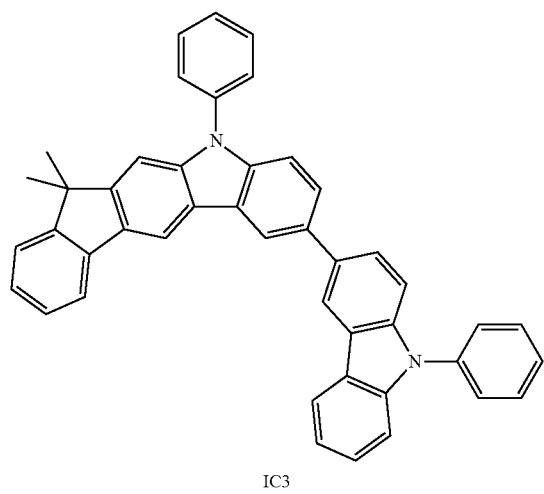
IC3

TABLE 3-continued
Structural formulae of the materials for the OLEDs
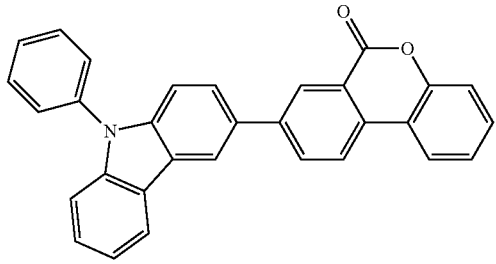 [SMILES: O=c1oc2ccccc2c2ccc(-c3ccc4c(c3)c3ccccc3n4-c3ccccc3)cc12]
EG1
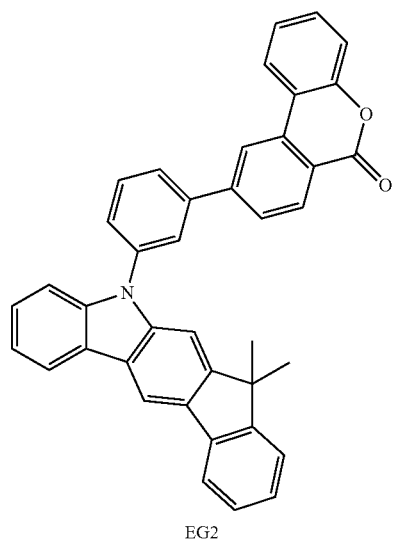
EG2
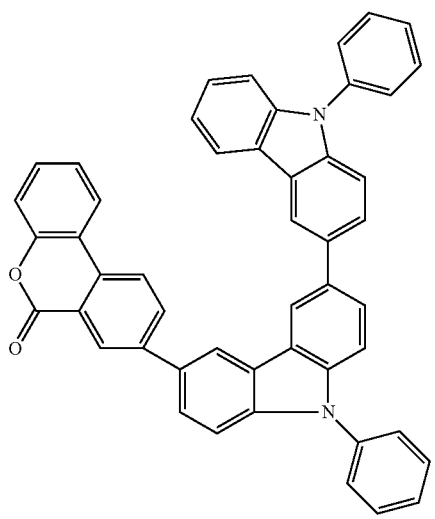 [SMILES: O=c1oc2ccccc2c2ccc(-c3ccc4c(c3)c3cc(-c5ccc6c(c5)c5ccccc5n6-c5ccccc5)ccc3n4-c3ccccc3)cc12]
EG3

TABLE 3-continued
Structural formulae of the materials for the OLEDs
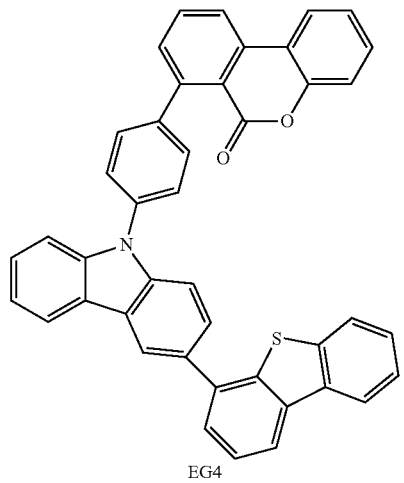
EG4
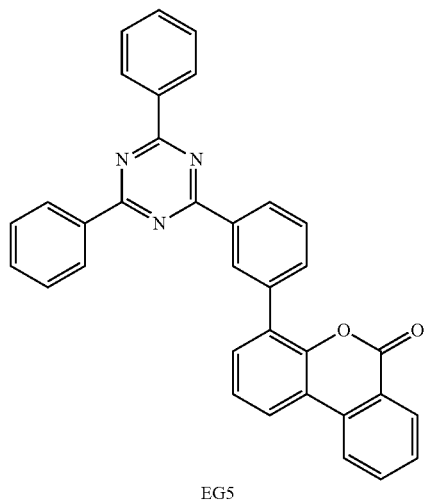
EG5
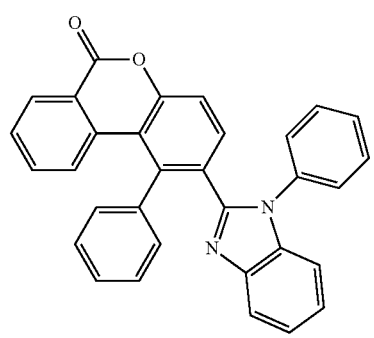 [SMILES: O=c1oc2ccc(-c3nc4ccccc4n3-c3ccccc3)c(-c3ccccc3)c2c2ccccc12]
EG6
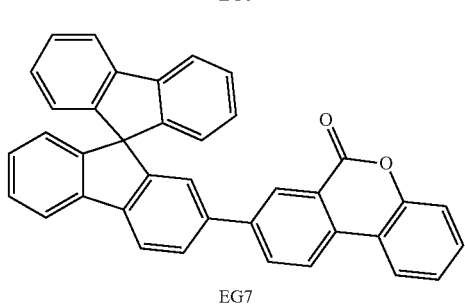
EG7

TABLE 3-continued
Structural formulae of the materials for the OLEDs
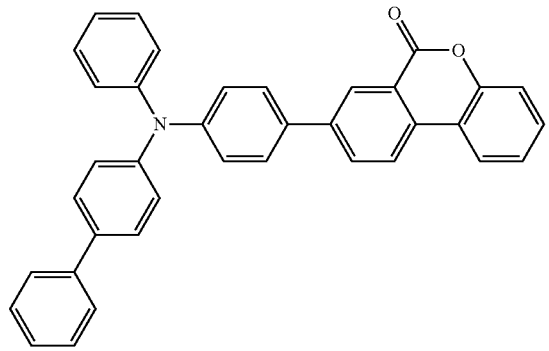 [SMILES: O=c1oc2ccccc2c2ccc(-c3ccc(N(c4ccccc4)c4ccc(-c5ccccc5)cc4)cc3)cc12]
EG8
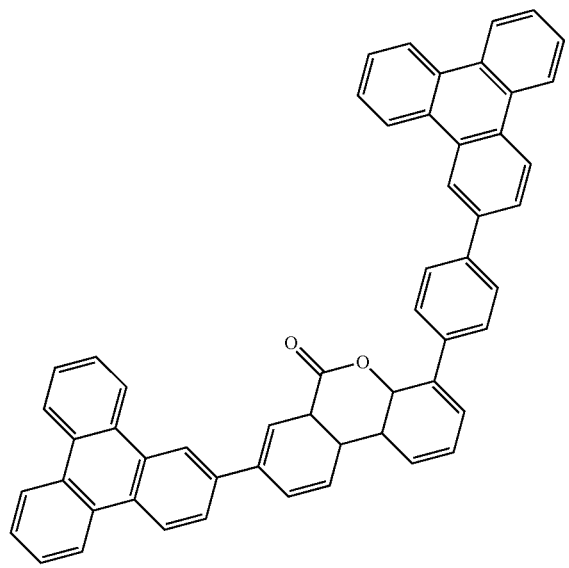 [SMILES: O=C1OC2C(c3ccc(-c4ccc5c6ccccc6c6ccccc6c5c4)cc3)=CC=CC2C2C=CC(c3ccc4c5ccccc5c5ccccc5c4c3)=CC12]
EG9
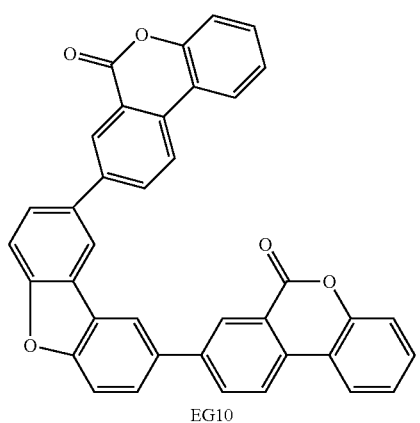
EG10

TABLE 3-continued
Structural formulae of the materials for the OLEDs
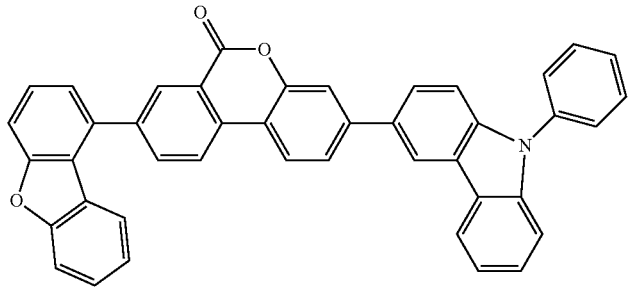 [SMILES: O=c1oc2cc(-c3ccc4c(c3)c3ccccc3n4-c3ccccc3)ccc2c2ccc(-c3cccc4oc5ccccc5c34)cc12]
EG11
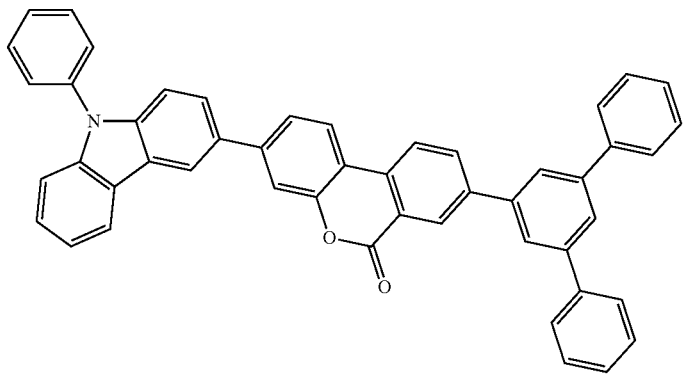 [SMILES: O=c1oc2cc(-c3ccc4c(c3)c3ccccc3n4-c3ccccc3)ccc2c2ccc(-c3cc(-c4ccccc4)cc(-c4ccccc4)c3)cc12]
EG12
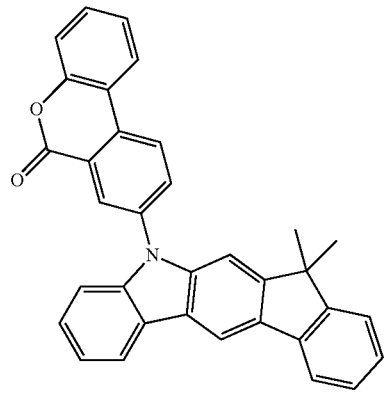 [SMILES: CC1(C)c2ccccc2-c2cc3c4ccccc4n(-c4ccc5c(c4)c(=O)oc4ccccc45)c3cc21]
EG13
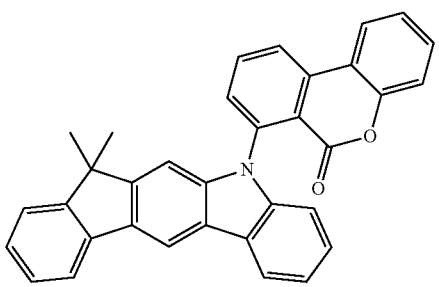 [SMILES: CC1(C)c2ccccc2-c2cc3c4ccccc4n(-c4cccc5c4c(=O)oc4ccccc45)c3cc21]
EG14

TABLE 3-continued

Structural formulae of the materials for the OLEDs

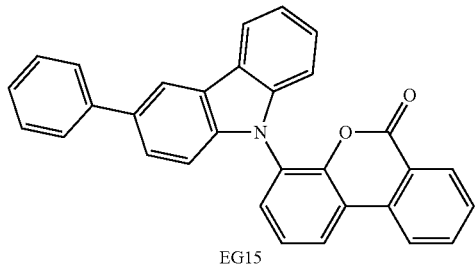

EG15

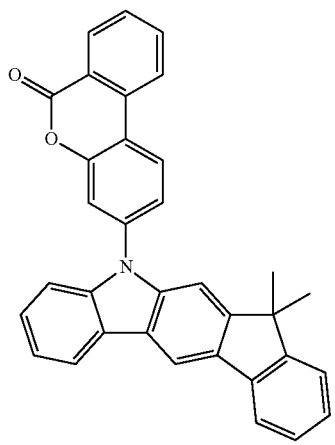 [SMILES: CC1(C)c2ccccc2-c2cc3c4ccccc4n(-c4ccc5c(c4)oc(=O)c4ccccc45)c3cc21]

EG16

The invention claimed is:

1. A compound having a molecular weight of not more than 5000 g/mol comprising structures of the formula (I)

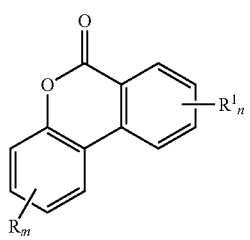

Formula (I)

where the symbols used are as follows:

R is the same or different at each instance and is H, D, F, Cl, Br, I, C(=O)Ar$^1$, CN, Si(R$^2$)$_3$, B(OR$^2$)$_2$, a straight-chain alkyl, or alkoxy group having 1 to 10 carbon atoms or an alkenyl group having 2 to 10 carbon atoms, or a branched or cyclic alkyl, or alkoxy group having 3 to 10 carbon atoms, each of which may be substituted by one or more R$^2$ radicals, where one or more hydrogen atoms may be replaced by D or F or an aromatic or heteroaromatic ring system which has 5 to 30 aromatic ring atoms, each of which may be substituted by one or more R$^2$ radicals, or an aryloxy or heteroaryloxy group which has 5 to 30 aromatic ring atoms and may be substituted by one or more R$^2$ radicals, or a combination of these systems; at the same time, two or more adjacent R substituents may also form a mono- or polycyclic aliphatic or aromatic ring system with one another, with the ring to which R is bonded, with a ring to which R is adjacent or with an R$^1$ radical;

R$^1$ is the same or different at each instance and is H, D, F, Cl, Br, I, C(=O)Ar$^1$, CN, Si(R$^2$)$_3$, B(OR$^2$)$_2$, a straight-chain alkyl or alkoxy group having 1 to 10 carbon atoms or an alkenyl group having 2 to 10 carbon atoms, or a branched or cyclic alkyl or alkoxy group having 3 to 10 carbon atoms, which are each substituted by one or more R$^2$ radicals, where one or more hydrogen atoms may be replaced by D or F, or an aromatic or heteroaromatic ring system which has 5 to 30 aromatic ring atoms, each of which may be substituted by one or more R$^2$ radicals; at the same time, two or more adjacent R$^1$ substituents may also form a mono- or polycyclic aliphatic or aromatic ring system with one another, with the ring to which R$^1$ is bonded, with a ring to which R$^1$ is adjacent or with an R radical;

R$^2$ is the same or different at each instance and is H, D, F, Cl, Br, I, CHO, C(=O)Ar$^1$, P(=O)(Ar$^1$)$_2$, S(=O)Ar$^1$, S(=O)$_2$Ar$^1$, CN, NO$_2$, Si(R$^3$)$_3$, B(OR$^3$)$_2$, OSO$_2$R$^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R$^3$ radicals, where one or more nonadjacent CH$_2$ groups may be replaced by C≡C, Si(R$^3$)$_2$, Ge(R$^3$)$_2$, Sn(R$^3$)$_2$, C=O, C=S, C=Se, P(=O)(R$^3$), SO, SO$_2$, O, S or CONR$^3$ and where one or more hydrogen atoms may be replaced by D, F, Cl, Br, I, CN or NO$_2$, or an aromatic or heteroaromatic ring system which has 5 to 40 aromatic ring atoms, each of which may be substituted by one or more R$^3$ radicals, or an aryloxy or heteroaryloxy group which has 5 to 40 aromatic ring atoms and may be substituted by one or more $R^3$ radicals, or a combination of these systems; at the same time, two or more adjacent $R^2$ substituents may also form a mono- or polycyclic, aliphatic or aromatic ring system with one another;

$Ar^1$ is the same or different at each instance and is an aromatic or heteroaromatic ring system which has 5 to 30 aromatic ring atoms and may be substituted by one or more $R^2$ radicals; at the same time, it is also possible for two $Ar^1$ radicals bonded to the same phosphorus atom to be joined to one another by a single bond or a bridge selected from $B(R^3)$, $C(R^3)_2$, $Si(R^3)_2$, $C=O$, $C=NR^3$, $C=C(R^3)_2$, $O$, $S$, $S=O$, $SO_2$, $N(R^3)$, $P(R^3)$ and $P(=O)R^3$;

$R^3$ is the same or different at each instance and is H, D, F or an aliphatic, aromatic and/or heteroaromatic hydrocarbyl radical having 1 to 20 carbon atoms, in which hydrogen atoms may also be replaced by F; at the same time, two or more adjacent $R^3$ substituents may also form a mono- or polycyclic, aliphatic or aromatic ring system with one another;

m, n are each independently 0, 1, 2, 3 or 4;

with the proviso that the sum of m and n is not less than 1;

at least one of the R and/or $R^1$ groups in formula (I) is at least one L group; and L is selected from the group consisting of Formula (L-1) to (L-42)

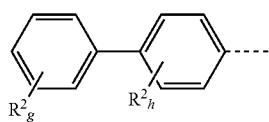

Formula (L-1)

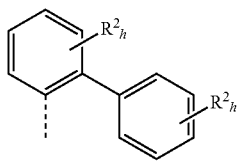

Formula (L-2)

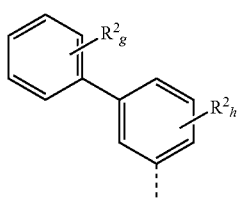

Formula (L-3)

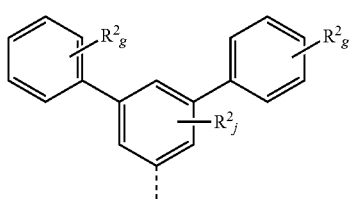

Formula (L-4)

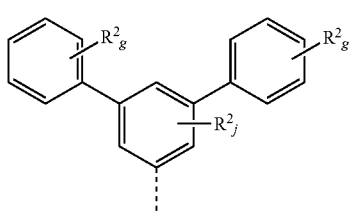

Formula (L-5)

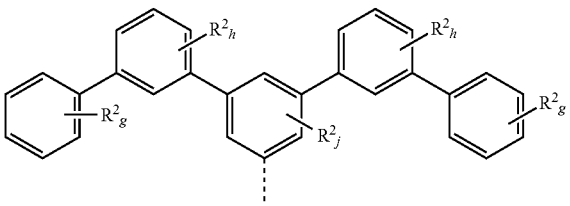

Formula (L-6)

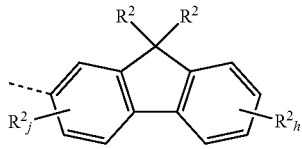

Formula (L-7)

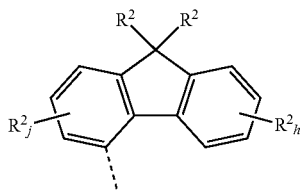

Formula (L-8)

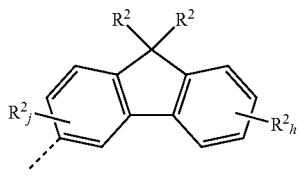

Formula (L-9)

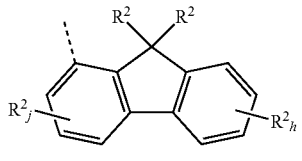

Formula (L-10)

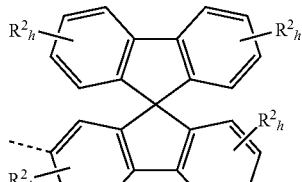

Formula (L-11)

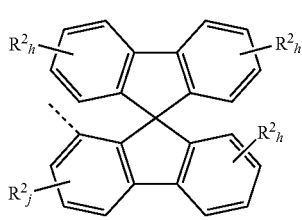

Formula (L-12)

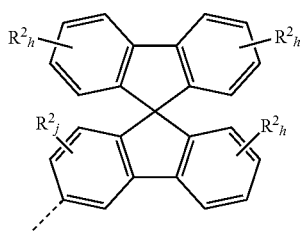

Formula (L-13)

-continued
Formula (L-14)
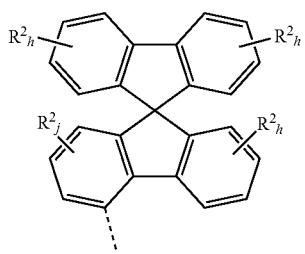
Formula (L-15)
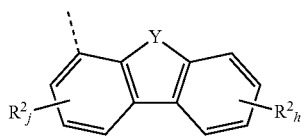
Formula (L-16)
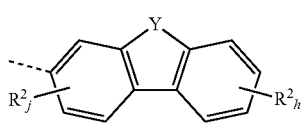
Formula (R1-17)
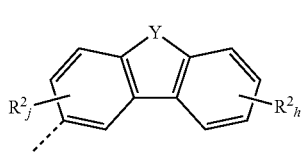
Formula (L-18)
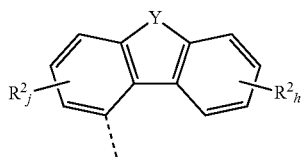
Formula (L-19)
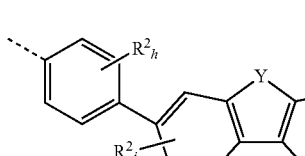
Formula (L-20)
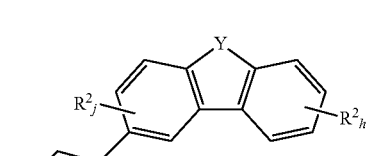
Formula (L-21)
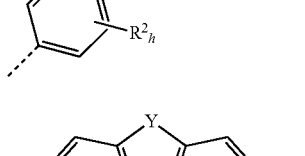
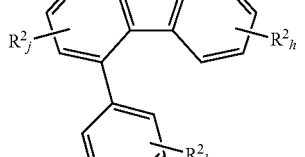
-continued
Formula (L-22)
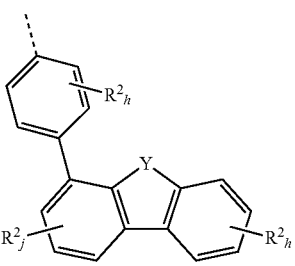
Formula (L-23)
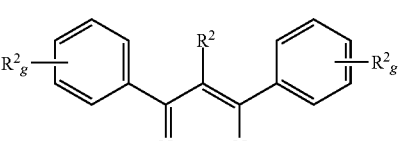
Formula (L-24)
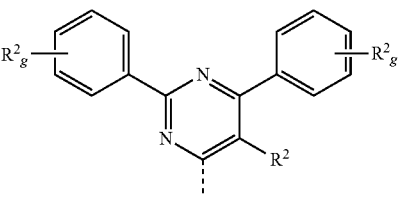
Formula (L-25)
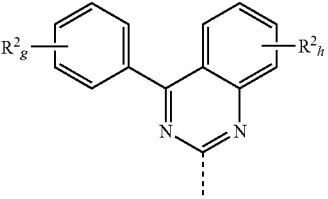
Formula (L-26)
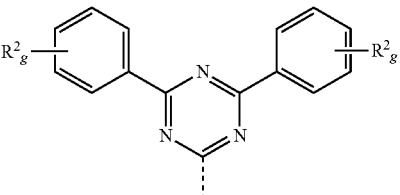
Formula (L-27)
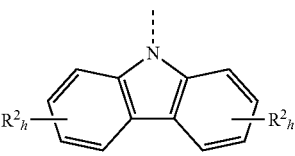
Formula (L-28)
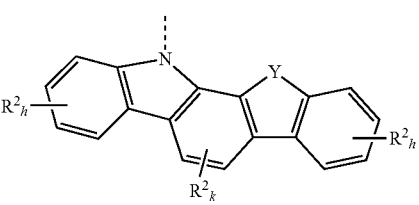

Formula (L-29)
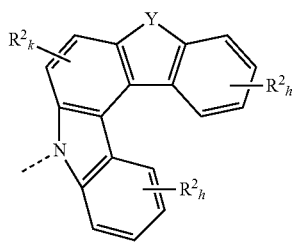

Formula (L-30)
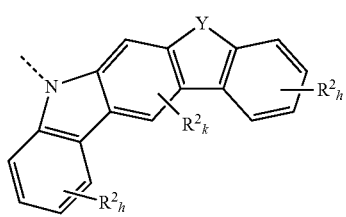

Formula (L-31)
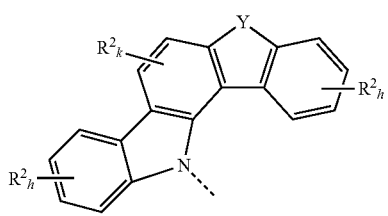

Formula (L-32)
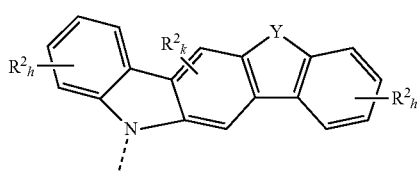

Formula (L-33)
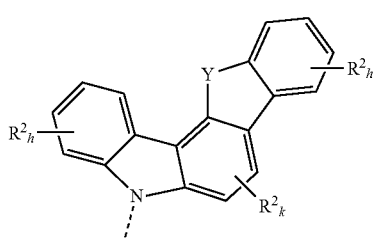

Formula (L-34)
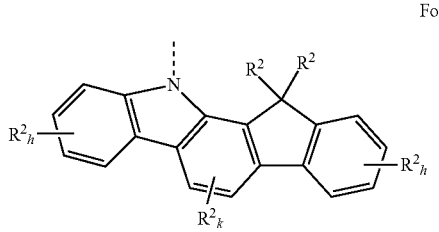

Formula (L-35)
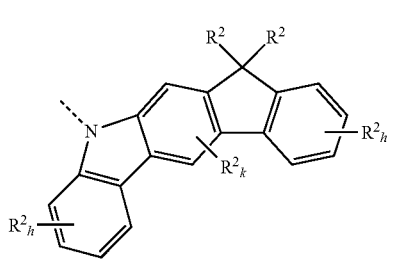

Formula (L-36)
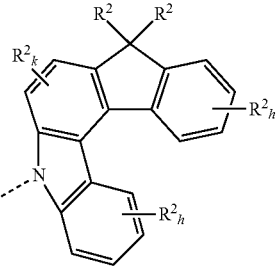

Formula (L-37)
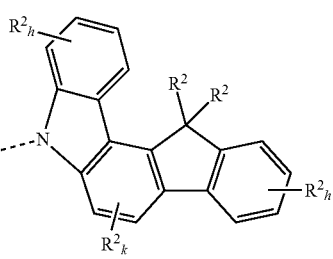

Formula (L-38)
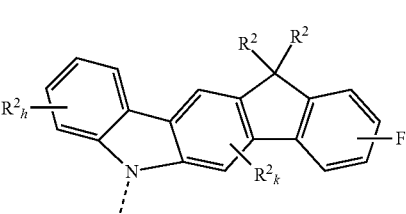

Formula (L-39)
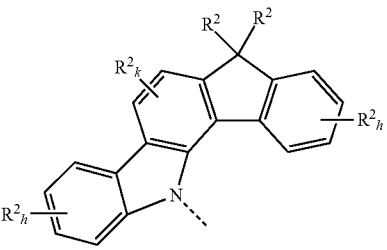

Formula (L-40)
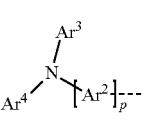

Formula (L-41)
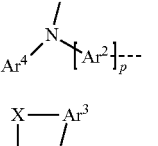

Formula (L-42)
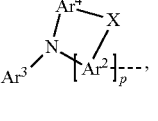

wherein the dashed bond marks the attachment position,
g is 0, 1, 2, 3, 4 or 5,
h is 0, 1, 2, 3 or 4,
j is 0, 1, 2 or 3,
Y is O, S or $N(R^1)$,
k is 0, 1 or 2,
$Ar^2$, $Ar^3$, $Ar^4$ are each independently an aryl group of 6 to 40 carbon atoms or a heteroaryl group of 3 to 40 carbon atoms, each of which is optionally substituted by one or more $R^1$;

p is 0 or 1,

X is a bond, $CR^1_2$, C=O, $N(R^1)$, $B(R^1)$, $SiR^1_2$, O or S.

2. An oligomer, polymer or dendrimer containing one or more compounds as claimed in claim 1, wherein one or more bonds of the compound to the polymer, oligomer or dendrimer are present.

3. A composition comprising at least one compound as claimed in claim 1 and at least one further compound selected from the group consisting of fluorescent emitters, phosphorescent emitters, host materials, matrix materials, electron transport materials, electron injection materials, hole conductor materials, hole injection materials, electron blocker materials and hole blocker materials.

4. A formulation comprising at least one compound as claimed in claim 1, and at least one solvent.

5. A process for preparing a compound as claimed in claim 1 comprising joining a coumarin compound to an aryl and/or heteroaryl group via a coupling reaction.

6. A product comprising the compound as claimed in claim 1, wherein the product is a hole transport material, hole injection material, hole blocker material, electron injection material, electron blocker material and/or electron transport material.

7. An electronic device comprising at least one compound as claimed in claim 1, wherein the electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field quench devices, light-emitting electrochemical cells and organic laser diodes.

8. The electronic device as claimed in claim 7, wherein the sum total of the indices m and n is not more than 3.

9. The electronic device as claimed in claim 7, wherein the structure of formula (I) has one or two L groups.

10. The electronic device as claimed in claim 7, wherein the L group in formula (I) comprises at least one biphenyl, fluorenyl and/or spirobifluorenyl group.

11. The electronic device as claimed in claim 7, wherein the index m is 1 or 2 and at least one of the R radicals is an L group, where the index n is 0.

12. The electronic device as claimed in claim 7, wherein the index n is 1 or 2 and at least one of the $R^1$ radicals is an L group, where the index m is 0.

13. The electronic device as claimed in claim 7, wherein the index m is 1 or 2 and the index n is 1 or 2, where at least one of the R radicals is an L group and at least one of the $R^1$ radicals is an L group.

14. The electronic device as claimed claim 7, wherein, in the structure of formula (I), at least one L radical is a group selected from the formulae (L-1) to (L-14)

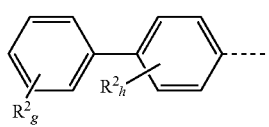

Formula (L-1)

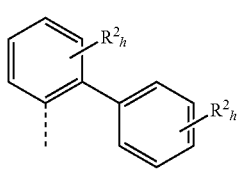

Formula (L-2)

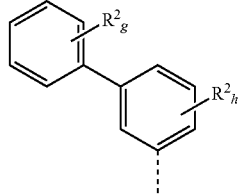

Formula (L-3)

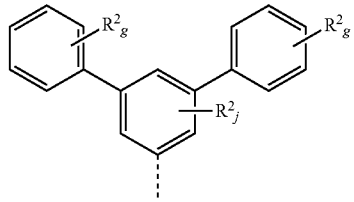

Formula (L-4)

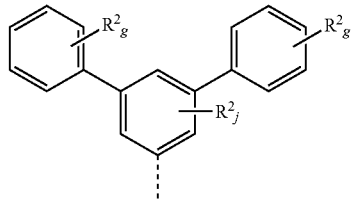

Formula (L-5)

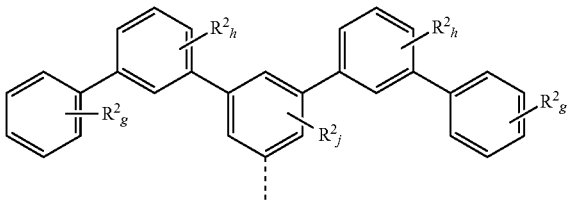

Formula (L-6)

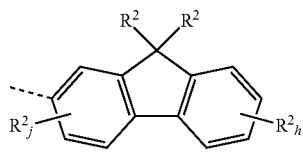

Formula (L-7)

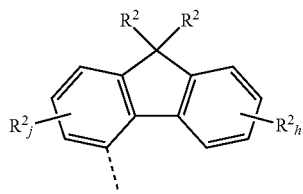

Formula (L-8)

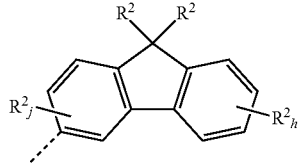

Formula (L-9)

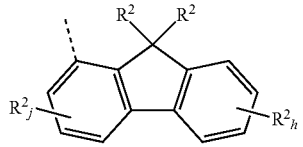

Formula (L-10)

-continued

Formula (L-11)

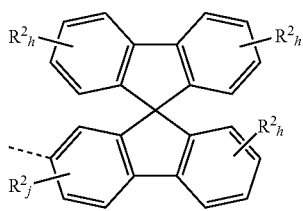

Formula (L-12)

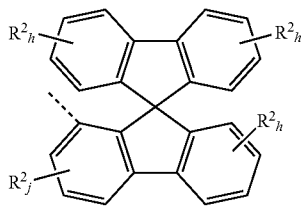

Formula (L-13)

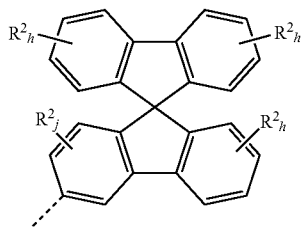

Formula (L-14)

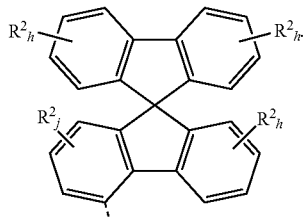

15. The electronic device as claimed in claim 7, wherein the L group in formula (I) comprises at least one heteroaryl group having a nitrogen atom.

16. The electronic device as claimed in claim 7, wherein the L group in formula (I) comprises at least one carbazole, diazine, triazine, benzothiophene and/or benzofuran group.

17. The electronic device as claimed in claim 7, wherein, in the structure of formula (I), at least one L radical is a group selected from the formulae (L-15) to (L-39)

Formula (L-15)

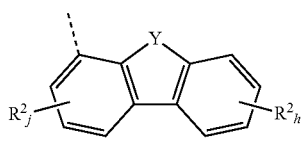

Formula (L-16)

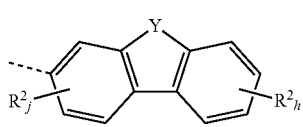

-continued

Formula (R¹-17)

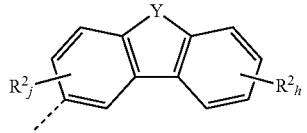

Formula (L-18)

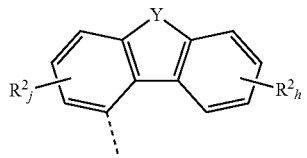

Formula (L-19)

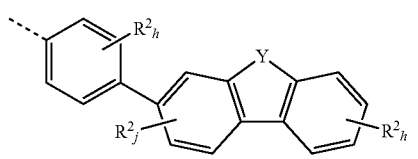

Formula (R¹-20)

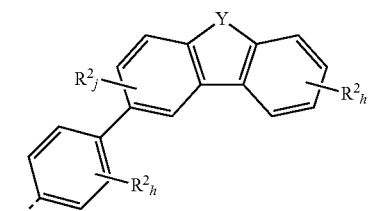

Formula (L-21)

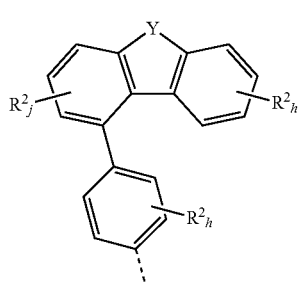

Formula (L-22)

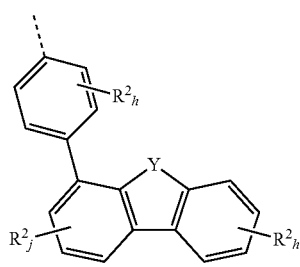

Formula (L-23)

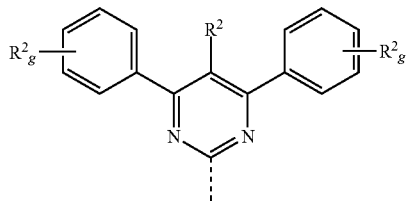

Formula (L-24)
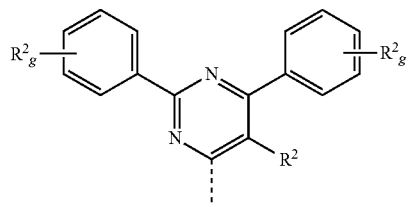
Formula (L-25)
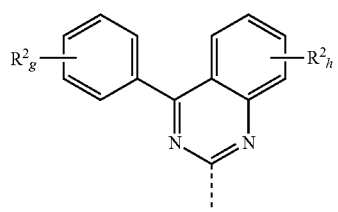
Formula (L-26)
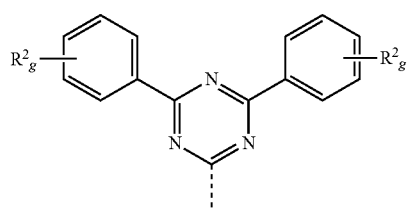
Formula (L-27)
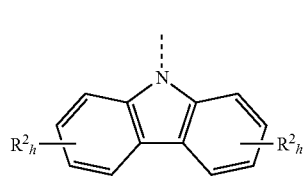
Formula (L-28)
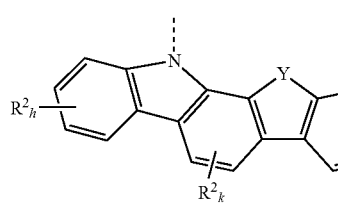
Formula (L-29)
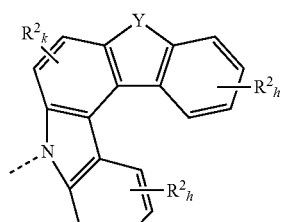
Formula (L-30)
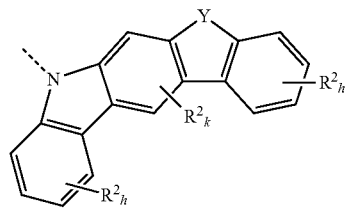
Formula (L-31)
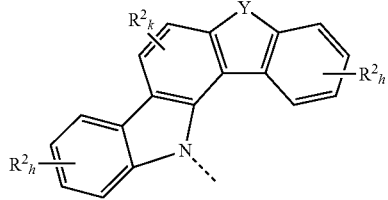
Formula (L-32)
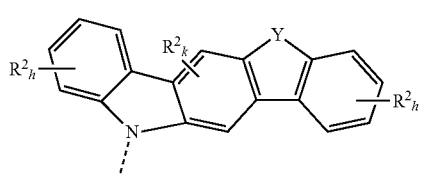
Formula (L-33)
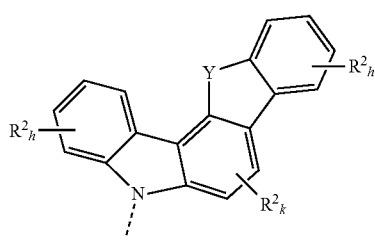
Formula (L-34)
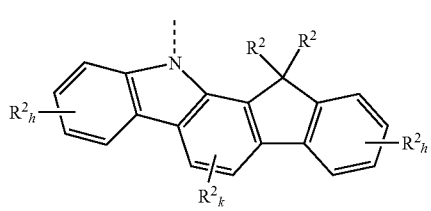
Formula (L-35)
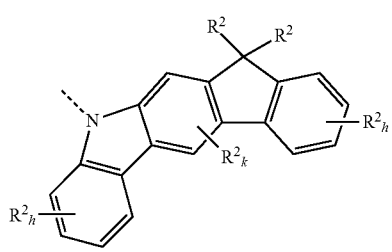
Formula (L-36)
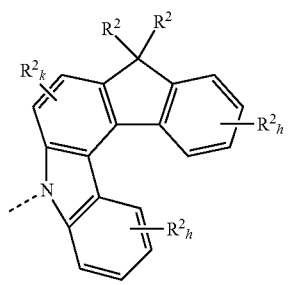

Formula (L-37)

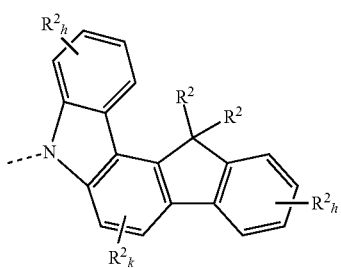

Formula (II)

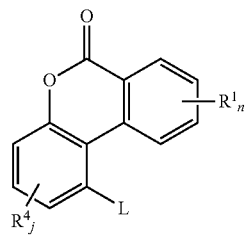

Formula (L-38)

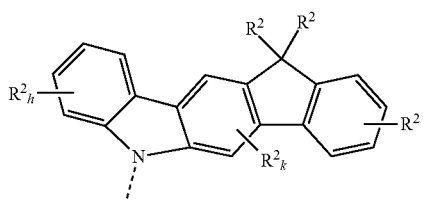

Formula (III)

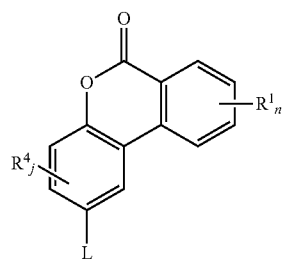

Formula (L-39)

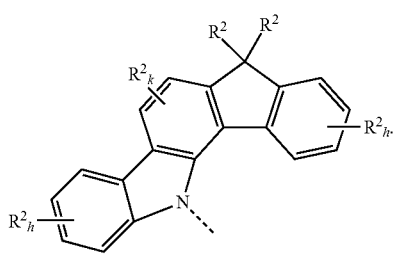

Formula (IV)

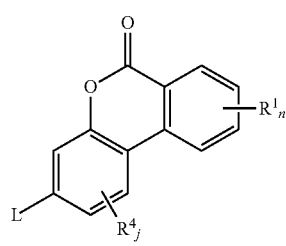

18. The electronic device as claimed in claim 7, wherein, in the structure of formula (I), at least one L radical is a group selected from the formulae (L-40) to (L-42)

Formula (L-40)

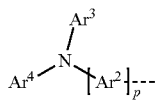

Formula (V)

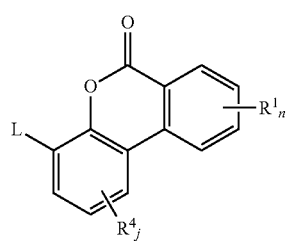

Formula (L-41)

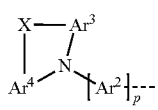

Formula (VI)

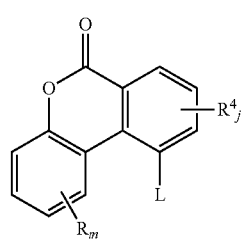

Formula (L-42)

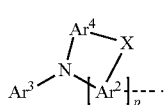

19. The electronic device as claimed claim 7, wherein the structure of formula (I) comprises not more than one reactive group.

20. The electronic device as claimed in claim 19, wherein the structure of formula (I) has at most the reactive group selected from Br, Cl and B(OR$^2$)$_2$.

21. The electronic device as claimed in claim 7, wherein the compound comprises structures of the formulae (II), (III), (IV), (V), (VI), (VII), (VIII) and/or (IX)

Formula (VII)

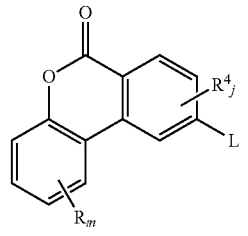

-continued

Formula (VIII)

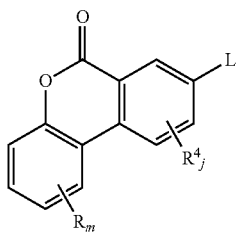

Formula (IX)

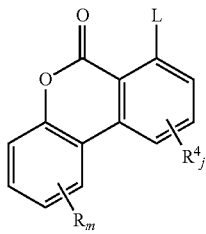

where

R⁴ is the same or different at each instance and is H, D, F, Cl, Br, I, CHO, C(=O)Ar¹, P(=O)(Ar¹)₂, S(=O)Ar¹, S(=O)₂Ar¹, CN, NO₂, Si(R²)₃, B(OR²)₂, OSO₂R², a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R² radicals, where one or more nonadjacent CH₂ groups may be replaced by R²C=CR², C≡C, Si(R²)₂, Ge(R²)₂, Sn(R²)₂, C=O, C=S, C=Se, P(=O)(R²), SO, SO₂, O, S or CONR² and where one or more hydrogen atoms may be replaced by D, F, Cl, Br, I, CN or NO₂, or an aromatic or heteroaromatic ring system which has 5 to 40 aromatic ring atoms, each of which may be substituted by one or more R² radicals, or an aryloxy or heteroaryloxy group which has 5 to 40 aromatic ring atoms and may be substituted by one or more R² radicals, where the R² and Ar¹ radicals have the definition given in claim 1, or a combination of these systems; at the same time, two or more adjacent R⁴ substituents may also form a mono- or polycyclic aliphatic or aromatic ring system with one another, with the ring to which R⁴ is bonded, with a ring to which R⁴ is adjacent or with an R or R¹ radical.

22. The electronic device as claimed in claim 7, wherein the compound comprises structures of the formulae (X), (XI), (XII), (XIII), (XIV), (XV), (XVI) and/or (XVII)

Formula (X)

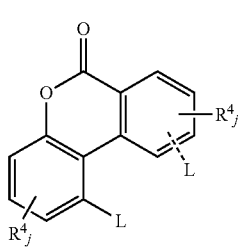

-continued

Formula (XI)

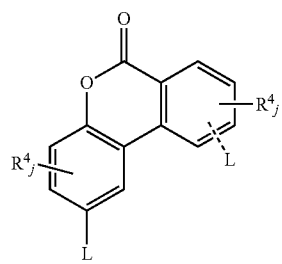

Formula (XII)

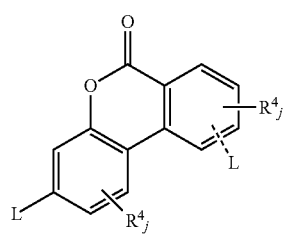

Formula (XIII)

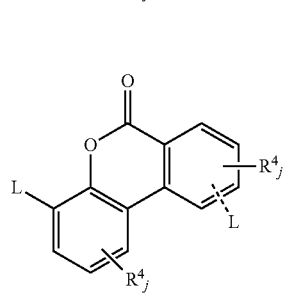

Formula (XIV)

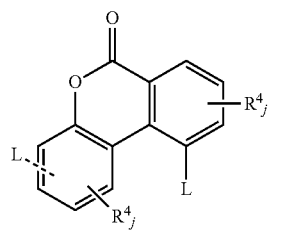

Formula (XV)

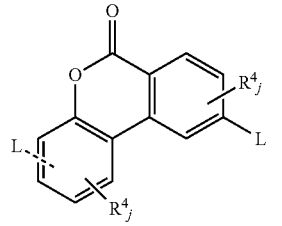

Formula (XVI)

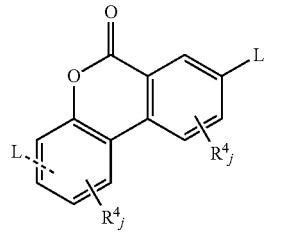

-continued

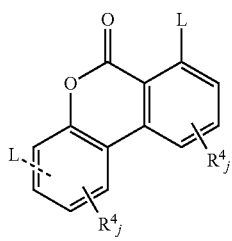

Formula (XVII)

where
R⁴ is the same or different at each instance and is H, D, F, Cl, Br, I, CHO, C(=O)Ar¹, P(=O)(Ar¹)₂, S(=O)Ar¹, S(=O)₂Ar¹, CN, NO₂, Si(R²)₃, B(OR²)₂, OSO₂R², a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R² radicals, where one or more nonadjacent CH₂ groups may be replaced by R²C=CR², C≡C, Si(R²)₂, Ge(R²)₂, Sn(R²)₂, C=O, C=S, C=Se, P(=O)(R²), SO, SO₂, O, S or CONR² and where one or more hydrogen atoms may be replaced by D, F, Cl, Br, I, CN or NO₂, or an aromatic or heteroaromatic ring system which has 5 to 40 aromatic ring atoms, each of which may be substituted by one or more R² radicals, or an aryloxy or heteroaryloxy group which has 5 to 40 aromatic ring atoms and may be substituted by one or more R² radicals, where the R² and Ar¹ radicals have the definition given in claim 1, or a combination of these systems; at the same time, two or more adjacent R⁴ substituents may also form a mono- or polycyclic aliphatic or aromatic ring system with one another, with the ring to which R⁴ is bonded or with a ring to which R⁴ is adjacent.

23. The electronic device as claimed in claim 21, wherein the R⁴ radical is not an aromatic group having 10 to 40 carbon atoms or a heteroaromatic group having 6 to 40 carbon atoms, where the aromatic and/or heteroaromatic group comprises at least two adjacent aromatic and/or heteroaromatic rings, each of which may be fused or unfused and/or may be substituted by one or more R² radicals.

* * * * *